US008604004B2

(12) United States Patent
Kahne et al.

(10) Patent No.: US 8,604,004 B2
(45) Date of Patent: Dec. 10, 2013

(54) MOENOMYCIN ANALOGS, METHODS OF SYNTHESIS, AND USES THEREOF

(75) Inventors: Daniel Kahne, Brookline, MA (US); Suzanne Walker Kahne, Brookline, MA (US); Masaatsu Adachi, Nagoya (JP); Emma Doud, Cambridge, MA (US); Shinichiro Fuse, Gumma (JP); Xiaonan Lin, Mendota Heights, MN (US); Yi Zhang, San Diego, CA (US); Hirokazu Tsukamoto, Cambridge, MA (US); Bohdan Ostash, L'viv (UA)

(73) Assignee: President and Fellows of Harvard College, Cambridge, MA (US)

(*) Notice: Subject to any disclaimer, the term of this patent is extended or adjusted under 35 U.S.C. 154(b) by 421 days.

(21) Appl. No.: 12/681,052

(22) PCT Filed: Oct. 3, 2008

(86) PCT No.: PCT/US2008/078771
§ 371 (c)(1),
(2), (4) Date: Jan. 4, 2011

(87) PCT Pub. No.: WO2009/046314
PCT Pub. Date: Apr. 9, 2009

(65) Prior Publication Data
US 2011/0136759 A1 Jun. 9, 2011

Related U.S. Application Data

(60) Provisional application No. 60/977,511, filed on Oct. 4, 2007.

(51) Int. Cl.
*A61K 31/702* (2006.01)
*A61K 31/715* (2006.01)
*A61K 31/7016* (2006.01)
*A61K 31/7028* (2006.01)
*C07H 5/04* (2006.01)
*C07H 5/06* (2006.01)

(52) U.S. Cl.
USPC ............... 514/61; 514/54; 514/25; 536/55.1; 536/53; 536/4.1

(58) Field of Classification Search
USPC .................. 514/61, 54, 25; 536/55.1, 53, 4.1
See application file for complete search history.

(56) References Cited

U.S. PATENT DOCUMENTS

| | | |
|---|---|---|
| 3,949,070 A | 4/1976 | Arai et al. |
| 3,992,263 A | 11/1976 | Dietrich et al. |
| 4,270,537 A | 6/1981 | Romaine |
| 4,522,811 A | 6/1985 | Eppstein et al. |
| 4,596,556 A | 6/1986 | Morrow et al. |
| 4,684,626 A | 8/1987 | Welzel et al. |
| 4,790,824 A | 12/1988 | Morrow et al. |
| 4,842,857 A | 6/1989 | Meyers et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,206,405 A | 4/1993 | Aretz et al. |
| 5,260,051 A | 11/1993 | Cho |
| 5,260,206 A | 11/1993 | Aretz et al. |
| 5,312,335 A | 5/1994 | McKinnon et al. |
| 5,315,038 A | 5/1994 | Aretz et al. |
| 5,316,929 A | 5/1994 | Aretz et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,454,971 A | 10/1995 | Sakai et al. |
| 5,466,220 A | 11/1995 | Brenneman |
| 5,480,381 A | 1/1996 | Weston |
| 5,503,627 A | 4/1996 | McKinnon et al. |
| 5,506,140 A | 4/1996 | Aretz et al. |
| 5,520,639 A | 5/1996 | Peterson et al. |
| 5,527,288 A | 6/1996 | Gross et al. |
| 5,569,189 A | 10/1996 | Parsons |

(Continued)

FOREIGN PATENT DOCUMENTS

EP  0 652 205 A2  5/1995
EP  1 069 130 A1  1/2001

(Continued)

OTHER PUBLICATIONS

Goldman et al. (Bioorganic & Medicinal Chemistry Letters (2000), 10(20), 2251-2254).*
International Search Report and Written Opinion for PCT/US2008/078771 mailed Mar. 10, 2009.
Adachi et al., Degradation and reconstruction of moenomycin A and derivatives: dissecting the function of the isoprenoid chain. J Am Chem Soc. Nov. 1, 2006;128(43):114012-3.

(Continued)

*Primary Examiner* — Shaojia Anna Jiang
*Assistant Examiner* — Michael C Henry
(74) *Attorney, Agent, or Firm* — Wolf, Greenfield & Sacks, P.C.; C. Hunter Baker

(57) ABSTRACT

The present invention provides novel moenomycin analogs as well as pharmaceutical compositions thereof, methods of synthesis, and methods of use in treating an infection by administering an inventive compound to a subject in need thereof. The moenomycin analogs may be prepared synthetically, biosynthetically, or semi-synthetically. The analogs are particularly useful in treating or preventing infections caused by Gram-positive organisms. Certain inventive compounds may have a broader spectrum of coverage, which includes Gram-negative organisms.

28 Claims, 46 Drawing Sheets

(56) References Cited

U.S. PATENT DOCUMENTS

| | | | |
|---|---|---|---|
| 5,599,302 | A | 2/1997 | Lilley et al. |
| 5,649,912 | A | 7/1997 | Peterson |
| 5,704,911 | A | 1/1998 | Parsons |
| 5,736,533 | A | 4/1998 | Simon et al. |
| 5,888,721 | A | 3/1999 | Rothstein et al. |
| 5,893,397 | A | 4/1999 | Peterson et al. |
| 5,986,089 | A | 11/1999 | Vertesy et al. |
| 5,993,412 | A | 11/1999 | Deily et al. |
| 6,077,830 | A | 6/2000 | Vertesy et al. |
| 6,114,309 | A | 9/2000 | Allanson et al. |
| 6,153,381 | A | 11/2000 | Rothstein |
| 6,207,820 | B1 | 3/2001 | Allanson et al. |
| 6,242,424 | B1 | 6/2001 | Riess et al. |
| 6,274,716 | B1 | 8/2001 | Allanson et al. |
| 6,461,829 | B1 | 10/2002 | Kahne |
| 6,534,278 | B1 | 3/2003 | Rothstein |
| 6,911,318 | B2 | 6/2005 | Kahne |
| 6,913,895 | B1 | 7/2005 | Goldman et al. |
| 7,129,229 | B2 | 10/2006 | Raddatz et al. |
| 7,186,813 | B1 | 3/2007 | Schweitzer et al. |
| 2003/0108969 | A1 | 6/2003 | DeSousa et al. |
| 2003/0129683 | A1 | 7/2003 | Kahne |
| 2003/0158093 | A1 | 8/2003 | Sun et al. |
| 2004/0018582 | A1 | 1/2004 | Eggert et al. |
| 2004/0042981 | A1 | 3/2004 | Vertesy et al. |
| 2004/0127403 | A1 | 7/2004 | Parenti et al. |
| 2004/0147441 | A1 | 7/2004 | Leach et al. |
| 2005/0026214 | A1 | 2/2005 | Biton et al. |
| 2005/0106555 | A1 | 5/2005 | Desousa |
| 2005/0186653 | A1 | 8/2005 | Helmann et al. |
| 2005/0287181 | A1 | 12/2005 | Murthy |
| 2005/0287198 | A1 | 12/2005 | Murthy |
| 2005/0287200 | A1 | 12/2005 | Murthy |
| 2005/0287219 | A1 | 12/2005 | Murthy |
| 2005/0287220 | A1 | 12/2005 | Murthy |
| 2006/0040891 | A1 | 2/2006 | Jiang et al. |
| 2006/0093632 | A1 | 5/2006 | Murthy |
| 2006/0094669 | A1 | 5/2006 | Murthy |
| 2006/0142217 | A1 | 6/2006 | Meutermans et al. |
| 2007/0060506 | A1 | 3/2007 | Walsh et al. |
| 2010/0279980 | A1 | 11/2010 | Walker et al. |

FOREIGN PATENT DOCUMENTS

| | | | |
|---|---|---|---|
| WO | WO 97/13537 A1 | 4/1997 | |
| WO | WO 97/37705 A1 | 10/1997 | |
| WO | WO 99/26956 A1 | 6/1999 | |
| WO | WO 99/34850 A1 | 7/1999 | |
| WO | WO 00/52035 A1 | 9/2000 | |
| WO | WO 00/64915 A1 | 11/2000 | |
| WO | WO 2008/021367 A2 | 2/2008 | |
| WO | WO 2009/046314 A2 | 4/2009 | |

OTHER PUBLICATIONS

Baizman et al., Antibacterial activity of synthetic analogues based on the disaccharide structure of moenomycin, an inhibitor of bacterial transglycosylase. Microbiology. Dec. 2000;146 Pt 12:3129-40.
Barrett et al., Kinetic characterization of the glycosyltransferase module of *Staphylococcus aureus* PBP2. J Bacteriol. Mar. 2005;187(6):2215-7.
Berge et al., Pharmaceutical salts. J Pharm Sci. Jan. 1977;66(1):1-19.
Blondelet-Rouault et al., Antibiotic resistance gene cassettes derived from the omega interposon for use in *E. coli* and *Streptomyces*. Gene, May 6, 1977;190(2):315-7.
Castro-Palomino et al., N-Tetrachlorophthaloyl-Protected Trichloroacetimidate of Glucosamine as Glycosyl Donor in Oligosaccharide Synthesis. Tetrahedron Lett. 1995;36:5343-46.
Chater, *Streptomyces* inside-out: a new perspective on the bacteria that provide us with antibiotics. Philos Trans R Soc Lond B Biol Sci. May 29, 2006;361(1479):761-8.
Chen et al., Vancomycin analogues active against vanA-resistant strains inhibit bacterial transglycosylase without binding substrate. Proc Natl Acad Sci U S A. May 13, 2003;100(10):5658-63. Epub Apr. 24, 2003.
Coates et al., Stereoselective Synthesis of Moenocinol and Assignment of its Carbon-13 Nuclear Magnetic Resonance Spectrum J Org Chem. 1980;45:2685-97.
Crich et al., Are Glycosyl Triflates Intermediates in the Sulfoxide Glycosylation Method? A Chemical and $^1$H, $^{13}$C, and $^{19}$F NMR Spectroscopic Investigation. J Am Chem Soc. 1997;119:11217-23.
Crich et al., Chapter 2. Gylcosylation with Sulfoxides and Sulfinates as Donors or Promoters. Org React. 2004;64:115-251.
Crich et al., Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxy-glucosamine derivatives in glycosylation. 2-Picolinyl ethers as reactivity-enhancing replacements for benzyl ethers. J Am Chem Soc. Jul. 18, 2001;123(28):6819-25.
Datsenko et al., One-step inactivation of chromosomal genes in *Escherichia coli* K-12 using PCR products. Proc Natl Acad Sci U S A. Jun. 6, 2000;97(12):6640-5.
Debenham et al., Two New Orthogonal Amine-Protecting Groups That Can Be Cleaved under Mild or Neutral Conditions. J Am Chem Soc. 1995;117:3302-03.
Ebenezer, Colabomycin Co-Metabolites. Synthesis of 2880-II, A Metabolite Related to Ferulic Acid. J Synth Commun. 1991;21:351-58.
Eichhorn et al., Characterization of moenomycin antibiotics from medicated chicken feed by ion-trap mass spectrometry with electrospray ionization. Rapid Commun Mass Spectrom. 2005;19(15):2179-86.
El-Abadla et al., Moenomycin A: The Role of the Methyl Group in the Moenuronamide Unit and a General Discussion of Struture-Activity Relationships. Tetrahedron. 1999;55(3):699-722.
Ellervik et al., A High Yieldig Chemical Synthesis of Sialyl Lewis x Tetrasaccharide and Lewis x Trisaccharide; Examples of Regio-and Stereodifferentiated Glycosylations. J Org Chem. 1998;63:9314-22.
Fehlhaber et al., Moenomycin A: A Strutural Revision and New Structure-Activity Relations. Tetrahedron. 1990;46(5):1557-68.
Flett et al., High efficiency intergeneric conjugal transfer of plasmid DNA from *Escherichia coli* to methyl DNA-restricting streptomycetes. FEMS Microbiol Lett. Oct. 15, 1997;15(2):223-9.
Garegg et al., Formation of Internucleotidic Bonds via Phosphonate Intermediates. Chem Scr. 1985;25:280-82.
Garneau et al., Synthesis of mono- and disaccharide analogs of moenomycin and lipid II for inhibition of transglycosylase activity of penicillin-binding protein 1b. Bioorg Med Chem. Dec. 15, 2004;12(24):6473-94.
Gildersleeve et al., Scavenging Byproducts in the Sulfoxide Glycosylation Reaction: Application to the Synthesis of Ciclamycin 0. J Am Chem Soc. 1999;121:6176-82.
Gildersleeve et al., Sulfenate Intermediates in the Sulfoxide Glycosylation Reaction. J Am Chem Soc. 1998;120:5961-69.
Goldman et al., Differential antibacterial activity of moenomycin analogues on gram-positive bacteria. Bioorg Med Chem Lett. Oct. 16, 2000;10(20):2251-4.
Goldman et al., Inhibition of Transglycosylation involved in bacterial peptidoglycan synthesis. Curr Med Chem. Aug. 2000;7(8):801-20.
Gust et al., PCR-targeted *Streptomyces* gene replacement identifies a protein domain needed for biosynthesis of the sesquiterpene soil odor geosmin. Proc Natl Acad Sci U S A. Feb. 18, 2003;100(4);1541-6. Epub Jan. 31, 2003.
Halliday et al., Targeting the forgotten transglycosylases. Biochem Pharmacol. Mar. 30, 2006;71(7):957-67. Epub Nov. 18, 2005.
He et al., Isolation and structural elucidation of AC326-alpha, a new member of the moenomycin group. J Antibiot (Tokyo). Feb. 2000;53(2):191-5.
Hebler-Klintz et al., The First Moenomycin Antibiotic Without the Methyl-Branched Uronic Acid Constituent.—Unexpected Structure Activity Relations. Tetrahedron. 1993;35:7667-78.
Hernández-Torres et al., Temperature-controlled regioselectivity in the reductive cleavage of p-methoxybenzylidene acetals. J Org Chem. Oct. 15, 2004;69(21):7206-11.

(56) References Cited

OTHER PUBLICATIONS

Hodgson, Primary metabolism and its control in *streptomycetes*: a most unusual group of bacteria. Adv Microb Physiol. 2000;42:47-238.

Jansson et al., 2-(Trimethylsily)ethyl Glycosides. Synthesis, Anomeric Deblocking, and Transformation into 1,2-Trans 1-*O*-Acyl Sugars. J Org Chem. 1988;53:5629-47.

Kahne et al., Glycosylation of Unreactive Substrates. J Am Chem Soc. 1989;111:6881-82.

Kartha et al., Iodine: A Versatile Reagent in Carbohydrate Chemistry III. Efficient Activation of Glycosyl Halides in Combination with $DDQ^1$. Tetrahedron Lett. 1996;37:8807-10.

Kuiper et al., A Selective and Mild Synthetic Route to Dialkyl Phosphates. Synthesis. 2003;5:695-98.

Lay et al., Synthesis of N-acetylglucosamine containing Lewis A and Lewis X building blocks based on N-tetrachlorophthaloyl protection—synthesis of Lewis X pentasaccharide. Carbohydr Res. Aug. 1998;310(3):157-71.

Leimkuhler et al., Differential inhibition of *Staphylococcus aureus* PBP2 by lycopeptides antibiotics. J Am Chem Soc. Mar. 16, 2005;127(10):3250-1.

Leskiw et al., TTA codons in some genes prevent their expression in a class of developmental, antibiotic-negative, *Streptomyces* mutants. Proc Natl Acad Sci U S A. Mar. 15, 1991;88(6):2461-5.

Linnett et al., Additional antibiotic inhibitors of peptidoglycan synthesis. Antimicrob Agents Chemother. Sep. 1973;4(3):231-6.

Liu et al., Acceptor specificity and inhibition of the bacterial cell-wall glycosyltransferase MurG. Chembiochem. Jul. 7, 2003;4(7):603-9.

Lovering et al., Structural insight into the transglycosylation step of bacterial cell-wall biosynthesis. Science. Mar. 9, 2007;315(5817):1402-5.

Marzian et al., Moenomycin A: Reactions at the Lipid Part. New Structure-Activity Relations. Tetrahedron. 1994;50:5299-308.

Metten et al., The Enzymatic Degradation Products of the Antibiotic Moenomycin A. Tetrahedron. 1992;48:8401-18.

Meyers et al., The Diumycins. New Members of an Antibiotic Family Having Prolonged in Vivo Activity. J Antibiot. 1969;22:490-93.

Müller et al., Utility of Glycosyl Phosphites as Glycosyl Donors-Fructofuranosyl and 2-Deoxyhexopyranosyl Phosphites in Glycoside Bond Formation. Tetrahedron Lett. 1994;35A:4763-66.

Ostash et al., A streamlined metabolic pathway for the biosynthesis of moenomycin A. Chem Biol. Mar. 2007;14(3):257-67.

Ostash et al., Bacterial transglycosylae inhibitors. Curr Opin Chem Biol. Oct. 2005;9(5):459-66.

Paulsen, Advances in Selective Chemical Syntheses of Complex Oligosaccharides. Angew Chem Int Ed Engl. 1982;21:155-73.

Petricek et al., Occurrence of two 5-aminolevulinate biosynthetic pathways in *Streptomyces nodosus* subsp. Asukaensis is linked with the production of asukamycin. J Bacteriol. Jul. 2006;188(14):5113-23.

Pfaller, Flavophospholipol use in animals: positive implications for antimicrobial resistance based on its microbiologic properties. Diagn Microbiol Infect Dis. Oct. 2006;56(2):115-21. Epub May 15, 2006.

Ritzeler et al., Search for new moenomycin structure-activity relationships Synthesis of a trisaccharide precursor of a moenomycin analogue. Tetrahedron. 1997;53:1665-74.

Schmidt et al., Nitriles as Solvents in Glycosylation Reactions: Highly Selective β-Glycoside Synthesis. Synlett. 1990;11:694-96.

Schuricht et al., Studies on the Biosynthesis of the Antibiotic Moenomycen A. J Prakt Chem. 2000;342(8):761-72.

Sekurova et al., In vivo analysis of the regulatory genes in the nystatin biosynthetic gene cluster of *Streptomyces noursei* ATCC 11455 reveals their differential control over antibiotic biosynthesis. J Bacteriol. Mar. 2004;186(5):1345-54.

Slusarchyk et al., The Structure of a Novel Lipid from the Antibiotic Diumycin. J Am Chem Soc. 1970;92:4486-88.

Slusarchyk et al., The structure of the lipid portion of the antibiotic prasinomycin. Tetrahedron Lett. Feb. 1969;8:659-62.

Srivastava et al., Combined chemical-enzymic synthesis of deoxygenated oligosaccharide analogs: transfer of deoxygenated D-GlcpNAc residues from their UDP-GlcpNAc derivatives using N-acetylglucosaminyltransferase I. Carbohydr Res. Oct. 25, 1990;207(2):259-76.

Stump et al., Synthesis of Moenocinol. Tetrahedron. 1986;42:5941-48.

Subramaniam-Niehaus et al., Isolation and analysis of moenomycin and its biosynthetic intermediates from *Streptomyces ghanaensis* (ATCC 14672) wildtype and selected mutants. Z Naturforsch C. Mar.-Apr. 1997;52(3-4):217-26.

Takahashi et al., Macarbomycin, a new antibiotic containing phosphorus. J Antibiot (Tokyo). Jan. 1970;23(1):48-50.

Taylor et al., The total synthesis of moenomycin A. J Am Chem Soc. Nov. 29, 2006;128(47):15084-5.

Tirado et al., Stereochemistry of the Iodocarbonation of *cis*- and *trans*-3-Methyl-4-pentene-1,2-diols: The Unusual Formation of Several Anti Iodo Carbonates. J Org Chem. 1993;58:5666-73.

Trepanier et al., The positive activator of cephamycin C and evalulanic acid production in *Streptomyces clavuligerus* is mistranslated in a bldA mutant. Microbiology. Mar. 2002;148(Pt 3):743-56.

Van Heuenoort, Formation of the glycan chains in the synthesis of bacterial peptidoglycan. Glycobiology. Mar. 2001;11(3):25R-36R.

Vogel et al., Some selective reactions of moenomycin A. Bioorg Med Chem Lett. Sep. 4, 2000;10(17):1963-5.

Vogel et al., Moenomycin analogues with modified lipid side chains from indium-mediated Barbier-type reaction. Tetrahedron. 2001;57:4139-46.

Volke et al., Characterisation of antibiotic moenomycin A intraction with phospholipid model membranes. Chem Phys Lipids. Feb. 28, 1997;85(2):115-23.

Wallhausser et al., Moenomycin, a new antibiotic. I. Fermentation and isolation. Antimicrob Agents Chemother (Bethesda). 1965;734-6.

Weisenborn et al., The prasinomycins: antibiotics containing phosphorus. Nature. Mar. 18, 1967;213(5081):1092-4.

Welzel et al., Moenomycin A: Minimum Structural Requirements for Biological Activity. Tetrahedron. 1987;43:585-98.

Welzel et al., [Moenomycin A: Spaltung Des Antibiotikums Mit Trifluoressigsaure/2-Propanol Und Bestimmung Der Verknupfung Von D-Glucose Und 2-Acetamido-2-Desoxy-D-Glucose.] Tetrahedron. 1981;37:97-104. German.

Welzel, Syntheses around the transglycosylation step in peptidoglycan biosynthesis. Chem Rev. Dec. 2005;105(12):4610-60.

Welzel, Transglycosylase Inhibition. In: Antibiotics and antiviral compounds—chemical synthesis and modification. Krohn et al., eds. Weinheim, Germany. 1993:373-78.

Welzel et al., [Zur Struktur Eines 2-Amino-Cyclopentandion-1,3, Galakturonsaure und Chinovos-Amin Enthaltenden Hydrolyseruchstucks Des Antibiotikums Moenomycin A.] Tetrahedron Lett. 1973;3:227-30. German.

Westerduin et al., Synthesis of the Fragment GlcNAc-α(I-P-6)-GlcNac of the Cell Wall Polymer of *Staphylococcus lactis* Having Repeating N-Acetyl-D-Glucosamine Phosphate Units, Tetrahedron Lett. 1986;27:6271-74.

White et al., New oligomeric catalyst for the hydrolytic kinetic resolution of terminal epoxides under solvent-free conditions. Tetrahedron Asymm. 2003;14:3633-38.

Wilen et al., Strategies in Optical Resolutions. Tetrahedron. 1977;33:2725-36.

Ye et al., Better substrates for bacterial transglycosylases. J Am Chem Soc. Apr. 4, 2001;123(13):3155-6.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zehl et al., Characterization of moenomycin antibiotic complex by multistage MALDI-IT/RTOF-MS and ESI-IT-MS. J Am Soc Mass Spectrom. Aug. 2006;17(8):1081-90. Epub May 30, 2006.

International Search Report and Written Opinion, mailed Sep. 30, 2008, in connection with PCT/US2007/017999.

International Preliminary Report on Patentability, mailed Feb. 26, 2009, in connection with PCT/US2007/017999.

International Preliminary Report on Patentabililty, mailed Apr. 15, 2010, in connection with PCT/US2008/078771.

(56) References Cited

OTHER PUBLICATIONS

Arai et al., Pholipomycin, a new member of phosphoglycolipid antibiotics. I. Taxonomy of producing organism and fermentation and isolation of pholipomycin. J Antibiot (Tokyo). Dec. 1977;30(12):1049-54.
Bardone et al., Teichomycins, new antibiotics from *Actinoplanes teichomyceticus* nov. sp. II. Extraction and chemical characterization. J Antibiot (Tokyo). Mar. 1978;31(3):170-7.
Belanger et al., Functional analysis of genes responsible for the synthesis of the B-band O antigen of *Pseudomonas aeruginosa* serotype O6 lipopolysaccharide. Microbiology. Dec. 1999;145 ( Pt 12):3505-21.
Bentley et al., Complete genome sequence of the model actinomycete *Streptomyces coelicolor* A3(2). Nature. May 9, 2009;417(6885):141-7.
Bibb, Regulation of secondary metabolism in streptomycetes. Curr Opin Microbiol. Apr. 2005;8(2):208-15.
Bierman et al., Plasmid cloning vectors for the conjugal transfer of DNA from *Escherichia coli* to *Streptomyces*spp. Gene. Jul. 1, 1992;116(1):43-9.
Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.
Chaffin et al., CpsK of *Streptococcus agalactiae* exhibits alpha2,3-sialyltransferase activity in *Haemophilus ducreyi*. Mol Microbiol. Jul. 2002;45(1):109-22.
Chang, Multidrug resistance ABC transporters. FEBS Lett. Nov. 27, 2003;555(1):102-5.
Cheng et al., Domain requirement of moenomycin binding to bifunctional transglycosylases and development of high-throughput discovery of antibiotics. Proc Natl Acad Sci U S A. Jan. 15, 2008;105(2):431-6. Epub Jan. 8, 2008.
Dairi, Studies on biosynthetic genes and enzymes of isoprenoids produced by actinomycetes. J Antibiot (Tokyo). Apr. 2005;58(4):227-43.
Decker et al., A general approach for cloning and characterizing dNDP-glucose dehydratase genes from actinomycetes. FEMS Microbiol Lett. Aug. 1, 1996;141(2-3):195-201.
Dirksen et al., Rapid oxime and hydrazone ligations with aromatic aldehydes for biomolecular labeling. Bioconjug Chem. Dec. 2008;19(12):2543-8.
Du et al., Identification and functional analysis of dTDP-glucose-4,6-dehydratase gene and its linked gene cluster in an aminoglycoside antibiotics producer of *Streptomyces tenebrarius* H6. Curr Microbiol. Aug. 2004;49(2):99-107.
Durr et al., Biosynthesis of the terpene phenalinolactone in *Streptomyces* sp. Tü6071: analysis of the gene cluster and generation of derivatives. Chem Biol. Apr. 2006;13(4):365-77.
Feng et al., Structure of the *Shigella dysenteriae* 7 O antigen gene cluster and identification of its antigen specific genes. Microb Pathog. Feb. 2004;36(2):109-15.
Fuse et al., Functional and Structural Analysis of a Key Region of the Cell Wall Inhibitor Moenomycin. ACS Chem Biol. 2010;5(7):701-711.
GENBANK Submission; NIH/NCBI, Accession No. AAF24002; Belanger et al.; Jan. 12, 2000.
GENBANK Submission; NIH/NCBI, Accession No. AAG34163; Yoo et al.; Mar. 6, 2001.
GENBANK Submission; NIH/NCBI, Accession No. AAO06921; Rascher et al.; Feb. 21, 2003.
GENBANK Submission; NIH/NCBI, Accession No. AAU93096; Ward et al.; Nov. 21, 2011.
GENBANK Submission; NIH/NCBI, Accession No. AAX98210; McAlpine et al.; Apr. 25, 2005.
GENBANK Submission; NIH/NCBI, Accession No. AY240962; Petricek et al.; Jul. 5, 2006.
GENBANK Submission; NIH/NCBI, Accession No. BAC68501; Omura et al.; Dec. 21, 2007.
GENBANK Submission; NIH/NCBI, Accession No. BAC68502; Omura et al.; Dec. 21, 2007.
GENBANK Submission; NIH/NCBI, Accession No. BAC70368; Omura et al.; Dec. 21, 2007.
GENBANK Submission; NIH/NCBI, Accession No. CAA22758; Bentley et al.; Oct. 23, 2008.
GENBANK Submission; NIH/NCBI, Accession No. CAC01594; Bentley et al.; Oct. 23, 2008.
GENBANK Submission; NIH/NCBI, Accession No. CAC37544; Bentley et al.; Oct. 23, 2008.
GENBANK Submission; NIH/NCBI, Accession No. CAC37545; Bentley et al.; Oct. 23, 2008.
GENBANK Submission; NIH/NCBI, Accession No. CAI08539; Rabus et al.; Sep. 11, 2009.
GENBANK Submission; NIH/NCBI, Accession No. EAM38951; Jun. 15, 2005.
GENBANK Submission; NIH/NCBI, Accession No. EAO07657; Jul. 26, 2005.
GENBANK Submission; NIH/NCBI, Accession No. EAS11435; Apr. 9, 2007.
GENBANK Submission; NIH/NCBI, Accession No. EAS23724; Mar. 22, 2006.
GENBANK Submission; NIH/NCBI, Accession No. EAS99725; Apr. 18, 2006.
GENBANK Submission; NIH/NCBI, Accession No. JC7965; Nemoto et al.; Mar. 15, 2004.
GENBANK Submission; NIH/NCBI, Accession No. NP_142754; Kawarabayasi et al.; Jan. 19, 2012.
GENBANK Submission; NIH/NCBI, Accession No. NP_220145; Griffiths et al.; Sep. 15, 2011.
GENBANK Submission; NIH/NCBI, Accession No. NP_630535; Hsiao et al.; Jan. 19, 2012.
GENBANK Submission; NIH/NCBI, Accession No. YP_074610; Ueda et al.; Jan. 23, 2012.
GENBANK Submission; NIH/NCBI, Accession No. YP_075255; Ueda et al.; Jan. 23, 2012.
GENBANK Submission; NIH/NCBI, Accession No. Y13_075256; Ueda et al.; Jan. 23, 2012.
GENBANK Submission; NIH/NCBI, Accession No. ZP_00616987; Heuts et al.; Jun. 28, 2007.
Gromyko et al., Generation of *Streptomyces globisporus* SMY622 strain with increased landomycin E production and it's initial characterization. J Antibiot (Tokyo). Jun. 2004;57(6):383-9.
Hang et al., Probing Glycosyltransferase Activities with the Staudinger Ligation. J Am Chem Soc. 2004;126(1):6-7.
Hang et al., Small molecule inhibitors of mucin-type O-linked glycosylation from a uridine-based library. Chem Biol. Mar. 2004;11(3):337-45.
Hang et al., The chemistry and biology of mucin-type O-linked glycosylation. Bioorg Med Chem. Sep. 1, 2005;13(17):5021-34.
Hong et al., A signal transduction system in *Streptomyces coelicolor* that activates the expression of a putative cell wall glycan operon in response to vancomycin and other cell wall-specific antibiotics. Mol Microbiol. Jun. 2002;44(5):1199-1211.
Hong et al., Inactivation of the carbamoyltransferase gene refines post-polyketide synthase modification steps in the biosynthesis of the antitumor agent geldanamycin. J Am Chem Soc. Sep. 15, 2004;126(36):11142-3.
Hopwood, Soil to genomics: the *Streptomyces* chromosome. Annu Rev Genet. 2006;40:1-23.
Ishikawa et al., FramePlot: a new implementation of the frame analysis for predicting protein-coding regions in bacterial DNA with a high G + C content. FEMS Microbiol Lett. May 15, 1999;174(2):251-3.
Iyobe et al., Sex pili mutants isolated by macarbomycin treatment. Antimicrob Agents Chemother. May 1973;3(5):614-20.
Jabbouri et al., Involvement of nodS in N-methylation and nodU in 6-O-carbamoylation of *Rhizobium* sp. NGR234 nod factors. J Biol Chem. Sep. 29, 1995;270(39):22968-73.
Kaplan et al., Genes involved in the synthesis and degradation of matrix polysaccharide in *Actinobacillus actinomycetemcomitans* and *Actinobacillus pleuropneumoniae* biofilms. J Bacteriol. Dec. 2004;186(24):8213-20.
Kaur, Expression and characterization of DrrA and DrrB proteins of *Streptomyces peucetius* in *Escherichia coli*: DrrA is an ATP binding protein. J Bacteriol. Feb. 1997;179(3):569-75.

(56) References Cited

OTHER PUBLICATIONS

Kawasaki et al., Biosynthesis of a natural polyketide-isoprenoid hybrid compound, furaquinocin A: identification and heterologous expression of the gene cluster. J Bacteriol. Feb. 2006;188(4):1236-44.
Kawasaki et al., Interconversion of the product specificity of type I eubacterial farnesyl diphosphate synthase and geranylgeranyl diphosphate synthase through one amino acid substitution. J Biochem. Jan. 2003;133(1):83-91.
Khidekel et al., A chemoenzymatic approach toward the rapid and sensitive detection of O-GlcNAc posttranslational modifications. J Am Chem Soc. Dec. 31, 2003;125(52):16162-3.
Knirel et al., Somatic antigens of *Shigella*: structure of the O-specific polysaccharide chain of the *Shigella dysenteriae* type 7 lipopolysaccharide. Carbohydr Res. Aug. 15, 1988;179:51-60.
Kudo et al., A new family of glucose-l-phosphate/glucosamine-l-phosphate nucleotidylyltransferase in the biosynthetic pathways for antibiotics. J Am Chem Soc. Feb. 16, 2005;127(6):1711-8.
Lehtovaara et al., A new method for random mutagenesis of complete genes: enzymatic generation of mutant libraries in vitro. Protein Eng. Apr. 1988;2(1):63-8.
Leskiw et al., Accumulation of bldA-specified tRNA is temporally regulated in *Streptomyces coelicolor* A3(2). J Bacteriol. Apr. 1993;175(7):1995-2005.
Lin et al., Sequence analysis and molecular characterization of genes required for the biosynthesis of type 1 capsular polysaccharide in *Staphylococcus aureus*. J Bacteriol. Nov. 1994;176(22):7005-16.
Lombo et al., The mithramycin gene cluster of *Streptomyces argillaceus* contains a positive regulatory gene and two repeated DNA sequences that are located at both ends of the cluster. J Bacteriol. Jan. 1999;181(2):642-7.
Luzhetskii et al., [Interspecies conjugation of *Escherichia coli-Streptomyces globisporus* 1912 using integrative plasmid pSET152 and its derivatives]. Genetika. Oct. 2001;37(10):1340-7. Russian, Abstract only.
Luzhetskyy et al., Iteratively acting glycosyltransferases involved in the hexasaccharide biosynthesis of landomycin A. Chem Biol. Jul. 2005;12(7):725-9.
McAlpine et al., Microbial genomics as a guide to drug discovery and structural elucidation: ECO-02301, a novel antifungal agent, as an example. J Nat Prod. Apr. 2005;68(4):493-6.
McKeegan et al., The structure and function of drug pumps: an update. Trends Microbiol. Jan. 2003;11(1):21-9.
Men et al., Substrate Synthesis and Activity Assay for MurG. J. Am. Chem. Soc. Feb. 1998;120(10):2484-2485.
Mendez et al., The role of ABC transporters in antibiotic-producing organisms: drug secretion and resistance mechanisms. Res Microbiol. Apr.-May 2001;152(3-4):341-50.
Murrell et al., Biochemical characterization of the SgcA1 alpha-D-glucopyranosyl-1-phosphate thymidylyltransferase from the enediyne antitumor antibiotic C-1027 biosynthetic pathway and overexpression of sgcA1 in *Streptomyces globisporus* to improve C-1027 production. J Nat Prod. Feb. 2004;67(2):206-13.
Muth et al., A vector sytem with temperature-sensitive replication for gene disruption and mutational cloning in *Streptomycetes*. Mol Gen Genet. 1989;219:341-48.
Nakagawa et al., Biosynthesis of asukamycin. Formation of the 2-amino-3-hydroxycyclopent-2-enone-moiety. J Chem Soc Chem Commun. 1985:519-21.
Nemoto et al., Purification and characterization of geranylgeranylglyceryl phosphate synthase from a thermoacidophilic archaeon, *Thermoplasma acidophilum*. J Biochem. May 2003;133(5):651-7.
Neundorf et al., Evidence for the combined participation of a C10 and a C15 precursor in the biosynthesis of moenocinol, the lipid part of the moenomycin antibiotics. Chembiochem. Nov. 7, 2003;4(11):1201-5.
Oh et al., Denaturation of circular or linear DNA facilitates targeted integrative transformation of *Streptomyces coelicolor* A3(2): possible relevance to other organisms. J Bacteriol. Jan. 1997;179(1):122-7.
Ostash et al., Complete characterization of the seventeen step moenomycin biosynthetic pathway. Biochemistry. Sep. 22, 2009;48(37):8830-41.
Pacholec et al., Characterization of the aminocoumarin ligase SimL from the simocyclinone pathway and tandem incubation with NovM,P,N from the novobiocin pathway. Biochemistry. Mar. 29, 2005;44(12):4949-56.
Paton et al., Molecular characterization of the locus encoding biosynthesis of the lipopolysaccharide O antigen of *Escherichia coli* serotype O113. Infect Immun. Nov. 1999;67(11):5930-7.
Ramakrishnan et al., Alpha-Lactalbumin (LA) stimulates milk beta-1,4-galactosyltransferase I (beta 4Gal-T1) to transfer glucose from UDP-glucose to N-acetylglucosamine. Crystal structure of beta 4Gal-T1 x LA complex with UDP-Glc. J Biol Chem. Oct. 5, 2001;276(40):37665-71. Epub Aug. 2, 2001.
Ramakrishnan et al., Structure-based design of beta 1,4-galactosyltransferase I (beta 4Gal-T1) with equally efficient N-acetylgalactosaminyltransferase activity: point mutation broadens beta 4Gal-T1 donor specificity. J Biol Chem. Jun. 7, 2002;277(23):20833-9. Epub Mar. 26, 2002.
Rascher et aL, Cloning and characterization of a gene cluster for geldanamycin production in *Streptomyces hygroscopicus* NRRL 3602. FEMS Microbiol Lett. Jan. 28, 2003;218(2):223-30.
Rebets et al., Expression of the regulatory protein LndI for landomycin E production in *Streptomyces globisporus* 1912 is controlled by the availability of tRNA for the rare UUA codon. FEMS Microbiol Lett. Mar. 2006;256(1):30-7.
Redenbach et al., The *Streptomyces lividans* 66 chromosome contains a 1 MB deletogenic region flanked by two amplifiable regions. Mol Gen Genet. Nov. 1993;241(3-4):255-62.
Riedl et al., Impact of flavophospholipol and vancomycin on conjugational transfer of vancomycin resistance plasmids. Antimicrob Agents Chemother. Nov. 2000;44(11):3189-92.
Rose et al., Consensus-degenerate hybrid oligonucleotide primers for amplification of distantly related sequences. Nucleic Acids Res. Apr. 1, 1998;26(7):1628-35.
Schuricht et al., The Biosynthesis of Moenocinol, the Lipid Part of the Moenomycin Antibiotics. Tetrahedron Lett. 2001;42:3835-37.
Shin et al., Total synthesis and structure of the ramoplanin A1 and A3 aglycons: two minor components of the ramoplanin complex. Proc Natl Acad Sci U S A. Aug. 17, 2004;101(33):11977-9. Epub Jun. 2, 2004.
Sletten et al., A bioorthogonal quadricyclane ligation. J Am Chem Soc. Nov. 9, 2011;133(44):17570-3. Epub Oct. 17, 2011.
Smith et al., The cps genes of *Streptococcus suis* serotypes 1, 2, and 9: development of rapid serotype-specific PCR assays. J Clin Microbiol. Oct. 1999;37(10):3146-52.
Soderberg et al., Geranylgeranylglyceryl phosphate synthase. Characterization of the recombinant enzyme from *Methanobacterium thermoautotrophicum*. Biochemistry. Dec. 11, 2001;40(49):14847-54.
Sosio et al., The gene cluster for the biosynthesis of the glycopeptide antibiotic A40926 by nonomuraea species. Chem Biol. Jun. 2003;10(6):541-9.
Stawinski, Chapter 8. Some Aspects of H-Phosphonate Chemistry. In: Handbook of Organophosphorus Chemistry. R. Engel ed. Marcel Dekker, New York. 1992:377-434.
Tachibana et al., Novel prenyltransferase gene encoding farnesylgeranyl diphosphate synthase from a hyperthermophilic archaeon, *Aeropyrum pernix*. Molecular evolution with alteration in product specificity. Eur J Biochem. Jan. 2000;267(2):321-8.
Tahlan et al., Three unlinked gene clusters are involved in clavam metabolite biosynthesis in *Streptomyces clavuligerus*. Can J Microbiol. Oct. 2004;50(10):803-10.
Tai et al., Parallel identification of O-GlcNAc-modified proteins from cell lysates. J Am Chem Soc. Sep. 1, 2004;126(34):10500-1.
Takahashi et al., A two-stage one-pot enzymatic synthesis of TDP-L-mycarose from thymidine and glucose-1-phosphate. J Am Chem Soc. Feb. 8, 2006;128(5):1432-3.

(56) References Cited

OTHER PUBLICATIONS

Thuy et al., Functional characterizations of novWUS involved in novobiocin biosynthesis from *Streptomyces spheroides*. Arch Biochem Biophys. Apr. 1, 2005;436(1):161-7.

Tschesche et al., Uber den Lipoidteil Moenocinol des Antibiotikums Moenomycin. Tetrahedron Letters. 1968;24:2905-09.

Vocadlo et al., A chemical approach for identifying O-GlcNAc-modified proteins in cells. Proc Natl Acad Sci U S A. Aug. 5, 2003;100(16):9116-21. Epub Jul. 21, 2003.

Vocadlo et al., A strategy for functional proteomic analysis of glycosidase activity from cell lysates. Angew Chem Int Ed Engl. Oct. 11, 2004;43(40):5338-42.

Wang et al., The pgaABCD locus of *Escherichia coli* promotes the synthesis of a polysaccharide adhesin required for biofilm formation. J Bacteriol. May 2004;186(9):2724-34.

Weber et al., Exploiting the genetic potential of polyketide producing streptomycetes. J Biotechnol. Dec. 19, 2003;106(2-3):221-32.

Westrich et al., Cloning and characterization of a gene cluster from *Streptomyces cyanogenus* S136 probably involved in landomycin biosynthesis. FEMS Microbiol Lett. Jan. 15, 1999;170(2):381-7.

Wilen, Tables of Resolving Agents and Optical Resolutions. E.L. Eliel, ed. Universtify of Notre Dame Press, Notre Dame, IN. 1972:268-98.

Wilson et al., Molecular analysis of tlrB, an antibiotic-resistance gene from tylosin-producing *Streptomyces fradiae*, and discovery of a novel resistance mechanism. J Antibiot (Tokyo). Mar. 1999;52(3):288-96.

Xiang et al., The crystal structure of *Escherichia coli* MoeA and its relationshhip to the multifunctional protein gephyrin. Structure. Apr. 4, 2001;9(4):299-310.

Yu et al., The biosynthetic gene cluster of the maytansinoid antitumor agent ansamitocin from *Actinosynnema pretiosum*. Proc Natl Acad Sci U S A. Jun. 11, 2002;99(12):7968-73.

Zalkin et al., Enzymes utilizing glutamine as an amide donor. Adv Enzymol Relat Areas Mol Biol. 1998;72:87-144.

Zhang et al., A Simple Statistical Parameter for Use in Evaluation and Validation of High Throughput Screening Assays. J Biomol Screen. 1999;4(2):67-73.

Zhang et al., Molecular and chemical characterization of the lipopolysaccharide O-antigen and its role in the virulence of *Yersinia enterocolitica* serotype O:8. Mol Microbiol. Jan. 1997;23(1):63-76.

Zhu et al., Identification of the function of gene IndM2 encoding a bifunctional oxygenase-reductase involved in the biodynthesis of the antitumor antibiotic landomycin E by *Streptomyces globisporus* 1912 supports the originally assigned structure for landomycinone. J Org Chem. Jan. 21, 2005;70(2):631-8.

\* cited by examiner

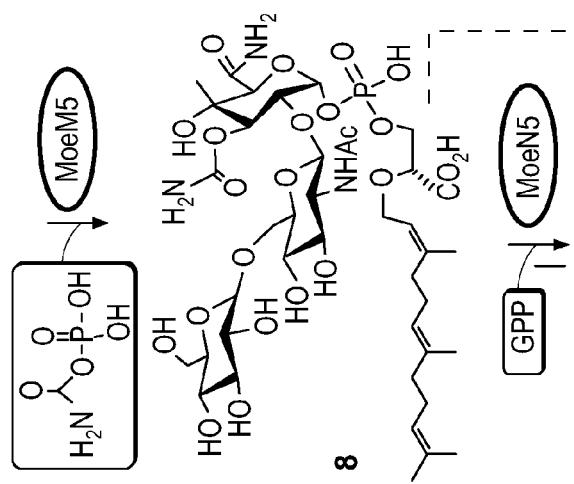
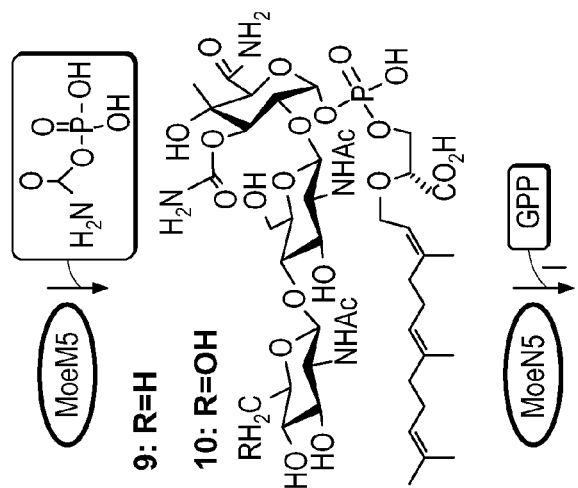
FIG. 4 (Continued)

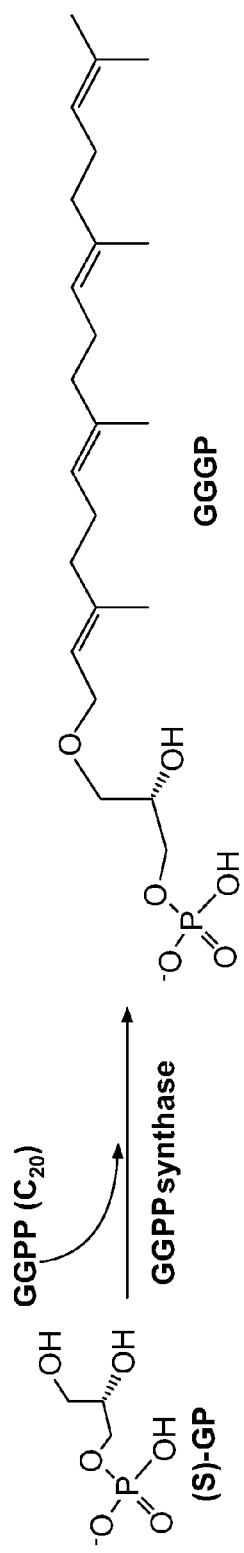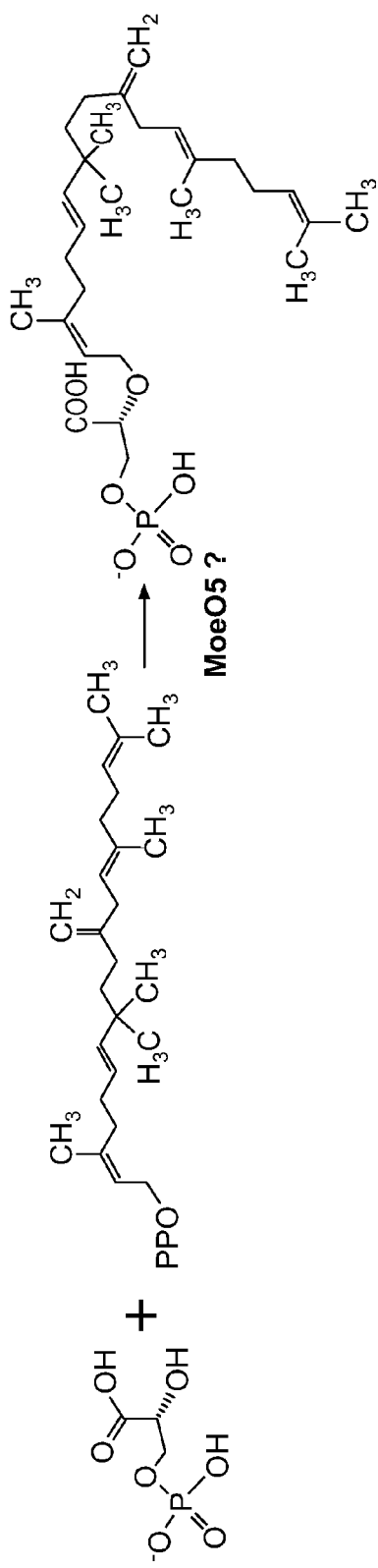
FIG. 8

Isolation of active compound is in progress

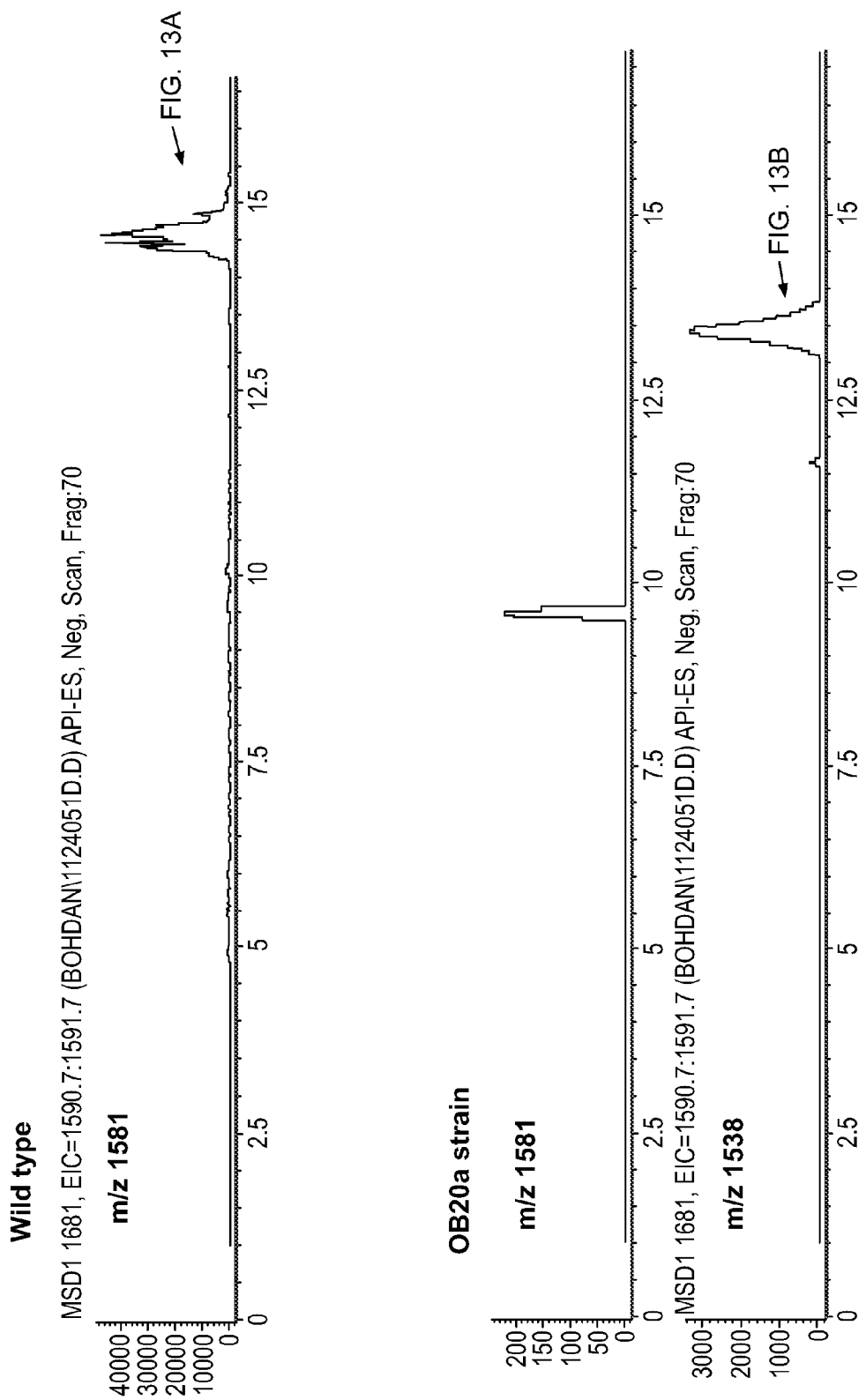

Moenomycin A

Moenomycin A without carbamoyl group

Moenomycin A

Pholipomycin

SEQUENCE LISTING

<160> NUMBER OF SEQ ID NOS: 18

<210> SEQ ID NO 1
<211> LENGTH: 45
<212> TYPE: DNA
<213> ORGANISM: Artificial sequence
<220> FEATURE:
<223> OTHER INFORMATION: Syntetic PCR primer for E. faecalis pbp2a gene, including NdeI restriction site

<400> SEQUENCE: 1
gagcatgtcc atatggaatc catggacaat cttaaacaat tttt        45

<210> SEQ ID NO 2
<211> LENGTH: 36
<212> TYPE: DNA
<213> ORGANISM: Artificial Sequence
<220> FEATURE:
<223> OTHER INFORMATION: Syntetic PCR primer for E. faecalis pbp2a gene,
including XhoI restriction site

<400> SEQUENCE: 2
actgcagtgc tcgagatttc ctaataagcc tccgaa                                 36

<210> SEQ ID NO 3
<211> LENGTH: 26
<212> TYPE: DNA
<213> ORGANISM: Artificial Sequence
<220> FEATURE:
<223> OTHER INFORMATION: Syntetic PCR primer MoeO5HinDIIIup

<400> SEQUENCE: 3
aaaaagcttc ggggcgtgcc ttcttc                                            26

<210> SEQ ID NO 4
<211> LENGTH: 26
<212> TYPE: DNA
<213> ORGANISM: Artificial Sequence
<220> FEATURE:
<223> OTHER INFORMATION: Syntetic PCR primer MoeO5XbaIrp

<400> SEQUENCE: 4
aaatctagac cgcccgctcc ccggac                                            26

<210> SEQ ID NO 5
<211> LENGTH: 25
<212> TYPE: DNA
<213> ORGANISM: Artificial Sequence
<220> FEATURE:
<223> OTHER INFORMATION: Syntetic PCR primer MoeGT1NdeI

<400> SEQUENCE: 5
aaacatatgg ctgcccccga ccgac                                             25

<210> SEQ ID NO 6
<211> LENGTH: 22
<212> TYPE: DNA
<213> ORGANISM: Artificial Sequence
<220> FEATURE:
<223> OTHER INFORMATION: Syntetic PCR primer MoeGT1NotI

<400> SEQUENCE: 6
ataaagcggc cgctcgggcg tc                                                22

<210> SEQ ID NO 7
<211> LENGTH: 33
<212> TYPE: DNA
<213> ORGANISM: Artificial Sequence
<220> FEATURE:
<223> OTHER INFORMATION: Syntetic PCR primer MoeF5NdeI

<400> SEQUENCE: 7
aaaaacatat gtgcggcttc gtcggattca gtg                                    33

<210> SEQ ID NO 8
<211> LENGTH: 22
<212> TYPE: DNA
<213> ORGANISM: Artificial Sequence
<220> FEATURE:

<223> OTHER INFORMATION: Syntetic PCR primer MoeF5NotI

<400> SEQUENCE: 8
aaaaagcggc cgcggagagg gc                                                  22

<210> SEQ ID NO 9
<211> LENGTH: 27
<212> TYPE: DNA
<213> ORGANISM: Artificial Sequence
<220> FEATURE:
<223> OTHER INFORMATION: Syntetic PCR primer MoeGT5NdeI

<400> SEQUENCE: 9
aaaacatatg gtgctgcgcc gtctggc                                           27

<210> SEQ ID NO 10
<211> LENGTH: 21
<212> TYPE: DNA
<213> ORGANISM: Artificial Sequence
<220> FEATURE:
<223> OTHER INFORMATION: Syntetic PCR primer MoeGT5XhoI

<400> SEQUENCE: 10
aaaaactcga ggcgcccggc g                                                      21

<210> SEQ ID NO 11
<211> LENGTH: 26
<212> TYPE: DNA
<213> ORGANISM: Artificial Sequence
<220> FEATURE:
<223> OTHER INFORMATION: Syntetic PCR primer MoeGT3Nde1

<400> SEQUENCE: 11
aaaacatatg gtggccgtcc tccgcg                                          26

<210> SEQ ID NO 12
<211> LENGTH: 26
<212> TYPE: DNA
<213> ORGANISM: Artificial Sequence
<220> FEATURE:
<223> OTHER INFORMATION: Syntetic PCR primer MoeGT3Not1

<400> SEQUENCE: 12
aaaaagcggc cgccaaacca ggaaac                                          26

<210> SEQ ID NO 13
<211> LENGTH: 32
<212> TYPE: DNA
<213> ORGANISM: Artificial Sequence
<220> FEATURE:
<223> OTHER INFORMATION: Syntetic PCR primer MoeE5BamHI

<400> SEQUENCE: 13
aaaaaggatc cggtgtcgag cgatacacac gg                                  32

<210> SEQ ID NO 14
<211> LENGTH: 30
<212> TYPE: DNA
<213> ORGANISM: Artificial Sequence
<220> FEATURE:
<223> OTHER INFORMATION: Syntetic PCR primer MoeE5XhoI

<400> SEQUENCE: 14
aaaaactcga gctacagccg cggcacggac                                      30

<210> SEQ ID NO 15

```
<211> LENGTH: 30
<212> TYPE: DNA
<213> ORGANISM: Artificial Sequence
<220> FEATURE:
<223> OTHER INFORMATION: Syntetic PCR primer MoeGT4KpnI

<400> SEQUENCE: 15
aaaaaggtac caggtgactt ctgagcccgc                               30

<210> SEQ ID NO 16
<211> LENGTH: 30
<212> TYPE: DNA
<213> ORGANISM: Artificial Sequence
<220> FEATURE:
<223> OTHER INFORMATION: Syntetic PCR primer MoeGT4XhoI

<400> SEQUENCE: 16
aaaaactcga gtcagctctc ctgacgcgtg                               30

<210> SEQ ID NO 17
<211> LENGTH: 40
<212> TYPE: DNA
<213> ORGANISM: Artificial Sequence
<220> FEATURE:
<223> OTHER INFORMATION: Syntetic PCR primer MoeM5NdeI

<400> SEQUENCE: 17
ggcgcgccca tatgaaggta ctgtcgctcc actccgccgg                    40

<210> SEQ ID NO 18
<211> LENGTH: 57
<212> TYPE: DNA
<213> ORGANISM: Artificial Sequence
<220> FEATURE:
<223> OTHER INFORMATION: Syntetic PCR primer MoeM5EcoRI

<400> SEQUENCE: 18
aaaataaaga attctcagtg gtggtggtgg tggtggtggt gccgcgcggc ggcgccc  57
```

MOENOMYCIN ANALOGS, METHODS OF SYNTHESIS, AND USES THEREOF

RELATED APPLICATIONS

The present application is a national stage filing under 35 U.S.C. §371 of international PCT application, PCT/US2008/078771, filed Oct. 3, 2008, which claims priority under 35 U.S.C. §119(e) to U.S. provisional patent application, U.S. Ser. No. 60/977,511, filed Oct. 4, 2007, each of which is incorporated herein by reference.

GOVERNMENT FUNDING

This invention was made with Government support under Grant GM66174 awarded by the National Institutes of Health. The Government has certain rights in the invention.

BACKGROUND OF THE INVENTION

Bacteria have the ability to generate resistance to antibiotics through lateral gene transfer, mutation of enzymes, or the expression of enzymes which actively pump the antibiotic out of the cell or break it down. Over the past 10 years, resistance to existing antibiotics has become a significant problem in many countries. Vancomycin is currently the drug of last resort to combat multidrug-resistant Gram-positive bacteria. In many places vancomycin-resistant *Staphylococcus aureus* and *Enterococci* (VRE) have been discovered. There is thus a desperate need for a new antibiotic drug to replace this drug of last resort.

There are a host of cytoplasmic targets for the development of new antibacterials, such as gyrase inhibitors, protein synthesis inhibitors, muramyl cascade inhibitors, and many more. The major hurdle in designing such drugs is that in addition to enzyme based activity these drugs need to cross the bacterial cell wall to exert their antibacterial effect. On the other hand, enzymes involved in synthesis of the bacterial cell wall exist on the cell wall exterior, and therefore drugs inhibiting these enzymes can exert their bactericidal or bacteriostatic effect without having to cross the cell wall. For example, penicillins, cephalosporins, and vancomycin are antibiotics that interact with bacterial transpeptidase enzymes. In particular, moenomycin A is an antibiotic which binds to bacterial transglycolsylase enzymes. Each of these antibiotics either controls and/or inhibits peptidoglycan biosynthesis in bacteria, and each exerts its effect without having to cross the bacterial cell wall.

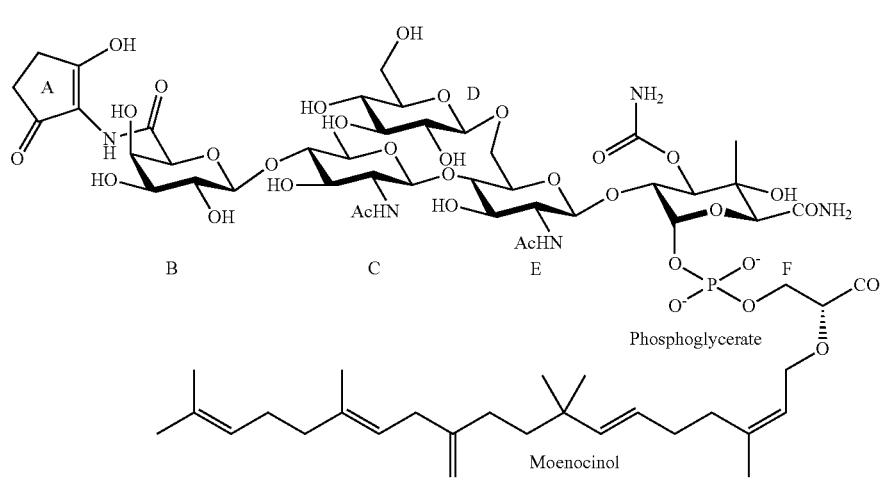

Moenomycin A

On a molar basis, moenomycin A is a thousand times more potent than vancomycin, but its absorption upon oral administration is relatively poor (van Heijenoort, *Glycobiology* (2001) 11:25R-36R). Structure-activity relationship studies of moneomycin analogs conducted on the sugar portion of the molecule have revealed that moenomycin analogs with at least three carbohydrate units (C, E, and F) are active in vivo against Gram-positive bacteria (for example, see Garneau et al., *Bioorganic & Medicinal Chemistry* (2004) 12:6473-6494, and references cited therein; each of which is incorporated herein by reference). However, to date, there has not been a comprehensive, systematic structure-activity relationship study of the entire moenomycin A structure.

SUMMARY OF THE INVENTION

The present invention provides inventive moenomycins and moenomycin analogs and the methodology for preparing these compounds based on the recent total synthesis of moenomycin A and an understanding of the biosynthesis of moenomycin A (see published PCT application, WO2008/021367, published Feb. 21, 2008; which is incorporated herein by reference. The inventive compounds may be prepared by total synthesis, biosynthesis, semi-synthesis, or a combination of these approaches. For example, inventive moenomycin compounds or moenomycin-like compounds may be prepared biosynthetically using wild type or genetically engineered bacteria or other organisms. The compounds may then be optionally further modified by chemical synthesis. For example, the sugar portion of a natural moenomycin (e.g., Moenomycin A, Moenomycin $A_{1.2}$, Moenomycin $C_1$, Moenomycin $C_3$, Moenomycin $C_4$, AC326-alpha, and/or Pholipomycin) may be removed and replaced with a different sugar portion, or the natural lipid side chain of moenomycin may be replace with a different lipid side chain. The different sugar portion may be a disaccharide, a trisaccharide, a tetrasaccharide, a pentasaccharide, or higher saccharide. In certain embodiments, the sugar portion of the inventive compound is derived from the natural products, Moenomycin A, Moenomycin $A_{1,2}$, Moenomycin $C_1$, Moenomycin $C_3$, Moenomycin $C_4$, AC326-alpha, or Pholipomycin. In other embodiments, the sugar portion is provided by chemical synthesis. A combination of these chemical and biosynthetic approaches allows for a comprehensive and systematic study of the structure-function relationship of the moenomycins (e.g., Moenomycin A, Moenomycin $A_{1,2}$, Moenomycin $C_1$, Moenomycin $C_3$, Moenomycin $C_4$, AC326-alpha, and/or Pholipomycin), allowing for the generation of better antibiotics. In certain embodiments, the compounds of the present invention are active against Gram-positive and/or Gram-negative bacteria. Therefore, the invention provides pharmaceutical compositions of the compounds described herein and methods of using these compounds to treat and/or prevent infection. In certain embodiments, the present invention provides an orally available antibiotic active against Gram-positive organisms. In certain embodiments, the present invention provides a broad spectrum antibiotic that is administered orally or parenterally.

In one aspect, the present invention provides moenomycin analogs of the formula (I), (II), (III), or (IV):

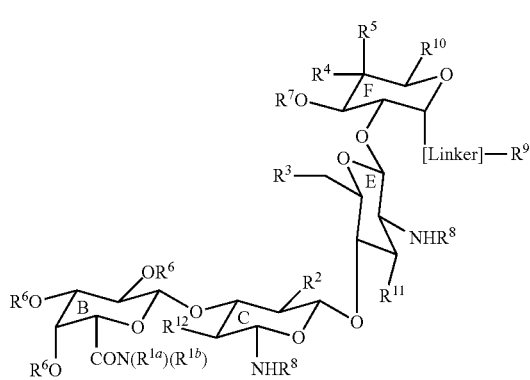

(I)

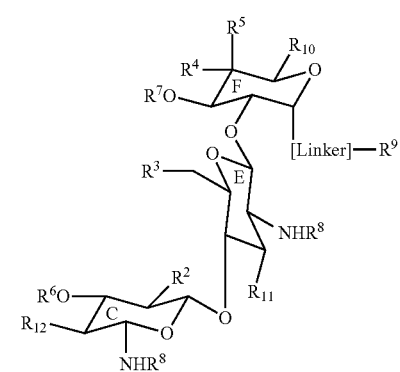

(II)

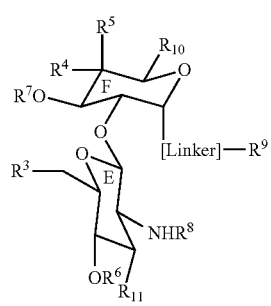

(III)

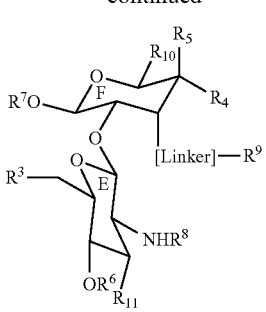

(IV)

or pharmaceutically acceptable forms thereof;
wherein:
[Linker] is the group:

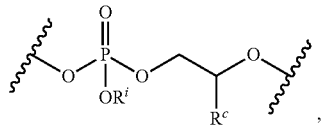

wherein:
$R^c$ is hydrogen, halogen, optionally substituted heteroaryl, —$OR^q$, —$N(R^q)_2$, —$SR^q$, —$NO_2$, —NC, —CN, —$N_3$, —$N(R^q)$=$NR^q$, —CHO, —C(=O)$R^q$, —C(=S)$R^q$, —C(=$NR^q$)$R^q$, —C(=O)$OR^q$, —C(=$NR^q$)$OR^q$, —C(=$NR^q$)$N(R^q)_2$, —C(=O)$N(R^q)_2$, —C(=S)$OR^q$, —C(=O)$SR^q$, —C(=S)$SR^q$, —P(=O)$(OR^q)_2$, —P(=O)$_2$$(OR^q)$, —S(=O)$(OR^q)$, —S(=O)$_2$$(OR^q)$, —P(=O)$N(R^q)_2$, —P(=O)$_2$$N(R^q)_2$, —C(=O)$NR^q$$S(=O)_2$$R^q$, —S(=O)$N(R^q)_2$, —S(=O)$_2$$N(R^q)_2$, or optionally substituted heteroaryl moiety; wherein each instance of $R^q$ is H, optionally substituted aliphatic, optionally substituted heteroaliphatic, optionally substituted aryl, optionally substituted heteroaryl, or a protecting group;

$R^i$ is H, optionally substituted aliphatic, optionally substituted heteroaliphatic, optionally substituted aryl, optionally substituted heteroaryl, or a hydroxyl protecting group;

$R^9$ is H or an optionally substituted $C_{1-30}$ aliphatic moiety, wherein 0 to 10 methylene units are optionally replaced with —O—, —$NR^x$—, —S—, —C(=O)—, —C(=$NR^x$)—, —S(=O)—, —S(=O)$_2$—, —N=N—, —C=N—, —C($R^y$)=C($R^y$)—, —N—O—, an optionally substituted arylene, or an optionally substituted heteroarylene moiety, wherein each instance of $R^x$ is, independently, H, optionally substituted aliphatic, optionally substituted heteroaliphatic, optionally substituted aryl, optionally substituted heteroaryl, or an amino protecting group, and each instance of $R^y$ is, independently, H, optionally substituted aliphatic, optionally substituted heteroaliphatic, optionally substituted aryl, or optionally substituted heteroaryl; and $R^{1a}$, $R^{2a}$, $R^3$, $R^4$, $R^5$, $R^6$, $R^7$, and $R^8$ are as defined herein.

In another aspect, the present invention provides a pharmaceutical composition comprising a compound of formula (I), (II), (III), or (IV), and optionally, a pharmaceutical excipient. In certain embodiments, the pharmaceutical composition comprises a therapeutically effective amount of the compound for treating or preventing an infection.

In yet another aspect, the present invention provides a method of slowing or inhibiting bacterial growth by contacting a bacterium with at least one compound of the formulae formula (I), (II), (III), or (IV), or a pharmaceutically acceptable form thereof.

In yet another aspect, the present invention provides a method of treating an infection (e.g., a bacterial infection) in a subject by administering a therapeutically effective amount of at least one compound of the formula (I), (II), (III), or (IV), or a pharmaceutically acceptable form thereof.

In still yet another aspect, the present invention provides various methods of synthesizing a compound of the formula (I), (II), (III), or (IV). The synthetic methods provided herein describe biosynthesis or degradation, chemical synthesis or degradation, and/or various combinations thereof. Various biosynthetic and chemical steps may be used to prepare an inventive compound.

This application refers to various issued patents, published patent applications, journal articles, and other publications, all of which are incorporated herein by reference. If there is a conflict between any of the incorporated references and the instant specification, the specification shall control.

The details of one or more embodiments of the invention are set forth in the accompanying Figures and the Detailed Description of Certain Embodiments, as described below. Other features, objects, and advantages of the invention will be apparent from the description, the figures, and from the claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position.

As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like) that results in the formation of a stable moiety. The present invention contemplates any and all such combinations in order to arrive at a stable substituent/moiety. For purposes of this invention, heteroatoms such as nitrogen may have hydrogen substituents and/or any suitable substituent as described herein which satisfy the valencies of the heteroatoms and results in the formation of a stable moiety.

The term "acyl," as used herein, refers to a group having the general formula —C(=O)R$^A$, —C(=O)OR$^A$, —C(=O)—O—C(=O)R$^A$, —C(=O)SR$^A$, —C(=O)N(R$^A$)$_2$, —C(=S)R$^A$, —C(=S)N(R$^A$)$_2$, and —C(=S)S(R$^A$), —C(=NR$^A$)R$^A$, —C(=NR$^A$)OR$^A$, —C(=NR$^A$)SR$^A$, and —C(=NR$^A$)N(R$^A$)$_2$, wherein R$^A$ is hydrogen; halogen; optionally substituted hydroxyl; optionally substituted thiol; optionally substituted amino; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups (for example, cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclooctenyl, cyclononenyl, cyclodecenyl, and the like, and which may bear one or more substituents). An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-30 carbon atoms (i.e., $C_{1-30}$ aliphatic) [in situations wherein the number of carbons is specified, such as a $C_{15}$ aliphatic, is meant a carbon chain 15 carbons in length]. In certain embodiments, the aliphatic group employed by the invention is an optionally substituted $C_2$-$C_{30}$ aliphatic group. In certain embodiments, the aliphatic group employed by the invention is an optionally substituted $C_5$-$C_{25}$ aliphatic group. In certain embodiments, the aliphatic group employed by the invention is an optionally substituted $C_1$-$C_{10}$ aliphatic group. In certain embodiments, the aliphatic group employed by the invention is an optionally substituted $C_{10}$-$C_{20}$ aliphatic group. In certain embodiments, the aliphatic group employed by the invention is an optionally substituted $C_{11}$-$C_{15}$ aliphatic group. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted, e.g., alkyl substituted with halogens such as perfluoroalkyl).

The term "alkyl," as used herein, refers to a saturated, straight- or branched-chain hydrocarbon radical derived from a hydrocarbon moiety which is optionally substituted with one or more functional groups. In some embodiments, the alkyl group employed in the invention contains 1-30 carbon atoms (i.e., $C_{1-30}$ alkyl) [in situations wherein the number of carbons is specified, such as a $C_{15}$ alkyl, is meant a fully saturated carbon chain 15 carbons in length]. In certain embodiments, the alkyl group employed by the invention is an optionally substituted $C_2$-$C_{30}$ alkyl group. In certain embodiments, the alkyl group employed by the invention is an optionally substituted $C_5$-$C_{25}$ alkyl group. In certain embodiments, the alkyl group employed by the invention is an optionally substituted $C_{10}$-$C_{20}$ alkyl group. In certain embodiments, the alkyl group employed by the invention is an optionally substituted $C_1$-$C_{10}$ alkyl group. In certain embodiments, the alkyl group employed by the invention is an optionally substituted $C_{11}$-$C_{15}$ alkyl group. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "alkenyl," as used herein, denotes a monovalent group derived from a straight- or branched-chain hydrocarbon moiety having at least one carbon-carbon double bond, and which is optionally substituted with one or more functional groups. In certain embodiments, the alkenyl group employed in the invention contains 2-30 carbon atoms (i.e., $C_{2-30}$ alkenyl) [in situations wherein the number of carbons is specified, such as a $C_{15}$ alkenyl, is meant a carbon chain 15 carbons containing at least one $sp^2$ (double bonded) carbon atom]. In certain embodiments, the alkenyl group employed by the invention is an optionally substituted $C_2$-$C_{30}$ alkenyl group. In certain embodiments, the alkenyl group employed by the invention is an optionally substituted $C_5$-$C_{25}$ alkenyl group. In certain embodiments, the alkenyl group employed by the invention is an optionally substituted $C_{10}$-$C_{20}$ alkenyl group. In certain embodiments, the alkenyl group employed by the invention is an optionally substituted $C_2$-$C_{10}$ alkenyl group. In certain embodiments, the alkenyl group employed by the invention is an optionally substituted $C_{11}$-$C_{15}$ alkenyl group. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "alkynyl," as used herein, refers to a monovalent group derived from a straight- or branched-chain hydrocarbon having at least one carbon-carbon triple bond, and which is optionally substituted with one or more functional groups. In certain embodiments, the alkynyl group employed in the invention contains 2-30 carbon atoms (i.e., $C_{2-30}$ alkenyl) [in situations wherein the number of carbons is specified, such as a $C_{15}$ alkynyl, is meant a carbon chain 15 carbons containing at least one sp (triple bonded) carbon atom]. In certain embodiments, the alkynyl group employed by the invention is an optionally substituted $C_2$-$C_{30}$ alkynyl group. In certain embodiments, the alkynyl group employed by the invention is an optionally substituted $C_5$-$C_{25}$ alkynyl group. In certain embodiments, the alkynyl group employed by the invention is an optionally substituted $C_2$-$C_{10}$ alkynyl group. In certain embodiments, the alkynyl group employed by the invention is an optionally substituted $C_{10}$-$C_{20}$ alkynyl group. In certain embodiments, the alkynyl group employed by the invention is an optionally substituted $C_{11}$-$C_{15}$ alkynyl group. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "amino," as used herein, refers to a group of the formula (—$NH_2$). An "substituted amino" refers to a mono-substituted amino group of the formula (—$NHR^B$) and a di-substituted amino group of the formula (—$NR^B_2$). Substituents include, but are not limited to, any of the substituents described herein, that result in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted). In certain embodiments, the $R^B$ substituents of the di-substituted amino group (—$NR^B_2$) form a 5- to 6-membered heterocyclic ring.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "arylene" as used herein, denotes a bivalent group derived from an aryl moiety, as defined herein. The term "heteroarylene" as used herein, denotes a bivalent group derived from a heteroaryl moiety, as defined herein.

The term "azido," as used herein, refers to a group of the formula (—$N_3$). An "optionally substituted azido" refers to a group of the formula (—$N_3R^C$), wherein $R^C$ can be any substitutent (other than hydrogen). Substituents include, but are not limited to, any of the substituents described herein, that result in the formation of a stable moiety (e.g., a suitable amino protecting group; aliphatic, alkyl, alkenyl, alkynyl, heteroaliphatic, heterocyclic, aryl, heteroaryl, acyl, and the like, each of which may or may not be further substituted (e.g., alkyl substituted with halogens such as perfluoroalkyl)).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, as used herein, the term "heteroalkyl" includes straight, branched and cyclic alkyl groups that contain one or more oxygen, sulfur, nitrogen, phosphorus, or silicon atoms, e.g., in place of carbon atoms. An analogous convention applies to other generic terms such as "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-30 carbon atoms (i.e., $C_{1-30}$ heteroaliphatic) [in situations wherein the number of carbons is specified, such as a $C_{15}$ heteroaliphatic, is meant a carbon chain 15 carbons in length]. In certain embodiments, the heteroaliphatic group employed by the invention is an optionally substituted $C_2$-$C_{30}$ heteroaliphatic group. In certain embodiments, the heteroaliphatic group employed by the invention is an optionally substituted $C_5$-$C_{25}$ heteroaliphatic group. In certain embodiments, the heteroaliphatic group employed by the invention is an optionally substituted $C_{10}$-$C_{20}$ heteroaliphatic group. In certain embodiments, the heteroaliphatic group employed by the invention is an optionally substituted $C_1$-$C_{10}$ heteroaliphatic group. In certain embodiments, the heteroaliphatic group employed by the invention is an optionally substituted $C_{11}$-$C_{15}$ heteroaliphatic group. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "heterocyclic," "heterocycles," or "heterocyclyl," as used herein, refers to a cyclic heteroaliphatic. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "heteroaryl," as used herein, refers to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted (e.g., alkyl substituted with halogens such as perfluoroalkyl)).

The term "hydroxy," or "hydroxyl," as used herein, refers to a group of the formula (—OH). An "optionally substituted hydroxyl" refers to a group of the formula (—OR$^D$), wherein R$^D$ can be hydrogen, or any substitutent which results in a stable moiety (e.g., a suitable hydroxyl protecting group; aliphatic, alkyl, alkenyl, alkynyl, heteroaliphatic, heterocyclic, aryl, heteroaryl, acyl, sulfinyl, sulfonyl, nitro, alkylaryl, arylalkyl, and the like, each of which may or may not be further substituted (e.g., alkyl substituted with halogens such as perfluoroalkyl)).

The term "imino," as used herein, refers to a group of the formula (=NR$^E$), wherein R$^E$ corresponds to hydrogen or any substitutent as described herein, that results in the formation of a stable moiety (for example, a suitable amino protecting group; aliphatic, alkyl, alkenyl, alkynyl, heteroaliphatic, heterocyclic, aryl, heteroaryl, acyl, sulfinyl, sulfonyl, amino, hydroxyl, alkylaryl, arylalkyl, and the like, each of which may or may not be further substituted (e.g., alkyl substituted with halogens such as perfluoroalkyl)).

The term "isocyano," as used herein, refers to a group of the formula (—NC).

The term "nitro," as used herein, refers to a group of the formula (—NO$_2$).

The term "oxo," as used herein, refers to a group of the formula (=O).

The term "thiooxo," as used herein, refers to a group of the formula (=S).

The term "thio," or "thiol," as used herein, refers to a group of the formula (—SH). An "optionally substituted thiol" refers to a group of the formula (—SR$^E$), wherein R$^E$ can be hydrogen, or any substitutent. Substituents include, but are not limited to, any of the substituents described herein, that result in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted (e.g., alkyl substituted with halogens such as perfluoroalkyl)).

The term "stable moiety," as used herein, preferably refers to a moiety which possess stability sufficient to allow manufacture, and which maintains its integrity for a sufficient period of time to be useful for the purposes detailed herein.

The term "protecting group" refers to an "amino-protecting group" if attached to a nitrogen atom, an "hydroxyl protecting group" if attached to an oxygen atom of an alcohol group, a "carboxylic acid protecting group" if attached to an oxygen atom of a carboxylate group, or a "thiol protecting group" if attached to a sulfur atom. Each of these protecting groups is described in more detail below.

An "amino protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "hydroxyl protecting group" as used herein, is well known in the art and include those described in detail in

*Protecting Groups in Organic Synthesis*, T. W. Greene and P. G. M. Wuts, 3rd edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "thiol protecting group" as used herein, is well known in the art and includes those described in detail in *Protecting Groups in Organic Synthesis*, T. W. Greene and P. G. M. Wuts, 3rd edition, John Wiley & Sons, 1999, the entirety of which is incorporated herein by reference. Suitable thiol protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl(CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TB- DPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

As used herein, a "pharmaceutically acceptable form thereof" includes any pharmaceutically acceptable salts, solvates, hydrates, co-crystals, prodrugs, tautomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in *The Organic Chemistry of Drug Design and Drug Interaction* by Richard Silverman, published by Academic Press (1992).

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers (e.g., enantiomers, diasteromers, etc.). For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and*

*Optical Resolutions* p. 268 (E. L. Eliel, Ed., Univ. of Notre Dame Press, Notre Dame, Ind. 1972).

As used herein, "polymorph" refers to a crystalline inventive compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

In situations wherein a "compound" of a parent molecule (such as Moenomycin A) is specified, such as the situation identifying a "moenomycin A compound wherein $R^{1a}$ and $R^{1b}$ are H," is meant that the structure of the moenomycin A compound is identical to the parent molecule (in this case, Moenomycin A) with one or more exceptions as specified (in this case, with the exception that Ring A has been replaced with a hydrogen).

BRIEF DESCRIPTION OF THE FIGURES

FIG. 3A shows a schematic of the moe gene clusters 1 and 2, and the relative positions of the identified ORFs and genes along the clusters. FIG. 3B shows a schematic of the moeno38-1 gene cluster; plasmid pOOB49f carries moeR5moeS5 under control of ermE promoter. White arrows separated by dotted line indicate 18 kb DNA segment that flanks moe cluster 1 and is not associated with MmA production.

FIG. 8. A schematic for the possible role of the moeO5 protein in moe biosynthesis.

FIG. 13. Graph of LC-MS analysis of moe extracts from wild-type and moeM5 deficient strain OB20a.

FIG. 15A. Southern analysis of BamHI and XhoI digests of total DNA of wild type *S. ghanaensis* (lanes 2 and 4, respectively) and MO12 strain with disrupted moeGT3 (lanes 3 and 5). Lane 1—mixture of plasmids pMO12, pMO14 and pOOB58 underdigested with PstI. FIG. 15B shows the results of a bioassay of semipurified extracts from 1 g (wet weight) of mycelia of wild type strain (WT) and MO12. FIG. 15C presents a scheme of moeGT3 disruption in the *S. ghanaensis* genome. X, H, E mark XhoI, HindIII, EcoRI sites, respectively.

DETAILED DESCRIPTION OF CERTAIN EMBODIMENTS OF THE INVENTION

Figure 20:
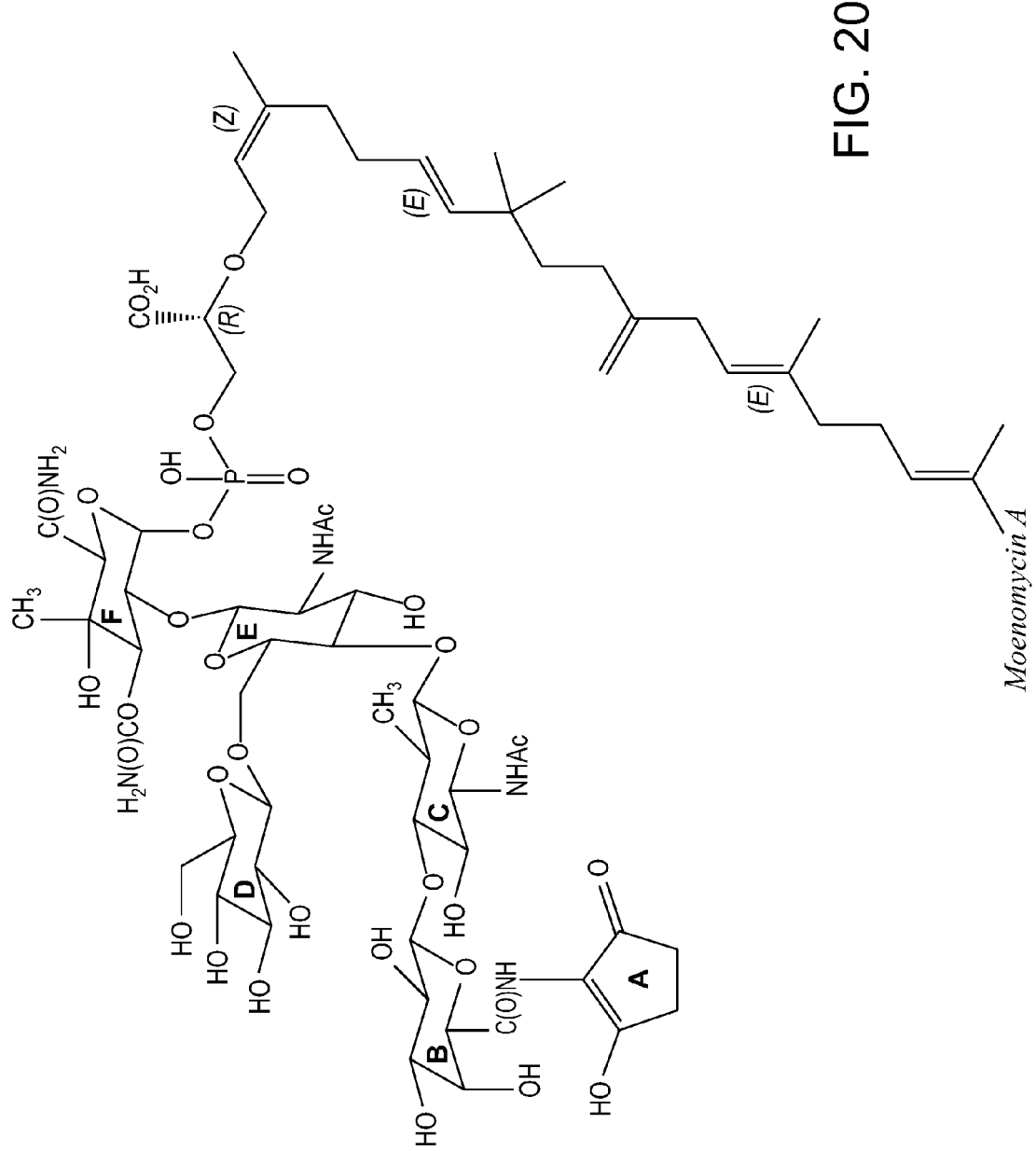
FIG. 20. Structure of Moenomycin A
Figure 21:
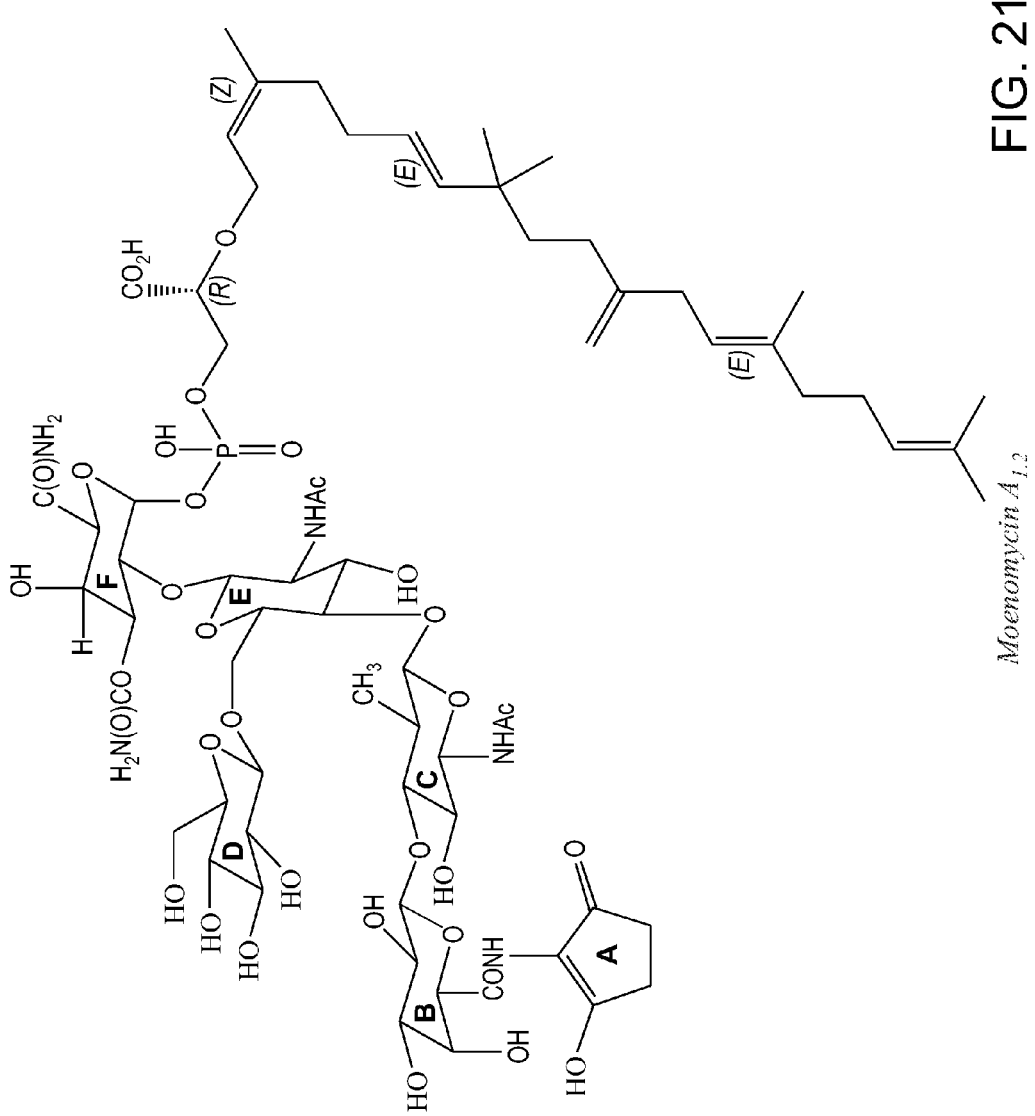
FIG. 21. Structure of Moenomycin $A_{1,2}$
Figure 22:
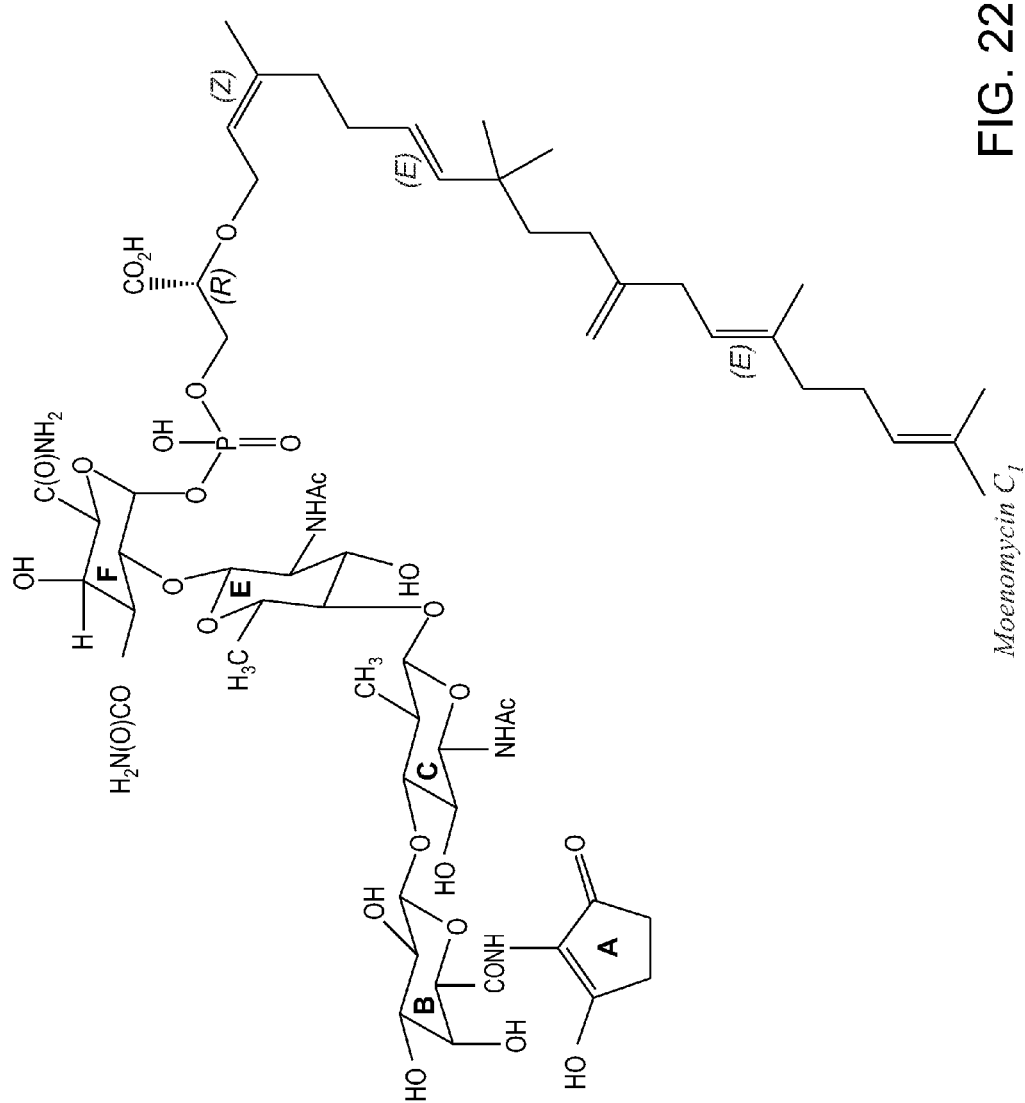
FIG. 22. Structure of Moenomycin $C_1$
Figure 23:
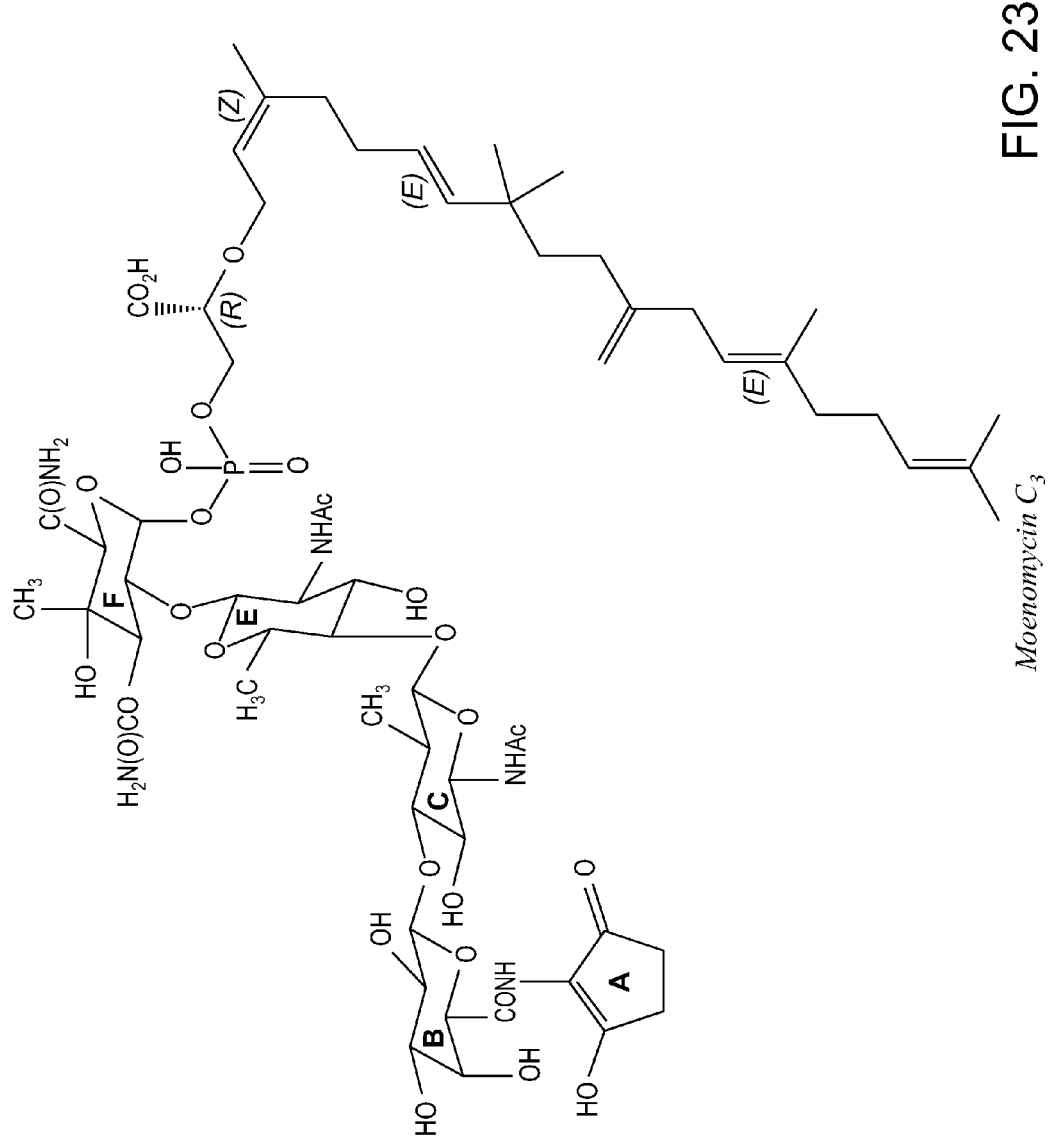
FIG. 23. Structure of Moenomycin $C_3$
Figure 24:
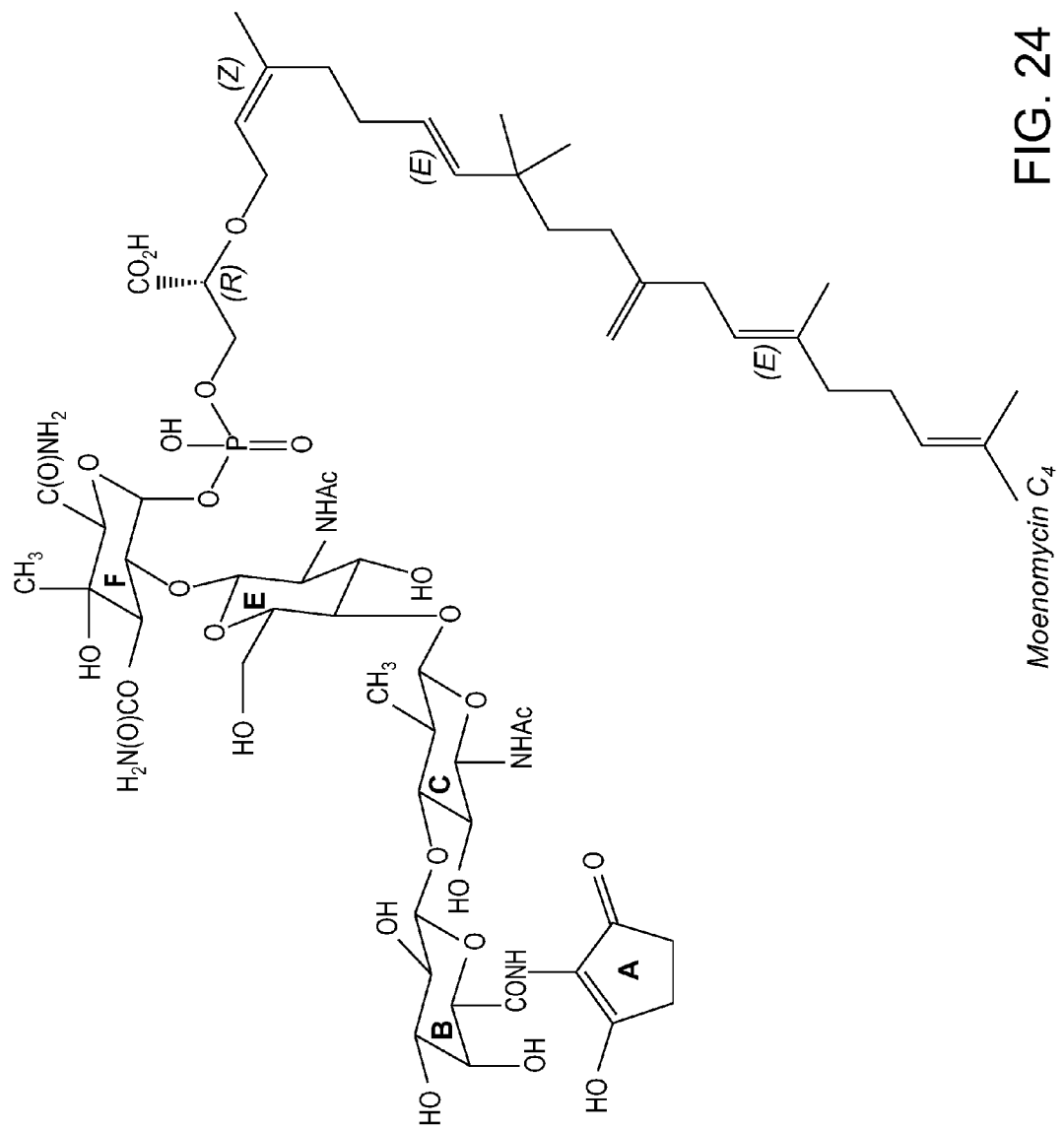
FIG. 24. Structure of Moenomycin $C_4$
Figure 25:
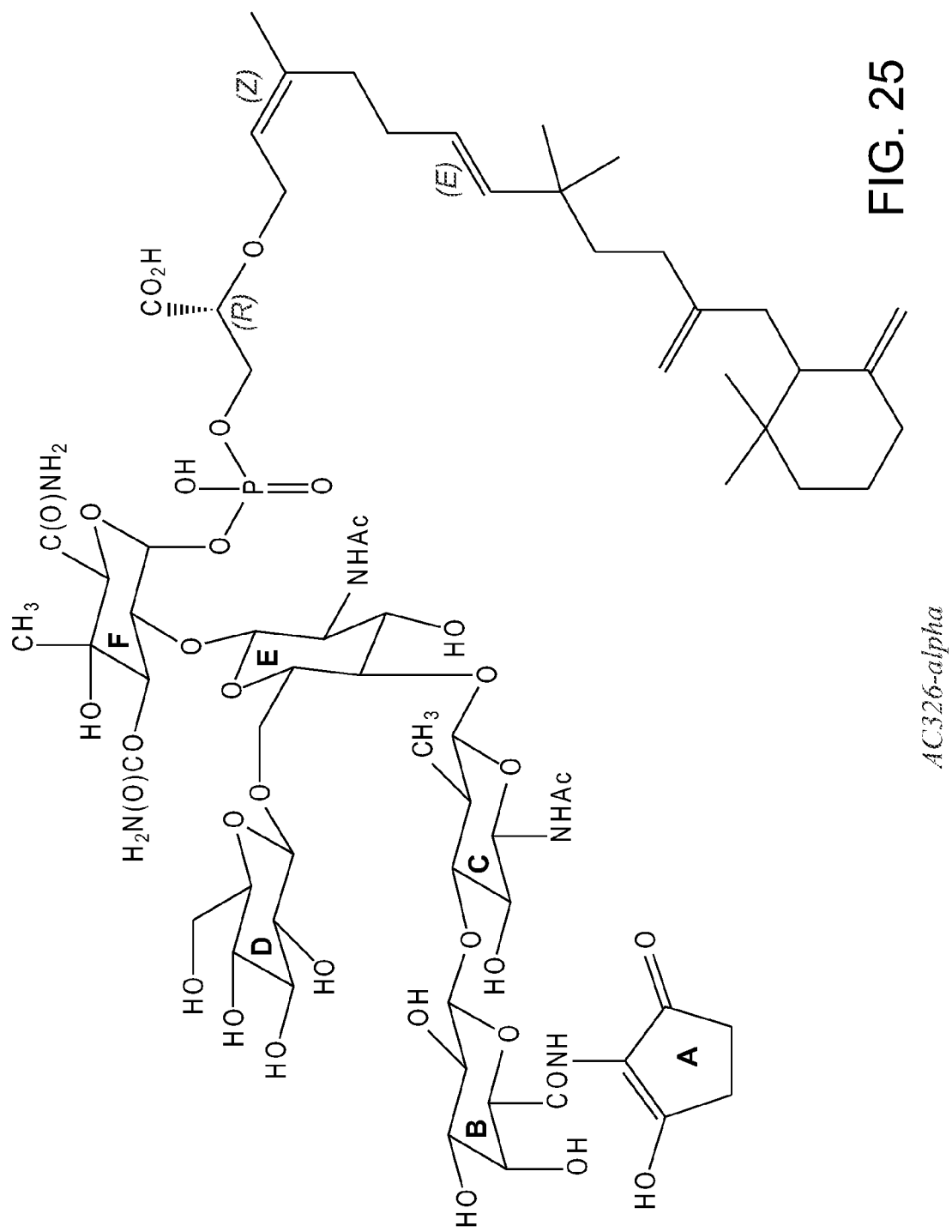
FIG. 25. Structure of AC326-alpha
Figure 26:
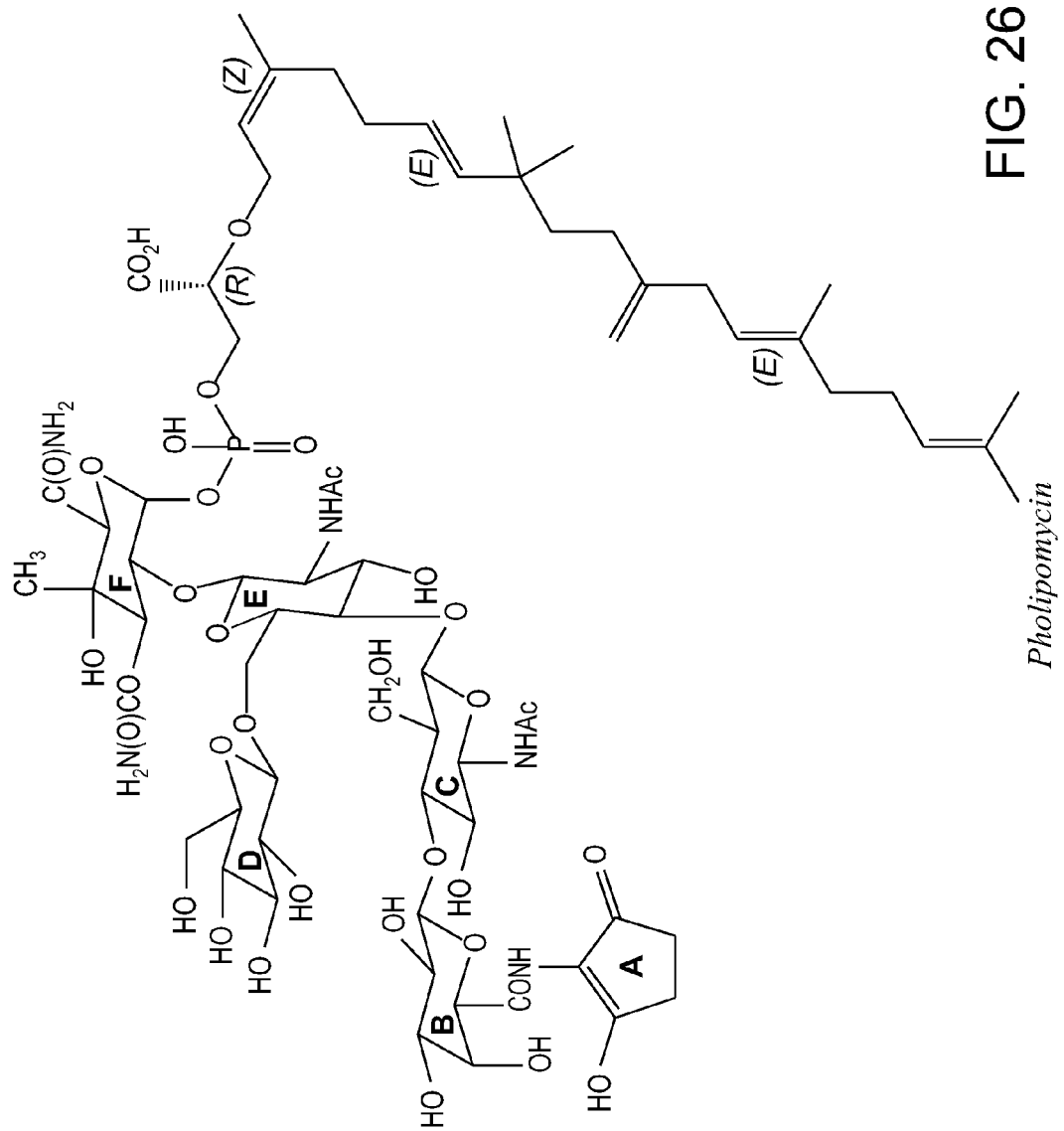
FIG. 26. Structure of Pholipomycin
Figure 27:
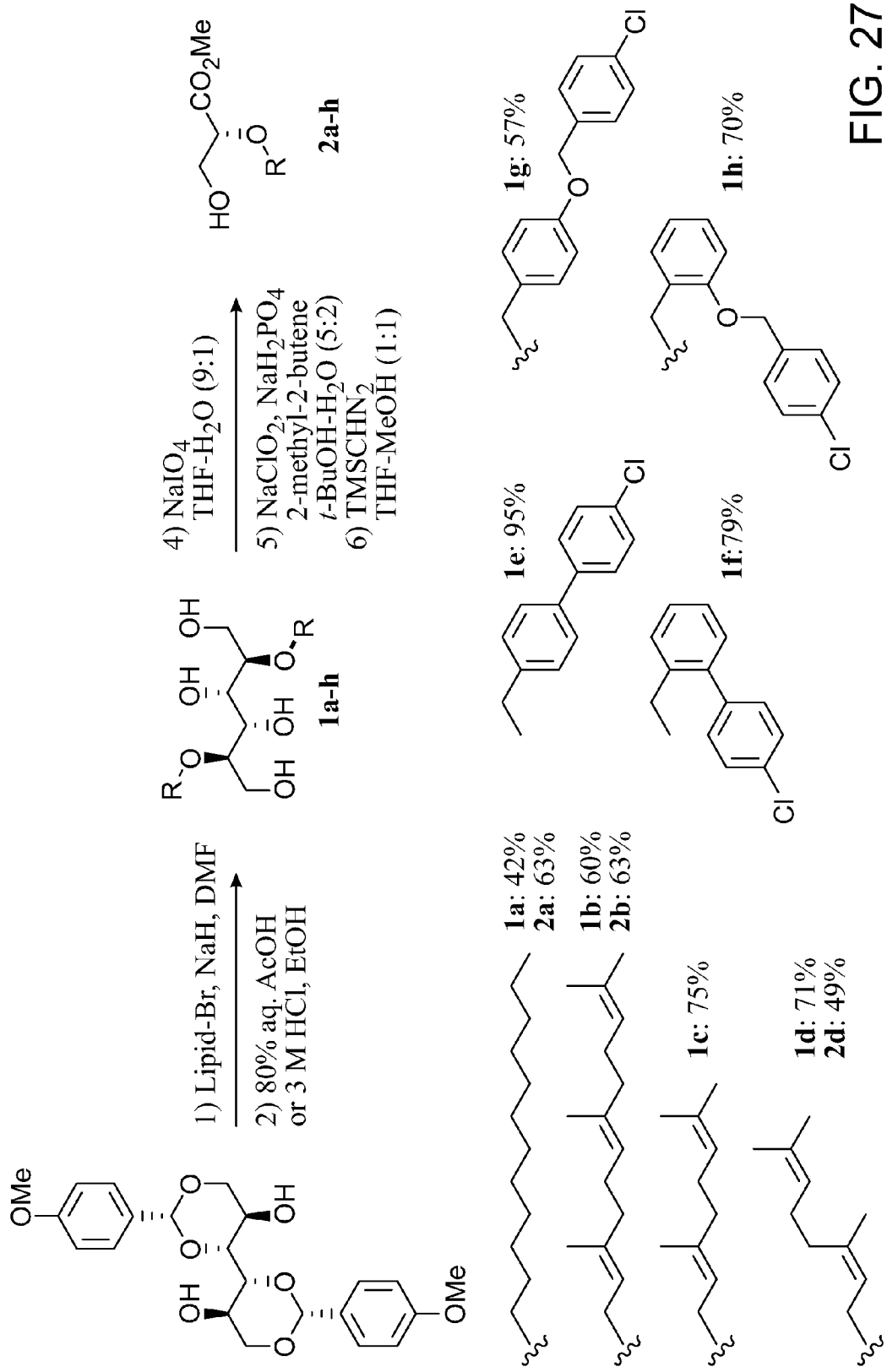
FIG. 27. Preparation of glycerate-lipid portion of moenomycin analogs.
Figure 28:
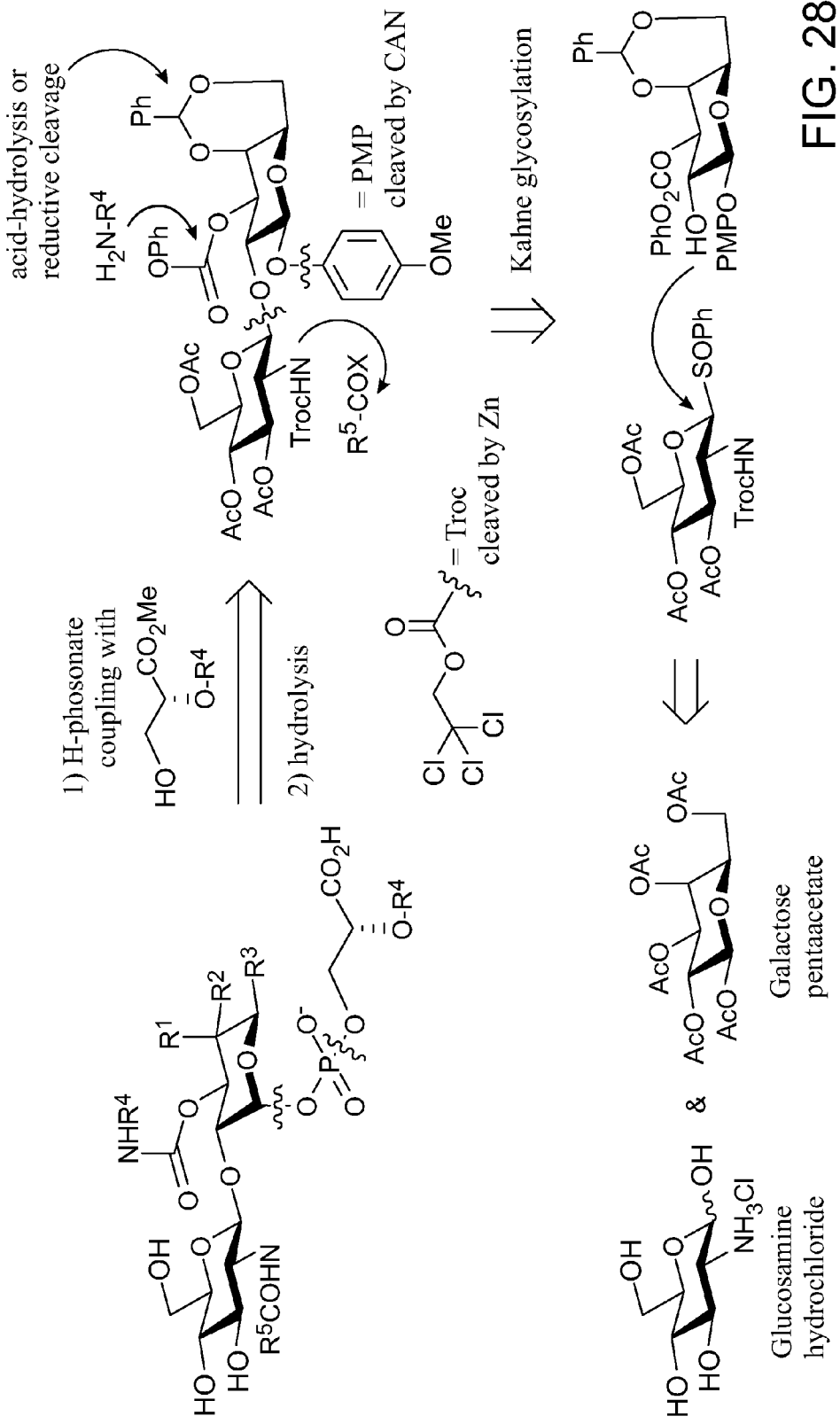
FIG. 28. Synthetic strategy for disaccharide moenomycin analogs.
Figure 29:
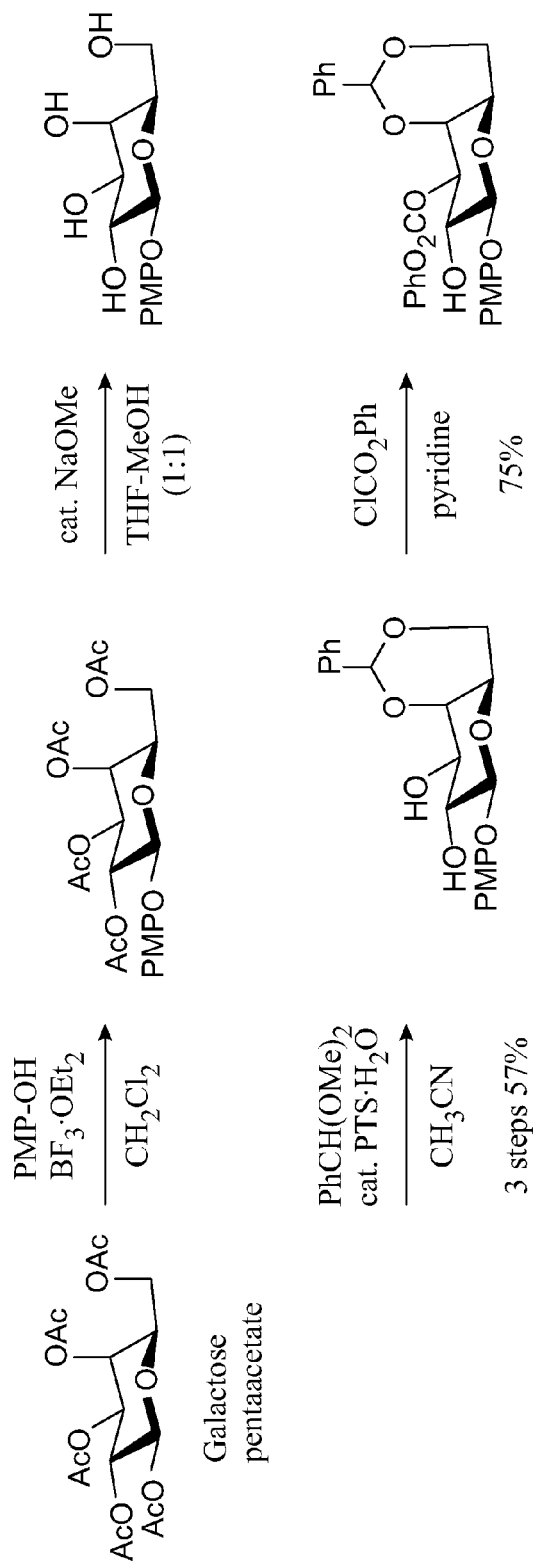
FIG. 29. Synthesis of galactose moiety.
Figure 30:
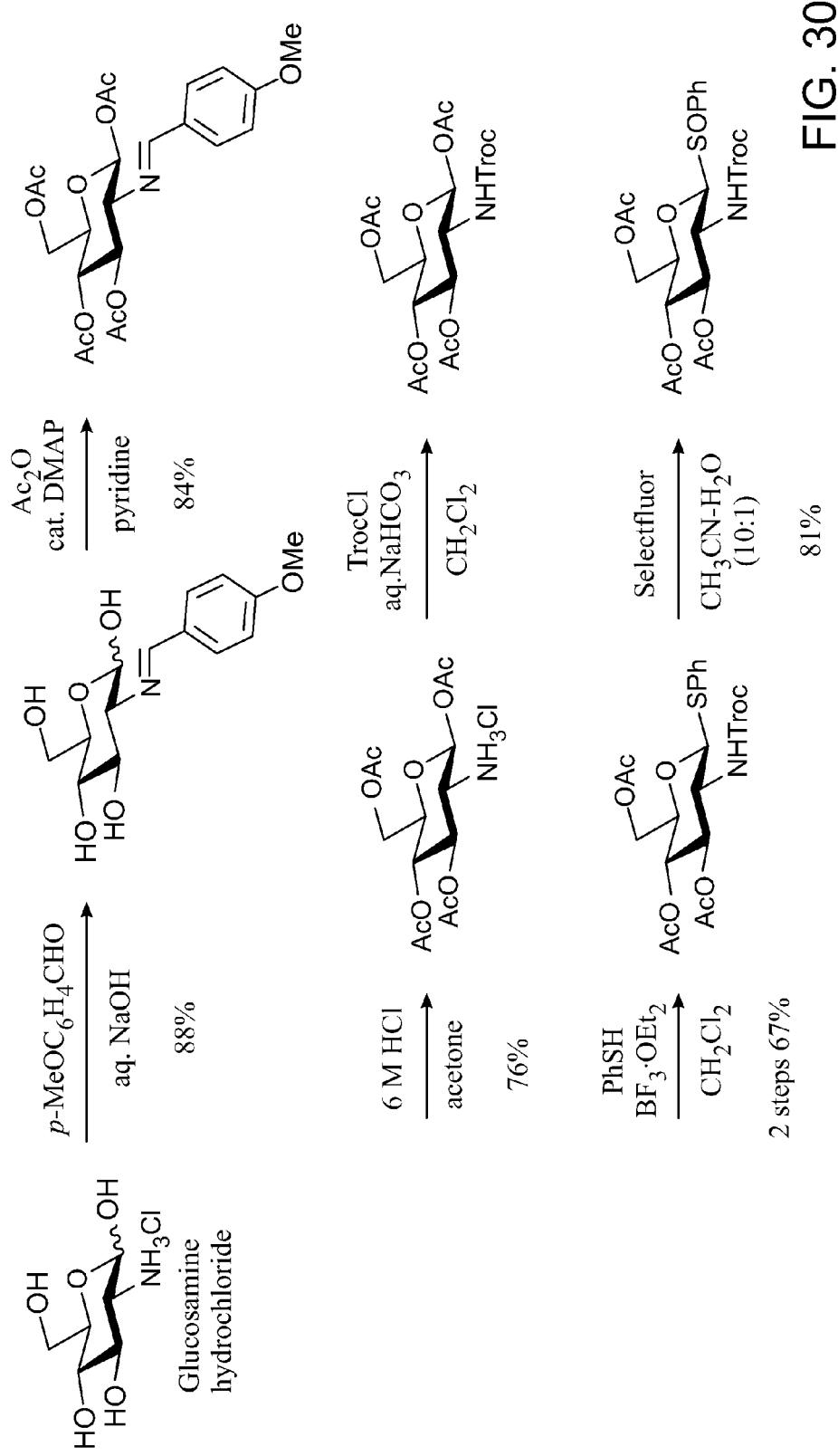
FIG. 30. Synthesis of glucosamine moiety.
Figure 31:
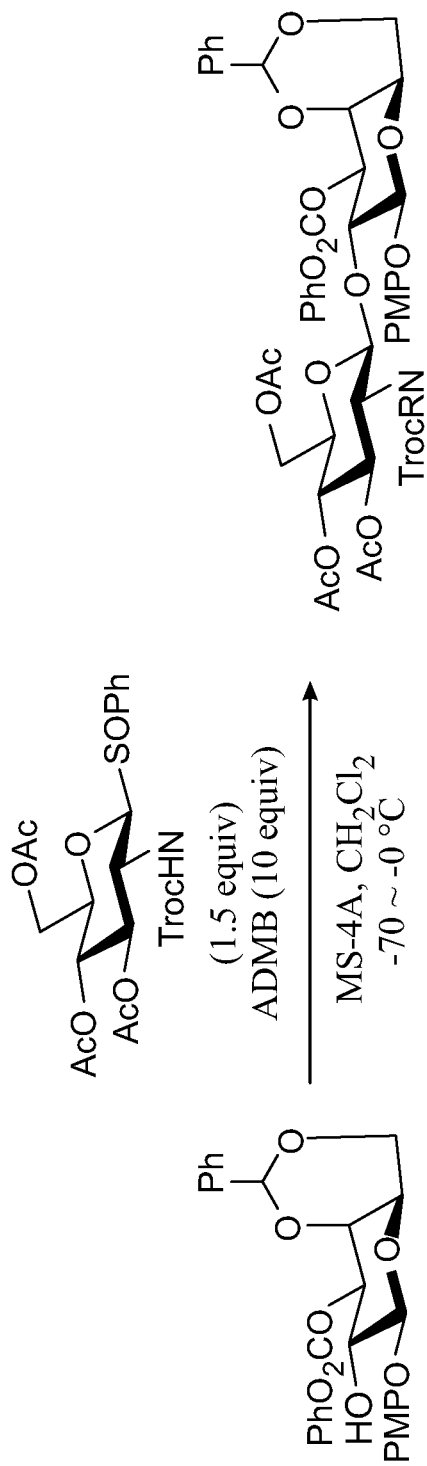
FIG. 31. Reaction conditions for Kahne glycosylation using 2-NHTroc glucosamine sulfoxide as glycosyl donor.
Figure 32:
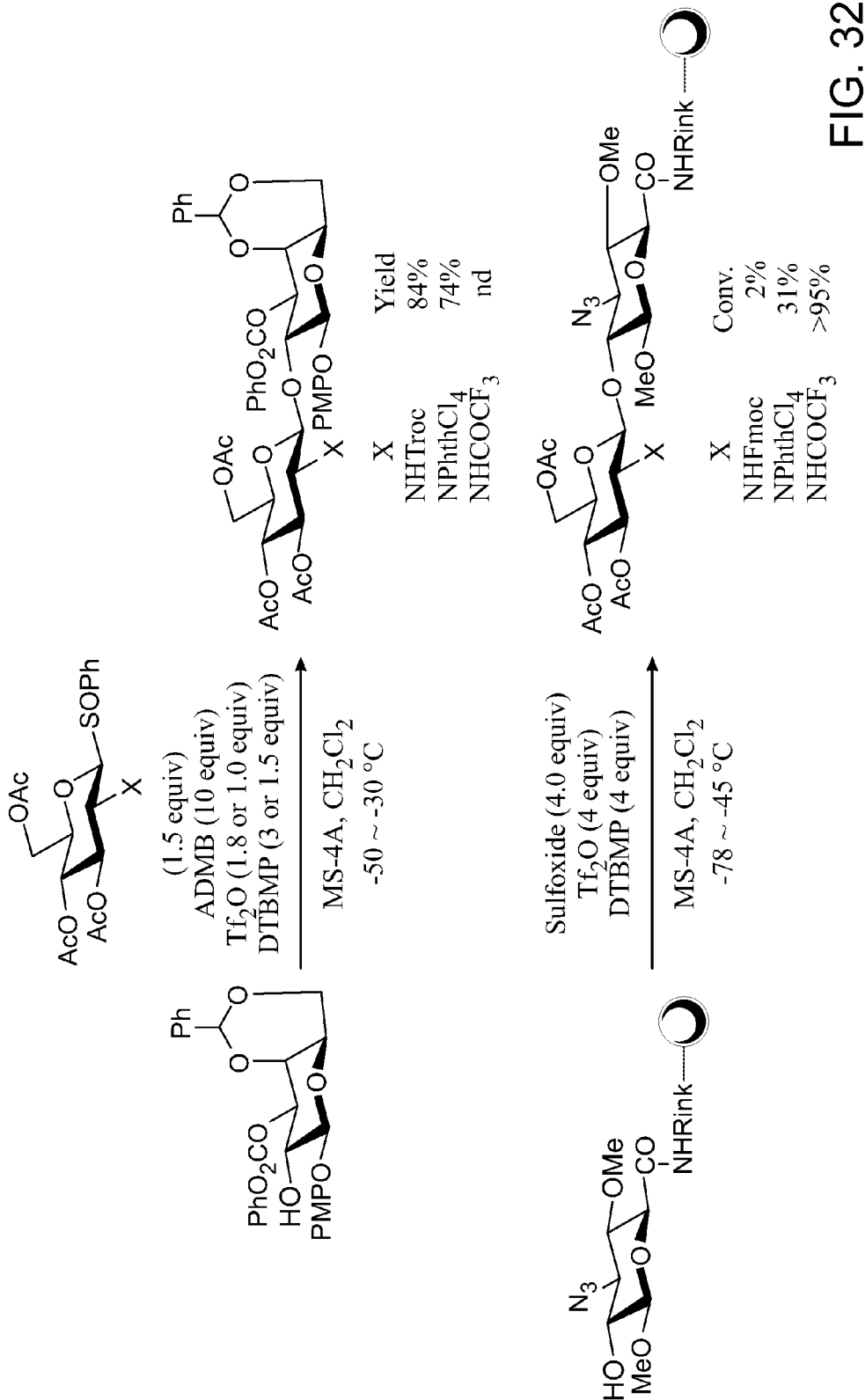
FIG. 32. Effect of N-2 protecting group of glucosamine sulfoxide on Kahne glycosylation.
Figure 33:
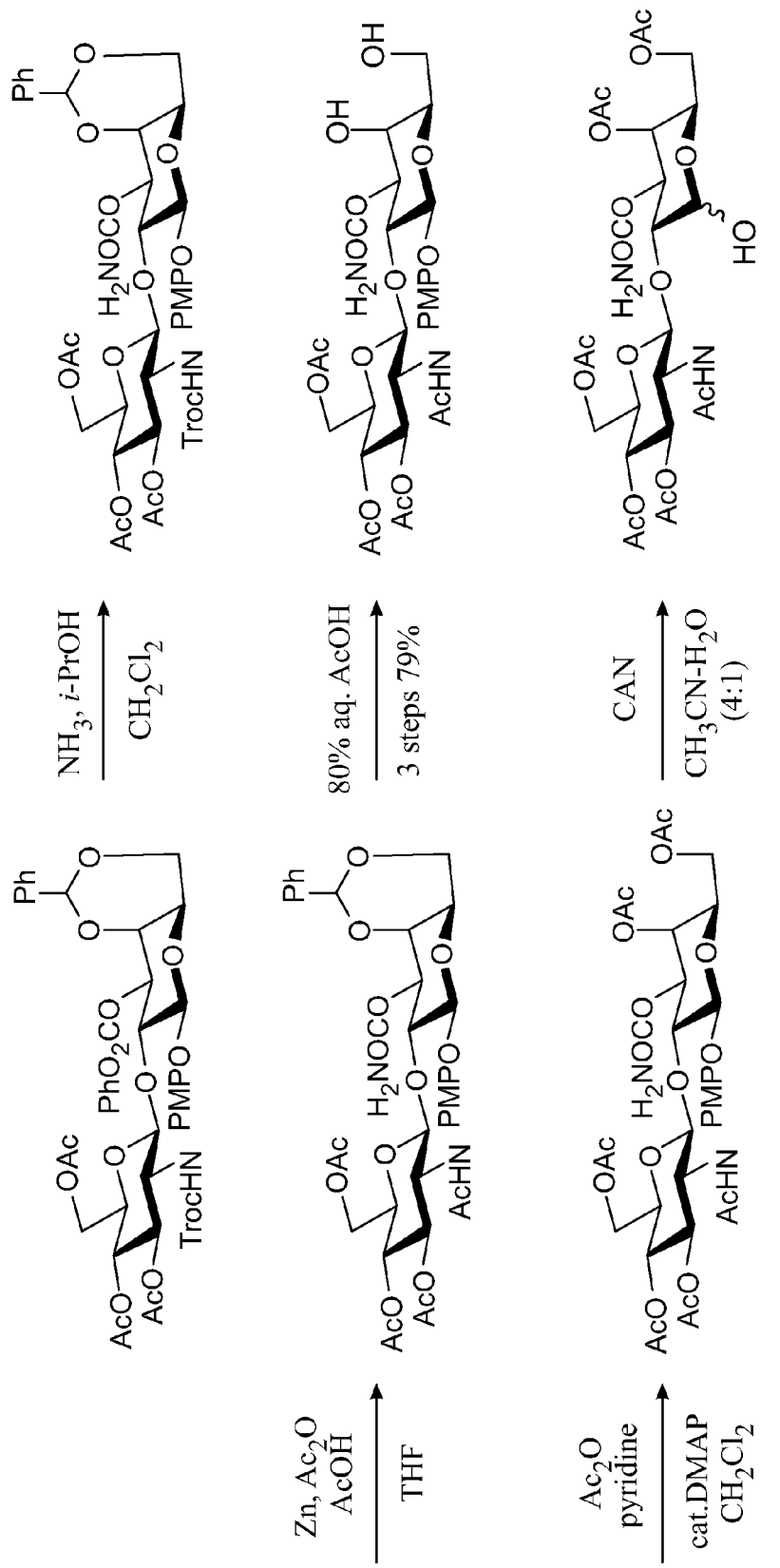
FIG. 33. Exemplary transformations of disaccharide.
Figure 34:
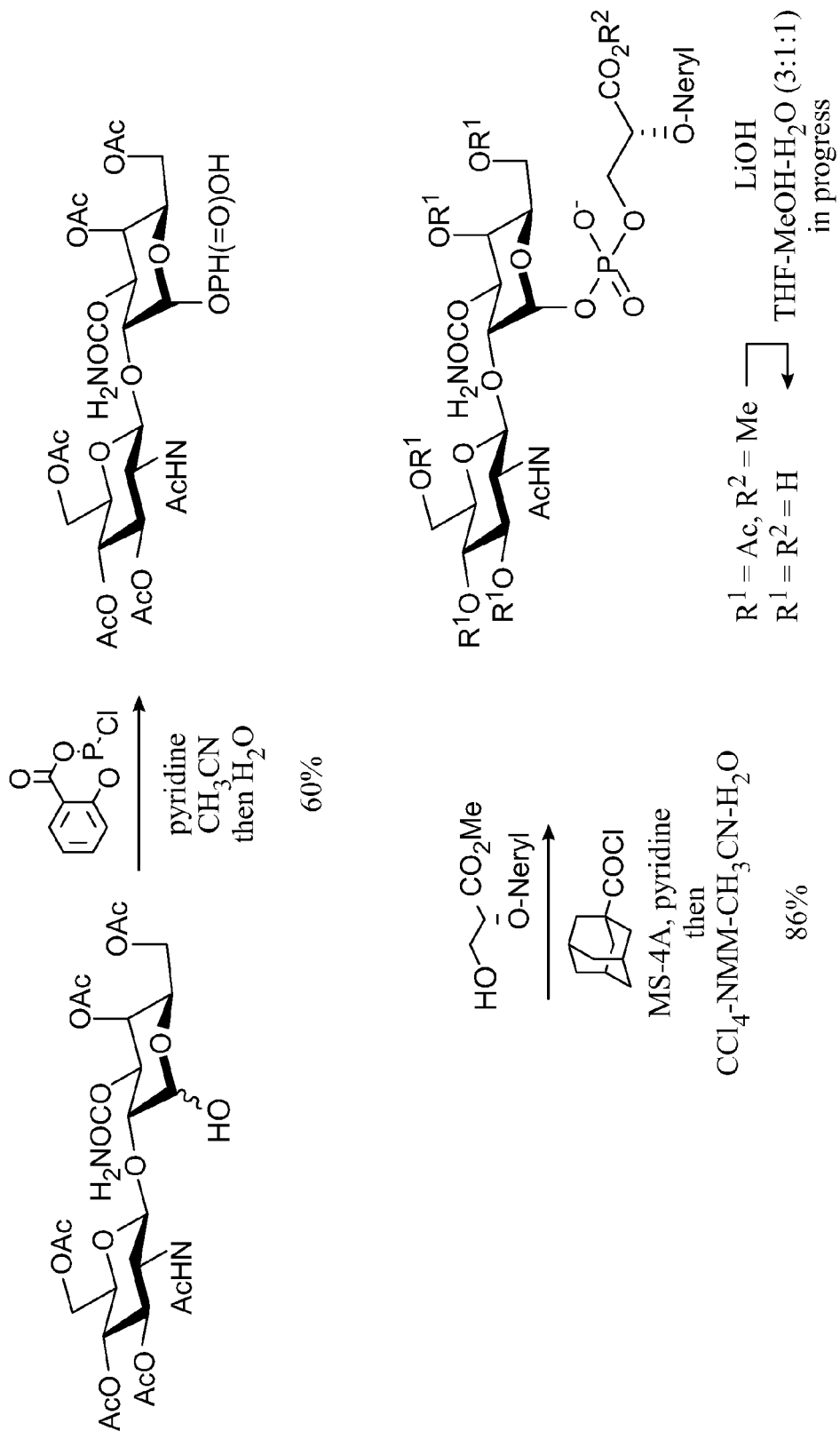
FIG. 34. Exemplary transformations of disaccharide.
Figure 35:
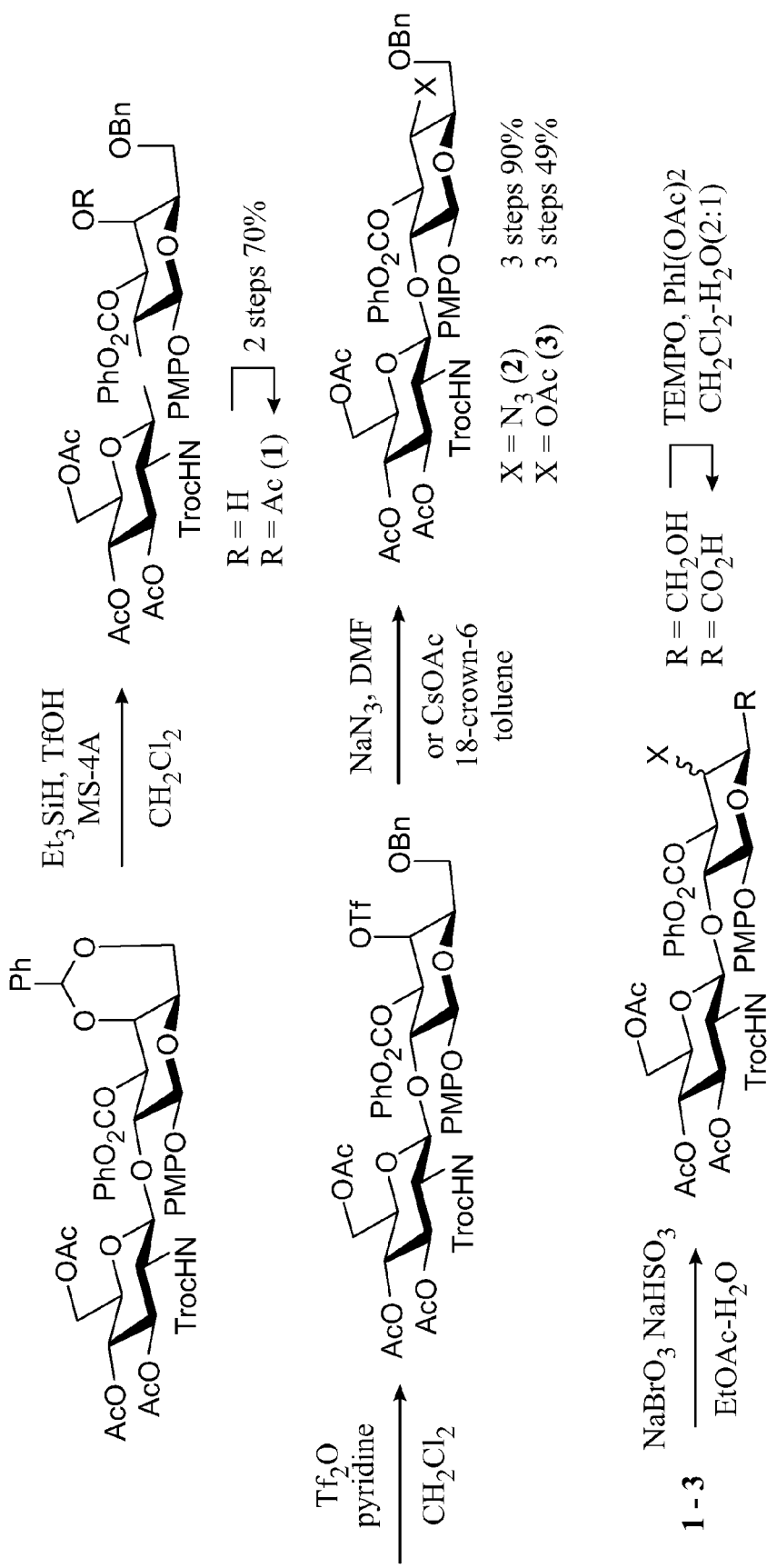
FIG. 35. Exemplary transformations of disaccharide.
Figure 36:
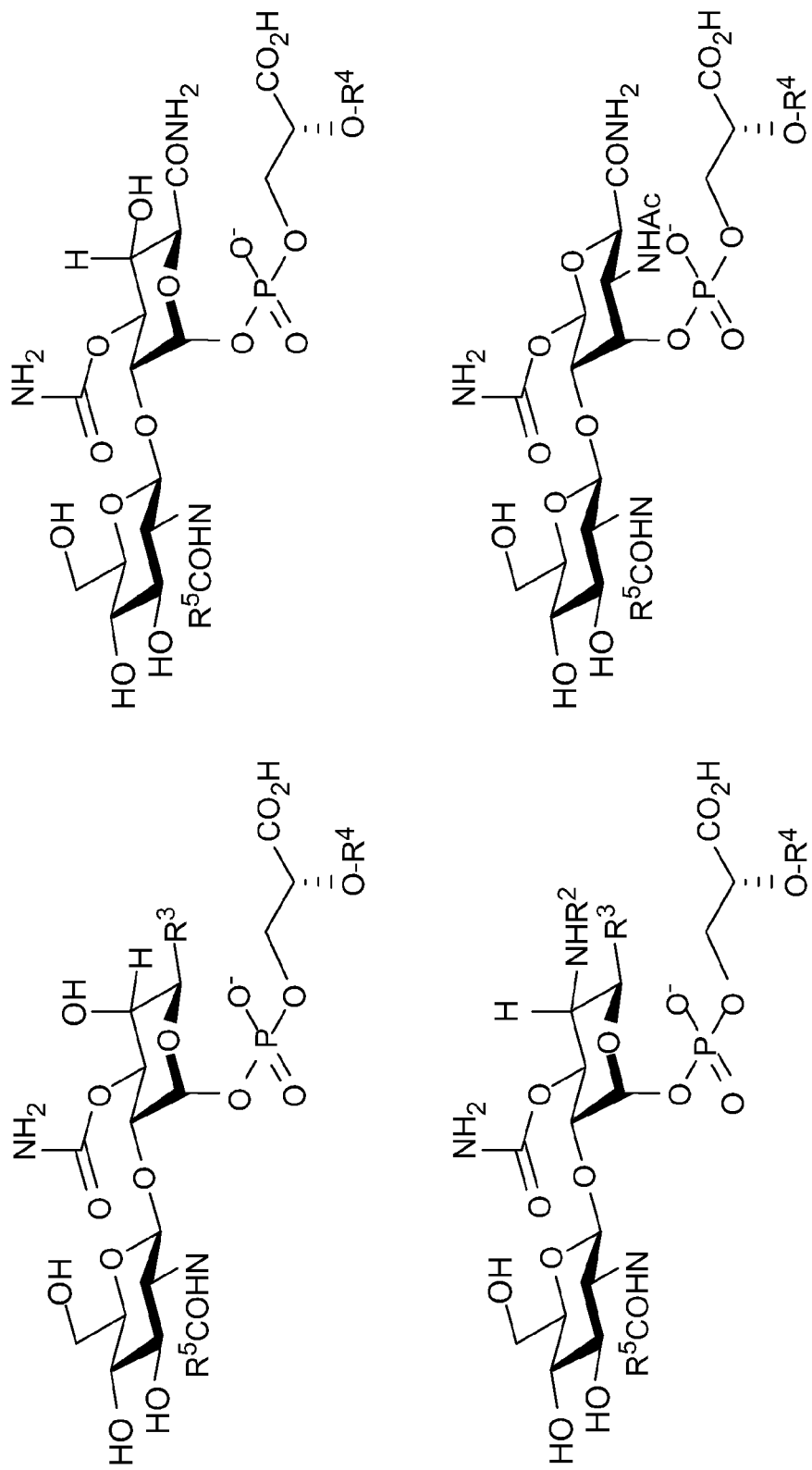
FIG. 36. Exemplary disaccharide-phosphoglycerate portions of moenomycin analogs.

Moenomycin A is a natural product that inhibits peptidoglycan biosynthesis by binding to bacterial transglycosylases (FIG. 20). Moenomycin A is a thousand times more potent than the antibiotic vancomycin, but poor pharmacokinetic properties related to the lipid side chain have prevented its use in humans. Removal of the natural lipid side chain completely abolishes biological activities. A comprehensive study of the effect of different side chains, optionally in combination with different sugar portions, on the anti-bacterial activity compared to natural moenomycins (e.g., Moenomycin A, Moenomycin $A_{1.2}$, Moenomycin $C_1$, Moenomycin $C_3$, Moenomycin $C_4$, AC326-alpha, and/or Pholipomycin), has been limited, as most synthetic transformations employed in the removal of the natural lipid side chain and in the addition of other different side chains have also altered other structural features of the molecule. The present invention seeks, in part, to solve these problems via new synthetic, biosynthetic, and semi-synthetic methodology as described herein, and to provide novel moenomycins and moenomycin analogs comprising different lipid side chains, linker groups, and/or different sugar portions.

Compounds

Thus, in one aspect, the present invention is directed to compounds of the formulae (I), (II), (III), or (IV):

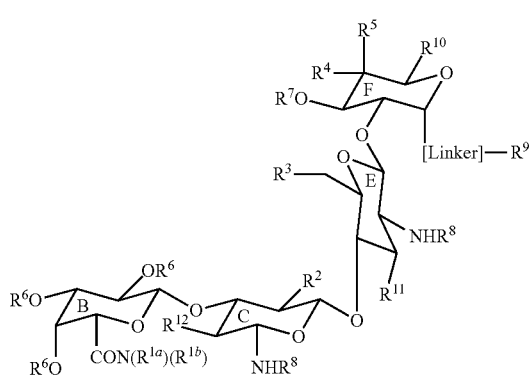

(I)

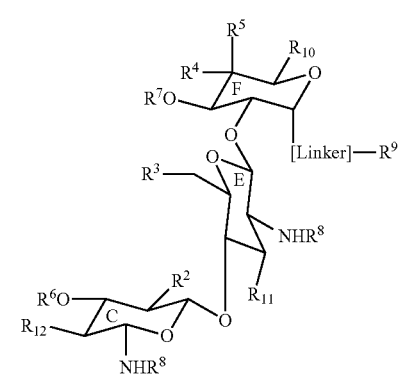

(II)

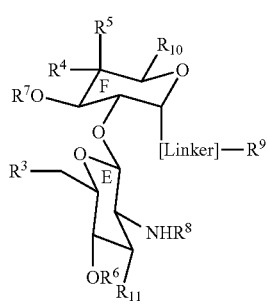

(III)

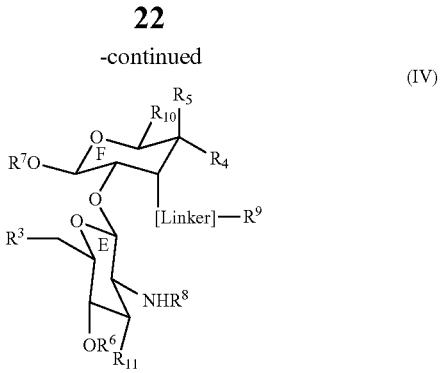

(IV)

or a pharmaceutically acceptable form thereof;
wherein:

$R^{1a}$ and $R^{1b}$ are, independently, H, an amino protecting group, optionally substituted aryl, optionally substituted heteroaryl, optionally substituted aliphatic, or optionally substituted heteroaliphatic;

each instance of $R^2$, $R^4$, and $R^5$ is, independently, H, $-OR^z$, $-N(R^z)_2$, optionally substituted aryl, optionally substituted heteroaryl, optionally substituted aliphatic, or optionally substituted heteroaliphatic, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety;

$R^3$ is, independently, H, $-OH$, $-NH_2$, $-SH$, $-OR^w$, $-NH(R^w)$, $N(R^w)_2$, $-SR^w$, $-O(C=O)R^w$, $-NH(C=O)R^w$, $-O(C=NH)R^w$, $-NH(C=NH)R^w$, $-S(C=NH)R^w$, $-NH(C=S)R^w$, $-S(C=O)R^w$, $-O(C=S)R^w$, $-S(=S)R^w$, optionally substituted aryl, optionally substituted heteroaryl, optionally substituted aliphatic, or optionally substituted heteroaliphatic, wherein $R^w$ is a carbohydrate moiety, optionally substituted aryl, optionally substituted heteroaryl, optionally substituted aliphatic, or optionally substituted heteroaliphatic;

each instance of $R^6$ and $R^7$ is, independently, H, a hydroxyl protecting group, optionally substituted aryl, optionally substituted heteroaryl, optionally substituted aliphatic, optionally substituted heteroaliphatic, a carbohydrate moiety, $-C(=O)N(R^Z)_2$, $-C(=O)OR^Z$, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety; and each instance of $R^8$ is, independently, H, an amino protecting group, optionally substituted aryl, optionally substituted heteroaryl, optionally substituted aliphatic, optionally substituted heteroaliphatic, a carbohydrate moiety, or $-C(=O)R^w$, wherein $R^w$ is a carbohydrate moiety, optionally substituted aryl, optionally substituted heteroaryl, optionally substituted aliphatic, or optionally substituted heteroaliphatic;

[Linker] is the group:

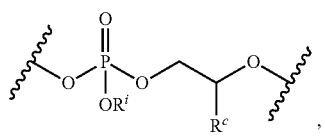

, wherein:

$R^c$ is hydrogen, halogen, optionally substituted heteroaryl, —$OR^q$, —$N(R^q)_2$, —$SR^q$, —$NO_2$, —NC, —CN, —$N_3$, —$N(R^q)=NR^q$, —CHO, —$C(=O)R^q$, —$C(=S)R^q$, —$C(=NR^q)R^q$, —$C(=O)OR^q$, —$C(=NR^q)OR^q$, —$C(=NR^q)N(R^q)_2$, —$C(=O)N(R^q)_2$, —$C(=S)OR^q$, —$C(=O)SR^q$, —$C(=S)SR^q$, —$P(=O)(OR^q)_2$, —$P(=O)_2(OR^q)$, —$S(=O)(OR^q)$, —$S(=O)_2(OR^q)$, —$P(=O)N(R^q)_2$, —$P(=O)_2N(R^q)_2$, —$C(=O)NR^qS(=O)_2R^q$, —$S(=O)N(R^q)_2$, —$S(=O)_2N(R^q)_2$, or an optionally substituted heteroaryl moiety; wherein each instance of $R^q$ is H, optionally substituted aliphatic, optionally substituted heteroaliphatic, optionally substituted aryl, optionally substituted heteroaryl, or a protecting group;

$R^i$ is H, optionally substituted aliphatic, optionally substituted heteroaliphatic, optionally substituted aryl, optionally substituted heteroaryl, or a hydroxyl protecting group; and $R^9$ is H or an optionally substituted $C_{1-30}$ aliphatic moiety, wherein 0 to 10 methylene units are optionally replaced with —O—, —$NR^x$—, —S—, —$C(=O)$—, —$C(=NR^x)$—, —$S(=O)$—, —$S(=O)_2$—, —N=N—, —C=N—, —$C(R^y)=C(R^y)$—, —N—O—, an optionally substituted arylene, or an optionally substituted heteroarylene moiety, wherein each instance of $R^x$ is, independently, H, optionally substituted aliphatic, optionally substituted heteroaliphatic, optionally substituted aryl, optionally substituted heteroaryl, or an amino protecting group, and each instance of $R^y$ is, independently, H, optionally substituted aliphatic, optionally substituted heteroaliphatic, optionally substituted aryl, or optionally substituted heteroaryl;

$R^{10}$ is —$C(=O)NHR^8$, —$CH_2OR^6$, or —$C(=O)OR^6$;

$R^{11}$ is —$OR^6$ or —$NHR^8$; and $R^{12}$ is —$OR^6$, —$NHR^8$.

(i) Compounds Encompassed by Formula (I)

Compounds of formula (I), and subsets thereof, as provided below, includes compounds comprising rings B, C, E and F, and optionally rings A and D, of the moenomycin sugar scaffold.

In certain embodiments, the present invention provides compounds of formula (I-a):

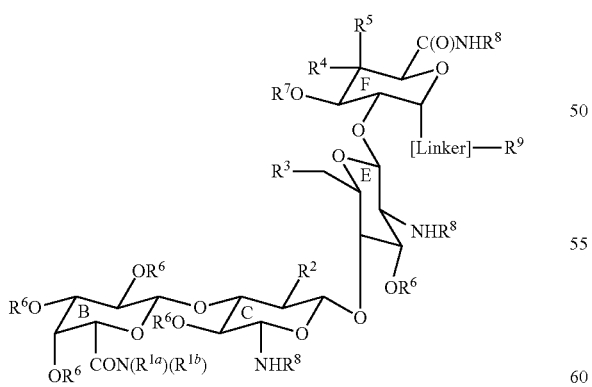

(I-a)

or pharmaceutically acceptable forms thereof; wherein $R^{1a}$, $R^{1b}$, $R^2$, $R^3$, $R^4$, $R^5$, $R^6$, $R^7$, $R^8$, $R^9$, and [Linker] are as defined herein.

In certain embodiments, the present invention provides compounds of formula (I-b):

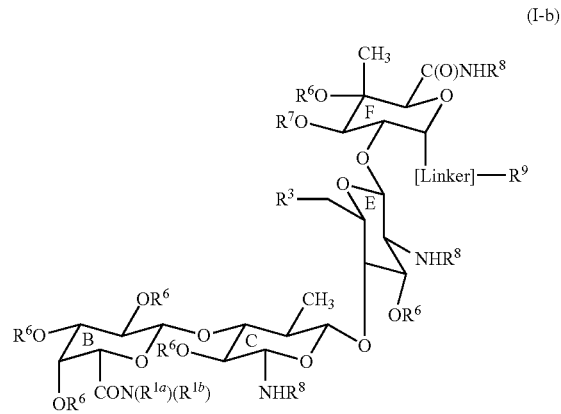

(I-b)

or pharmaceutically acceptable forms thereof; wherein $R^{1a}$, $R^{1b}$, $R^6$, $R^7$, $R^8$, $R^9$ and [Linker] are as defined above and herein.

In other embodiments, the present invention provides compounds of formula (I-c):

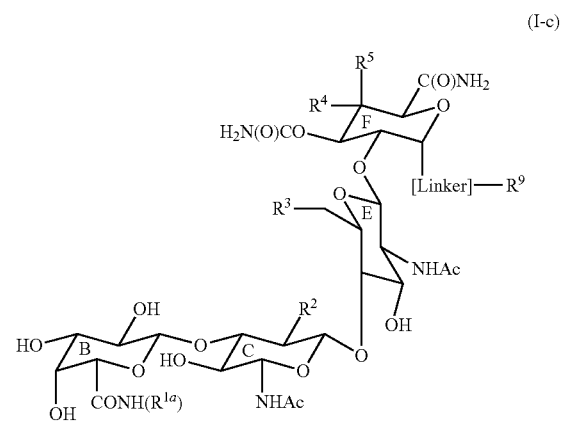

(I-c)

or pharmaceutically acceptable forms thereof; wherein $R^{1a}$, $R^2$, $R^3$, $R^4$, $R^5$, $R^9$, x and [Linker] are as defined herein.

In other embodiments, the present invention provides compounds of formula (I-d):

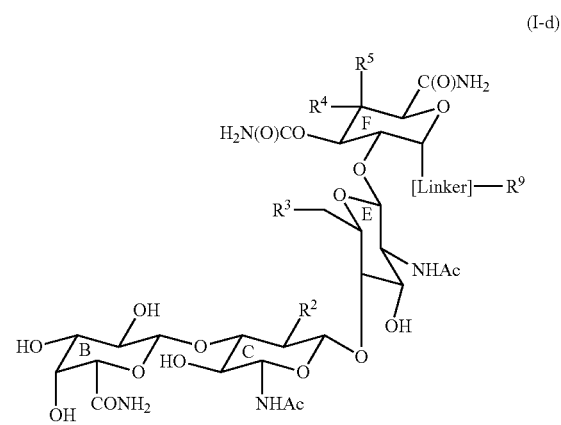

(I-d)

or pharmaceutically acceptable forms thereof; wherein $R^2$, $R^3$, $R^4$, $R^5$, $R^9$, and [Linker] are as defined herein.

In other embodiments, the present invention provides compounds of formula (I-e):

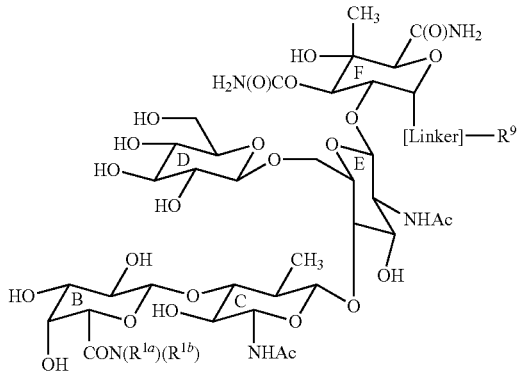

(I-e)

or pharmaceutically acceptable forms thereof; wherein $R^{1a}$, $R^{1b}$, $R^9$ and [Linker] are as defined herein.

In other embodiments, the present invention provides compounds of formula (I-f):

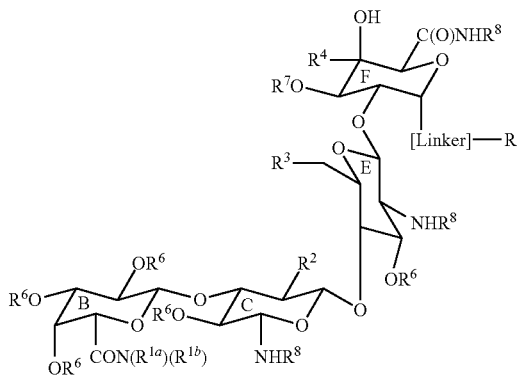

(I-f)

or pharmaceutically acceptable forms thereof; wherein $R^{1a}$, $R^{1b}$, $R^2$, $R^3$, $R^4$, $R^5$, $R^6$, $R^7$, $R^8$, $R^9$, and [Linker] are as defined herein.

In other embodiments, the present invention provides compounds of formula (I-g):

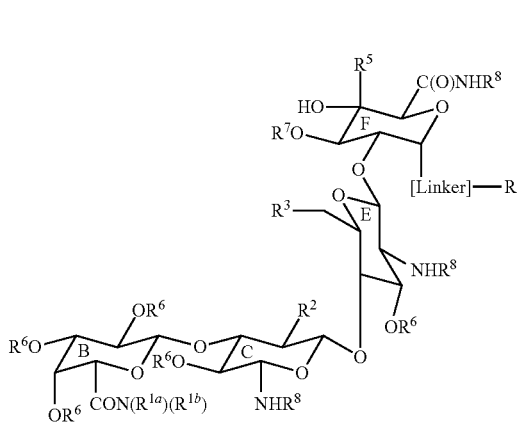

(I-g)

or pharmaceutically acceptable forms thereof; wherein $R^{1a}$, $R^{1b}$, $R^2$, $R^3$, $R^4$, $R^5$, $R^6$, $R^7$, $R^8$, $R^9$, and [Linker] are as defined herein.

In other embodiments, the present invention provides compounds of formula (I-h):

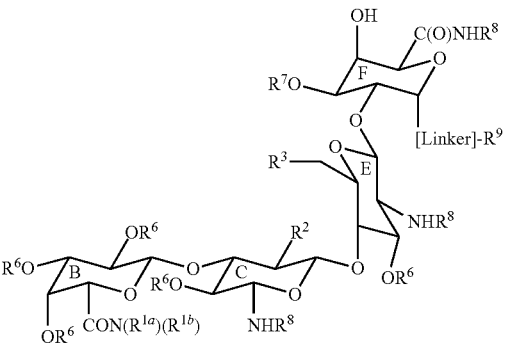

(I-h)

or pharmaceutically acceptable forms thereof; wherein $R^{1a}$, $R^{1b}$, $R^2$, $R^3$, $R^6$, $R^7$, $R^8$, $R^9$, and [Linker] are as defined herein.

In other embodiments, the present invention provides compounds of formula (I-i):

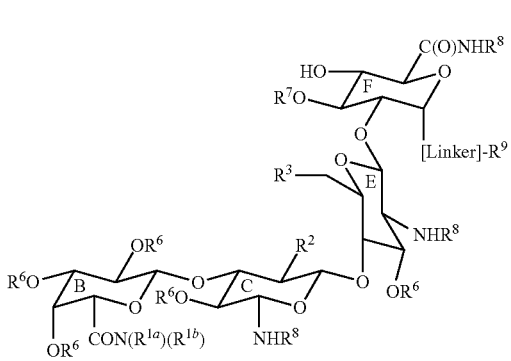

(I-i)

or pharmaceutically acceptable forms thereof; wherein $R^{1a}$, $R^{1b}$, $R^2$, $R^3$, $R^6$, $R^7$, $R^8$, $R^9$, and [Linker] are as defined herein.

In yet other embodiments, the present invention provides compounds of formula (I-j):

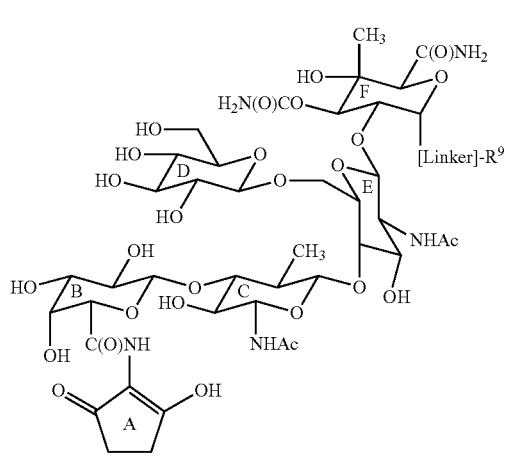

(I-j)

or pharmaceutically acceptable forms thereof; wherein $R^9$ and [Linker] are as defined herein.

In still yet other embodiments, the present invention provides compounds of formula (I-k):

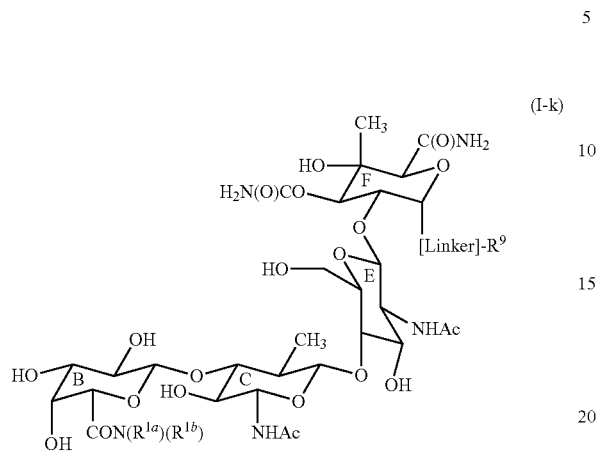

or pharmaceutically acceptable forms thereof; wherein $R^{1a}$, $R^{1b}$, $R^9$, and [Linker] are as defined herein.

In certain embodiments, the present invention provides compounds of formula (I) wherein the sugar portion comprising Rings A, B, C, E and F, and optionally Ring D, is derived from the natural products, Moenomycin A, Moenomycin $A_{1.2}$, Moenomycin $C_1$, Moenomycin $C_3$, Moenomycin $C_4$, AC326-alpha, and Pholipomycin. In other embodiments, intermediate moenomycin compounds are generated from bacteria (e.g., wild type or genetically engineered bacteria) and further synthetically modified to provide compounds of the present invention. As is appreciated by one of skill in the art, the various functional groups (e.g., hydroxyl and amino groups) of the sugar portion may optionally be protected (e.g., with hydroxyl and/or amino protecting groups, as defined above and herein).

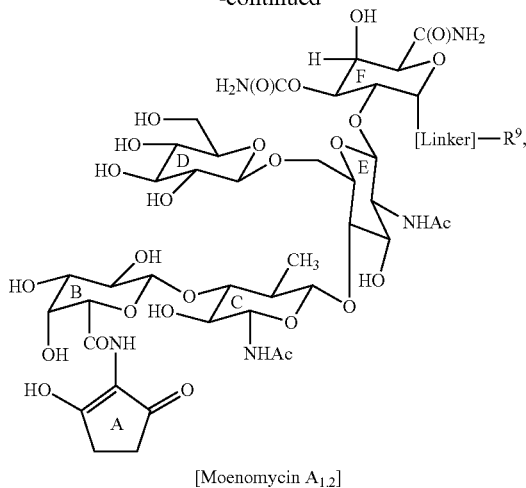

[Moenomycin $A_{1.2}$]

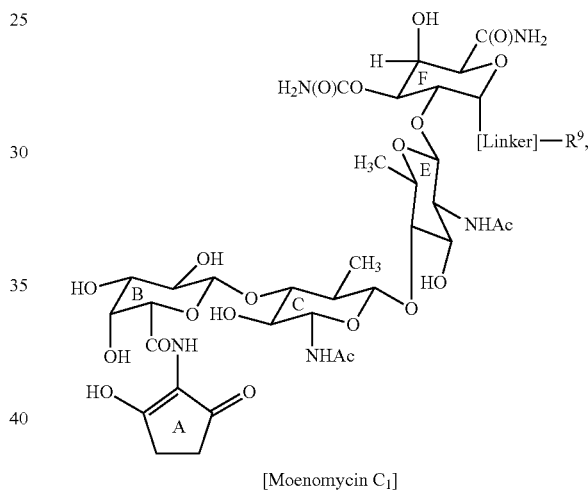

[Moenomycin $C_1$]

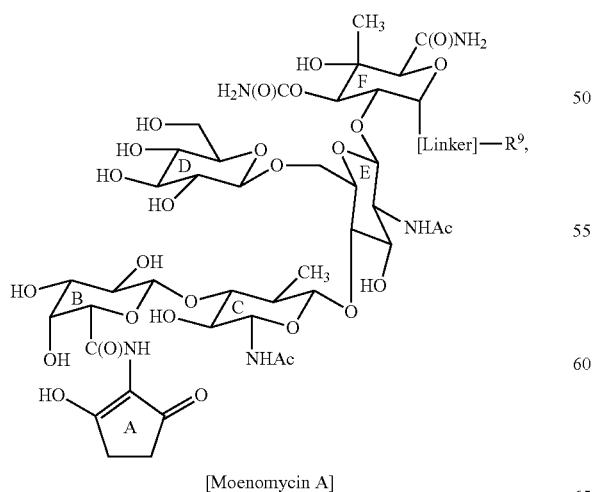

[Moenomycin A]

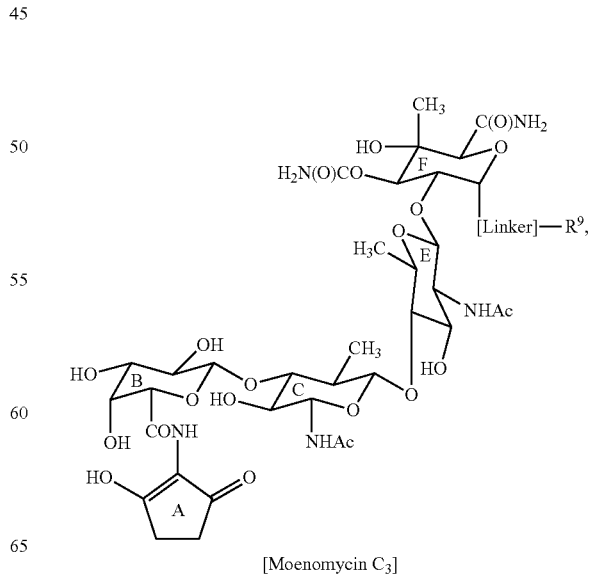

[Moenomycin $C_3$]

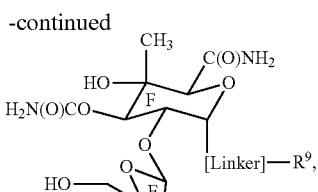

[Moenomycin C4]

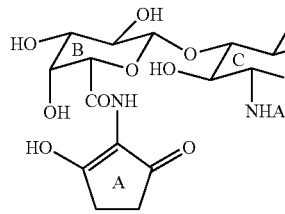

[AC326-alpha]

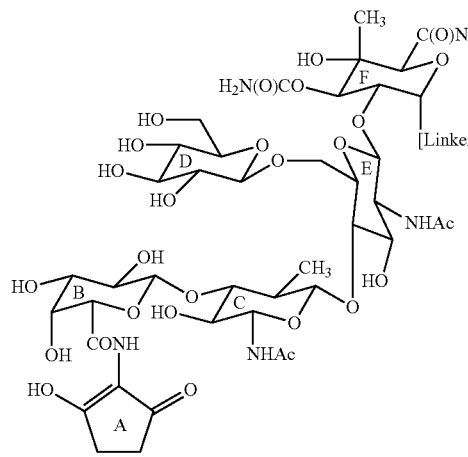

[Pholipomycin]

In certain embodiments, the present invention provides compounds of formula (II) wherein the sugar portion comprising Rings B, C, E and F, and optionally Ring D, is derived from the natural products, Moenomycin A, Moenomycin $A_{1.2}$, Moenomycin $C_1$, Moenomycin $C_3$, Moenomycin $C_4$, AC326-alpha, and Pholipomycin. In certain embodiments, Ring A is enzymatically or chemically cleaved to provide such compounds. In other embodiments, intermediate moenomycin-like compounds (i.e., provided without Ring A) are generated from bacteria (e.g., wild type or genetically engineered bacteria) and further synthetically modified to provide compounds of the present invention. As is appreciated by one of skill in the art, the various functional groups (e.g., hydroxyl and amino groups) of the sugar portion may optionally be protected (e.g., with hydroxyl and/or amino protecting groups, as defined above and herein).

Exemplary sugar portions include:

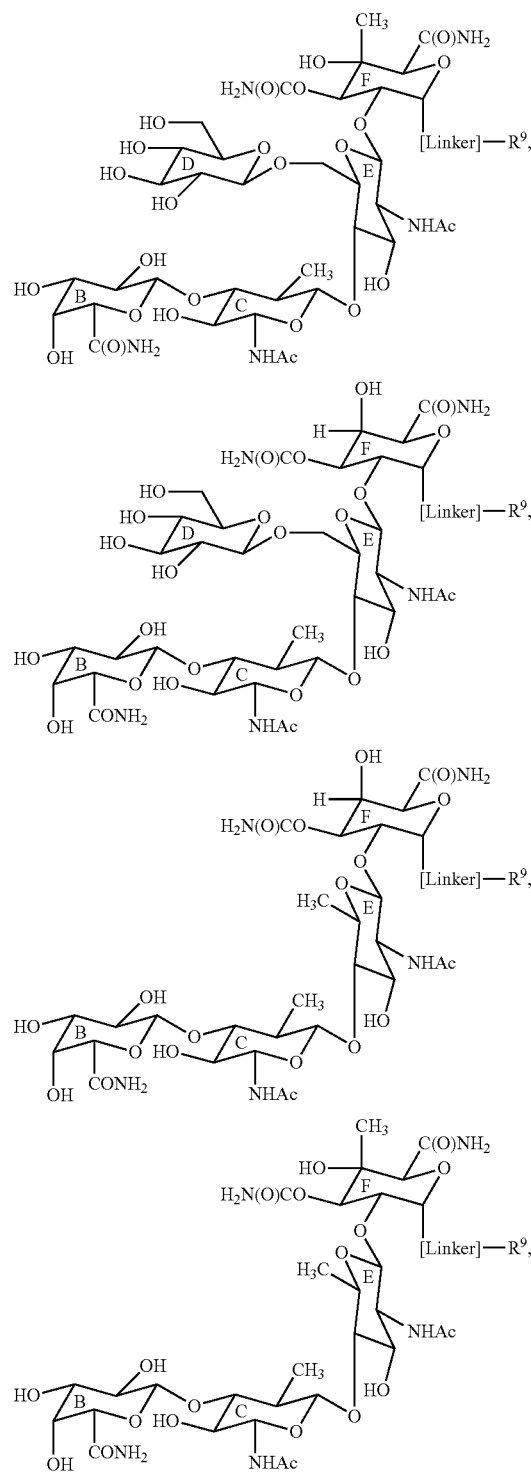

31
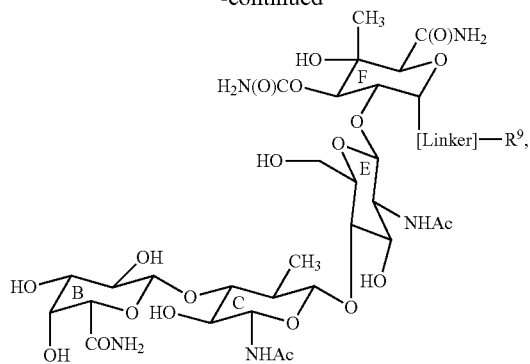
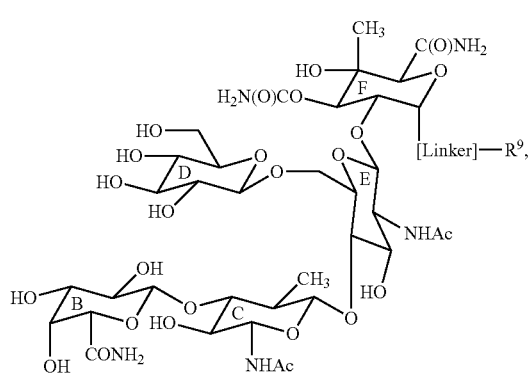
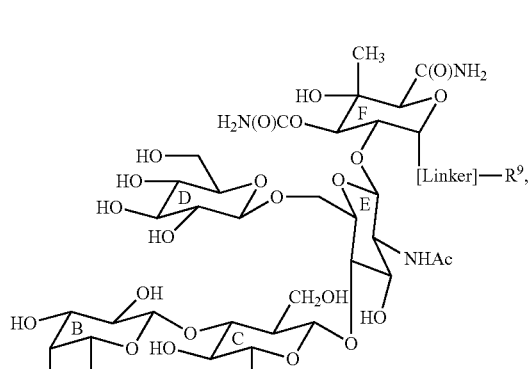
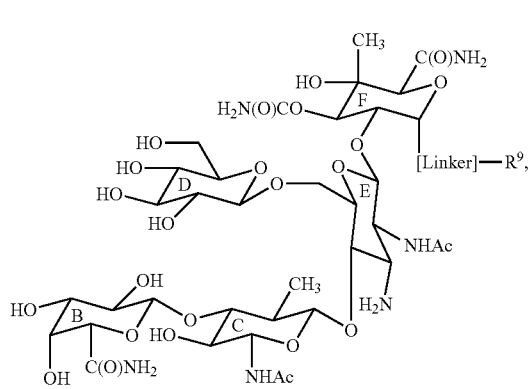
32
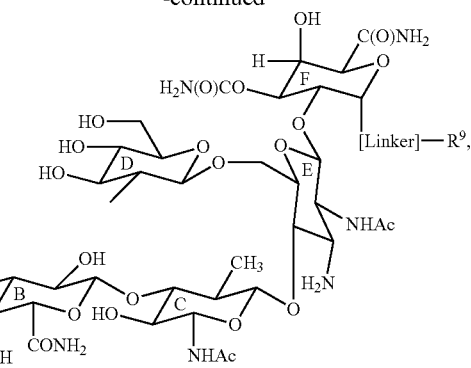
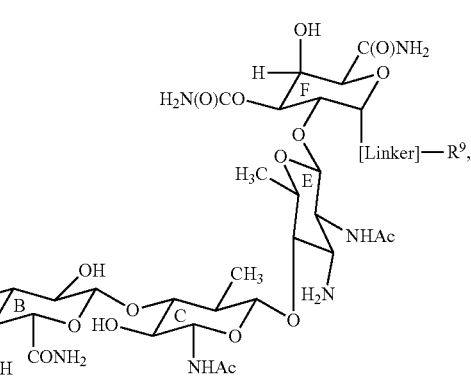

-continued

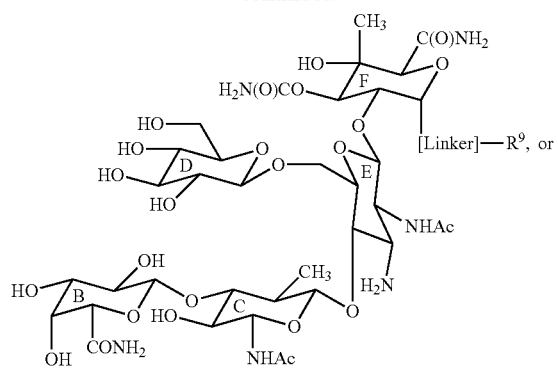

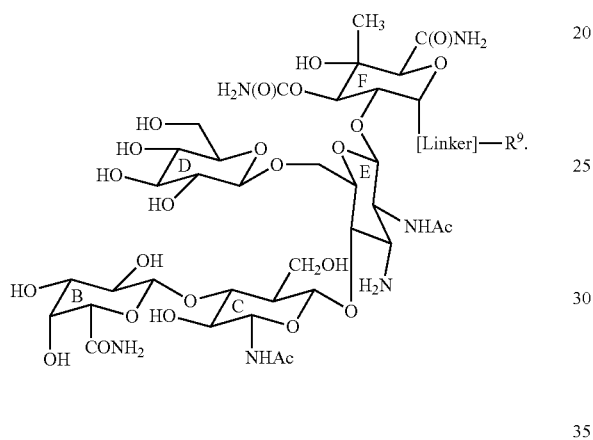

(ii) Compounds Encompassed by Formula (II)

Compounds encompassed by formula (II), and subsets thereof, as provided below, includes compounds comprising rings C, E and F, and optionally ring D, of the moenomycin sugar scaffold.

In certain embodiments, the present invention provides compounds of formula (II-a):

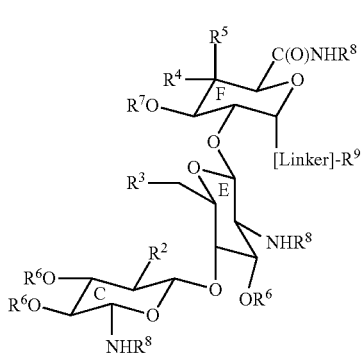

or pharmaceutically acceptable forms thereof; wherein $R^6$, $R^7$, $R^8$, $R^9$, and [Linker] are as defined herein.

In certain embodiments, the present invention provides compounds of formula (II-b):

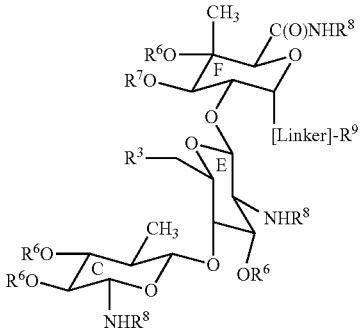

or pharmaceutically acceptable forms thereof; wherein $R^3$, $R^4$, $R^5$, $R^6$, $R^7$, $R^8$, $R^9$, and [Linker] are as defined herein.

In certain embodiments, the present invention provides compounds of formula (II-c):

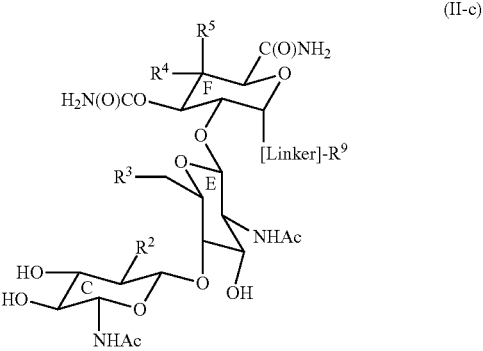

or pharmaceutically acceptable forms thereof; wherein $R^2$, $R^3$, $R^4$, $R^5$, $R^9$, and [Linker] are as defined herein.

In other embodiments, the present invention provides compounds of formula (II-d):

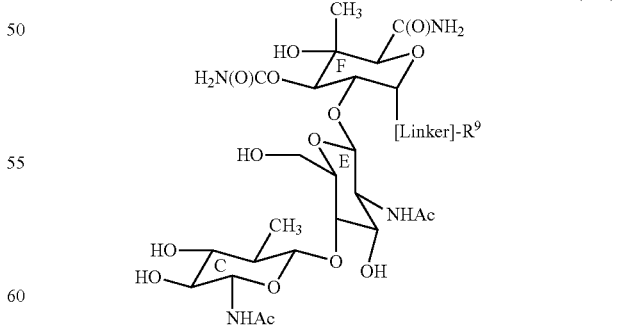

or pharmaceutically acceptable forms thereof; wherein $R^9$ and [Linker] are as defined herein.

In certain embodiments, the present invention provides compounds of formula (II-e):

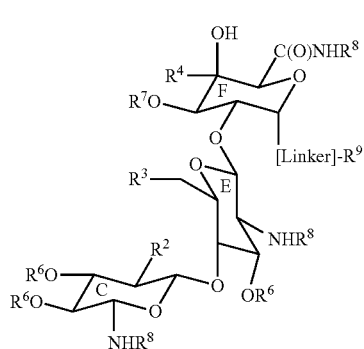

(II-e)

or pharmaceutically acceptable forms thereof; wherein $R^6$, $R^7$, $R^8$, $R^9$, and [Linker] are as defined herein.

In certain embodiments, the present invention provides compounds of formula (II-f):

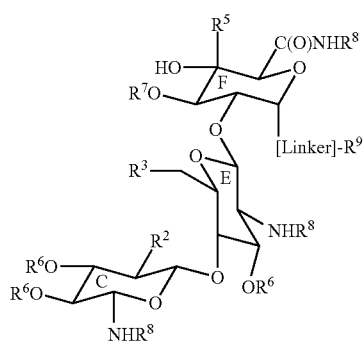

(II-f)

or pharmaceutically acceptable forms thereof; wherein $R^6$, $R^7$, $R^8$, $R^9$, and [Linker] are as defined herein.

In certain embodiments, the present invention provides compounds of formula (II-g):

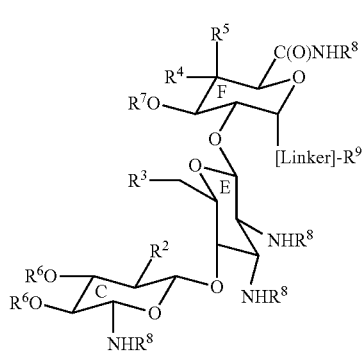

(II-g)

or pharmaceutically acceptable forms thereof; wherein $R^6$, $R^7$, $R^8$, $R^9$, and [Linker] are as defined herein.

In certain embodiments, the present invention provides compounds of formula (II-h):

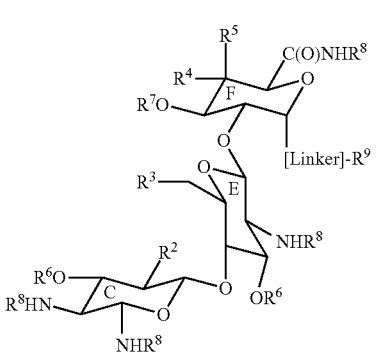

(II-h)

or pharmaceutically acceptable forms thereof; wherein $R^6$, $R^7$, $R^8$, $R^9$, and [Linker] are as defined herein.

In certain embodiments, the present invention provides compounds of formula (II-i):

(II-i)

or pharmaceutically acceptable forms thereof; wherein $R^6$, $R^7$, $R^8$, $R^9$ and [Linker] are as defined herein.

In certain embodiments, the present invention provides compounds of formula (II) wherein the sugar portion comprising Rings C, E and F, and optionally Ring D, is derived from the natural products, Moenomycin A, Moenomycin $A_{1.2}$, Moenomycin $C_1$, Moenomycin $C_3$, Moenomycin $C_4$, AC326-alpha, and Pholipomycin. In certain embodiments, Rings A and B are enzymatically or chemically cleaved to provide such compounds. In other embodiments, intermediate moenomycin-like compounds (i.e., provided without Rings A and B) are generated from bacteria (e.g., wild type or genetically engineered bacteria) and further synthetically modified to provide compounds of the present invention. As is appreciated by one of skill in the art, the various functional groups (e.g., hydroxyl and amino groups) of the sugar portion may optionally be protected (e.g., with hydroxyl and/or amino protecting groups, as defined above and herein).

Exemplary saccharide portions include:

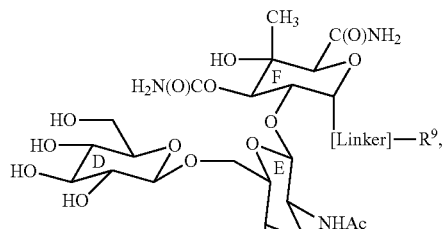
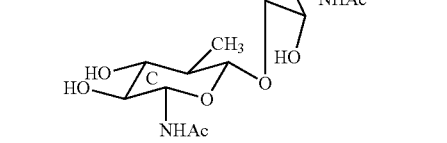

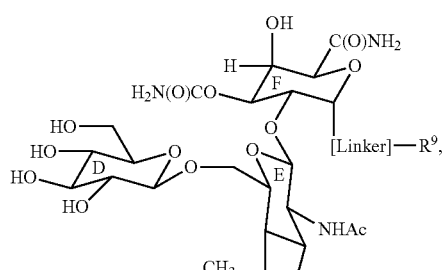
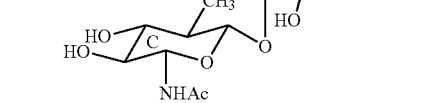

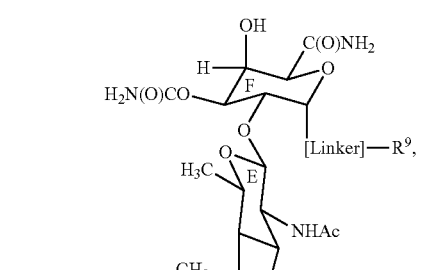
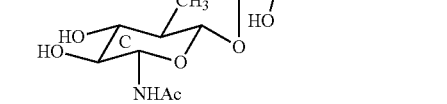

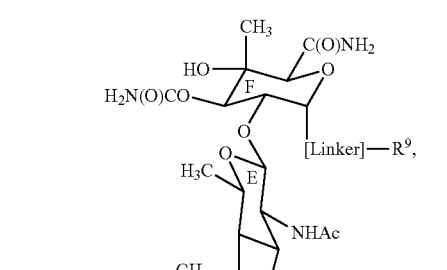
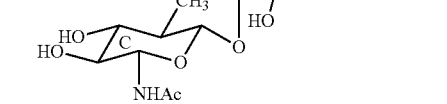

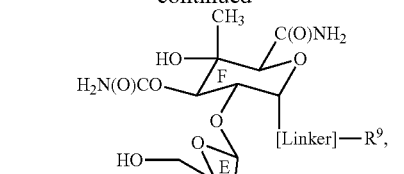

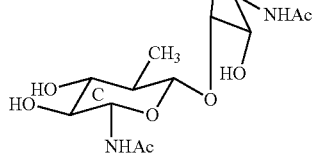

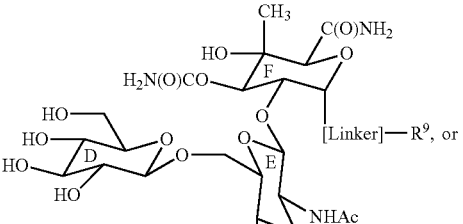

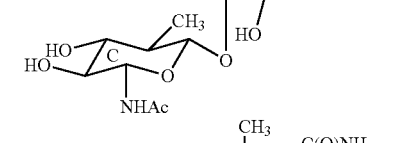

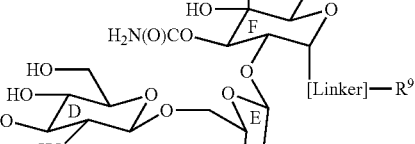

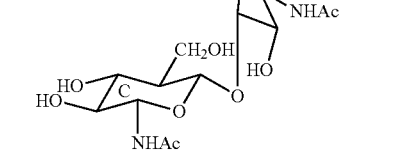

(iii) Compounds Encompassed by Formula (III)

Compounds encompassed by formula (III), and subsets thereof, as provided below, includes compounds comprising rings E and F, and optionally ring D, of the moenomycin sugar scaffold.

In certain embodiments, the present invention provides compounds of formula (III-a):

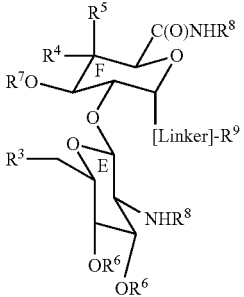

(III-a)

or pharmaceutically acceptable forms thereof; wherein $R^3$, $R^4$, $R^5$, $R^6$, $R^7$, $R^8$, $R^9$, and [Linker] are as defined herein.

In certain embodiments, the present invention provides compounds of formula (III-b):

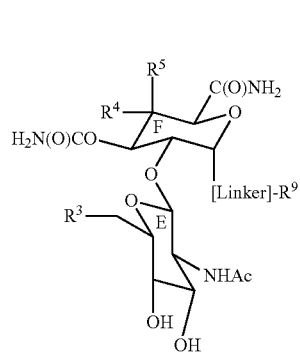

(III-b)

or pharmaceutically acceptable forms thereof; wherein $R^3$, $R^4$, $R^5$, $R^9$, and [Linker] are as defined herein.

In certain embodiments, the present invention provides compounds of formula (III-c):

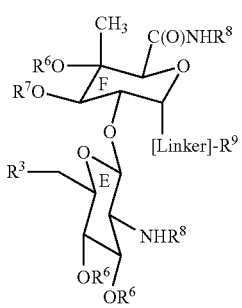

(III-c)

or pharmaceutically acceptable forms thereof; wherein $R^3$, $R^6$, $R^7$, $R^8$, $R^9$, and [Linker] are as defined herein.

In certain embodiments, the present invention provides compounds of formula (III-d):

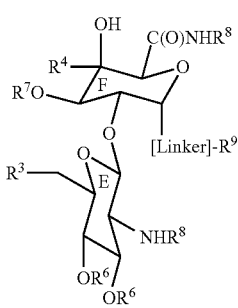

(III-d)

or pharmaceutically acceptable forms thereof; wherein $R^3$, $R^4$, $R^6$, $R^7$, $R^8$, $R^9$, and [Linker] are as defined herein.

In certain embodiments, the present invention provides compounds of formula (III-e):

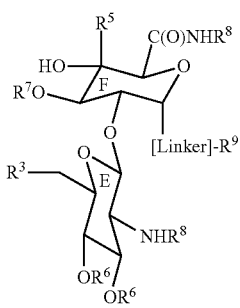

(III-e)

or pharmaceutically acceptable forms thereof; wherein $R^3$, $R^5$, $R^6$, $R^7$, $R^8$, $R^9$, and [Linker] are as defined herein.

In certain embodiments, the present invention provides compounds of formula (III-f):

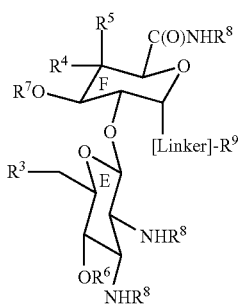

(III-f)

or pharmaceutically acceptable forms thereof; wherein $R^3$, $R^4$, $R^5$, $R^6$, $R^7$, $R^8$, $R^9$, and [Linker] are as defined herein.

In certain embodiments, the present invention provides compounds of formula (III) wherein the sugar portion comprising rings E and F, and optionally ring D, is derived from the natural products, Moenomycin A, Moenomycin $A_{1.2}$, Moenomycin $C_1$, Moenomycin $C_3$, Moenomycin $C_4$, AC326-alpha, and Pholipomycin. In certain embodiments, rings A, B and C are enzymatically or chemically cleaved to provide such compounds. In other embodiments, intermediate moenomycin-like compounds (i.e., provided without rings A, B and C) are generated from bacteria (e.g., wild type or genetically engineered bacteria) and further synthetically modified to provide compounds of the present invention. As will be appreciated by one of skill in the art, the various functional groups (e.g., hydroxyl and amino groups) of the sugar portion may optionally be protected (e.g., with hydroxyl and/or amino protecting groups, as defined above and herein).

Exemplary saccharide portions include:
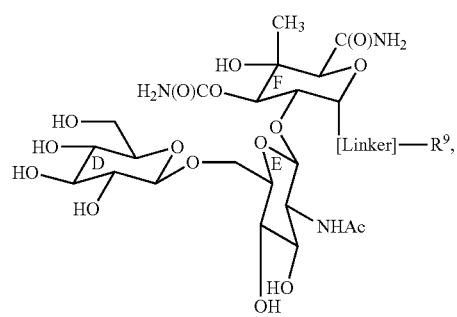
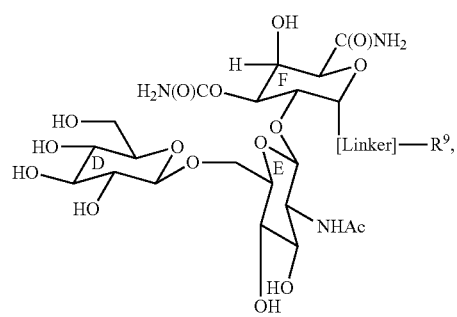
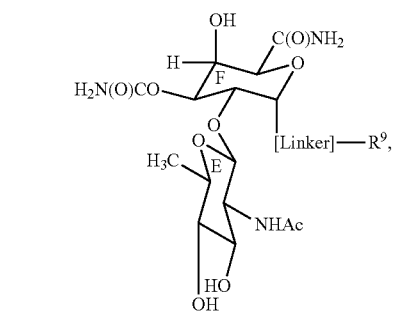
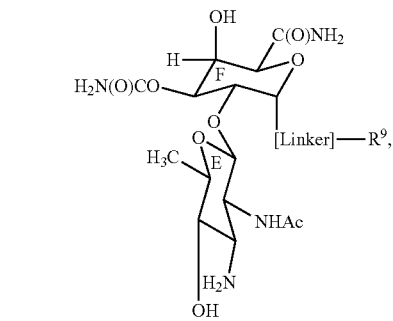
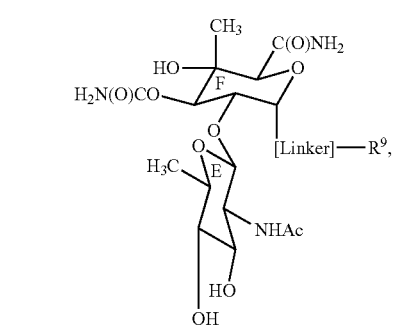
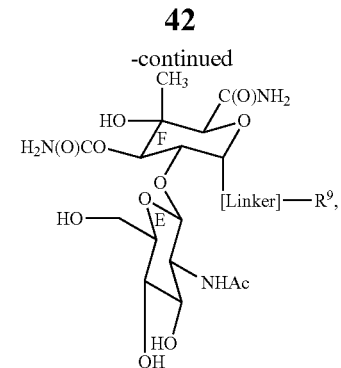
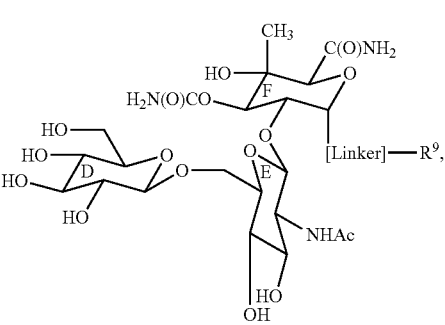
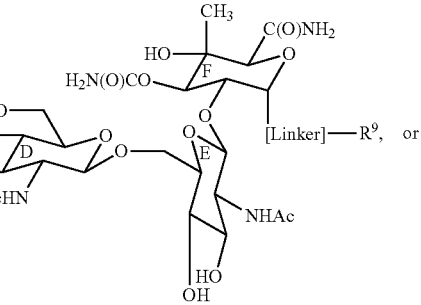
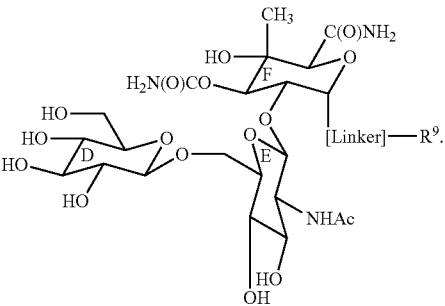
(ii) Compounds Encompassed by Formula (IV)
Compounds encompassed by formula (II), and subsets thereof, as provided below, includes compounds comprising rings E and F, and optionally ring D, of the moenomycin sugar scaffold.
In certain embodiments, the present invention provides compounds of formula (IV-a):

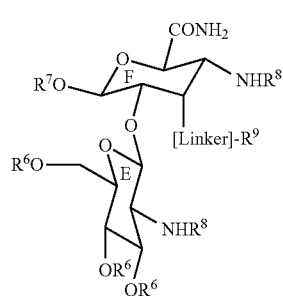
(IV-a)

or pharmaceutically acceptable forms thereof; wherein $R^6$, $R^7$, $R^8$, $R^9$, and [Linker] are as defined herein.

In certain embodiments, the present invention provides compounds of formula (IV-b):

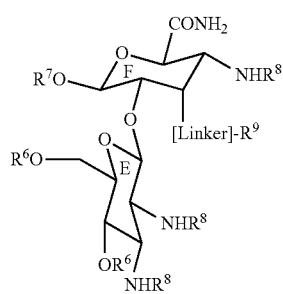
(IV-b)

or pharmaceutically acceptable forms thereof; wherein $R^6$, $R^7$, $R^8$, $R^9$, and [Linker] are as defined herein.

In certain embodiments, the present invention provides compounds of formula (IV-c):

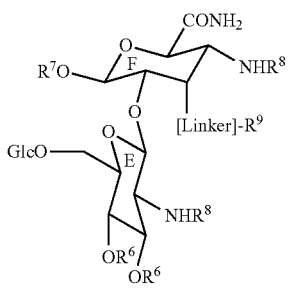
(IV-c)

or pharmaceutically acceptable forms thereof; wherein $R^5$, $R^6$, $R^9$, and [Linker] are as defined herein.

In other embodiments, the present invention provides compounds of formula (IV-d):

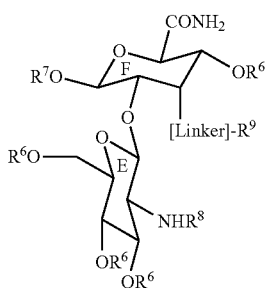
(IV-d)

or pharmaceutically acceptable forms thereof; wherein $R^5$, $R^6$, $R^9$, and [Linker] are as defined herein.

In certain embodiments, the present invention provides compounds of formula (IV-e):

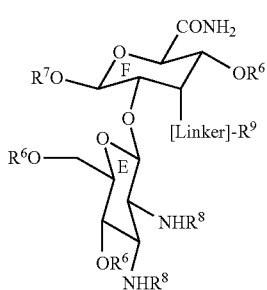
(IV-e)

or pharmaceutically acceptable forms thereof; wherein $R^6$, $R^7$, $R^8$, $R^9$, and [Linker] are as defined herein.

In certain embodiments, the present invention provides compounds of formula (II) wherein the sugar portion comprising rings C and E, and optionally Ring D, is derived from the natural products, Moenomycin A, Moenomycin $A_{1-2}$, Moenomycin $C_1$, Moenomycin $C_3$, Moenomycin $C_4$, AC326-alpha, and Pholipomycin. In certain embodiments, rings A, B, and C (and optionally ring D) are enzymatically or chemically cleaved to provide such compounds. In other embodiments, intermediate moenomycin-like compounds (i.e., provided without Rings A, B, and C, and optionally D) are generated from bacteria (e.g., wild type or genetically engineered bacteria) and further synthetically modified to provide compounds of the present invention. As is appreciated by one of skill in the art, the various functional groups (e.g., hydroxyl and amino groups) of the sugar portion may optionally be protected (e.g., with hydroxyl and/or amino protecting groups, as defined above and herein).

Exemplary sugar portions for formula (IV) include:

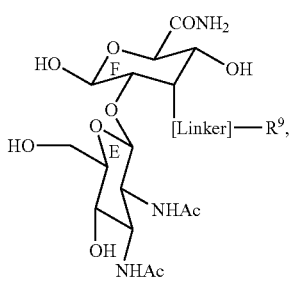

-continued

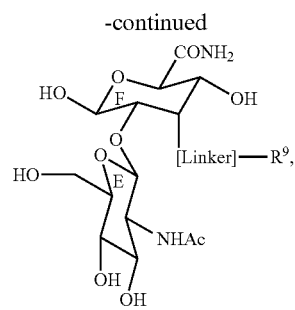,

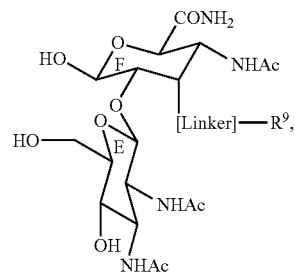,

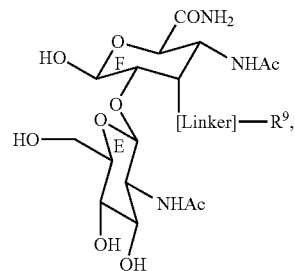,

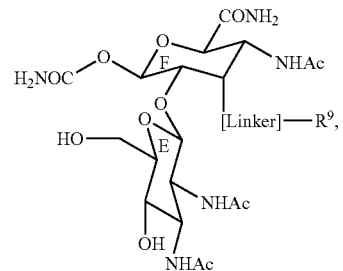,

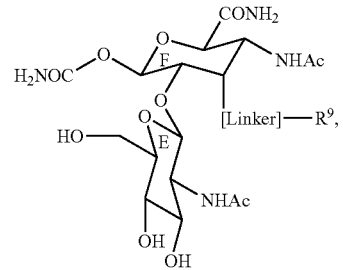,

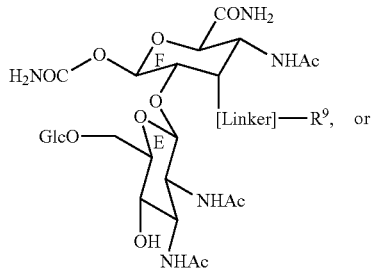 or

-continued

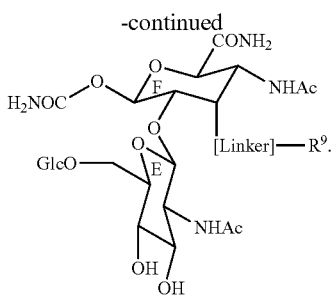.

As defined generally above, $R^{1a}$ and $R^{1b}$ are, independently, H, an amino protecting group, optionally substituted aryl, optionally substituted heteroaryl, optionally substituted aliphatic, or optionally substituted heteroaliphatic.

In certain embodiments, $R^{1a}$ and $R^{1b}$ are, independently, H, an amino protecting group, or an optionally substituted aliphatic. In certain embodiments, $R^{1a}$ and $R^{1b}$ are, independently, H or an optionally substituted aliphatic. In certain embodiments, both $R^{1a}$ and $R^{1b}$ are H.

In certain embodiments, $R^{1a}$ and $R^{1b}$ are, independently, H or the group:

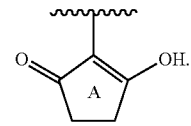

In certain embodiments, $R^{1a}$ is H and $R^{1b}$ is the group:

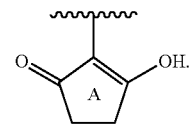

As defined generally above, $R^2$ is, independently, H, —$OR^z$, optionally substituted aryl, optionally substituted heteroaryl, optionally substituted aliphatic, or optionally substituted heteroaliphatic, wherein $R^z$ is H, a hydroxyl protecting group, optionally substituted aryl, optionally substituted heteroaryl, or optionally substituted aliphatic, optionally substituted heteroaliphatic.

In certain embodiments, $R^2$ is H, —$OR^z$, optionally substituted aliphatic, or optionally substituted heteroaliphatic. In certain embodiments, $R^2$ is H, —$OR^z$, or an optionally substituted aliphatic group. In certain embodiments, $R^2$ is —$OR^z$ or an optionally substituted aliphatic group. In certain embodiments, $R^2$ is —$OR^z$. In certain embodiments, $R^2$ is —OH. In certain embodiments, $R^2$ is optionally substituted $C_{1-6}$ alkyl. In certain embodiments, $R^2$ is —$CH_3$. In certain embodiments, $R^2$ is —$CH_2OH$. In certain embodiments, $R^2$ is —$CO_2H$. In certain embodiments, $R^2$ is —CHO.

As defined generally above, $R^3$ is H, —OH, —$NH_2$, —SH, —$OR^w$, —$NH(R^w)$, —$N(R^w)_2$, —$SR^w$, —O(C=O)$R^w$, —NH(C=O)$R^w$, —O(C=NH)$R^w$, —NH(C=NH)$R^w$, —S(C=NH)$R^w$, —NH(C=S)$R^w$, —S(C=O)$R^w$, —O(C=S)$R^w$, —S(=S)$R^w$, optionally substituted aryl, optionally substituted heteroaryl, optionally substituted aliphatic, or optionally substituted heteroaliphatic, wherein $R^w$ is a carbohydrate moiety, optionally substituted aryl, optionally substituted heteroaryl, optionally substituted aliphatic, optionally substituted heteroaliphatic.

In certain embodiments, $R^3$ is H, —OH, —NH$_2$, —SH, —OR$^w$, —NH(R$^w$), —N(R$^w$)$_2$, —SR$^w$, —O(C═O)R$^w$, —NH(C═O)R$^w$, —O(C═NH)R$^w$, —NH(C═NH)R$^w$, —S(C═NH)R$^w$, —NH(C═S)R$^w$, —S(C═O)R$^w$, —O(C═S)R$^w$, —S(═S)R$^w$, optionally substituted aryl, optionally substituted heteroaryl, optionally substituted C$_{1-6}$ alkyl, or optionally substituted C$_{1-6}$ heteroalkyl, wherein R$^w$ is a carbohydrate moiety, optionally substituted aryl, optionally substituted heteroaryl, optionally substituted aliphatic, optionally substituted heteroaliphatic.

In certain embodiments, $R^3$ is optionally substituted C$_{1-6}$ alkyl or optionally substituted C$_{1-6}$ heteroalkyl. In certain embodiments, $R^3$ is optionally substituted C$_{1-6}$ alkyl.

In certain embodiments, $R^3$ is H, —OH, —NH$_2$, —SH, —OR$^w$, —NH(R$^w$), —N(R$^w$)$_2$, —SR$^w$, —O(C═O)R$^w$, —NH(C═O)R$^w$, —O(C═NH)R$^w$, —NH(C═NH)R$^w$, —S(C═NH)R$^w$, —NH(C═S)R$^w$, —S(C═O)R$^w$, —O(C═S)R$^w$, or —S(═S)R$^w$. In certain embodiments, $R^3$ is H, —OH, —OR$^w$, —NH$_2$, —NH(R$^w$), —N(R$^w$)$_2$, —O(C═O)R$^w$, —O(C═NH)R$^w$, or —O(C═S)R$^w$. In certain embodiments, $R^3$ is H, —OH, —OR$^w$, —NH$_2$, —NH(R$^w$), —N(R$^w$)$_2$, or —O(C═O)R$^w$. In certain embodiments, $R^3$ is —NH$_2$, —NH(R$^w$), —N(R$^w$)$_2$. In certain embodiments, $R^3$ is —NH$_2$. In certain embodiments, $R^3$ is H, —OH, or —OR$^w$. In certain embodiments, $R^3$ is —OH. In certain embodiments, $R^3$ is —OR$^w$. In certain embodiments, $R^3$ is H.

As defined generally above, R$^w$ is a carbohydrate moiety, optionally substituted aryl, optionally substituted heteroaryl, optionally substituted aliphatic, optionally substituted heteroaliphatic. R$^w$ is a carbohydrate moiety or an optionally substituted aliphatic group. In certain embodiments, R$^w$ is a carbohydrate moiety. Carbohydrate moeities include monosaccharides (e.g., erythrose, threose, erythrulose, arabinose, deoxyribose, lyxose, ribose, ribulose, xylose, xylulose, allose, altrose, galactose, glucose, gulose, idose, mannose and talose, fructose, psicose, sorbose and tagatose, fucose, and rhamnose), disaccharides (e.g., sucrose, lactose, trehalose, and maltose) and trisaccharides (e.g., acarbose, raffinose, melezitose). In certain embodiments, R$^w$ is a monosaccharide moiety. In certain embodiments, R$^w$ is the monosaccharide moiety:

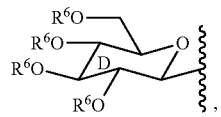

wherein R$^6$ is as defined herein. In certain embodiments, R$^w$ is the monosaccharide moiety:

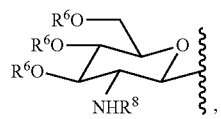

wherein R$^6$ and R$^8$ are as defined herein.

In certain embodiments, $R^3$ is —OR$^w$, and R$^w$ is a carbohydrate moiety, as defined above. For example, the R$^w$ carbohydrate moiety of —OR$^w$ may include monosaccharides (e.g., erythrose, threose, erythrulose, arabinose, deoxyribose, lyxose, ribose, ribulose, xylose, xylulose, allose, altrose, galactose, glucose, gulose, idose, mannose, talose, fructose, psicose, sorbose and tagatose, fucose, and rhamnose), disaccharides (e.g., sucrose, lactose, trehalose, and maltose), and trisaccharides (e.g., acarbose, raffinose, melezitose). In certain embodiments, R$^w$ of —OR$^w$ is a monosaccharide moiety. In certain embodiments, R$^w$ of —OR$^w$ is the monosaccharide moiety:

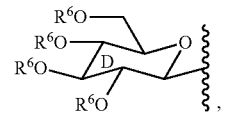

wherein R$^6$ is as defined herein. In certain embodiments, $R^3$ is —OR$^w$, and R$^w$ is D-glucose. In certain embodiments, R$^w$ of —OR$^w$ is the monosaccharide moiety:

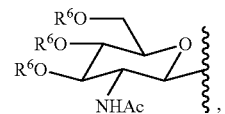

wherein R$^6$ is as defined herein.

As defined generally above, each instance of $R^4$ and $R^5$ is, independently, H, —OR$^z$, —N(R$^z$)$_2$, optionally substituted aryl, optionally substituted heteroaryl, optionally substituted aliphatic, or optionally substituted heteroaliphatic, wherein R$^z$ is H, a hydroxyl protecting group, optionally substituted aryl, optionally substituted heteroaryl, or optionally substituted aliphatic, optionally substituted heteroaliphatic.

In certain embodiments, $R^4$ and $R^5$ are, independently, H, —OR$^z$, —N(R$^z$)$_2$, optionally substituted aliphatic, or optionally substituted heteroaliphatic. In certain embodiments, $R^4$ and $R^5$ are, independently, H, —OR$^z$, —N(R$^z$)$_2$, or optionally substituted aliphatic. In certain embodiments, $R^4$ and $R^5$ are, independently, H, —CH$_3$, —N(R$^z$)$_2$, or —OR$^z$. In certain embodiments, $R^4$ and $R^5$ are, independently, —CH$_3$ or —OR$^z$. In certain embodiments, $R^4$ is —OH. In certain embodiments, $R^5$ is —CH$_3$.

In certain embodiments, $R^4$ is H and $R^5$ is —CH$_3$. In certain embodiments, $R^5$ is H and $R^4$ is —CH$_3$.

In certain embodiments, $R^4$ is H and $R^5$ is —OR$^z$. In certain embodiments, $R^4$ is H and $R^5$ is —OH. In certain embodiments, $R^5$ is H and $R^4$ is —OR$^z$. In certain embodiments, $R^5$ is H and $R^4$ is —OH.

In certain embodiments, $R^4$ is H and $R^5$ is —N(R$^z$)$_2$. In certain embodiments, $R^4$ is H and $R^5$ is —NHR$^z$. In certain embodiments, $R^4$ is H and $R^5$ is —NH$_2$. In certain embodiments, $R^4$ is H, and $R^5$ is —NHAc. In certain embodiments, $R^5$ is H, and $R^4$ is —N(R$^z$)$_2$. In certain embodiments, $R^5$ is H, and $R^4$ is —NHR$^z$. In certain embodiments, $R^5$ is H, and $R^4$ is —NH$_2$. In certain embodiments, $R^5$ is H, and $R^4$ is —NHAc.

In certain embodiments, $R^4$ is —CH$_3$ and $R^5$ is —OR$^z$. In certain embodiments, $R^4$ is —CH$_3$ and $R^5$ is —OH. In certain embodiments, $R^5$ is —CH$_3$ and $R^4$ is —OR$^z$. In certain embodiments, $R^5$ is —CH$_3$ and $R^4$ is —OH.

In certain embodiments, $R^4$ is —CH$_3$ and $R^5$ is —N(R$^z$)$_2$. In certain embodiments, $R^4$ is —CH$_3$ and $R^5$ is —NHR$^z$. In certain embodiments, $R^4$ is —CH$_3$ and $R^5$ is —NH$_2$. In certain embodiments, $R^4$ is —CH$_3$ and $R^5$ is —NHAc. In certain embodiments, $R^5$ is —CH$_3$ and $R^4$ is —N(R$^z$)$_2$. In certain embodiments, $R^5$ is —CH$_3$ and $R^4$ is —NHR$^z$. In certain embodiments, $R^5$ is —$CH_3$ and $R^4$ is —$NH_2$. In certain embodiments, $R^5$ is —$CH_3$ and $R^4$ is —NHAc.

In certain embodiments, both $R^4$ and $R^5$ are H. In certain embodiments, both $R^4$ and $R^5$ are —$CH_3$. In certain embodiments, both $R^4$ and $R^5$ are —$OR^z$. In certain embodiments, both $R^4$ and $R^5$ are —OH. In certain embodiments, both $R^4$ and $R^5$ are —$N(R^z)_2$. In certain embodiments, both $R^4$ and $R^5$ are —$NHR^z$. In certain embodiments, both $R^4$ and $R^5$ are —$NH_2$. In certain embodiments, both $R^4$ and $R^5$ are —NHAc.

As defined generally above, each instance of $R^6$ and $R^7$ is, independently, H, a hydroxyl protecting group, optionally substituted aryl, optionally substituted heteroaryl, optionally substituted aliphatic, or optionally substituted heteroaliphatic.

In certain embodiments, each instance of $R^6$ and $R^7$ is, independently, H, a hydroxyl protecting group, or an optionally substituted aliphatic group. In certain embodiments, each instance of $R^6$ and $R^7$ is, independently, H or a hydroxyl protecting group. In certain embodiments, each instance of $R^6$ and $R^7$ is, independently, H or $C_1$-$C_6$ alkyl. In certain embodiments, each instance of $R^6$ and $R^7$ is, independently, H or acyl. In certain embodiments, each instance of $R^6$ is, independently, H or —$C(=O)CH_3$ (i.e., -Ac, Acetyl). In certain embodiments, all $R^6$ are H. In certain embodiments, all $R^6$ are —$C(=O)CH_3$.

In certain embodiments, $R^7$ is H, —$C(=O)CH_3$, or —$C(=O)NH_2$. In certain embodiments, $R^7$ is H. In certain embodiments, $R^7$ is —$C(=O)CH_3$. In certain embodiments, $R^7$ is —$C(=O)NH_2$.

In certain embodiments, $R^7$ is a carbohydrate moiety, as defined above. For example, $R^7$ may include monosaccharides (e.g., erythrose, threose, erythrulose, arabinose, deoxyribose, lyxose, ribose, ribulose, xylose, xylulose, allose, altrose, galactose, glucose, gulose, idose, mannose, talose, fructose, psicose, sorbose and tagatose, fucose, and rhamnose), disaccharides (e.g., sucrose, lactose, trehalose, and maltose), and trisaccharides (e.g., acarbose, raffinose, melezitose). In certain embodiments, $R^7$ is a monosaccharide moiety. In certain embodiments, $R^7$ is the monosaccharide moiety:

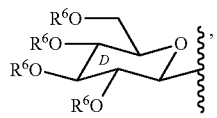

wherein $R^6$ is as defined herein. In certain embodiments, $R^7$ is D-glucose. In certain embodiments, $R^7$ is the monosaccharide moiety:

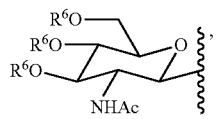

wherein $R^6$ is as defined herein.

As defined generally above, each instance of $R^8$ is, independently, H, an amino protecting group, optionally substituted aryl, optionally substituted heteroaryl, optionally substituted aliphatic, or optionally substituted heteroaliphatic. In certain embodiments, each instance of $R^8$ is, independently, H, an amino protecting group, or an optionally substituted aliphatic group. In certain embodiments, each instance of $R^8$ is, independently, H or an amino protecting group. In certain embodiments, each instance of $R^8$ is, independently, H or —$C(=O)CH_3$. In certain embodiments, each instance of $R^8$ is hydrogen. In certain embodiments, each instance of $R^8$ is acyl. In certain embodiments, each instance of $R^8$ is —$C(=O)CH_3$ (Ac). In certain embodiments, each instance of $R^8$ is $C_1$-$C_6$ alkyl.

As is defined generally above, the [Linker] is the group:

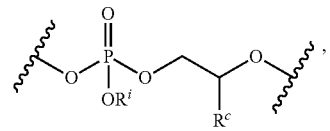

wherein:

$R^c$ is —$OR^q$, —$N(R^q)_2$, —$SR^q$, —$NO_2$, —NC, —CN, —$N_3$, —$N(R^q)=NR^q$, —CHO, —$C(=O)R^q$, —$C(=S)R^q$, —$C(=NR^q)R^q$, —$C(=O)OR^q$, —$C(=NR^q)OR^q$, —$C(=NR^q)N(R^q)_2$, —$C(=O)N(R^q)_2$, —$C(=S)OR^q$, —$C(=O)SR^q$, —$C(=S)SR^q$, —$P(=O)(OR^q)_2$, —$P(=O)_2(OR^q)$, —$S(=O)(OR^q)$, —$S(=O)_2(OR^q)$, —$P(=O)N(R^q)_2$, —$P(=O)_2N(R^q)_2$, —$C(=O)NR^qS(=O)_2R^q$, —$S(=O)N(R^q)_2$, —$S(=O)_2N(R^q)_2$, or optionally substituted heteroaryl; wherein each instance of $R^q$ is H, optionally substituted aliphatic, optionally substituted heteroaliphatic, optionally substituted aryl, optionally substituted heteroaryl, or a protecting group; and $R^i$ is H, optionally substituted aliphatic, optionally substituted heteroaliphatic, optionally substituted aryl, optionally substituted heteroaryl or a hydroxyl protecting group.

In certain embodiments, $R^c$ is —$NO_2$, —CN, —$C(=O)R^q$, —$C(=S)R^q$, —$C(=NR^q)R^q$, —$C(=O)OR^q$, —$C(=NR^q)OR^q$, —$C(=NR^q)N(R^q)_2$, —$C(=O)N(R^q)_2$, —$C(=S)OR^q$, —$C(=O)SR^q$, —$C(=S)SR^q$, —$P(=O)(OR^q)_2$, —$P(=O)_2(OR^q)$, —$S(=O)(OR^q)$, —$S(=O)_2(OR^q)$, —$P(=O)N(R^q)_2$, —$P(=O)_2N(R^q)_2$, —$S(=O)N(R^q)_2$, or —$S(=O)_2N(R^q)_2$. In certain embodiments, $R^c$ is —$C(=O)R^q$, —$C(=S)R^q$, —$C(=NR^q)R^q$, —$C(=O)OR^q$, —$C(=NR^q)OR^q$, —$C(=NR^q)N(R^q)_2$, —$C(=O)N(R^q)_2$, —$C(=S)OR^q$, —$C(=O)SR^q$, or —$C(=S)SR^q$. In certain embodiments, $R^c$ is —$C(=O)R^q$, —$C(=O)OR^q$, —$C(=O)N(R^q)_2$, or —$C(=O)SR^q$. In certain embodiments, $R^c$ is —$C(=O)R^q$, —$C(=O)OR^q$, or —$C(=O)N(R^q)_2$. In certain embodiments, $R^c$ is —$C(=O)H$, —$C(=O)OH$, or —$C(=O)NH_2$. In certain embodiments, $R^c$ is —$C(=O)OH$. In certain embodiments, $R^c$ is —$C(=O)NHS(=O)_2R^q$. In certain embodiments, $R^c$ is —$C(=O)NHS(=O)_2CH_3$. In certain embodiments, $R^c$ is —$C(=O)NHS(=O)_2$—$CH=CH_2$.

In certain embodiments, $R^i$ is H, optionally substituted aliphatic or a hydroxyl protecting group. In certain embodiments, $R^i$ is H or a hydroxyl protecting group. In certain embodiments, $R^i$ is a hydroxyl protecting group. In certain embodiments, $R^i$ is H. In certain embodiments, $R^i$ is $C_1$-$C_6$ alkyl. In certain embodiments, $R^i$ is methyl.

In certain embodiments, the stereochemistry of the [Linker] is defined as below:

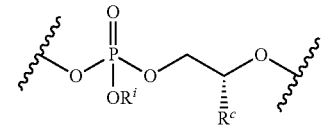

wherein $R^i$ and $R^c$ are as defined herein.

In certain embodiments, the stereochemistry of the [Linker] is defined as below:

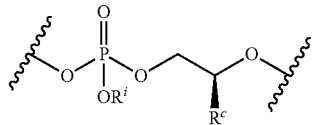

wherein $R^i$ and $R^c$ are as defined herein.

In certain embodiments, the stereochemistry of the [Linker] is defined as below:

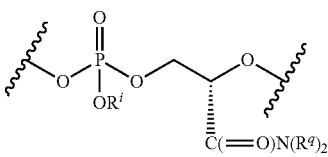

wherein $R^i$ and $R^q$ are as defined herein.

In certain embodiments, the stereochemistry of the [Linker] is defined as below:

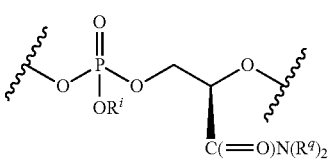

wherein $R^i$ and $R^q$ are as defined herein.

In certain embodiments, the stereochemistry of the [Linker] is defined as below:

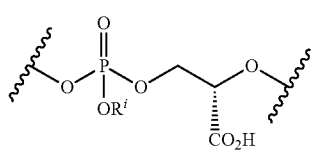

wherein $R^i$ is as defined herein.

In certain embodiments, the stereochemistry of the [Linker] is defined as below:

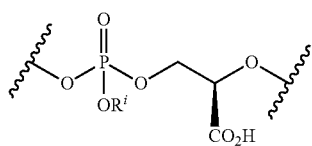

wherein $R^i$ is as defined herein.

In certain embodiments, the stereochemistry of the [Linker] is defined as below:

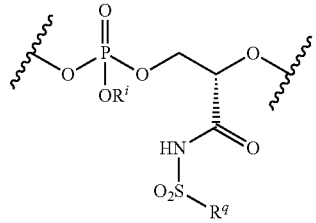

wherein $R^i$ and $R^q$ are as defined herein.

In certain embodiments, the stereochemistry of the [Linker] is defined as below:

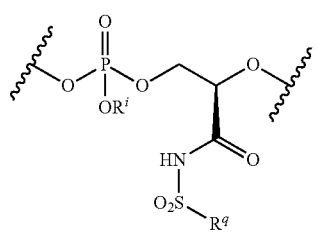

wherein $R^i$ and $R^q$ are as defined herein.

In certain embodiments, the stereochemistry of the [Linker] is defined as below:

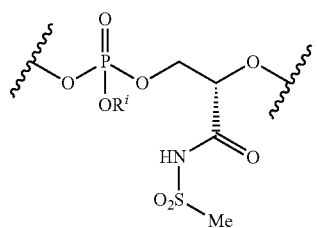

wherein $R^i$ is as defined herein.

In certain embodiments, the stereochemistry of the [Linker] is defined as below:

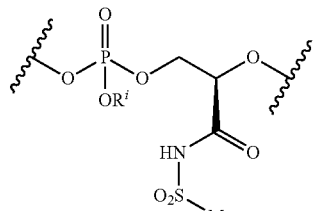

wherein $R^i$ is as defined herein.

In certain embodiments, the stereochemistry of the [Linker] is defined as below:

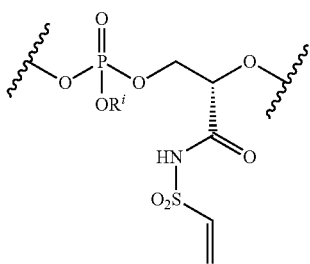

wherein $R^i$ is as defined herein.

In certain embodiments, the stereochemistry of the [Linker] is defined as below:

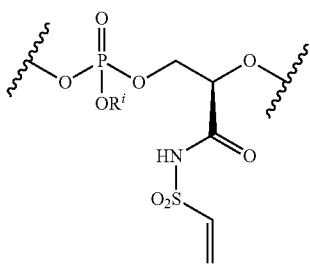

wherein $R^i$ is as defined herein.

In certain embodiments, the stereochemistry of the [Linker] is defined as below:

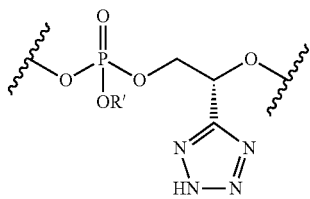

wherein $R^i$ is as defined herein.

In certain embodiments, the stereochemistry of the [Linker] is defined as below:

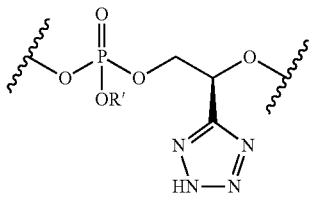

wherein $R^i$ is as defined herein.

As defined generally above, $R^9$ is H or an optionally substituted, optionally unsaturated, $C_{1-30}$ aliphatic moiety, wherein 0 to 10 methylene units are optionally replaced with —O—, —$NR^x$—, —S—, —C(=O)—, —C(=$NR^x$)—, —S(=O)—, —S(=O)$_2$—, —N=N—, —C=N—, —C($R^y$)=C($R^y$)—, —N—O—, an optionally substituted arylene, or an optionally substituted heteroarylene moiety, wherein each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl.

In certain embodiments, $R^9$ is H.

In certain embodiments, $R^9$ is an optionally substituted, optionally unsaturated, $C_{1-30}$ aliphatic moiety, wherein 0 to 10 methylene units are optionally replaced with —O—, —$NR^x$—, —S—, —C(=O)—, —C(=$NR^x$)—, —S(=O)—, —S(=O)$_2$—, —N=N—, —C=N—, —C($R^y$)=C($R^y$)—, —N—O—, an optionally substituted arylene or an optionally substituted heteroarylene moiety, wherein each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl.

Exemplary aliphatic moieties include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), hexadecyl ($C_{16}$), heptadecyl ($C_{17}$), octadecyl ($C_{18}$), nonadecyl ($C_{19}$), eicosyl ($C_{20}$), and so on up to ($C_{30}$). In certain embodiments, the aliphatic moiety is a straight chain alkyl moiety, including, but not limited to, methyl ($C_1$), ethyl ($C_2$), n-propyl ($C_3$), n-butyl ($C_4$), n-pentyl ($C_5$), n-hexyl ($C_6$), n-heptyl ($C_7$), n-octyl ($C_8$), n-nonyl ($C_9$), n-decyl ($C_{10}$), n-undecyl ($C_{11}$), n-dodecyl ($C_{12}$), n-tridecyl ($C_{13}$), n-tetradecyl ($C_{14}$), n-pentadecyl ($C_{15}$), n-hexadecyl ($C_{16}$), n-heptadecyl ($C_{17}$), n-octadecyl ($C_{18}$), n-nonadecyl ($C_{19}$), n-eicosyl ($C_{20}$), and so on, up to ($C_{30}$).

Exemplary substituents include are described throughout, and include optionally substituted aliphatic (e.g., alkyl, alkenyl, alkynyl), optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=$NR^v$)$R^v$, —C(=O)$OR^q$, —C(=$NR^q$)$OR^q$, —C(=$NR^v$)$N(R^v)_2$, —C(=O)$N(R^v)_2$, —C(=S)$OR^v$, —C(=O)$SR^v$, —C(=S)$SR^v$, —P(=O)($OR^v$)$_2$, —P(=O)$_2$($OR^v$), —S(=O)($OR^v$), —S(=O)$_2$($OR^v$), —P(=O)$N(R^v)_2$, —P(=O)$_2$$N(R^v)_2$, —S(=O)$N(R^v)_2$, or —S(=O)$_2$$N(R^v)_2$; wherein each instance of $R^v$ is H, optionally substituted aliphatic, optionally substituted heteroaliphatic, optionally substituted aryl, optionally substituted heteroaryl or a protecting group. In certain embodiments, the $R^9$ hydrocarbon chain is substituted with one or more optionally substituted aliphatic moieties, optionally substituted heteroaliphatic moieties, optionally substituted aryl moieties, optionally substituted heteroaryl moieties, halogen moieties, —$OR^v$ moieties, —$N(R^v)_2$ moieties, or —$SR^v$ moieties. In certain embodiments, the $R^9$ hydrocarbon chain is substituted with one or more optionally substituted aliphatic moieties or —$OR^v$ moieties. In certain embodiments, the $R^9$ hydrocarbon chain is substituted with one or more optionally substituted aliphatic moieties. In certain embodiments, the $R^9$ hydrocarbon chain is substituted with one or more optionally substituted $C_{1-6}$ alkyl moieties. In certain embodiments, the $R^9$ hydrocarbon chain is substituted with one or more —$CH_3$ moieties.

In certain embodiments, $R^9$ is an optionally substituted, optionally unsaturated, $C_{5-20}$ hydrocarbon chain, wherein 0 to 10 methylene units are optionally replaced with —O—, —$NR^x$—, —S—, —C(=O)—, —C(=$NR^x$)—, —S(=O)—, —S(=O)$_2$—, —N=N—, —C=N—, —C(R$^y$)=C(R$^y$)—, —N—O—, an optionally substituted arylene or an optionally substituted heteroarylene moiety.

In certain embodiments, R$^9$ is an optionally substituted, optionally unsaturated, C$_{10-20}$ hydrocarbon chain, wherein 0 to 8 methylene units are optionally replaced with —O—, —NR$^x$—, —S—, —(=O)—, —C(=NR$^x$)—, —S(=O)—, —S(=O)$_2$—, —N=N—, —C=N—, —C(R$^y$)=C(R$^y$)—, —N—O—, an optionally substituted arylene or an optionally substituted heteroarylene moiety.

In certain embodiments, R$^9$ is an optionally substituted, optionally unsaturated, C$_{10-20}$ hydrocarbon chain, wherein 0 to 6 methylene units are optionally replaced with —O—, —NR$^x$—, —S—, —(=O)—, —C(=NR$^x$)—, —S(=O)—, —S(=O)$_2$—, —N=N—, —C=N—, —C(R$^y$)=C(R$^y$)—, —N—O—, an optionally substituted arylene or an optionally substituted heteroarylene moiety.

In certain embodiments, R$^9$ is an unsubstituted, optionally unsaturated hydrocarbon chain.

In certain embodiments, R$^9$ is an unsubstituted and saturated hydrocarbon chain. In certain embodiments, R$^9$ is an unsubstituted hydrocarbon and saturated hydrocarbon chain wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, R$^9$ is an unsubstituted and unsaturated hydrocarbon chain. In certain embodiments, R$^9$ is an unsubstituted hydrocarbon and unsaturated hydrocarbon chain, wherein 1 to 10 methylene units are replaced with —O—, —NR$^x$—, —S—, —C(=O)—, —C(=NR$^x$)—, —S(=O)—, —S(=O)$_2$—, —N=N—, —C=N—, —C(R$^y$)=C(R$^y$)—, —N—O—, an optionally substituted arylene or an optionally substituted heteroarylene moiety.

In certain embodiments, R$^9$ is a substituted and saturated hydrocarbon chain. In certain embodiments, R$^9$ is a substituted and saturated hydrocarbon chain, wherein 0 to 10 methylene units are replaced with —O—, —NR$^x$—, —S—, —C(=O)—, —C(=NR$^x$)—, —S(=O)—, —S(=O)$_2$— or —N—O—.

In certain embodiments, R$^9$ is a substituted, optionally unsaturated hydrocarbon chain. In certain embodiments, R$^9$ is a substituted and unsaturated hydrocarbon chain. In certain embodiments, R$^9$ is a substituted hydrocarbon and unsaturated hydrocarbon chain wherein 1 to 10 methylene units are replaced with —O—, —NR$^x$—, —S—, —C(=O)—, —C(=NR$^x$)—, —S(=O)—, —S(=O)$_2$—, —N=N—, —C=N—, —C(R$^y$)=C(R$^y$)—, —N—O—, an optionally substituted arylene or an optionally substituted heteroarylene moiety.

In certain embodiments, R$^9$ is an optionally substituted, optionally unsaturated, C$_{10}$-C$_{16}$ aliphatic moiety. In certain embodiments, R$^9$ is an optionally substituted, C$_8$-C$_{16}$ alkyl moiety. In certain embodiments, R$^9$ is an optionally substituted, C$_{10}$-C$_{14}$ alkyl moiety.

In certain embodiments, R$^9$ is of one of the formulae:

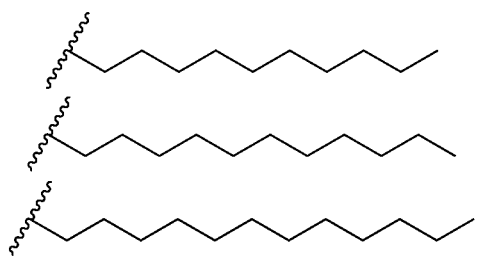

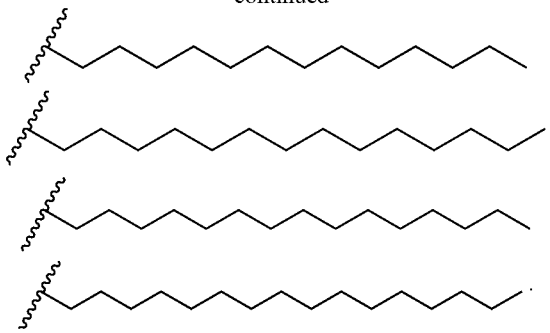

In certain embodiments, R$^9$ is of the formula:

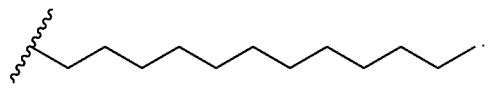 [SMILES: *CCCCCCCCCCCC]

In certain embodiments, R$^9$ is fluorinated. R$^9$ may be perfluorinated or partially fluorinated. In certain embodiments, all the hydrogen atoms of R$^9$ are replaced with fluorine atoms. In certain embodiments, only a portion of the hydrogen atoms of R$^9$ are replaced with fluorine atoms. In certain embodiments, at least 10%, at least 20%, at least 30%, at least 40%, at least 50%, at least 60%, at least 70%, at least 80%, or at least 80% of the hydrogen atoms are replaced with fluorine atoms. In certain embodiments, R$^9$ compriese at least 1, 2, 3, 4, 5, 6, 7, 8, 9, 10, 15, 20, or more fluorine atoms. In certain embodiments, R$^9$ may include substituents that are or are not fluorinated. In certain embodiments, R$^9$ is a fluorinated, optionally unsaturated, C$_{10}$-C$_{16}$ aliphatic moiety. In certain embodiments, R$^9$ is a perfluorinated, optionally unsaturated, C$_{10}$-C$_{16}$ aliphatic moiety. In certain embodiments, R$^9$ is a partially fluorinated, optionally unsaturated, C$_{10}$-C$_{16}$ aliphatic moiety. In certain embodiments, R$^9$ is a C$_8$-C$_{16}$ alkyl moiety. In certain embodiments, R$^9$ is a perfluorinated, C$_8$-C$_{16}$ alkyl moiety. In certain embodiments, R$^9$ is a partially fluorinated, C$_8$-C$_{16}$ alkyl moiety. In certain embodiments, R$^9$ is a fluorinated, C$_{10}$-C$_{14}$ alkyl moiety. In certain embodiments, R$^9$ is a perfluorinated, C$_{10}$-C$_{14}$ alkyl moiety. In certain embodiments, R$^9$ is a partially fluorinated, C$_{10}$-C$_{14}$ alkyl moiety.

In certain embodiments, R$^9$ is a perfluorinated, optionally unsaturated C$_{10}$-C$_{16}$ alkyl moiety. In certain embodiments, R$^9$ is one of the formulae:

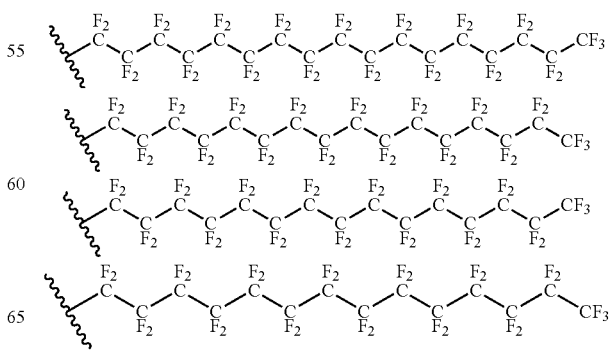

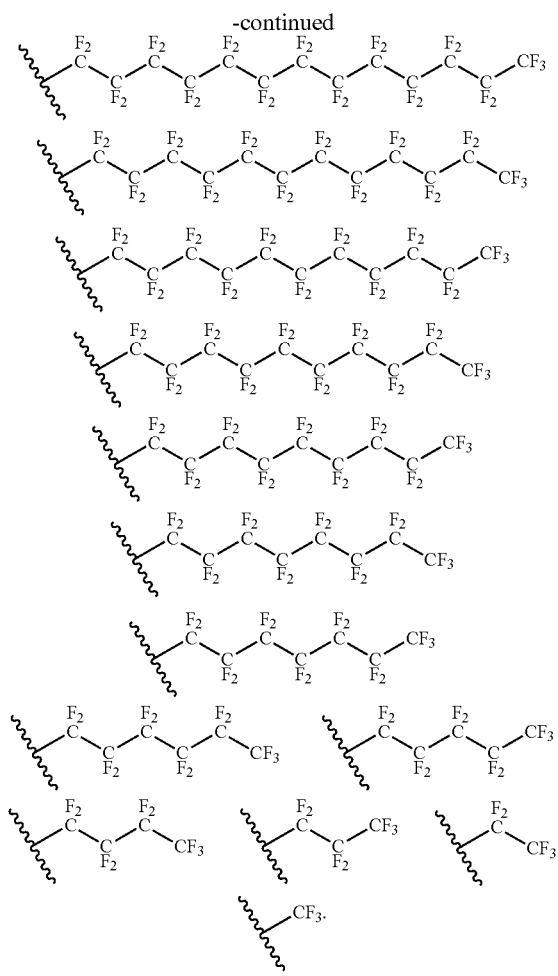

In certain embodiments, $R^9$ is of one of the formulae:

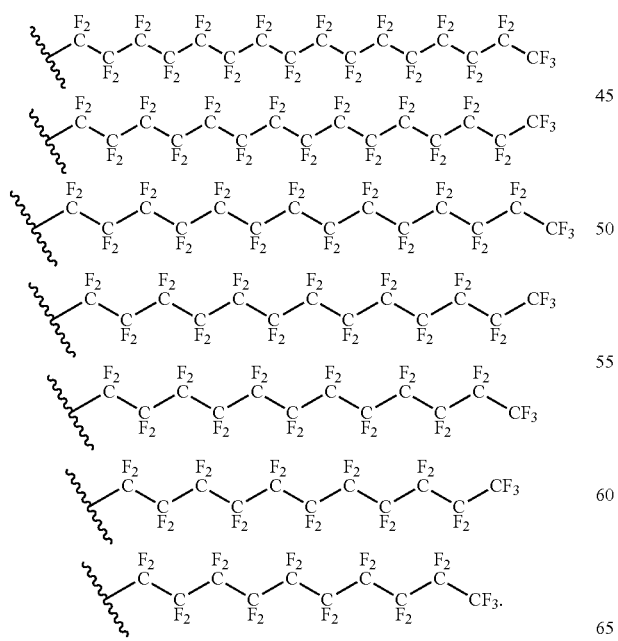

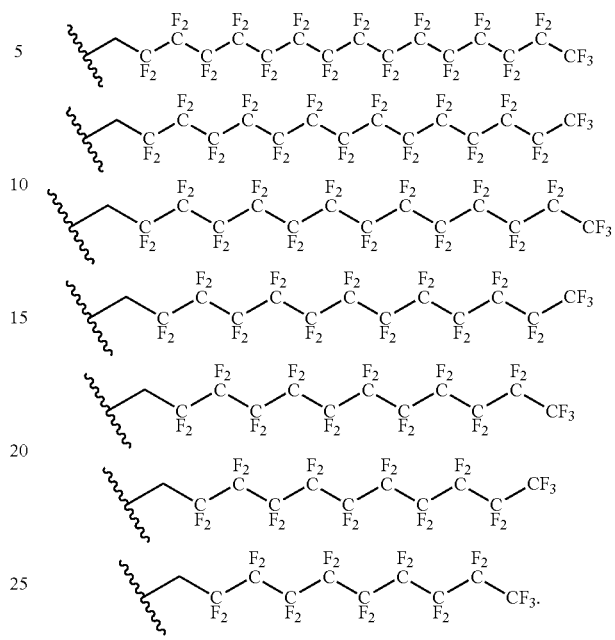

In certain embodiments, $R^9$ is an optionally substituted, unsaturated, $C_{5-20}$ hydrocarbon chain, wherein 1 to 10 methylene units are replaced —C(R$^y$)=C(R$^y$)—. In certain embodiments, $R^9$ is an optionally substituted, unsaturated, $C_{5-20}$ hydrocarbon chain, wherein 1 to 4 methylene units are replaced —C(R$^y$)=C(R$^y$)—. In certain embodiments, $R^9$ is an optionally substituted, unsaturated, $C_{10-20}$ hydrocarbon chain, wherein 1 to 4 methylene units are replaced —C(R$^y$)=C(R$^y$)—. In certain embodiments, $R^9$ is an optionally substituted, unsaturated, $C_{10-18}$ hydrocarbon chain, wherein 1 to 4 methylene units are replaced —C(R$^y$)=C(R$^y$)—.

For example, in certain embodiments, $R^9$ is a substituted or unsubstituted optionally unsaturated $C_{2-30}$ hydrocarbon chain of the formulae:

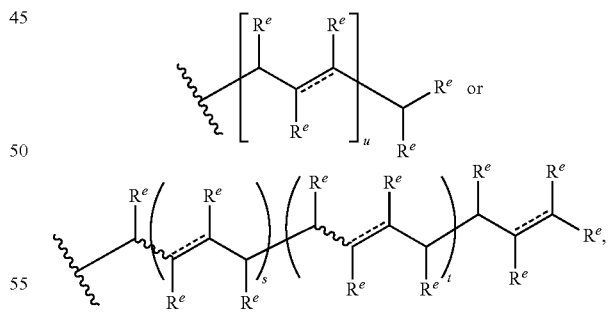

wherein ⋰ is a single or double bond, and each instance of $R^e$ is, independently, H, optionally substituted aliphatic, optionally substituted heteroaliphatic, optionally substituted aryl, optionally substituted heteroaryl, halogen, —OR$^v$, —N(R$^v$)$_2$, —SR$^v$, —NO$_2$, —NC, —CN, —N$_3$, —N(R$^v$)=NR$^v$, —CHO, —C(=O)R$^v$, —C(=S)R$^v$, —C(=NR$^v$)R$^v$, —C(=O)OR$^q$, —C(=NR$^q$)OR$^q$, —C(=NR$^v$)N(R$^v$)$_2$, —C(=O)N(R$^v$)$_2$, —C(=S)OR$^v$, —C(=O)SR$^v$, —C(=S)SR$^v$, —P(=O)(OR$^v$)$_2$, —P(=O)$_2$(OR$^v$), —S(=O)(OR$^v$), —S(=O)$_2$(OR$^v$), —P(=O)N(R$^v$)$_2$, —P(=O)$_2$N(R$^v$)$_2$, —S(=O)N(R$^v$)$_2$, or —S(=O)$_2$N(R$^v$)$_2$; wherein each instance of R$^v$ is H, optionally substituted aliphatic, optionally substituted heteroaliphatic, optionally substituted aryl, optionally substituted heteroaryl or a protecting group; and each instance of u, s and t is, independently, 0, 1, 2, 3, 4, or 5.

In certain embodiments, R$^e$ is, independently, H or optionally substituted aliphatic, optionally substituted heteroaliphatic, optionally substituted aryl, optionally substituted heteroaryl, halogen, —OR$^v$ or —N(R$^v$)$_2$. In certain embodiments, R$^e$ is, independently, H, optionally substituted aliphatic, optionally substituted heteroaliphatic, optionally substituted aryl or optionally substituted heteroaryl. In certain embodiments, R$^e$ is, independently, optionally substituted aliphatic or optionally substituted heteroaliphatic. In certain embodiments, R$^e$ is, independently, H or optionally substituted aliphatic. In certain embodiments, R$^e$ is, independently, H or —CH$_3$.

For example, in certain embodiments, R$^9$ is a fully saturated hydrocarbon group of the formula:

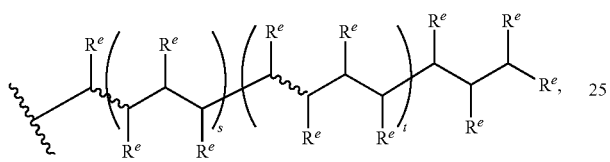

wherein R$^e$, s and t are as defined above and herein.

In certain embodiments, R$^9$ is a fully saturated hydrocarbon group of the formulae:

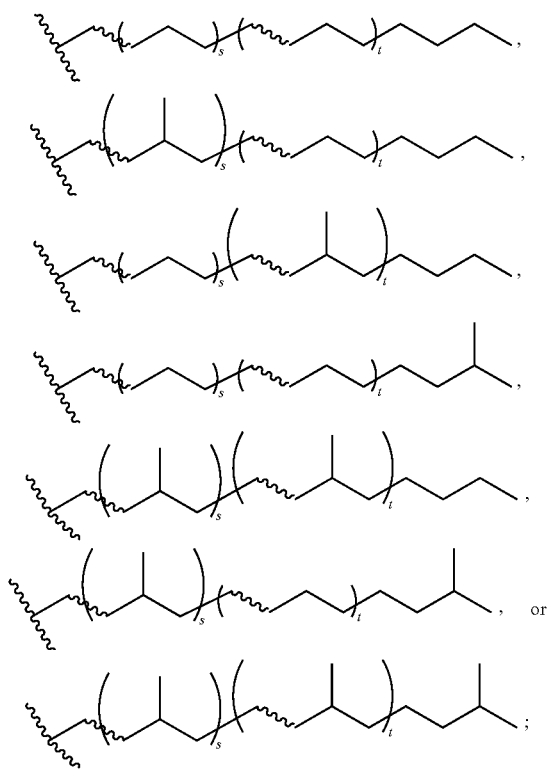

wherein s and t are as defined above and herein.

In certain embodiments, R$^9$ is an unsaturated group of the formulae:

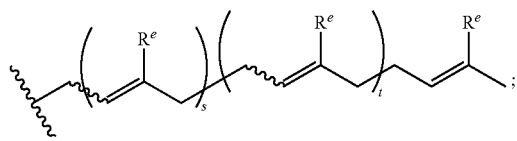

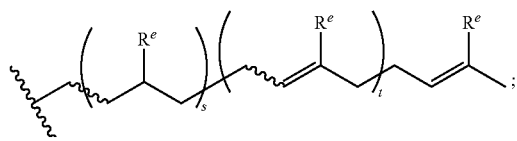

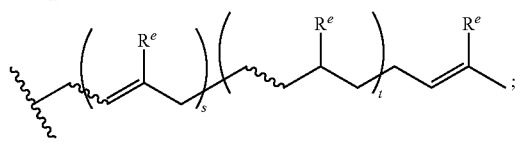

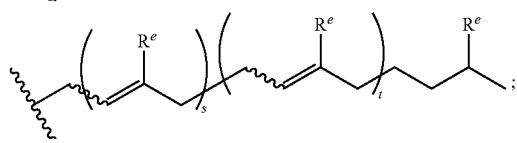

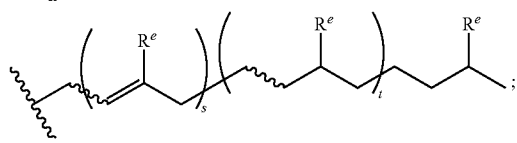

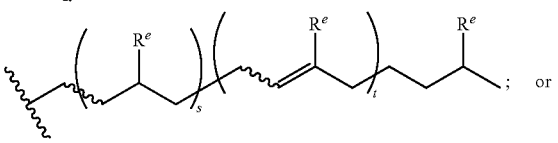

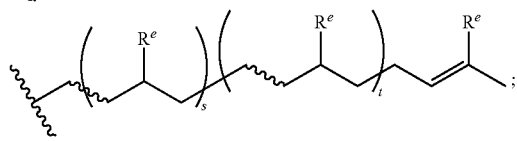

wherein R$^e$, s, and t are as defined herein.

In another aspect, in certain embodiments, R$^9$ is a group of the formulae:

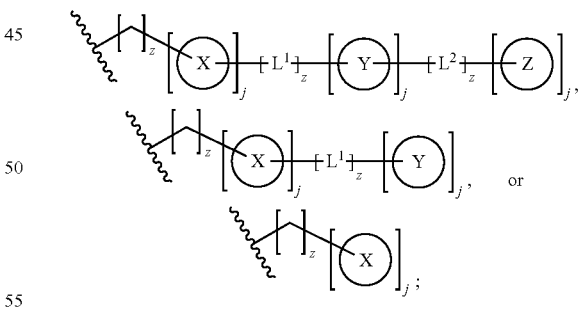

wherein Ring X, Ring Y and Ring Z are, independently, an optionally substituted arylene or an optionally substituted heteroarylene moiety;

z is 0 to 3;

each instance of j is, independently, 1 or 2; and each instance of L$^1$ and L$^2$ are, independently, —(C(R$^o$)$_2$—, —O—, —NR$^x$—, —S—, —C(=O)—, —C(=O)O—, —C(=O)NR$^x$—, —C(=O)S—, —C(=NR$^x$)—, —C(=NR$^x$)O—, —C(=NR$^x$)NR$^x$—, —C(=NR$^x$)S—, —S(=O)—, —S(=O)$_2$—, —N=N—, —C=N—, —C(R$^y$)=C(R$^y$)—, or —N—O—, wherein R$^o$ is H, optionally substituted aliphatic, optionally substituted heteroaliphatic, optionally substituted aryl, optionally substituted heteroaryl, each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl.

Exemplary optionally substituted arylene groups include, but are not limited to:

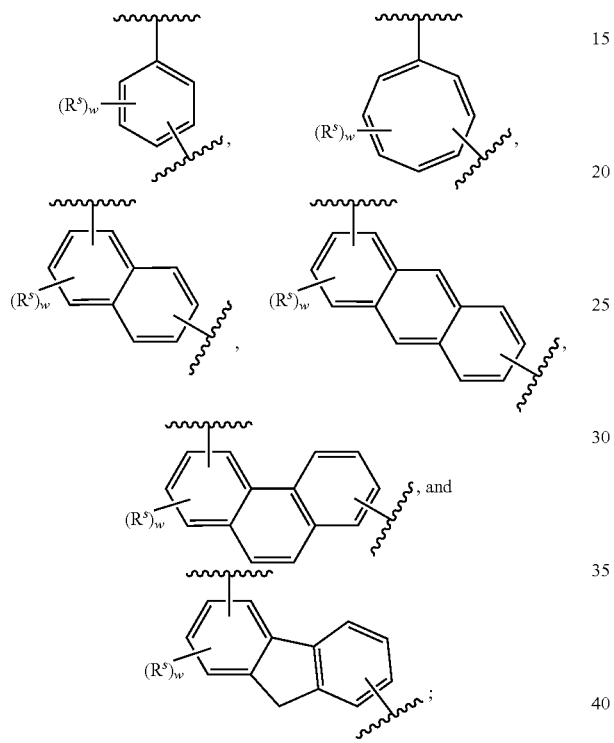

wherein each instance of $R^s$ is, independently, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)$=$NR^v$, —CHO, —C(=O)$R^v$, —C(=S)$R^v$, —C(=$NR^v$)$R^v$, —C(=O)$OR^q$, —C(=$NR^q$)$OR^q$, —C(=$NR^v$)N($R^v$)$_2$, —C(=O)N($R^v$)$_2$, —C(=S)$OR^v$, —C(=O)$SR^v$, —C(=S)$SR^v$, —P(=O)(O$R^v$)$_2$, —P(=O)$_2$(O$R^v$), —S(=O)(O$R^v$), —S(=O)$_2$(O$R^v$), —P(=O)N($R^v$)$_2$, —P(=O)$_2$N($R^v$)$_2$, —S(=O)N($R^v$)$_2$, or —S(=O)$_2$N($R^v$)$_2$; wherein each instance of $R^v$ is H, optionally substituted aliphatic, optionally substituted heteroaliphatic, optionally substituted aryl, optionally substituted heteroaryl or a protecting group; and w is an integer between 0 to 10, inclusive.

Exemplary optionally substituted heteroarylene groups include, but are not limited to:

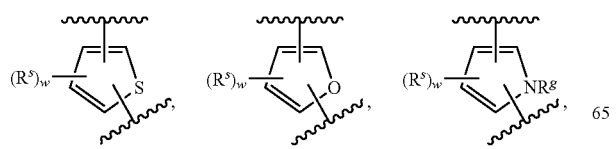

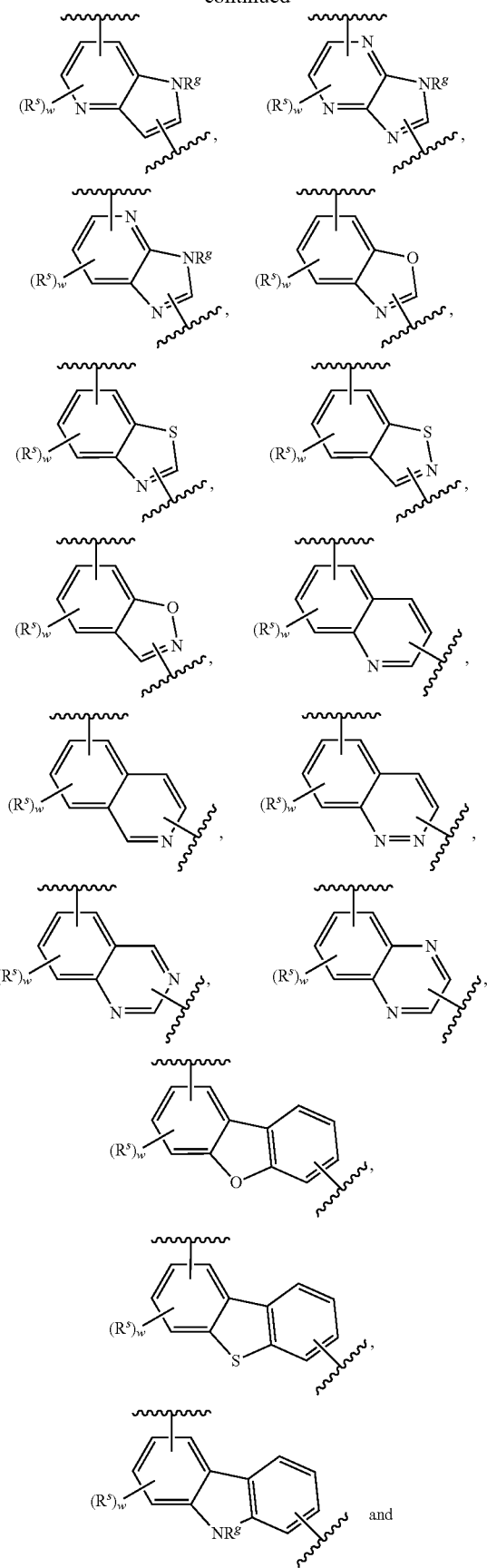

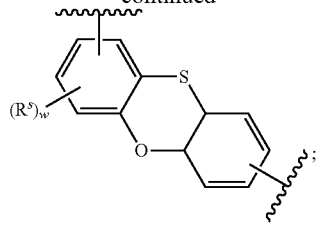

wherein each instance of $R^s$ is, independently, optionally substituted aliphatic, optionally substituted heteroaliphatic, optionally substituted aryl, optionally substituted heteroaryl, halogen, —$OR^v$, —$N(R^v)_2$, —$SR^v$, —$NO_2$, —NC, —CN, —$N_3$, —$N(R^v)=NR^v$, —CHO, —C(=O)$R^v$, —C(=S)$R^v$, —C(=$NR^v$)$R^v$, —C(=O)$OR^q$, —C(=$NR^q$)$OR^q$, —(=$NR^v$)$N(R^v)_2$, —C(=O)$N(R^v)_2$, —C(=S)$OR^v$, —C(=O)$SR^v$, —C(=S)$SR^v$, —P(=O)$(OR^v)_2$, —P(=O)$_2$(OR$^v$), —S(=O)(OR$^v$), —S(=O)$_2$(OR$^v$), —P(=O)$N(R^v)_2$, —P(=O)$_2N(R^v)_2$, —S(=O)$N(R^v)_2$, or —S(=O)$_2N(R^v)_2$; wherein each instance of $R^v$ is H, optionally substituted aliphatic, optionally substituted heteroaliphatic, optionally substituted aryl, optionally substituted heteroaryl or a protecting group; and w is an integer between 0 to 10, inclusive, and each instance of $R^g$ is, independently, H, optionally substituted aliphatic, optionally substituted heteroaliphatic, optionally substituted aryl, optionally substituted heteroaryl or an amino protecting group.

In certain embodiments, Ring X, Ring Y and Ring Z are, independently, an optionally substituted arylene moiety. In certain embodiments, Ring X, Ring Y and Ring Z are, independently, an optionally substituted phenylene moiety. For example, in certain embodiments, $R^9$ is an group of the formulae:

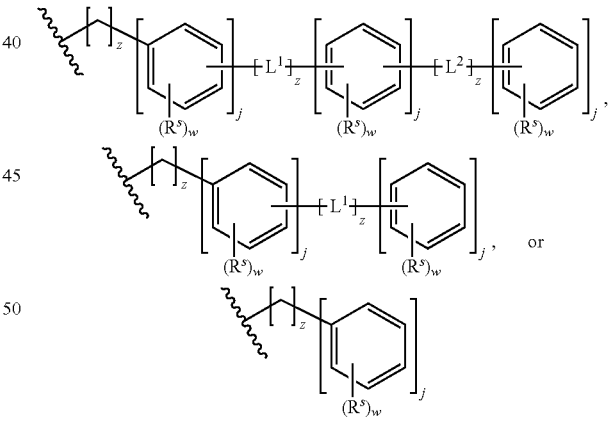

wherein z, w, j, $L^1$, $L^2$, and $R^s$ are as defined above and herein.
In certain embodiments, $R^9$ is of one or the formulae:

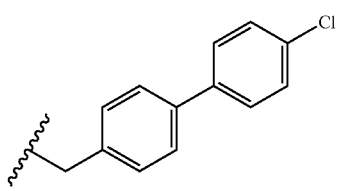

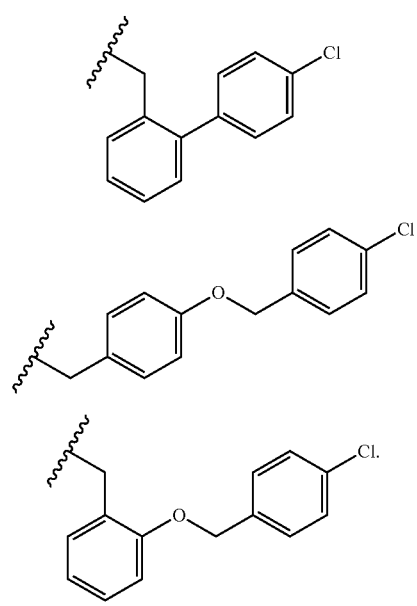
In certain embodiments, $R^9$ is any one of the following groups:
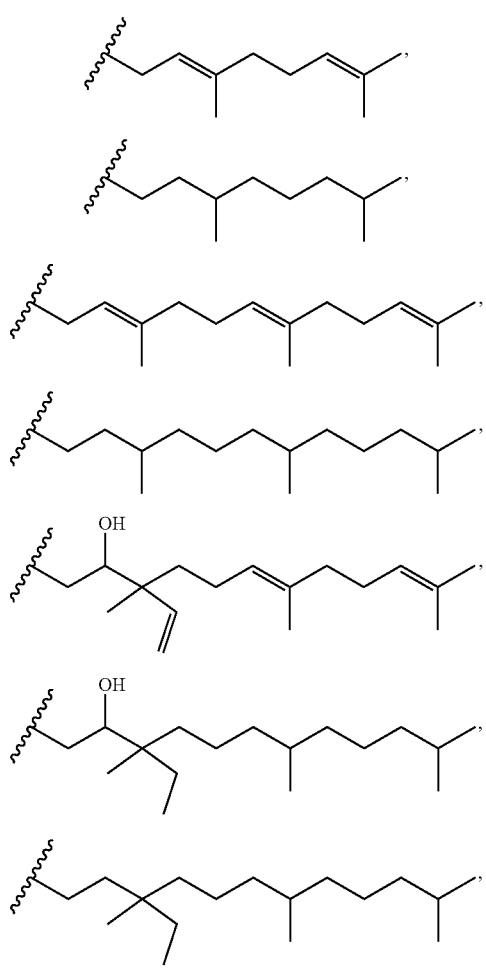
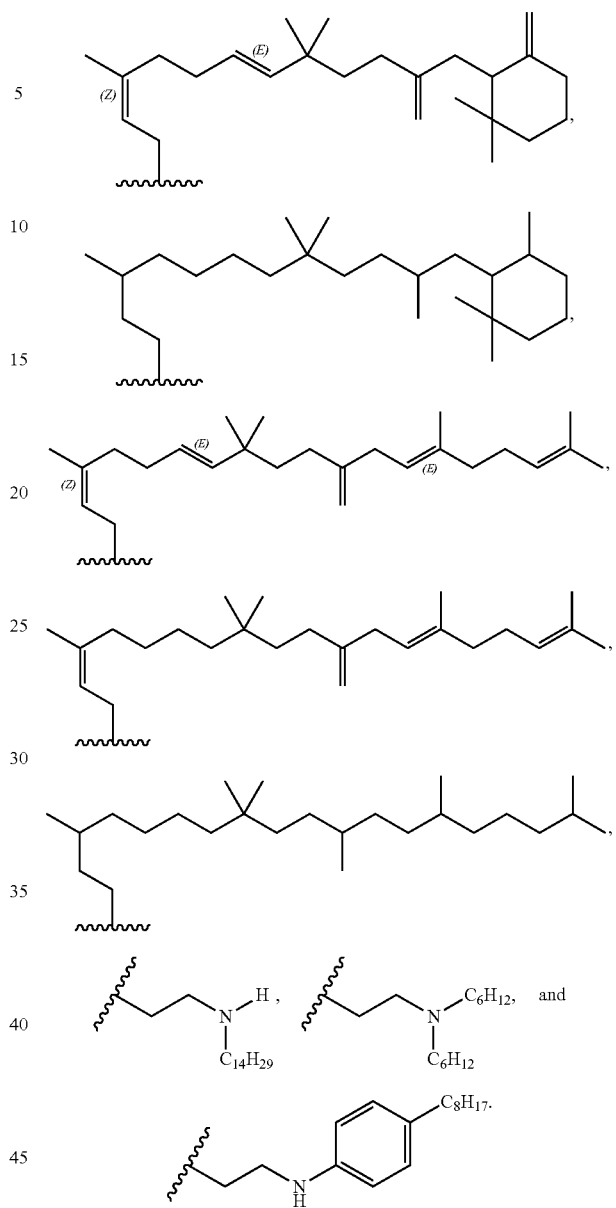
In certain embodiments, $R^9$ is the geranyl group:
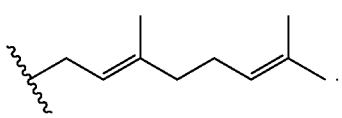 [SMILES: *C/C=C(\C)CCC=C(C)C]
In certain embodiments, $R^9$ is the farnesyl group:
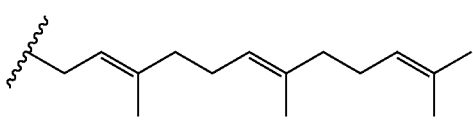

In certain embodiments, $R^9$ is $C_{12}$ alkyl of the formula:

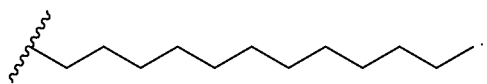 [SMILES: *CCCCCCCCCCCC]

In certain embodiments, $R^9$ is the nerolyl group:

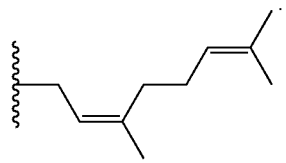 [SMILES: *C/C=C(/C)CCC=C(C)C]

In certain embodiments, $R^9$ is of the formula:

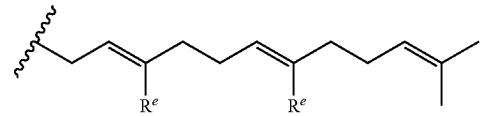

wherein each occurrence of $R^e$ is independently hydrogen or an optionally substituted aliphatic moiety. In certain embodiments, $R^e$ is hydrogen or $C_1$-$C_6$ aliphatic. In certain embodiments, $R^e$ is hydrogen, $C_1$-$C_6$ alkyl, or $C_1$-$C_6$ alkenyl. In certain embodiments, $R^e$ is vinyl. In certain embodiments, $R^e$ is allyl. In certain embodiments, $R^e$ is isopropyl. In certain embodiments, $R^e$ is n-propyl. In certain embodiments, $R^e$ is isobutyl. In certain embodiments, $R^e$ is n-butyl. In certain embodiments, $R^e$ is t-butyl. In certain embodiments, $R^e$ is n-pentyl. In certain embodiments, $R^e$ is isopentyl. In certain embodiments, $R^e$ is neopentyl. In certain embodiments, $R^e$ is 3-methyl-but-2-enyl. Exemplary $R^9$ include:

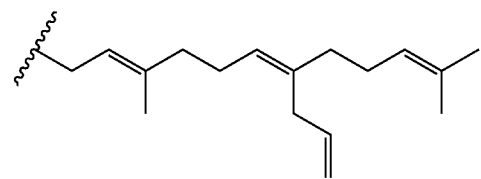

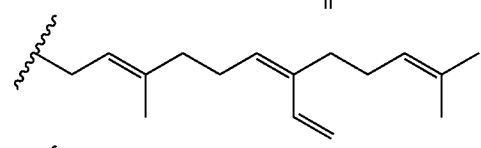

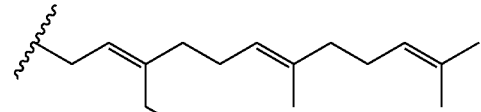

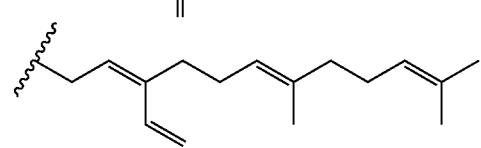

-continued

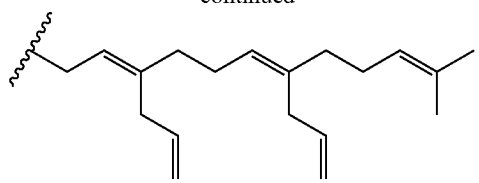

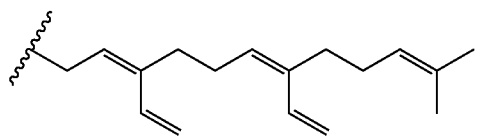

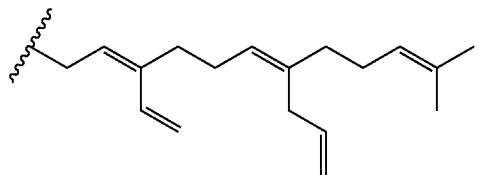

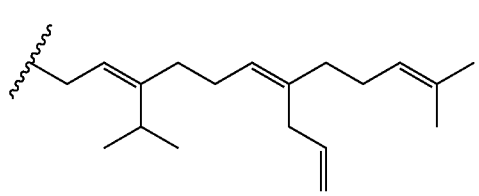

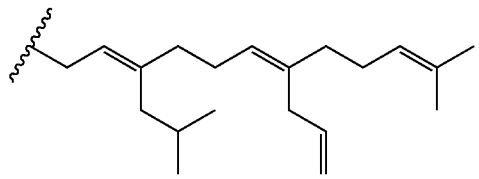

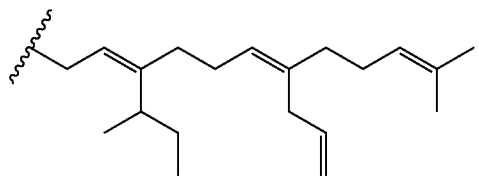

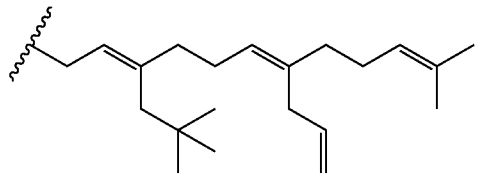

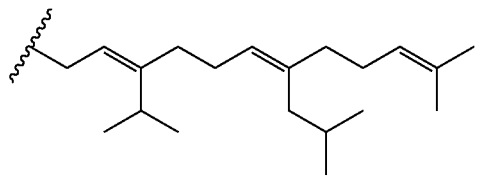

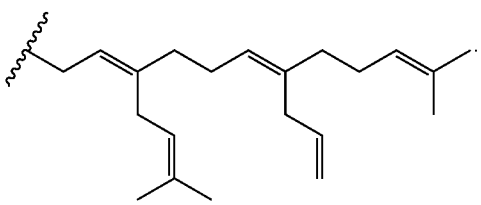

In certain embodiments, $R^9$ is of the formula:

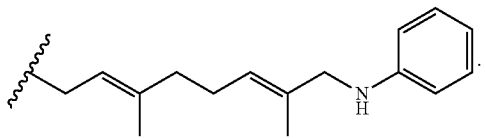 [SMILES: *C/C=C(\C)CC/C=C(\C)CNc1ccccc1]

However, in certain embodiments, the following $R^9$ groups are specifically excluded:

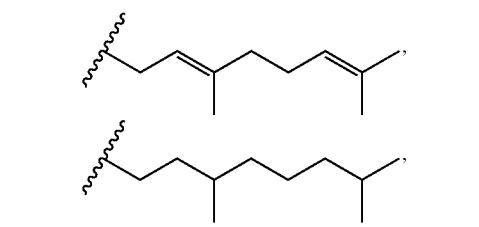

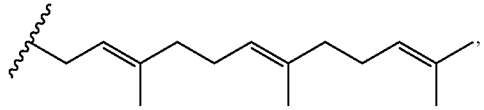

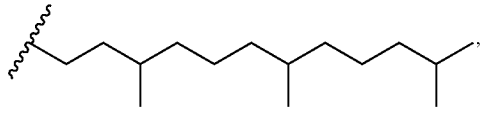

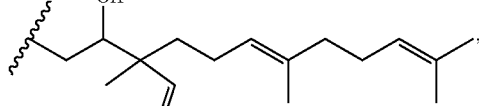

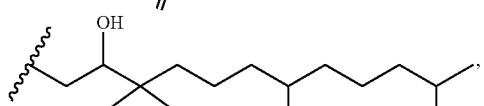

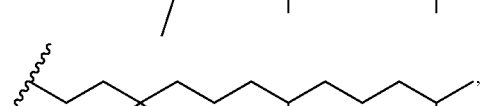

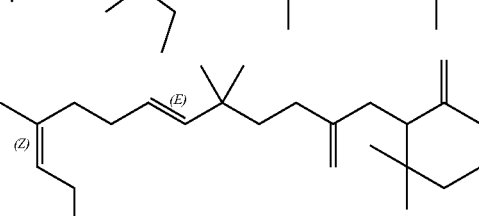

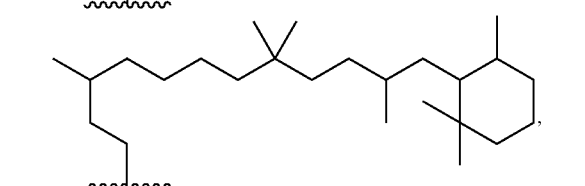

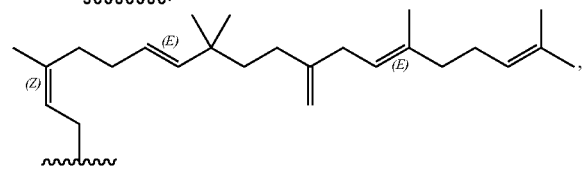

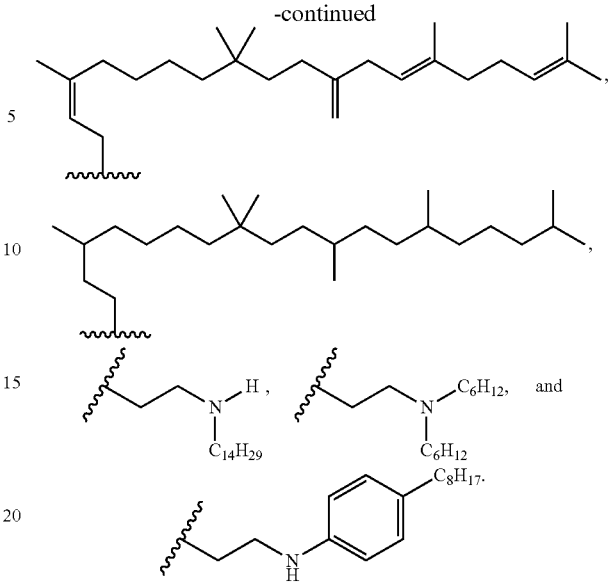

As defined generally above, $R^{10}$ is —C(=O)NHR$^8$, —CH$_2$OR$^6$, or —C(=O)OR$^6$, wherein $R^6$ and $R^8$ are as defined herein. In certain embodiments, $R^{10}$ is —C(=O)NHR$^8$. In certain embodiments, $R^{10}$ is —C(=O)NH$_2$. In certain embodiments, $R^{10}$ is —CH$_2$OR$^6$. In certain embodiments, $R^{10}$ is —CH$_2$OH. In certain embodiments, $R^{10}$ is —C(=O)OR$^6$. In certain embodiments, $R^{10}$ is —C(=O)OH. In certain embodiments, $R^{10}$ is —C(=O)OMe.

As defined generally above, $R^{11}$ is —OR$^6$ or —NHR$^8$, wherein $R^6$ and $R^8$ are as defined herein. In certain embodiments, $R^{11}$ is —OR$^6$. In certain embodiments, $R^{11}$ is —OH. In certain embodiments, $R^{11}$ is —OAc. In certain embodiments, $R^{11}$ is —OR$^6$, wherein $R^6$ is N-acetyl-D-glucosamine (GlcNAc). In certain embodiments, $R^{11}$ is —OR$^6$, wherein $R^6$ is C3-amino-N-acetyl-D-glucosamine. In certain embodiments, $R^{11}$ is —NHR$^8$. In certain embodiments, $R^{11}$ is —NHAc. In certain embodiments, $R^{11}$ is —NH$_2$.

As defined generally above, $R^{12}$ is —OR$^6$ or —NHR$^8$, wherein $R^6$ and $R^8$ are as defined herein. In certain embodiments, $R^{12}$ is —OR$^6$. In certain embodiments, $R^{12}$ is —OH. In certain embodiments, $R^{12}$ is —OAc. In certain embodiments, $R^{12}$ is —NHR$^8$. In certain embodiments, $R^{12}$ is —NHAc. In certain embodiments, $R^{12}$ is —NH$_2$.

Known compounds which may be encompassed by any of the general formulae (I), (II), (III), or (IV), or any subsets thereof, are not intended to be covered by the present invention. For example, known compounds which may be encompassed by any of the general formulae (I), (II), (III), or (IV), or any subsets thereof, and are taught in following literature references and patent documents are specifically excluded: Adachi et al., *J. Am. Chem. Soc.* (2006) 128:14012-14013; Taylor et al., *J. Am. Chem. Soc.*, 128:15084-15085; Welzel, *Chem. Rev.* (2005) 105:4610-4660; Slusarchyk et al., *J. Am. Chem. Soc.* (1970) 92-4487-4488; Slusarchyk and Weisenborn, *Tet. Lett.* (1969) 8:659-662; Welzel et al., *Tetrahedron* (1987) 43:585-598; Weisenborn et al., *Nature* (1967) 1092-1094; Eichhorn and Aga, *Rapid Comm. Mass Spectr.* (2005) 19:2179-2186; Ostash et al., *Chemistry & Biology* (2007) 14:257-267; Pfaller, *Diagnosic Microbiology & Infectious Disease* (2006) 56:115-121; Hebler-Klintz et al., *Tetrahedron* (1993) 35:7667-7678; Linnett and Strominger, *Antimicrobial Agents & Chemotherapy* (1973) 231-236; Vogel et al., *Bioorg. Med. Chem. Lett.* (2000) 10:1963-1965; Baizman et al., *Microbiology* (2000) 146:3129-3140; Garneau et al., *Bioorg. Med. Chem.* (2004) 12:6473-6494; Halliday et al., *Biochemical Pharm.* (2006) 71:957-967; Goldman et al, *Current Med. Chem.* (2000) 7:801-820; and Goldman et al., *Bioorg. Med. Chem. Lett.* (2000) 10:2251-2254; U.S. Pat. Nos. 6,911,318, 6,461,829, 6,114,309; 6,274,716; 6,242,424; 4,684,626; 6,077,830; 6,207,820; 5,986,089; and 3,992,263; U.S. Patent Application Publication Nos. 2003/0158093, US 2004/0018582, 2006/0142217 and 2005/0026214; PCT Application PCT/US2007/017999, and International Application Publication Nos. WO/2000/64915 and W0/1999/26596; the entirety of each of which is hereby incorporated herein by reference.

In certain embodiments, one or more of the following compounds (e.g., as defined by formula (I), or any subsets thereof), are specifically excluded:

Moenomycin A (Welzel, *Chem. Rev.* (2005) 105:4610-4660);

moenomycin A compounds provided in wherein $R^{1a}$ and $R^{1b}$ are H (Ostash et al., *Chemistry & Biology* (2007) 14:257-267);

moenomycin A compound wherein $R^{1a}$ and $R^{1b}$ are H, and $PG^2$ is alkyl;

moenomycin A compound wherein $R^7$ is H (Ostash et al., *Chemistry & Biology* (2007) 14:257-267;

moenomycin A compound wherein $R^{1a}$ and $R^{1b}$ are H and $R^2$ is —$CH_2OH$ (Ostash et al., *Chemistry & Biology* (2007) 14:257-267);

moenomycin A compound wherein $R^3$ is —OH and $R^2$ is —$CH_2OH$ (U.S. Pat. No. 6,242,424).

moenomycin A compound wherein $R^6$ is -Ac (Adachi et al., *J. Am. Chem. Soc.* (2006) 128:14012-14013; Taylor et al., *J. Am. Chem. Soc.*, 128:15084-15085), moenomycin A compound wherein $R^{1a}$ is Group A:

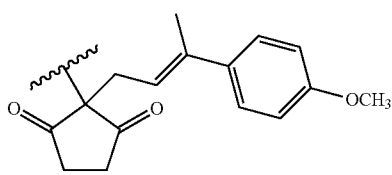 [SMILES: *C1(C/C=C(\C)c2ccc(OC)cc2)C(=O)CCC1=O]

Group A (Vogel et al., *Bioorg. Med. Chem. Lett.* (2000) 10:1963-1965);

moenomycin A compound wherein $R^7$ is H, and $R^{1a}$ is Group A (Vogel et al., *Bioorg. Med. Chem. Lett.* (2000) 10:1963-1965);

moenomycin A compound wherein $R^9$ is:

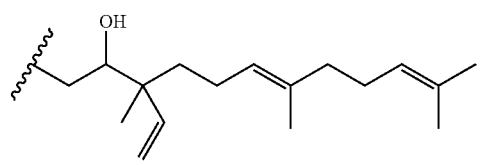 [SMILES: *CC(O)C(C)(C=C)CC/C=C(\C)CCC=C(C)C]

Group B (Vogel et al., *Bioorg. Med. Chem. Lett.* (2000) 10:1963-1965);

moenomycin A compound wherein $R^9$ is:

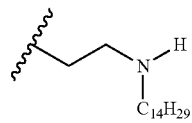

Group C (Vogel et al., *Bioorg. Med. Chem. Lett.* (2000) 10:1963-1965);

moenomycin A compound wherein $R^9$ is:

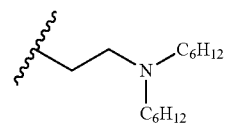

Group D (Vogel et al., *Bioorg. Med. Chem. Lett.* (2000) 10:1963-1965);

moenomycin A compound wherein $R^9$ is:

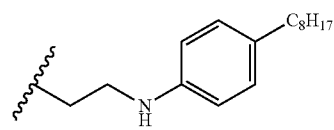

Group E (Vogel et al., *Bioorg. Med. Chem. Lett.* (2000) 10:1963-1965);

moenomycin A compound wherein $R^9$ is:

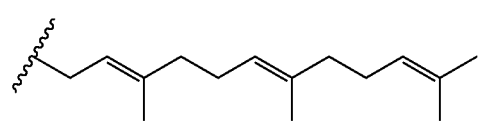 [SMILES: *C/C=C(\C)CC/C=C(\C)CCC=C(C)C]

Group F (PCT/US2007/017999);

moenomycin A compound wherein $R^9$ is:

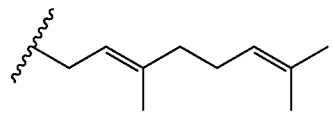 [SMILES: *C/C=C(\C)CCC=C(C)C]

Group G (PCT/US2007/017999);

moenomycin A compound wherein $R^{1a}$ and $R^{1b}$ are H, and $R^9$ is Group B, C, D, E, F or G (Vogel et al., *Bioorg. Med. Chem. Lett.* (2000) 10:1963-1965);

moenomycin A compound wherein $R^{1a}$ and $R^{1b}$ are H, $R^9$ is Group B, C, D, E, F or G, and $R^7$ is H (Vogel et al., *Bioorg. Med. Chem. Lett.* (2000) 10:1963-1965);

dihydromoenomycin A (US 2005/0026214);

[$^3$H] moenomycin A (US 2005/0026214);

[$^2$H] moenomycin A (US 2005/0026214);

decahydromoenomycin A (Welzel et al., *Tetrahedron* (1987) 43:585-598);

decahydromoenomycin A compound wherein $R^{1a}$ and $R^{1b}$ are H (Welzel et al., *Tetrahedron* (1987) 43:585-598; U.S. Pat. No. 6,242,424);

decahydromoenomycin A compound wherein $R^{1a}$ and $R^{1b}$ are H and $PG^2$ is alkyl (Welzel et al., *Tetrahedron* (1987) 43:585-598; U.S. Pat. No. 6,242,424);

Moenomycin $A_{1.1}$;
moenomycin $A_{1.1}$ compound wherein $R^{1a}$ and $R^{1b}$ are H;
decahydromoenomycin $A_{1.1}$;
decahydromoenomycin $A_{1.1}$ compound wherein $R^{1a}$ and $R^{1b}$ are H;
Moenomycin $A_{1.2}$ (Welzel, *Chem. Rev.* (2005) 105:4610-4660);
moenomycin $A_{1.2}$ compound wherein $R^{1a}$ and $R^{1b}$ are H;
decahydromoenomycin $A_{1.2}$;
decahydromoenomycin $A_{1.2}$ compound wherein $R^{1a}$ and $R^{1b}$ are H;
Moenomycin $B_1$
decahydromoenomycin $B_1$;
Moenomycin $B_2$
decahydromoenomycin $B_2$;
Moenomycin $C_1$ (Welzel, *Chem. Rev.* (2005) 105:4610-4660);
moenomycin $C_1$ compound wherein $R^{1a}$ and $R^{1b}$ are H;
decahydromoenomycin $C_1$ (U.S. Pat. No. 6,242,424);
decahydromoenomycin $C_1$ compound wherein $R^{1a}$ and $R^{1b}$ are H (U.S. Pat. No. 6,242,424);
Moenomycin $C_2$
decahydromoenomycin $C_2$;
Moenomycin $C_3$ (Welzel, *Chem. Rev.* (2005) 105:4610-4660);
moenomycin $C_3$ compound wherein $R^{1a}$ and $R^{1b}$ are H;
decahydromoenomycin $C_3$ (U.S. Pat. No. 6,242,424);
decahydromoenomycin $C_3$ compound wherein $R^{1a}$ and $R^{1b}$ are H (U.S. Pat. No. 6,242,424);
Moenomycin $C_4$ (Welzel, *Chem. Rev.* (2005) 105:4610-4660);
moenomycin $C_4$ compound wherein $R^{1a}$ and $R^{1b}$ are H;
decahydromoenomycin $C_4$;
decahydromoenomycin $C_4$ compound wherein $R^{1a}$ and $R^{1b}$ are H;
AC326-alpha (Welzel, *Chem. Rev.* (2005) 105:4610-4660)
AC326-alpha compound wherein $R^{1a}$ and $R^{1b}$ are H;
octahydro-AC326-alpha;
AC326-alpha compound wherein $R^{1a}$ and $R^{1b}$ are H;
Pholipomycin (Welzel, *Chem. Rev.* (2005) 105:4610-4660);
pholipomycin compound wherein $R^{1a}$ and $R^{1b}$ are H;
pholipomycin compound wherein $R^3$ is OH (Hebler-Klintz et al., *Tetrahedron* (1993) 35:7667-7678);
decahydropholipomycin;
decahydropholipomycin compound wherein $R^{1a}$ and $R^{1b}$ are H;
decahydropholipomycin compound wherein $R^{1a}$ and $R^{1b}$ are H and $R^3$ is OH;
Diumycin (Slusarchyk et al., *J. Am. Chem. Soc.* (1970) 92-4487-4488)
Prasinomycin (Slusarchyk et al., *J. Am. Chem. Soc.* (1970) 92-4487-4488; Slusarchyk and Weisenborn, *Tet. Lett.* (1969) 8:659-662); and
Bambermycin (Pfaller, *Diagnosic Microbiology & Infectious Disease* (2006) 56:115-121).

In certain embodiments, known products degradation or cleavage products of any of the above listed known compounds that are encompassed by any of formulae (I), (II) (III), or (IV), or subsets thereof, are specifically excluded (e.g., see Hebler-Klintz et al., *Tetrahedron* (1993) 35:7667-7678; Baizman et al., *Microbiology* (2000) 146:3129-3140; Garneau et al., *Bioorg. Med. Chem.* (2004) 12:6473-6494; Halliday et al., *Biochemical Pharm.* (2006) 71:957-967; and Goldman et al., *Bioorg. Med. Chem. Lett.* (2000) 10:2251-2254, Goldman et al., *Current Med. Chem.* (2000) 7:801-820; and U.S. Pat. No. 4,684,626). For example, in certain embodiments, degradation products resulting from cleavage of ring A from any of the above listed known compounds are specifically excluded. In certain embodiments, degradation products resulting from cleavage of ring B of any of the above listed known compounds are specifically excluded (e.g., see Halliday et al.). In certain embodiments, degradation products resulting from cleavage of ring C of any of the above listed known compounds are specifically excluded. In certain embodiments, degradation products resulting from cleavage of ring D of any of the above listed known compounds are specifically excluded.

Pharmaceutical Compositions and Formulations

The present invention also provides pharmaceutical compositions comprising a compound of the formulae (I), (II), (III), or (IV). The pharmaceutical composition typically includes a therapeutically effective amount of the inventive compound. In certain embodiments, the therapeutically effective amount is the amount necessary to treat or prevent an infection in a subject. In certain embodiments, the infection is caused by a Gram-positive organism. The pharmaceutical compositions may also include a pharmaceutically acceptable excipient.

For the purposes of the present invention, the phrase "active ingredient" generally refers to an inventive compound, as described herein.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Exemplary pharmaceutically acceptable excipients include any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with at substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation—exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits comprising one or more inventive compounds (or pharmaceutically acceptable forms thereof), and/or an inventive pharmaceutical composition. Kits are typically provided in a suitable container (e.g., for example, a foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

Methods of Use

The present invention also provides methods of slowing or inhibiting bacterial growth by contacting a bacterium with at least one compound of the formulae (I), (II), (III), or (IV), or a pharmaceutically acceptable form thereof. In certain embodiments, the bacterium is a Gram-positive bacterium.

Additionally, the present invention provides methods of treating an infection in a subject by administering a therapeutically effective amount of at least one compound of the formulae (I), (II), (III), or (IV), or a pharmaceutically acceptable form thereof. In certain embodiments, the causative organism of the infection is a Gram-positive bacterium.

Subjects to which administration is contemplated include, but are not limited to, humans (e.g., male, female, infant, child, adolescent, adult, elderly adult, etc.) and/or other primates; mammals, including domesticated mammals such as cattle, pigs, horses, sheep, cats, and/or dogs; and including commercially relevant birds such as chickens, ducks, geese, and/or turkeys. In certain embodiments, the inventive compound or a pharmaceutical composition thereof is administered orally. In other embodiments, the inventive compound or a pharmaceutical composition thereof is administered parenterally (e.g., intravenously).

"Treating," as used herein, refers to partially or completely inhibiting, ameliorating, reducing, delaying, or diminishing the severity of a bacterial infection or symptoms related to an infection from which the subject is suffering. "Therapeutically effective amount," as used herein, refers to the minimal amount or concentration of an inventive compound or inventive pharmaceutical composition that when administered is sufficient in treating the subject. In certain embodiments of the present invention a "therapeutically effective amount" of the inventive compound or pharmaceutical composition is that amount effective for killing or inhibiting the growth of bacteria. In certain embodiments, a therapeutically effective amount is the amount administered to a subject to achieve a concentration at the site of infection sufficient to inhibit the growth of the causative organism. In certain embodiments, a therapeutically effective amount is the amount administered to a subject to achieve the mean inhibitory concentration at the site of infection for the causative organism.

In certain embodiments, the infection is a bacterial infection. In certain embodiments, the bacterial infection is caused by Gram-negative bacteria or Gram-positive bacteria. In certain embodiments, the infection is caused by Gram-positive bacteria. In other embodiments, the infection is caused by Gram-negative bacteria.

In certain embodiments, the bacterial infection is caused by caused Gram-negative bacteria. Exemplary Gram-negative bacteria include, but are not limited to, *Escherichia coli*, *Salmonella* (e.g., *Salmonella enteritidis*, and *Salmonella typhi*), *Hemophilus influenzae, Klebsiella pneumoniae, Legionella pneumophila, Pseudomonas aeruginosa, Proteus mirabilis, Enterobacter cloacae, Serratia marcescens, Helicobacter pylori, Pseudomonas, Moraxella* (e.g., *Moraxella catarrhalis*), *Helicobacter, Stenotrophomonas, Bdellovibrio*, acetic acid bacteria, *Legionella*, and *Neisseria* (e.g., *Neisseria gonorrhoeae, Neisseria meningitidis*).

In certain embodiments, the infection is caused by caused Gram-positive bacteria. Exemplary Gram-positive bacteria include, but are not limited to, *Streptococci* bacteria such as *Streptococcus* Group A, *Streptococcus* Group B, *Streptococcus* Group G (e.g., *Streptococcus anginosus, Streptococcus pneumoniae*), *Streptococcus viridans, Streptococcus pyogenes* (e.g., ATCC8668); *Staphylococci* bacteria such as *Staphylococcus aureaus* (e.g., *Staphylococcus aureus* (e.g., ATCC29213), *Staphylococcus aureus* (e.g., ATCC43300) MSA) *Staphylococcus saprophyticus*, and other bacteria such as *Micrococcus luteus* (e.g., ATCC272), *Enterococcus faecalis* (e.g., ATCC29212) and *Enterococcus faecalis* (e.g., ATCC51299).

In certain embodiments, the bacterial infection is caused by vancomycin-resistant bacteria. In certain embodiments, the bacterial infection is caused by vancomycin-resistant Gram-negative or Gram-positive bacteria. In certain embodiments, the bacterial infection is caused by vancomycin-resistant Gram-positive bacteria. In certain embodiments, the bacterial infection is caused by vancomycin-resistant *Staphylococcus aureus*. In certain embodiments, the bacterial infection is caused by vancomycin-resistant Gram-positive enterococci (VRE). In certain embodiments, the bacterial infection is caused by methicillin-resistant bacteria. In certain embodiments, the bacterial infection is caused by methicillin-resistant *Staphylococcus aureus*.

In certain embodiments, the infection is a viral infection. In certain embodiments, the infection is a fungal infection. In certain embodiments, the infection is a parasitic infection.

The methods and pharmaceutical compositions may be used to treat any infection including, but not limited to, anthrax, bacterial meningitis, botulism, brucellosis, campylobacteriosis, cholera, diphtheria, gonorrhea, impetigo, legionellosis, leprosy (Hansen's disease), leptospirosis, listeriosis, lyme disease, melioidosis, MRSA infection, nocardiosis, pertussis (whooping cough), plague, pneumococcal pneumonia, psittacosis, Q fever, rocky mountain spotted fever (RMSF), scarlet fever, shigellosis, syphilis, tetanus, trachoma, tuberculosis, tularemia, typhoid fever, typhus, urinary tract infection (UTI), skin infections, gastrointestinal infections, genito-urinary infections, and systemic infections.

Particularly useful compounds of the present invention include those with biological activity. In certain embodiments, the compounds of the invention exhibit antibacterial activity. For example, the compound may have a mean inhibitory concentration, with respect to a particular bacteria, of less than 50 µg/mL, preferably less than 25 µg/mL, more preferably less than 5 µg/mL, and most preferably less than 1 µg/mL.

A method for the treatment of infection is provided comprising administering a therapeutically effective amount of an inventive compound, or a pharmaceutical composition comprising an inventive compound to a subject in need thereof, in such amounts and for such time as is necessary to achieve the desired result. The compounds and compositions, according to the method of the present invention, may be administered using any amount and any route of administration effective for killing or inhibiting the growth of bacteria. The exact amount required will vary from subject to subject, depending on the species, age, and general condition of the subject, the severity of the infection, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, a therapeutically effective amount of an inventive compound is delivered to a patient and/or organism prior to, simultaneously with, and/or after diagnosis of a bacterial infection. In some embodiments, a therapeutic amount of an inventive composition is delivered to a patient and/or organism prior to, simultaneously with, and/or after onset of symptoms associated with a bacterial infection. In some embodiments, the amount of inventive compound is sufficient to treat, alleviate, ameliorate, relieve, delay onset of, inhibit progression of, reduce severity of, and/or reduce incidence of one or more symptoms or features associated with a bacterial infection.

The inventive compounds and compositions of the present invention may be administered by any route. In some embodiments, the inventive compounds and compositions are administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

The exact amount of a compound required to achieve a therapeutically effective amount will vary from subject to subject, depending on species, age, and general condition of a subject, severity of the side effects or disorder, identity of the particular compound(s), mode of administration, and the like. In certain embodiments of the present invention, a therapeutically effective amount of an inventive compound for administration one or more times a day to a 70 kg adult human may comprise about 0.001 mg/kg to about 100 mg/kg of an inventive compound per unit dosage form. It will be appreciated that dose ranges as described herein provide guidance for the administration of inventive pharmaceutical compositions to an adult. The amount to be administered to, for example, a child or an adolescent can be determined by a medical practitioner or person skilled in the art and can be lower or the same as that administered to an adult.

In certain embodiments, the compounds of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be also appreciated that an inventive compound or composition, as described above and herein, can be employed in combination with one or more additional therapeutically active agents. By "in combination with," it is not intended to imply that the agents must be administered at the same time and/or formulated for delivery together, although these methods of delivery are within the scope of the invention. The compositions can be administered concurrently with, prior to, or subsequent to, one or more other additional therapeutically active agents.

In general, each agent will be administered at a dose and/or on a time schedule determined for that agent.

Additionally, the invention encompasses the delivery of the inventive pharmaceutical compositions in combination with agents that may improve their bioavailability, reduce and/or modify their metabolism, inhibit their excretion, and/or modify their distribution within the body.

In will further be appreciated that the additional therapeutically active agent utilized in this combination may be administered together in a single composition or administered separately in different compositions.

In general, it is expected that additional therapeutically active agents utilized in combination be utilized at levels that do not exceed the levels at which they are utilized individually. In some embodiments, the levels utilized in combination will be lower than those utilized individually.

The particular combination to employ in a regimen will take into account compatibility of the inventive compound with the additional therapeutically active agent and/or the desired therapeutic effect to be achieved.

It will also be appreciated that the therapy employed may achieve a desired effect for the same disorder (for example, an inventive compound may be administered in combination with another antibacterial agent), and/or they may achieve different effects (e.g., control of any adverse effects).

Therapeutically active agents include organic molecules that are drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, and vitamins. Therapeutically active agents include any substance used as a medicine for treatment, prevention, delay, reduction or amelioration of a disease, condition, or disorder, and refers to a substance that is useful for therapy, including prophylactic and therapeutic treatment. A therapeutically active agent also includes a compound that increases the effect or effectiveness of another compound, for example, by enhancing potency or reducing adverse effects of the other compound.

For example, in certain embodiments, an additional therapeutically active agent is an antibacterial agent. Exemplary antibacterial agents include aminoglycosides, glycoproteins (e.g. vancomycin, teicoplanin), penicillins, vephalosporins, carbapenems (e.g., imipenem, cilastin, ertapenem), chloramphenicol, macrolides (e.g., erythromycin), lincosamides (e.g., lincomycin, clindamycin), fusidic acid, tetracyclines, streptogramins, quinolones (e.g., fluoroquinolones, ciprofloxacin, levofloxacin), rifampicin, nitrofurans, polymyxins, daptomycin, sulphonamides, diaminopyrimidines, etc.

In certain embodiments, an additional therapeutically active agent is a pain relieving agent. Exemplary pain relieving agents include, but are not limited to, analgesics such as non-narcotic analgesics or narcotic analgesics; anti-inflammatory agents such as non-steroidal anti-inflammatory agents (NSAIDs), steroids or anti-rheumatic agents; migraine preparations such as beta adrenergic blocking agents, ergot derivatives, or isometheptene; tricyclic antidepressants such as amitryptyline, desipramine, or imipramine; anti-epileptics such as gabapentin, carbamazepine, topiramate, sodium valproate or phenytoin; $\alpha_2$ agonists; selective serotonin reuptake inhibitors (SSRIs), selective norepinepherine uptake inhibitors, or combinations thereof. One skilled in the art will recognize that some agents described herein act to relieve multiple conditions such as pain and inflammation, while other agents may just relieve one symptom such as pain. A specific example of an agent having multiple properties is aspirin, where aspirin is anti-inflammatory when given in high doses, but at lower doses is just an analgesic. The pain relieving agent may include any combination of the afore-mentioned agents, for example, the pain relieving agent may be a non-narcotic analgesic in combination with a narcotic analgesic.

Exemplary non-narcotic analgesics include, but are not limited to, salicylates such as aspirin, ibuprofen (MOTRIN®, ADVIL®), ketoprofen (ORUDIS®), naproxen (NAPROSYN®), acetaminophen, indomethacin or combinations thereof. Exemplary narcotic analgesic agents include, but are not limited to, opioid analgesics such as fentenyl, sufentanil, morphine, hydromorphone, codeine, oxycodone, and buprenorphine. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl) benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

Methods of Synthesis

The present invention also provides methods of synthesizing the inventive compounds. The synthetic methods include the use of biosynthetic and chemical reactions. These reactions may be synthetic (i.e., building up) as well as degradative (i.e., breaking down). Biosynthetic reactions may include the use of enzymes, cells, cell lysates, or cell cultures. The steps used to prepare an intermediate or an inventive compound may be a combination of biological and chemical reactions. For example, a saccharide portion may be prepared by cleavage from a natural product, and the purified saccharide portion may be added synthetically to a novel linker and/or lipid tail.

Examples of biodegradative reactions are well known in the art; see for example, U.S. Pat. Nos. 5,206,405; 5,260,206;

5,315,038; and 5,506,140, the entirety of each of which is incorporated herein by reference. For example, the biodegradative step may be catalyzed by an enzyme (e.g., lipase, esterase, transferase, etc.). The biodegradation step may be accomplished using an enzyme, a cell lysate, a cell, a cell culture, or the like. The cell or enzyme may be a wild-type or genetically engineered cell or enzyme. In certain embodiments, a natural product is contacted with an enzyme under suitable conditions to prepare a sugar portion of a moenomycin analogy by cleave of the sugar portion from the natural product.

Examples of biosynthetic reactions useful in preparing the inventive compounds are also known in the art, see for example, PCT application PCT/US2007/017999, published as WO 2008/021367 on Feb. 21, 2008, the entirety of which is incorporated herein by reference. For example, the biosynthetic step may be catalyzed by an enzyme (e.g., lipase, esterase, ligase, synthase, transferase, epimerase, etc.). The biosynthetic step may be accomplished using an enzyme, using a cell lysate, using a cell, using a cell culture, or the like. The cell may be a wild-type or genetically engineered cell. The enzyme may be wild type or genetically engineered.

In certain embodiments, the biosynthetic method or reaction is one as described in PCT/US2007/017999. For example, PCT/US2007/017999 describes the isolation and characterization of enzymes involved in the biosynthesis of moenomycin A and moenomycin-like compounds, e.g., moeA4 moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and/or moeGT5. The product of biosynthesis (e.g., the final product, a by-product, or an intermediate in the biosynthetic process) may be isolated using conventional methods well known to those skilled in the art, such as methods as described in PCT/US2007/017999. In certain embodiments, MoeO5 is used in the synthesis of an inventive compound. In certain embodiments, MoeGT1 is used in the synthesis of an inventive compound. For example, MoeGT1 may be used to transfer a lipid tail to the carbohydrate portion of the inventive compound. In certain embodiments, MoeGT3 is used in the synthesis of an inventive compound. In certain embodiments, MoeGT4 is used in the synthesis of an inventive compound. In certain embodiments, MoeGT5 is used in the synthesis of an inventive compound. In certain embodiments, MoeF5 is used in the synthesis of an inventive compound. In certain embodiments, MoeM5 is used in the synthesis of an inventive compound. MoeGT3, MoeGT4, or MoeGT5 may be used to add sugar moieties to the inventive compound. These enzyme may be used with their natural substrate or with a different sugar substrate.

An intermediate compound may refer to a natural product, a product obtained from a chemical synthesis or chemical degradation, or a by-product obtained (e.g., an enzymatic by-product) from a biosynthesis or biodegradation. An intermediate compound may also be, for example, a moenomycin natural product (e.g., such as Moenomycin A, Moenomycin $A_{1.2}$, Moenomycin $C_1$, and the like), or a moenomycin-like molecule (e.g., molecules which have a partial moenomycin structure, or bear structural similarity to a moenomycin natural product). PCT/US2007/017999 provides exemplary moenomycin-like molecules which may be isolated from cell culture and modified via one or more chemical synthetic, chemical degradative, biosynthetic or biodegradative steps to provide compounds of the formulae (I), (II), (III), or (IV).

In certain embodiments, the first step in the synthesis of a compound of formulae (I), (II), (III), or (IV) is a degradation step (i.e., removing functional group/moieties from the molecule, such as removing one or more sugar moieties, removing the side chain moeity, removing one or more protecting groups, etc.). For example, in certain embodiments, the present invention provides a method of synthesizing a compound of formulae (I), (II), (III), or (IV) by chemical degradation or biodegradation. In certain embodiments, the present invention provides method of synthesizing a compound of formulae (I), (II), (III), or (IV) utilizing chemical degradation or biodegradation of an intermediate compound [such as a natural product (e.g., such as Moenomycin A, Moenomycin $A_{1.2}$, Moenomycin $C_1$, and the like), a product previously obtained from a chemical synthesis or chemical degradation, or a by-product previously obtained (e.g., an enzymatic by-product) from a biosynthesis or biodegradation]. In certain embodiments, the present invention provides method of synthesizing a compound of formulae (I), (II), (III), or (IV) involving chemical degradation of an intermediate compound. In certain embodiments, the present invention provides method of synthesizing a compound of formulae (I), (II), (III), or (IV) involving biodegradation of an intermediate compound. In certain embodiments, the above method further comprises one or more chemical synthetic or chemical degradation steps. Alternatively, in certain embodiments, the above method further comprises one and/or more biosynthetic and/or biodegradation steps.

In other embodiments, the first step in the synthesis of a compound of formulae (I), (II), (III), or (IV) is a synthetic step (i.e., adding a functional group/moiety to the molecule, such as adding one or more sugar moieties, adding a side chain moiety, adding and/or removing one or more protecting groups, etc.). For example, in certain embodiments, the present invention provides method of synthesizing a compound of formulae (I), (II), (III), or (IV) utilizing chemical synthesis or biosynthesis. In certain embodiments, the present invention provides method of synthesizing a compound of formulae (I), (II), (III), or (IV) by chemical synthesis or biosynthesis from an intermediate compound [such as a natural product (e.g., such as Moenomycin A, Moenomycin $A_{1.2}$, Moenomycin $C_1$, and the like), a product previously obtained from a chemical synthesis or chemical degradation, or a by-product previously obtained (e.g., an enzymatic by-product) from a biosynthesis or biodegradation]. In certain embodiments, the present invention provides methods of synthesizing a compound of formulae (I), (II), (III), or (IV) by chemical synthesis from an intermediate compound. In certain embodiments, the present invention provides method of synthesizing a compound of formulae (I), (II), (III), or (IV) by biosynthesis from an intermediate compound. In certain embodiments, the above method further comprises one or more chemical synthetic and/or chemical degradation steps. Alternatively, in certain embodiments, the above method further comprises one or more biosynthetic and/or biodegradation steps.

Various combinations of the synthetic approaches are envisioned. For example, the first step can be chemical, and the second step can employ biological conditions; the first step can be biological (e.g., enzymatic) and the second step can be chemical; the first and second steps can be both chemical, or the first and second steps can both employ biological conditions. The syntheses may also be wholly or partially biological (i.e., employing biosynthetic or biodegradative steps) or may be all chemical (i.e., employing synthetic steps which are not biosynthetic or biodegradative). In certain embodiments, the synthesis is partially biosynthetic (i.e., employing a combination of (i) chemical synthetic and/or chemical degradative steps, and (ii) biosynthetic and/or biodegradative steps).

Thus, in certain embodiments, the present invention provides a method of synthesizing a compound of the formulae (I), (II), (III), or (IV) comprising (i) providing a first intermediate, and (ii) synthetically modifying the first intermediate (e.g., for example, via a chemical synthetic step by replacing a sugar moeity or lipid side chain moiety of the first intermediate with a different sugar moeity or different side chain moiety, respectively; by synthetically protecting the first intermediate, or via a chemical degradation step by removing a sugar moiety or lipid chain moiety of the first intermediate, by deprotecting the first intermediate, etc.) to afford a second intermediate. In certain embodiments, the method further comprises, after the synthetic modification step (ii), a biosynthetic step (iii) (e.g., for example, by contacting the second intermediate with a second cell culture or second enzyme to obtain a third/different intermediate). In certain embodiments, the method further comprises, after the synthetic modification step (ii), a second synthetic modification step (iii).

In certain embodiments, step (i) comprises providing the first intermediate by biosynthesis. In certain embodiments, step (i) comprises providing the first intermediate by biodegradation. In other embodiments, step (i) comprises providing the first intermediate by chemical synthesis. In other embodiments, step (i) comprises providing the first intermediate by chemical degradation.

In certain embodiments, the first intermediate is a moenomycin natural product or a moenomycin-like molecule. In certain embodiments, the first intermediate is a moenomycin natural product. In certain embodiments, the first intermediate is a moenomycin-like molecule.

In certain embodiments, the above method comprises isolating the first intermediate from a cell culture. In certain embodiments, the above method further comprises purifying the first intermediate.

In certain embodiments, the cell culture is a bacterial cell culture. In certain embodiments, the bacterial cell culture is *Streptomyces*. In certain embodiments, the *Streptomyces* bacterial cell culture is *Streptomyces ghanaensis* or *Streptomyces lividans*.

In certain embodiments, the bacteria is a wild-type bacteria. In certain embodiments, the bacteria is genetically engineered bacteria. PCT application No. PCT/US2007/017999 provides genetically modified bacteria and wild-type bacteria useful in the present invention. In certain embodiments, the bacteria produces a specific enzyme for a biosynthetic or biodegradative step. In certain embodiments, a specific enzyme is deleted from the bacterial genome or inhibited in some manner. In certain embodiments, the enzyme that is affected is selected from the group consisting of moeA4, moeB4, moeC4, moeB5, moe A5, moeD5, moeJ5, moeE5, moeF5, moeH5, moeK5, moeM5, moeN5, moeO5, moeX5, moeP5, moeR5, moeS5, moeGT1, moeGT2, moeGT3, moeGT4, and moeGT5.

In certain embodiments, the step (ii) of synthetically modifying the first intermediate comprises replacing the lipid side chain moiety of the first intermediate with a different side chain moiety $R^9$ to afford a second intermediate, wherein $R^9$ is optionally substituted $C_{1-30}$ aliphatic moiety, wherein 0 to 10 methylene units are optionally replaced with —O—, $NR^x$—, —S—, —C(=O)—, —C(=$NR^x$)—, —S(=O)—, —S(=O)$_2$—, —N=N—, —C=N—, —C($R^y$)=C($R^y$)—, —N—O—, an optionally substituted arylene or an optionally substituted heteroarylene moiety, wherein each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl.

In certain embodiments, the lipid side chain moiety of the first intermediate is:

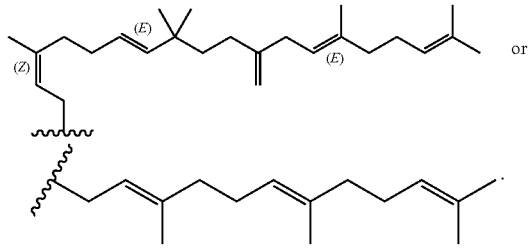

In other embodiments, the present invention provides a method of synthesizing a compound of formula (I), comprising (i) exchanging the lipid side chain moiety of a natural product consisting of Moenomycin A, Moenomycin $A_{1,2}$, Moenomycin $C_1$, Moenomycin $C_3$, Moenomycin $C_4$, AC326-alpha, or Pholipomycin with a different side chain moiety, $R^9$, wherein $R^9$ is optionally substituted $C_{2-30}$ hydrocarbon chain wherein 0 to 10 methylene units are optionally replaced with —O—, —$NR^x$—, —S—, —C(=O)—, —C(=$NR^x$)—, —S(=O)—, —S(=O)$_2$—, —N=N—, —C=N—, —C($R^y$)=C($R^y$)—, —N—O—, an optionally substituted arylene or an optionally substituted heteroarylene moiety, wherein each instance of $R^x$ is, independently, H, optionally substituted aliphatic, optionally substituted heteroaliphatic, optionally substituted aryl, optionally substituted heteroaryl or an amino protecting group, and each instance of $R^y$ is, independently, H, optionally substituted aliphatic, optionally substituted heteroaliphatic, optionally substituted aryl, or optionally substituted heteroaryl. The above method may be modified to provide compounds of formulae (II) or (III). For example, any of the method may comprise an additional step of degrading the natural product (chemically and/or biodegradatively) by cleaving of two or more rings A, B, C and/or D of the natural product prior to step (i).

In certain embodiments, the step of exchanging involves (i) treating the natural product with a base suitable for removing the lipid side chain moiety to provide an intermediate; and (iii) treating the intermediate with one or more coupling reagents and an alcohol of the formula $R^9OH$ (wherein $R^9$ is defined above and herein). In certain embodiments, the base employed is an organic or inorganic base. In certain embodiments, the base is an organic base. Exemplary organic bases include, but are not limited to, triethylamine, diisopropylethyl amine (DIEA), pyridine Py), and dimethylaminopyridine (DMAP). In certain embodiments, the base is pyridine. In certain embodiments, the base is an inorganic base. Exemplary inorganic bases include, but are not limited to, NaOH, KOH, LiOH, Ca(OH)$_2$, Ca$_2$CO$_3$, and K$_2$CO$_3$.

Any suitable coupling agent in the art may be used. In certain embodiments, the coupling agent is a coupling agent used in H-phosphate chemistry. In certain embodiments, the coupling reagent is adamantanecarbonyl chloride.

Exemplary syntheses of inventive compounds are described below in the examples. As would be appreciated by one of skill in the art, the steps described below may be mixed and matched to prepare a wide variety of inventive moenomycin analogs. A variety of approaches may be used to prepare a compound. Transformations that cannot be achieved using wild type enzymes in the moenomycin biosynthetic pathway may be achieved using chemical synthesis, or enzymes may be engineered to catalyse the desired reaction. For example, the substrate specificity of an enzyme may be changed by mutagenesis.

EXAMPLES

In order that the invention described herein may be more fully understood, the following examples are set forth. It should be understood that these examples are for illustrative purposes only and are not to be construed as limiting this invention in any manner.

Example 1

Degradation and Reconstruction of Moenomycin A and Derivatives: Dissecting the Function of the Isoprenoid Chain

This Examples describes a degradation/reconstruction route to manipulate the reducing end of moenomycin A. We evaluate the enzyme inhibitory activity of moenomycin A and an analog containing a nerol chain against membrane-free TGases from the clinically relevant pathogens *Staphylococcus aureus* and vancomycin-resistant *Enterococcus faecalis*. This work provides insight into the different structural requirements for TGase inhibition and biological activities.

Moenomycin A was extracted and purified from feed stock Flavomycin® and fully protected by sequential acetylation of hydroxyls followed by esterification of the acids on the phosphoglycerate moiety. The glycidyl ether linkage was then cleaved by treatment with TMSOTf to produce 2. Workup in the presence of saturated sodium bicarbonate produced the desired anomeric lactol 3 in 75% yield, presumably via ejection of the cyclic glycerol phosphate (Scheme 1).

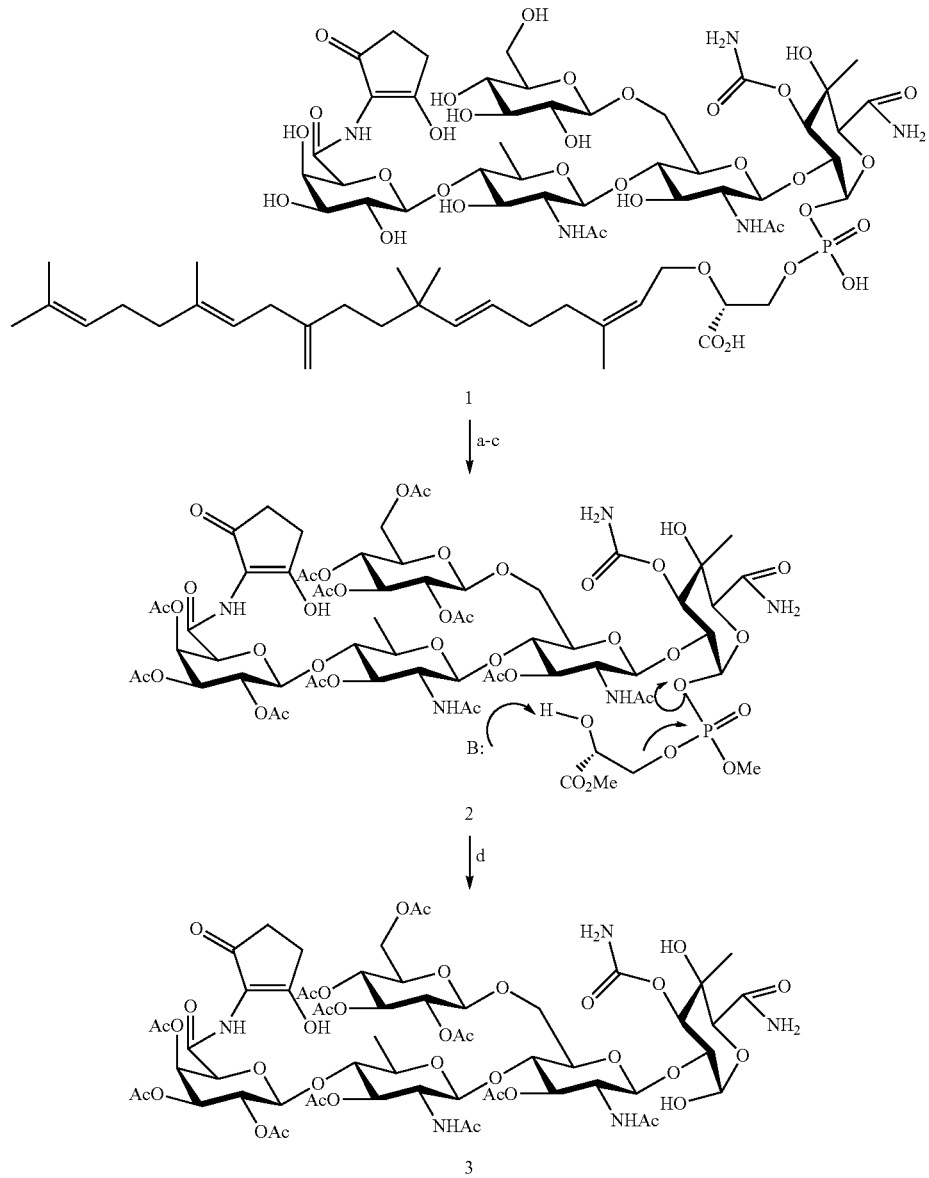

Scheme 1. Degradation of moenomycin A[a]

[a]Conditions: (a) Ac$_2$O, Py, rt; (b) TMSCHN$_2$, CH$_2$Cl$_2$/MeOH, -78° C., 61% two steps; (c) TMSOf, MS 4Å, CH$_2$Cl$_2$, -78° C. to 0° C; (d) sat. NaHCO$_3$, rt, 75% two steps We next required a route to moenocinyl glycerate 11. Our synthetic approach was patterned after the routes to moenocinol developed by Coates[10] and Schmidt[11]. To form the glycidyl ether linkage, moenocinol was converted to the corresponding allylic bromide and then alkylated to a 1,3-protected glycerol 7, which was obtained using the elegant chemistry developed by Jacobsen[12]. Efficient etherification required a specific 7:1 ratio of THF:DMF and the use of the triisopropyl silyl (TIPS) group to prevent silyl protecting group migration. Under these conditions, alkylation proceeded in 66% yield. Following formation of the allyl ether linkage, enantiopure 8 was treated with TBAF to remove TIPS group. Oxidation of the deprotected glycerol 9, followed by esterification to generate 10, and finally oxidative deprotection gave the desired compound 11.

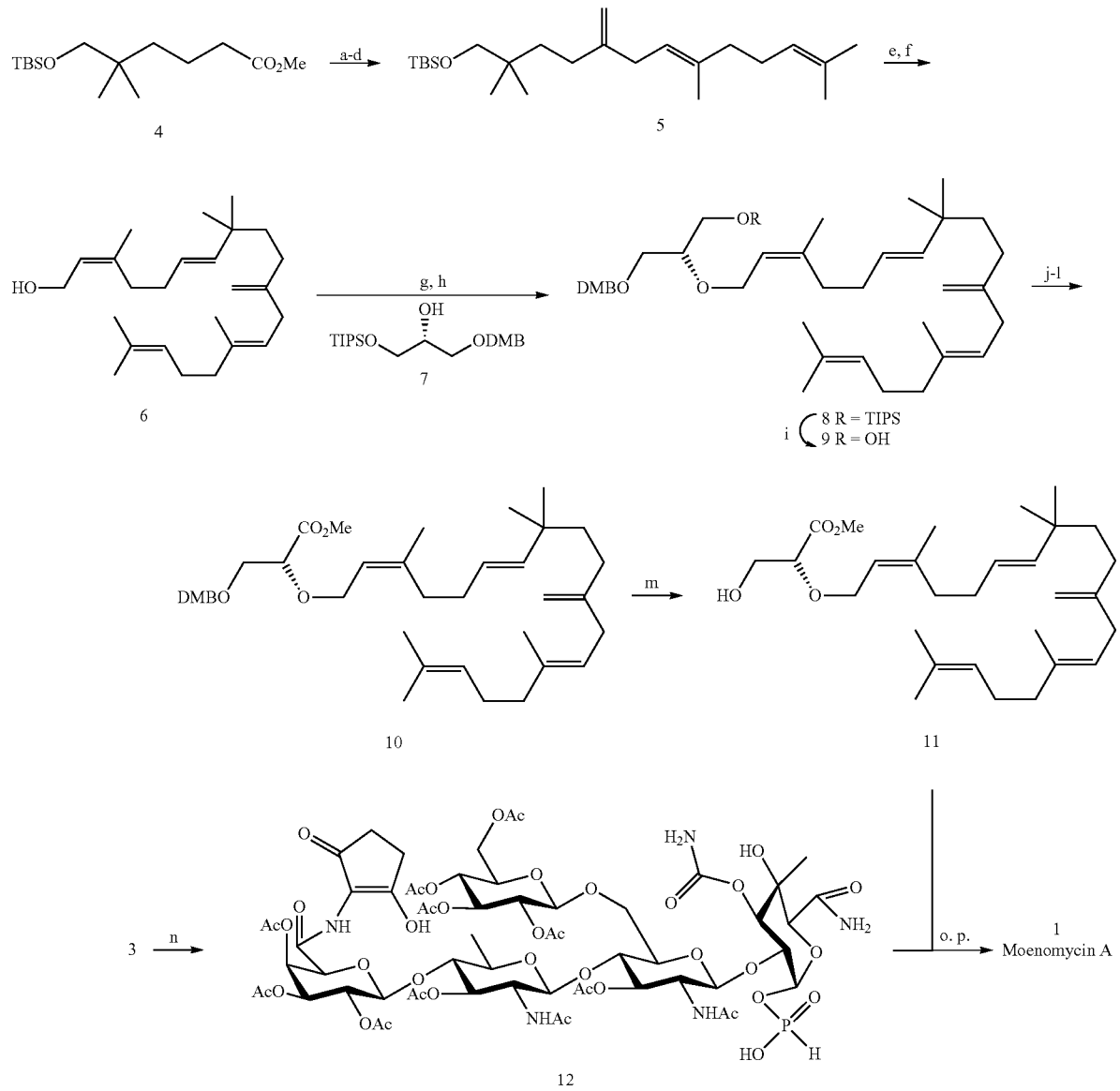

Scheme 2. Reconstruction of moenomycin A[a]

[a]Conditions: (a) LDA, PhSeCl, THF, -78° C. to -5° C., 77%; (b) LDA, geranyl bromide, -78° C. to -5° C; (c) DIBAL, toluene, 0° C., 54% two steps; (d) (CF$_3$CO)$_2$O, TEA, then NaOMe, MeOH, 63%; (e) TBAF, THF, rt, 99%; (f) ref. 10; (g) PBr$_3$, Et$_2$O, 0° C., 80%; (h) 7, NaH, THF/DMF (7:1), 0° C. to rt, 66%; (i) TBAF, THF, 0° C., 97%; (j) Dess-Martin periodinane, NaHCO$_3$, CH$_2$Cl$_2$, rt; (k) NaClO$_2$, NaH$_2$PO$_4$, 2-methyl-2-butene, t-BuOH, H$_2$O; (l) TMSCHN$_2$, CH$_2$Cl$_2$/MeOH (1:1), -60° C., 57% three steps; (m) DDQ, CH$_2$Cl$_2$/pH 7 buffer (10:1), 61% (recovered starting material 34%); (n) 2-Chloro-1,3,2-benzodioxa-phosphorin-4-one, 85%; (o) Py, MS 4Å, rt, 1-adamantanecarbonyl chloride, then NMM/CCl$_4$/Py/CH$_3$CN/H$_2$O (1:2.5:6:1:1), 2 h, 62%; (p) 0.1 N LiOH, THF/H$_2$O (1:1), rt, then AcOH, 47%.

Using H-phosphate chemistry[13], derivative 12, generated from 3, was coupled with 11 using 1-adamantanecarbonyl chloride. Mild oxidation proceeded regioselectively in the presence of NMM/CCl$_4$[14] to produce the corresponding phosphate in 53% yield from 3 without affecting the lipid chain olefins or the 2-amino-3-hydroxycyclopent-2-enone unit (Scheme 2). Global deprotection using LiOH afforded moenomycin A (1).

Using the same route, we were also able to prepare neryl derivative 15 in good yield (Scheme 3). We evaluated the ability of 15 and moenomycin A to inhibit TGases from *S. aureus*[6] and *E. faecalis* (Table 1). The inhibitory activity of 15 is comparable to that of moenomycin A. However, the MICs for 15 against *S. aureus*[6] and *E. faecalis* are several orders of magnitude higher than for moenomycin A. Access to the transglycosylases, which are anchored to the bacterial membrane and operate on membrane-bound substrates, may require that moenomycin partition into membranes[3,7,15]

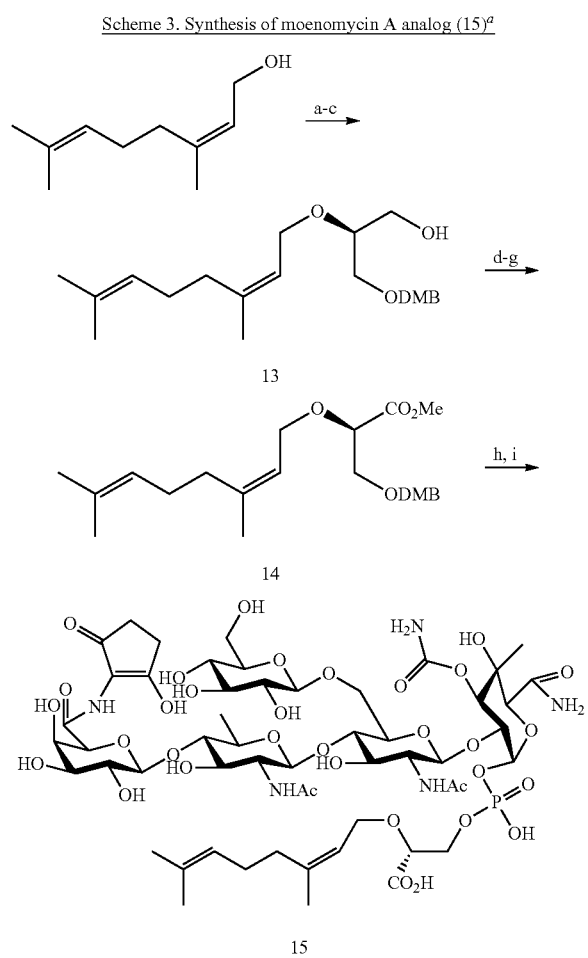

Scheme 3. Synthesis of moenomycin A analog (15)$^a$ $^a$Conditions: (a) PBr$_3$, Et$_2$O, 0° C., 100%; (b) NaH, THF/DMF (7:1), 0° C. to rt, 96%; (c) TBAF, THF, 0° C., 92%; (d) Dess-Martin, NaHCO$_3$, CH$_2$Cl$_2$, rt; (e) NaClO$_2$, NaH$_2$PO$_4$, 2-methyl-2-butene, t-BuOH; (f) TMSCHN$_2$, CH$_2$Cl$_2$/MeOH (1:1), -60° C., 49% three steps; (g) DDQ, CH$_2$Cl$_2$/pH 7 buffer (10:1), 70%; (h) 12, adamantanecarbonyl chloride, Py, MS 4Å, rt, then NMM/CCl$_4$/Py/CH$_3$CN/H$_2$O (1:2.5:6:1:1), 51%; (i) 1.3 M KOH, THF/H$_2$O (2:1), rt, then AcOH, 92%.

REFERENCES 1. van Heijenoort, J. *Glycobiology* 2001, 11, 25R-36R.
2. Goldman, R. C.; Gange, D. *Curr. Med. Chem.* 2000, 7, 801-820.
3. Marzian, S.; Happel, M.; Wagner, U.; Müller, D.; Welzel, P.; Fehlhaber, H. W.; Stark, A.; Schütz, H. J.; Markus, A.; Limbert, M.; van Heijenoort, Y.; van Heijenoort, J. *Tetrahedron* 1994, 50, 5299-5308.
4. (a) Vogel, S.; Stembera, K.; Hennig, L.; Findeisen, M.; Giesa, S.; Welzel, P.; Lampilas, M. *Tetrahedron* 2001, 57, 4139-4146 (b) Vogel, S.; Stembera, K.; Hennig, L.; Findeisen, M.; Giesa, S.; Welzel, P.; Tillier, C.; Bonhomme, C.; Lampilas, M. *Tetrahedron* 2001, 57, 4147-4160.
5. See references (1) and (2) for reviews on moenomycin A inhibition of TGases in the presence of biological membranes.
6. (a) Barrett, D.; Leimkuhler, C.; Chen, L.; Walker, D.; Kahne, D.; Walker, S. *J. Bact.*, 187, 2215-2217 (b) Leimkuhler, C.; Chen, L.; Barrett, D.; Panzone, G.; Sun, B. Y.; Falcone, B.; Oberthür, M.; Donadio, S.; Walker, S.; Kahne, D. *J. Am. Chem. Soc.* 2005, 127, 3250-3251.
7. Volke, F.; Waschipky, R.; Pampel, A.; Donnerstag, A.; Lantzsch, G.; Pfeiffer, H.; Richter, W.; Klose, G.; Welzel, P. *Chem. Phys. Lipids* 1997, 85, 115-123.
8. (a) Welzel, P.; Witteler, F. J.; Müller, D. *Tetrahedron lett.* 1976, 20, 1665-1668 (b) Metten, K. H.; Hobert, K.; Marzian, S.; Hackler, U. E.; Heinz, U.; Welzel, P.; Aretz, W.; Bottger, D.; Hedtmann, U.; Seibert, G.; Markus, A.; Limbert, M.; van Heijenoort, Y.; van Heijenoort, J. *Tetrahedron* 1992, 48, 8401-8418 (c) Welzel, P.; Knupp, G.; Witteler, F. J.; Schubert, T.; Duddeck, H.; Müller, D.; Hofle, G. *Tetrahedron* 1981, 37, 97-104 (d) Welzel, P.; Kunisch, F.; Kruggel, F.; Stein, H.; Scherkenbeck, J.; Hiltmann, A.; Duddeck, H.; Müller, D.; Maggio, J. E.; Fehlhaber, H. W.; Seibert, G.; van Heijenoort, Y.; van Heijenoort, J. *Tetrahedron* 1987, 43, 585-598.
9. Welzel, P. *Chem. Rev.* 2005, 105, 4610-4660.
10. Coates, R. M.; Johnson, M. W. *J. Org. Chem.* 1980, 45, 2685-2697.
11. Stumpp, M. C.; Schmidt, R. R. *Tetrahedron* 1986, 42, 5941-5948.
12. White, D. E.; Jacobsen, E. N. *Tetrahedron: Asymmetry* 2003, 14, 3633-3638.
13. (a) Garegg, P. J.; Regberg, T.; Stawinski, J.; Strömberg, R. *Chem. Scr.* 1985, 25, 280-282 (b) Westerduin, P.; Veeneman, G. H.; van der Marel, G. A.; van Boom, J. H. *Tetrahedron Lett.* 1986, 27, 6271-6274.
14. Kuiper, J. M.; Hulst, R.; Engberts, J. *Synthesis* 2003, 5, 695-698.
15. Subramaniam-Niehaus, B.; Schneider, T.; Metzger, J. W.; Wohlleben, W. *Z. Naturforsch., C: J. Biosci.* 1997, 52, 217-226.

General Methods.

NMR spectra were recorded on a Varian Inova 400 (400 MHz for $^1$H, 100 MHz for $^{13}$C and 162 MHz for $^{31}$P) or a Varian Inova 500 (500 MHz for $^1$H and 125 MHz for $^{13}$C) or a BRUKER DMX 500 (500 MHz for $^1$H, 125 MHz for $^{13}$C) instrument in the indicated solvent. Chemical shift are reported in units parts per million (ppm). $^1$H NMR spectra date are reported as follows: CDCl$_3$ (7.26 ppm) or CD$_3$OD (3.30 ppm) or D$_2$O (4.80 ppm). $^{13}$C NMR spectra date are reported as follows: CDCl$_3$ (77.0 ppm) or CD$_3$OD (49.0 ppm). $^{31}$P NMR spectra date are reported as follows: phosphoric acid (0 ppm) was used as a external standard. Multiplicities are reported by using the following abbreviations: s=singlet, d=doublet, t=triplet, q=quartet, m=multiplet, br=broad, J=coupling constant in Hertz.

Unless otherwise noted, all reactions were conducted under an argon atmosphere using anhydrous solvent (either distilled or passed through an activated alumina column) Commercially available reagents were used without further purification. Reactions were monitored by thin layer chromatography on glass plates precoated with silica gel (250 µm, Sorbent Technologies), with detection by UV and p-anisaldehyde or ceric sulfate or ethanolic phosphomolybdic acid as developing agent. Flash chromatography was carried out on silica gel (60 Å, 32-63 µm), purchased from Sorbent Technologies. Analytical HPLC was performed on a Hewlett-Packard 1100 series instrument using Phenomenex Luna 5 µm C18 column (250 mm×4.6 mm) Preparative HPLC was performed on a Hitachi L6200 instrument (flow-rate: 7.5 mL/min) using a Phenomenex Luna 5 µm C18 column (250× 21.2 mm) Low-resolution mass spectra (LRMS) were obtained on an Agilent Technolgies LC/MSD instrument (Model #G1956B) using electrospray ionization (ESI), while high-resolution mass spectra (HRMS), ESI mode, were obtained at the Harvard University Mass Spectrometry Facilities.

The pET-42 *Escherichia coli* expression vector was purchased from Novagen. *E. coli* BL21 (DE3) competent cells were purchased from Novagen. Restriction enzymes and T4 ligase were purchased from New England Biolabs. The Ni-NTA resin was purchased from Qiagen and the Econo column was purchased from BioRad.

Example (1-a)

Flavomycin (500 g) was dissolved in CH$_2$Cl$_2$ (1.50 L) and the solution was stirred at room temperature for 12 h. The washed Flavomycin was collected by filtration and air dried to remove residual solvent. The dried product was extracted twice with methanol (2.00 Li) at room temperature for 4 h. The combined methanol extract was concentrated in vacuo. To a solution of the residue in Tris buffer (pH=8) (1.00 L) was added HP20P adsorption resin (2.00 kg, washed with acetone/methanol (4/1, 1.00 L)), methanol (1.00 L) and cold water (1.00 L). After being stirred at room temperature for 12 h, the reaction mixture was filtered. The absorption resin was washed with water (1.00 L) and water/methanol (2/1, 1.00 L), followed by elution with methanol (2.00 L). The methanol extract containing moenomycin A was concentrated in vacuo. The residue was purified by silica gel chromatography (2-propanol: 2 M ammonium hydroxide=7:3) to give moenomycin A (9.60 g) as a white solid.

$^1$H NMR (500 MHz, CD$_3$OD): δ 5.88 (dd, F-1, $^3$J$_{1,P}$=6.5 Hz, J$_{1,2}$=4.0 Hz, 1H), 5.43 (t, I-2, J$_{1,2}$=6.5 Hz, 1H), 5.37 (d, I-7, J$_{6,7}$=15.5 Hz, 1H), 5.28 (dt, I-6, J$_{5,6}$=6.5 Hz, J$_{6,7}$=15.5 Hz, 1H), 5.13 (t, I-13, J$_{12,13}$=7.5 Hz, 1H), 5.10 (t, I-17, J$_{16,17}$=6.5 Hz, 1H), 5.05 (d, F-3, J$_{2,3}$=10.5 Hz, 1H), 4.66 (d, I-22, J=5.5 Hz, 2H), 4.57 (d, C-1, J$_{1,2}$=8.5 Hz, 1H), 4.49 (d, B-1, J$_{1,2}$=7.0 Hz, 1H), 4.42-4.47 (m, E-1, D-1, F-5, 3H), 4.08-4.39 (m, B-4, B-5, E-6, H-1, H-2, H-2', I-1, I-1', 8H), 3.95 (br-d, D-6, J$_{6,6}$=10.0 Hz, 1H), 3.73-3.80 (m, C-2, E-2, 2H), 3.53-3.71 (m, B-2, B-3, C-3, C-5, D-6', E-3, E-5, E-6', F-2, 9H), 3.47 (m, E-4, 1H), 3.45 (dd, D-3, J$_{2,3}$=9.0 Hz, J$_{3,4}$=9.5 Hz, 1H), 3.26-3.40 (m, C-4, D-4, D-5, 3H), 3.24 (dd, D-2, J$_{1,2}$=8.0 Hz, J$_{2,3}$=9.0 Hz, 1H), 2.68 (d, I-12, J$_{12,13}$=8.0 Hz, 2H), 2.43 (s, A-4, A-4', A-5, A-5' 4H), 2.00-2.13 (m, I-4, I-4', I-5, I-5', I-15, I-15', I-16, I-16', 8H), 2.04 (s, C-2-NAc, 3H), 2.01 (s, E-2-NAc, 3H), 1.89 (m, I-10, I-10', 2H), 1.76 (s, I-25, 3H), 1.66 (s, I-19, 3H), 1.60 (s, I-21, 3H), 1.59 (s, I-20, 3H), 1.42 (d, C-6, J$_{5,6}$=6.0 Hz, 3H), 1.36 (m, I-9, 2H), 1.24 (s, F-4-Me, 3H), 0.96 (s, I-23, I-24, 6H); $^{13}$C NMR (100 MHz, CD$_3$OD): δ 194.72 (br-s, A-1), 175.10 (H-1), 174.66 (F-5-C'), 174.07 (E-2-C'), 173.87 (C-2-C'), 170.50 (B-5-C'), 159.10 (F-3-C'), 151.08 (I-11), 142.07 (I-3), 141.57 (I-7), 137.33 (I-14), 132.19 (I-18), 126.84 (I-6), 125.37 (I-17), 123.51 (I-2), 122.78 (I-13), 113.05 (A-2), 109.25 (I-22), 104.77 (B-1), 104.44 (D-1), 104.28 (E-1), 103.07 (C-1), 96.09 (d, F-1, $^2$J$_{C,P}$=6.1 Hz), 85.03 (C-4), 82.28 (E-4), 79.18 (d, H-2, $^3$J$_{C,P}$=6.8 Hz), 78.82 (d, F-2, $^3$J$_{C,P}$=9.1 Hz), 78.18 (D-5), 78.11 (D-3), 76.43 (B-5), 75.81 (F-3), 75.12 x2 (D-2, E-5), 74.14, 74.17, 73.83, 73.79, 73.67 (B-3, C-3, E-3, F-4, F-5), 72.71 (C-5), 72.21 (B-2), 71.68 (D-4), 70.66 (B-4), 69.52 (E-6), 68.36 (d, H-3, $^2$J$_{C,P}$=5.2 Hz), 67.28 (I-1), 62.26 (D-6), 57.39 (E-2), 56.18 (C-2), 42.86 (I-9), 40.85 (I-15), 36.45 (I-8), 35.93 (I-12), 33.48 (I-4), 32.67 (I-5), 32.34 (I-10), 30.73 (br-s, A-4, A-5), 27.85 x2, 27.70 (I-16, I-23, I-24), 25.95 (I-19), 23.97 (I-25), 23.48 (C-2-NAc), 23.38 (E-2-NAc), 18.07 (C-6), 17.80 (I-20), 16.45 (F-4-Me), 16.12 (I-21); $^{13}$C NMR (125 MHz, CD$_3$OD): δ 194.71 (br-s, A-1), 175.63 x2 (F-5-C', H-1), 174.85 (E-2-C'), 174.71 (C-2-C'), 171.37 (B-5-C'), 159.89 (F-3-C'), 151.89 (I-11), 142.84 (I-3), 142.34 (I-7), 138.08 (I-14), 132.93 (I-18), 127.60 (I-6), 126.09 (I-17), 124.22 (I-2), 123.47 (I-13), 113.94 (A-2), 109.90 (I-22), 105.45 (B-1), 105.14 (D-1), 104.84 (E-1), 103.73 (C-1), 96.69 (d, F-1, $^2$J$_{C,P}$=6.1 Hz), 85.71 (C-4), 82.94 (E-4), 79.71 (d, H-2, $^3$J$_{C,P}$=8.3 Hz), 79.33 (d, F-2, $^3$J$_{C,P}$=9.2 Hz), 78.79 (D-5), 78.72 (D-3), 77.01 (B-5), 76.42 (F-3), 75.74 x2 (D-2, E-5), 75.02, 74.78, 74.38 x2, 74.19 (B-3, C-3, E-3, F-4, F-5), 73.30 (C-5), 72.79 (B-2), 72.33 (D-4), 71.21 (B-4), 70.11 (E-6), 68.76 (br-d, H-3), 67.91 (I-1), 63.23 (D-6), 57.96 (E-2), 56.81 (C-2), 43.37 (I-9), 41.36 (I-15), 36.94 (I-8), 36.41 (I-12), 33.94 (I-4), 33.12 (I-5), 32.81 (I-10), 31.07 (br-s, A-4, A-5), 28.29 x2, 28.16 (I-16, I-23, I-24), 26.38 (I-19), 24.38 (I-25), 23.88 (C-2-NAc), 23.79 (E-2-NAc), 18.48 (C-6), 18.20 (I-20), 16.89 (F-4-Me), 16.53 (I-21); $^{31}$P NMR (162 MHz, CD$_3$OD): δ–1.11; LRMS (ESI) calcd for C$_{69}$H$_{107}$N$_5$O$_{34}$P [M–NH$_3$–H]$^-$ 1580.7. found 1580.6.

Example (1-b)

Synthesis of N₁-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl)-(1→2)-3-O-carbamoyl-1-O-{[(R)-2-methoxycarbonyl-2-(2Z,6E,13E)-3,8,8,14,18-pentamethyl-11-methylene-nonadeca-2,6,13,17-tetraen-1-yloxy)-ethoxy]-methoxyphosphoryl}-4-C-methyl-α-D-glucopyranuronamide (1.1)

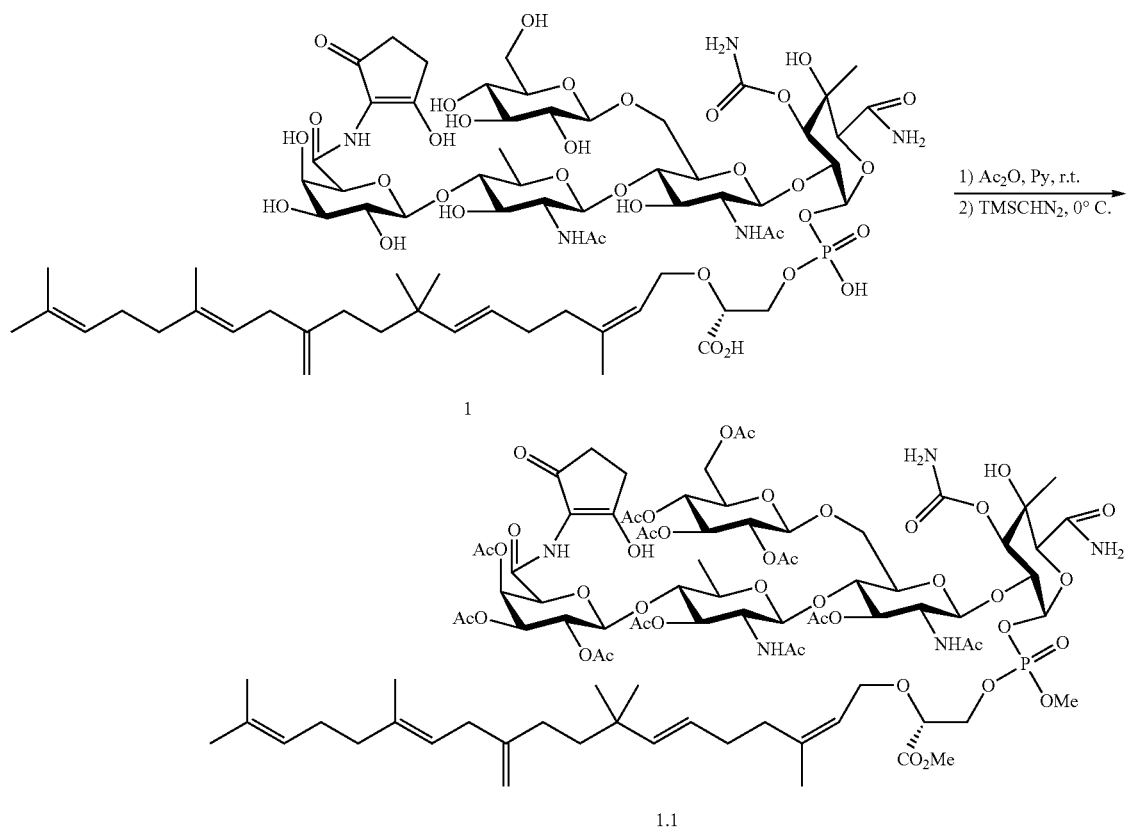

To a solution of moenomycin A (1) (1.00 g, 0.619 mmol, 1.00 eq.) in pyridine (5.00 mL, 61.9 mmol, 100 eq.) was added acetic anhydride (1.05 mL, 11.1 mmol, 18.0 eq.) at room temperature. After being stirred at the same temperature for 20 h, the reaction mixture was concentrated in vacuo. The residue was used for the next reaction without further purification.

To a solution of the residue in methanol was added Dowex 50WX8-400 (0.70 g) at room temperature. After being stirred at the same temperature for 30 min, the reaction mixture was filtered and the filtrate was concentrated in vacuo. The residue was used for the next reaction without further purification.

To a solution of the residue in dry methanol (30 mL) and dry dichloromethane (30 mL) was added 2 M (trimethylsilyl) diazomethane solution in hexane (1.40 mL, 2.79 mmol, 4.50 eq.) at −78° C. After being stirred at the same temperature for 15 min, the reaction mixture was quenched by addition of acetic acid (1.50 mL), allowed to warm to room temperature and concentrated in vacuo. The residue was purified by silica gel chromatography (chloroform:methanol:acetic acid: $H_2O$=80:20:0.5:0.5) to give nonaacetyl moenomycin A methyl diester (1.1) (745 mg, 0.374 mmol, 61% in 3 steps) as a white solid.

$^1$H NMR (500 MHz, CD$_3$OD): δ 6.03 (dd, F-1, $^3J_{1,P}$=7.0 Hz, $J_{1,2}$=3.5 Hz, 1H), 5.68 (br-d, B-4, $J_{3,4}$=2.5 Hz), 5.40 (dd, D-3, $J_{2,3}$=9.5 Hz, $J_{3,4}$=9.5 Hz, 1H), 5.38 (d, I-7, $J_{6,7}$=15.5 Hz, 1H), 5.37 (t, I-2, $J_{1,2}$=6.0 Hz, 1H), 5.29 (dt, I-6, $J_{5,6}$=6.5 Hz, $J_{6,7}$=15.5 Hz, 1H), 5.20 (dd, B-3, $J_{2,3}$=9.5 Hz, $J_{3,4}$=3.0 Hz, 1H), 5.19 (dd, C-3, $J_{2,3}$=9.5 Hz, $J_{3,4}$=9.5 Hz, 1H), 5.05-5.13 (m, B-2, E-3, F-3, I-13, I-17, 5H), 5.04 (dd, D-4, $J_{3,4}$=9.5 Hz, $J_{4,5}$=10.0 Hz, 1H), 5.01 (d, B-1, $J_{1,2}$=8.5 Hz, 1H), 4.93 (d, D-1, $J_{1,2}$=8.5 Hz, 1H), 4.88 (dd, D-2, $J_{1,2}$=8.5 Hz, $J_{2,3}$=9.0

Hz, 1H), 4.66 (m, C-1 or E-1, I-22, I-22', 3H), 4.63 (br-s, B-5, 1H), 4.58 (d, C-1 or E-1, $J_{1,2}$=8.5 Hz, 1H), 4.40 (s, F-5, 1H), 4.19-4.37 (m, D-6, H-2, H-3, H-3', I-1, 5H), 4.15 (br-d, D-6', $J_{6,6'}$=11.0 Hz, 1H), 4.03-4.10 (m, D-5, E-6, I-1', 3H), 3.87 (d, OMe, $^3J_{H,P}$=11.0 Hz, 3H), 3.59-3.83 (m, C-2, C-4, E-2, E-4, E-5, E-6', F-2, OMe, 10H), 3.49 (dq, C-5, $J_{4,5}$=9.0 Hz, $J_{5,6}$=6.0 Hz, 1H), 2.70 (d, I-12, $J_{12,13}$=7.0 Hz, 2H), 2.54 (s, A-4, A-4', A-5, A-5', 4H), 1.89-2.16 (m, OAc x9, NAc x2, I-4, I-4', I-5, I-5', I-10, I-10', I-15, I-15', I-16, I-16', 43H), 1.75 (s, I-25, 3H), 1.66 (s, I-19, 3H), 1.61 (s, I-21, 3H), 1.60 (s, I-20, 3H), 1.38 (m, I-9, 2H), 1.31 (d, C-6, $J_{5,6}$=6.0 Hz, 3H), 1.25 (s, F-4-Me, 3H), 0.97 (s, I-23, I-24, 6H); $^{13}$C NMR (100 MHz, CD$_3$OD): δ 191.05 (br-s), 173.51, 173.46, 172.45, 171.91, 171.66, 171.52, 171.44, 171.36, 171.25, 171.17, 171.00, 167.82, 158.53, 151.09, 142.72, 141.63, 137.35, 132.21, 126.75, 125.37, 123.50, 122.17, 113.57, 109.26, 103.54, 101.99, 101.91, 101.69, 97.74 (d, $^2J_{C,P}$=5.3 Hz), 82.00, 78.69 (d, $^3J_{C,P}$=7.5 Hz), 77.34 (d, $^3J_{C,P}$=7.6 Hz), 76.31, 75.18, 74.74, 74.65, 74.58, 74.34, 74.25, 73.89, 73.23, 72.67, 72.07, 71.89, 70.50, 69.79, 69.73, 69.27, 68.85 (d, $^2J_{C,P}$=5.3 Hz), 67.94, 63.21, 56.49 (d, $^2J_{C,P}$=7.0 Hz), 56.46, 55.39, 52.96, 42.82, 40.88, 36.49, 35.96, 33.34, 32.50, 32.32, 30.41 (br-d), 27.98, 27.82, 25.98, 23.81, 23.08, 23.05, 21.35, 21.33, 21.08, 20.85, 20.77, 20.67, 20.63, 20.50, 20.46, 18.28, 17.82, 16.64, 16.14; $^{31}$P NMR (162 MHz, CD$_3$OD): δ−1.02; LRMS (ESI) calcd for C$_{89}$H$_{131}$N$_5$O$_{43}$P [M+H]$^+$ 1988.8. found 1988.8.

Example (1-c)

Synthesis of N$_1$-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl-(1→2)-3-O-carbamoyl-4-C-methyl-α-D-glucopyranuronamide (3)

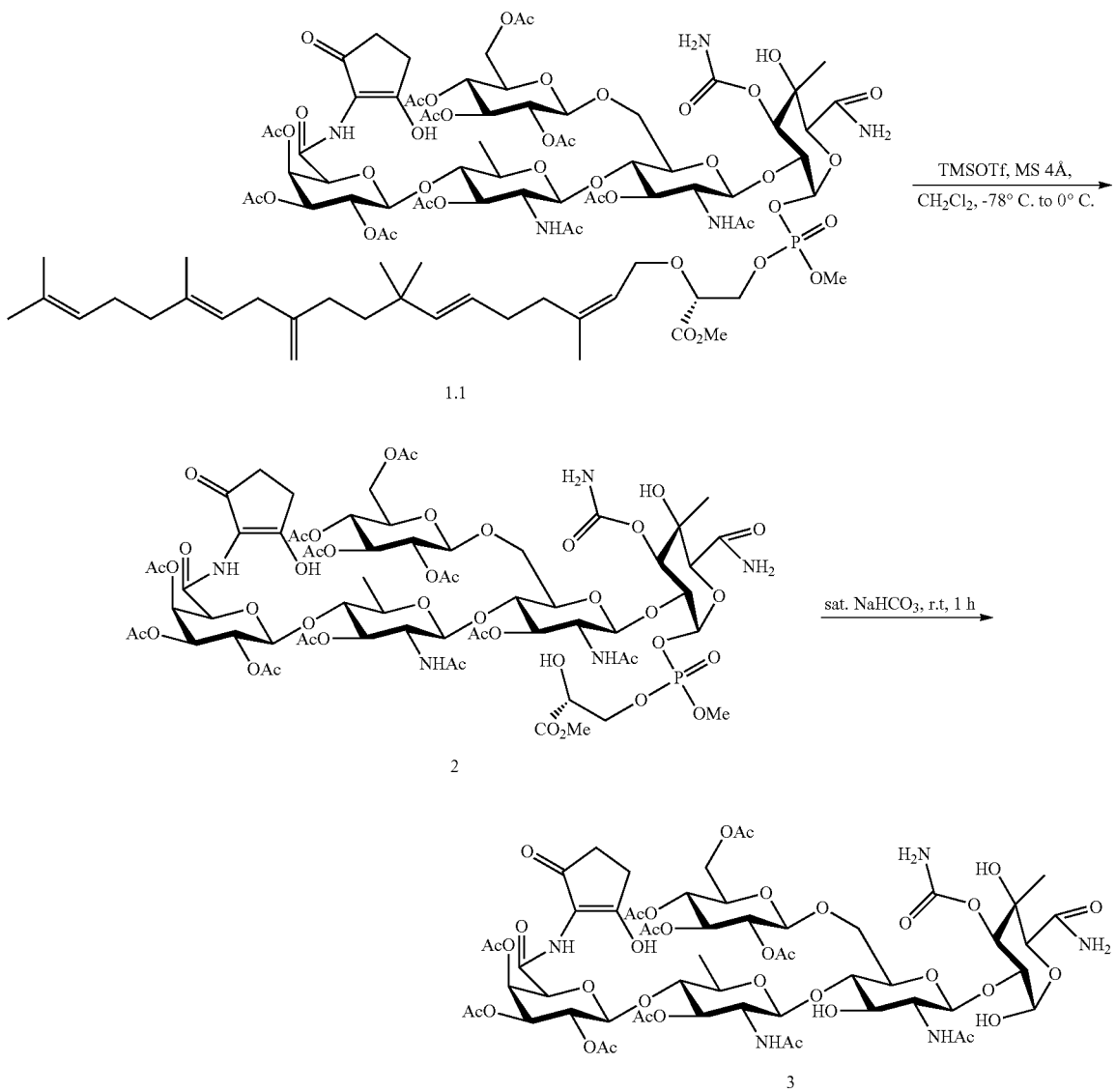

A mixture of nonaacetyl moenomycin A methyl diester (1.1) (292 mg, 0.147 mmol, 1.00 eq.) and pulverized activated MS 4 Å in dry dichloromethane (7.00 mL) was stirred at room temperature for 30 min to remove a trace of water. Then the reaction mixture was cooled to −78° C. Trimethylsilyl trifluoromethanesulfonate (0.33 mL, 1.84 mmol, 12.5 eq.) was added to the reaction mixture at the same temperature. After being stirred for 15 min, the reaction mixture was allowed to warm to 0° C. over 2 h. After 1 h, saturated aq. NaHCO$_3$ (7.00 mL) was added to the reaction mixture at the same temperature. After being stirred for 1 h at the same temperature, the reaction mixture was neutralized with acetic acid, filtered and concentrated in vacuo. The residue was purified by reversed-phase HPLC (gradient 30-40% acetonitrile/water with 0.1% TFA over 60 min) to give nonaacetyl moenomycin A pentasaccharide lactol (3) (160 mg, 0.110 mmol, 75%) as a white solid.

Characterization of Compound (3):

$^1$H NMR (500 MHz, CD$_3$OD) δ 5.68 (dd, B-4, $J_{3,4}$=3.5 Hz, $J_{4,5}$=1.5 Hz, 1H), 5.45 (d, F-1, $J_{1,2}$=3.0 Hz, 1H), 5.27 (dd, D-3, $J_{2,3}$=9.5 Hz, $J_{3,4}$=9.5 Hz, 1H), 5.22 (dd, C-3, $J_{2,3}$=9.5 Hz, $J_{3,4}$=9.5 Hz, 1H), 5.20 (dd, B-3, $J_{2,3}$=10.5 Hz, $J_{3,4}$=3.5 Hz, 1H), 5.15 (dd, E-3, $J_{2,3}$=10.5 Hz, $J_{3,4}$=8.0 Hz, 1H), 5.13 (d, F-3, $J_{2,3}$=10.0 Hz, 1H), 5.05 (dd, B-2, $J_{1,2}$=8.5 Hz, $J_{2,3}$=9.5 Hz, 1H), 5.04 (dd, D-4, $J_{3,4}$=9.5 Hz, $J_{4,5}$=7.5 Hz, 1H), 4.77 (d, D-1, $J_{1,2}$=8.5 Hz, 1H), 4.64 (m, C-1, E-1, 2H), 4.63 (s, B-5, 1H), 4.39 (s, F-5, 1H), 4.33 (dd, D-6, $J_{5,6}$=4.5 Hz, $J_{6,6'}$=12.5 Hz, 1H), 4.17 (dd, D-6', $J_{5,6'}$=2.0 Hz, $J_{6,6'}$=12.0 Hz, 1H), 4.01 (br-d, E-6, $J_{6,6'}$=10.0 Hz, 1H), 3.89 (ddd, D-5, $J_{4,5}$=10.0 Hz, $J_{5,6}$=4.5 Hz, $J_{5,6'}$=2.5 Hz, 1H), 3.81 (dd, E-6', $J_{5,6'}$=6.0 Hz, $J_{6,6'}$=11.5 Hz, 1H), 3.74 (dd, E-2, $J_{1,2}$=9.0 Hz, $J_{2,3}$=10.5 Hz, 1H), 3.68 (dd, E-4, $J_{3,4}$=9.0 Hz, $J_{4,5}$=9.5 Hz, 1H), 3.57-3.63 (m, C-2, C-4, E-5, 3H), 3.49-3.54 (m, F-2, F-5, 2H), 2.57 (s, A-4, A-4', A-5, A-5', 4H), 2.09 (s, Ac, 3H), 2.08 (s, Ac, 3H), 2.06 (s x2, Ac, 6H), 2.02 (s, Ac, 3H), 2.01 (s, Ac, 3H), 2.00 (s, Ac, 3H), 1.96 (s, Ac, 3H), 1.92 (s, Ac, 3H), 1.91 (s, Ac, 3H), 1.89 (s, Ac, 3H), 1.32 (d, C-6, $J_{5,6}$=6.0 Hz, 3H), 1.22 (s, F-4-Me, 3H); $^{13}$C NMR (125 MHz, CD$_3$OD): Compound was decomposed in CD$_3$OD; $^1$H NMR (500 MHz, D$_2$O): δ 5.77 (d, B-4, $J_{3,4}$=3.2 Hz, 1H), 5.54 (d, F-1, $J_{1,2}$=3.7 Hz, 1H), 5.38 (dd, D-3, $J_{2,3}$=9.2 Hz, $J_{3,4}$=9.6 Hz, 1H), 5.32 (dd, B-3, $J_{2,3}$=9.2 Hz, $J_{3,4}$=3.2 Hz, 1H), 5.10-5.20 (m, E-3, 1H), 5.15 (dd, D-4, $J_{3,4}$=9.6 Hz, $J_{4,5}$=8.7 Hz, 1H), 5.14 (dd, C-3, $J_{2,3}$=9.6 Hz, $J_{3,4}$=9.6 Hz, 1H), 5.10 (dd, B-2, $J_{1,2}$=8.2 Hz, $J_{2,3}$=9.2 Hz, 1H), 5.07 (d, B-1, $J_{1,2}$=8.2 Hz, 1H), 5.05 (d, F-3, $J_{2,3}$=10.5 Hz, 1H), 4.89 (d, D-1, $J_{1,2}$=7.8 Hz, 1H), 4.67-4.77 (m, C-1, E-1, 2H), 4.71 (s, B-5, 1H), 4.47 (s, F-5, 1H), 4.46 (dd, D-6, $J_{5,6}$=3.7 Hz, $J_{6,6'}$=12.4 Hz, 1H), 4.28 (dd, D-6', $J_{5,6'}$=4.2 Hz, $J_{6,6'}$=12.4 Hz, 1H), 4.00-4.10 (m, D-5, 1H), 4.04 (br-d, E-6, $J_{6,6'}$=12.3 Hz, 1H) 3.78-4.00 (m, C-2, C-4, E-2, E-4, E-6', 5H), 3.77 (dd, F-2, $J_{1,2}$=3.7 Hz, $J_{2,3}$=10.5 Hz, 1H), 3.67-3.75 (m, E-5, 1H), 3.58-3.67 (m, C-5, 1H), 2.46 (s, A-4, A-4', A-5, A-5', 4H), 2.21 (s, Ac, 3H), 2.18 (s, Ac, 3H), 2.17 (s, Ac, 3H), 2.16 (s, Ac, 3H), 2.14 (s, Ac, 3H), 2.12 (s, Ac, 3H), 2.11 (s, Ac, 3H), 2.08 (s, Ac, 3H), 2.03 (s, Ac, 3H), 2.00 (s, Ac, 3H), 1.99 (s, Ac, 3H), 1.34 (d, C-6, $J_{5,6}$=6.4 Hz, 3H), 1.26 (s, F-4-Me, 3H); $^{13}$C NMR (125 MHz, D$_2$O): δ 199.98, 175.32, 175.08, 174.63, 174.43, 174.26, 173.99, 173.96, 173.86, 173.77, 173.71, 173.53, 173.47, 167.79, 159.15, 110.71, 102.39, 101.73, 101.21, 100.82, 92.64, 80.92, 78.67, 77.01, 75.68, 75.11, 74.56, 74.24, 74.15, 74.07, 74.00, 73.86, 72.83, 72.59, 72.26, 71.87, 71.67, 70.06, 69.88, 69.10, 62.80, 55.64, 54.74, 31.03, 23.03, 22.98, 21.52, 21.23, 21.23, 21.19, 21.15, 21.00, 20.97, 20.91, 20.91, 17.74, 15.68; LRMS (ESI) calcd for C$_{59}$H$_{82}$N$_5$O$_{37}$ [M+H]$^+$ 1452.5. found 1452.5.

Characterization of Compound (2):

N$_1$-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-β-D-glucopyranosyl-(1→6)]-2-acetamido-3-O-acetyl-2-deoxy-(3-D-glucopyranosyl)-(1→2)-3-O-carbamoyl-1-O-{[(R)-2-hydroxy-2-methoxycarbonyl-ethoxy]-methoxyphosphoryl}-4-C-methyl-α-D-glucopyranuronamide (2).

$^1$H NMR (500 MHz, CD$_3$OD): δ 6.04 (dd, F-1, $^3J_{1,P}$=7.0 Hz, $J_{1,2}$=4.0 Hz, 1H), 5.69 (br-s, B-4, 1H), 5.39 (dd, D-3, $J_{2,3}$=10.0 Hz, $J_{3,4}$=9.0 Hz, 1H), 5.10-5.19 (m, B-3, C-3, E-3, F-3, 4H), 5.05 (dd, B-2, $J_{1,2}$=8.0 Hz, $J_{2,3}$=10.0 Hz, 1H), 5.00 (d, B-1, $J_{1,2}$=8.5 Hz, 1H), 4.91 (d, D-1, $J_{1,2}$=8.0 Hz, 1H), 4.87 (dd, D-2, $J_{1,2}$=8.5 Hz, $J_{2,3}$=10.0 Hz, 1H), 4.65 (d, C-1 or E-1, $J_{1,2}$=8.0 Hz, 1H), 4.60 (s, B-5, 1H), 4.59 (d, C-1 or E-1, $J_{1,2}$=8.0 Hz, 1H), 4.44 (m, H-3, 1H), 4.39 (s, F-5, 1H), 4.27-4.34 (m, D-6, H-2, H-3', 3H), 4.15 (dd, D-6', $J_{5,6}$=2.0 Hz, $J_{6,6'}$=12.0 Hz, 1H), 4.08 (ddd, D-5, $J_{4,5}$=10.0 Hz, $J_{5,6}$=4.5 Hz, $J_{5,6'}$=2.0 Hz, 1H), 4.04 (br-d, E-6, $J_{6,6'}$=12.0 Hz, 1H), 3.88 (d, OMe, $^3J_{H,P}$=12.0 Hz, 3H), 3.75-3.83 (m, C-2, E-2, E-6', OMe, 6H), 3.58-3.70 (m, C-4, E-4, E-5, F-2, 4H), 3.48 (dq, C-5, $J_{4,5}$=9.0 Hz, $J_{5,6}$=6.0 Hz, 1H), 2.48 (s, A-4, A-4', A-5, A-5', 4H), 2.08 (s x3, Ac, 9H), 2.05 (s, Ac, 3H), 2.02 (s x2, Ac, 6H), 2.01 (s, Ac, 3H), 1.96 (s, Ac, 3H), 1.92 (s x2, Ac, 6H), 1.90 (s, Ac, 3H), 1.32 (d, C-6, $J_{5,6}$=6.0 Hz, 3H), 1.25 (s, F-4-Me, 3H); $^{13}$C NMR (100 MHz, CD$_3$OD): δ 192.56 (br-s), 173.45, 172.97, 172.48, 171.92, 171.69, 171.57, 171.40, 171.33, 171.21, 171.03, 167.65, 158.58, 112.93, 105.55, 101.97 x2, 101.64, 97.74 (d, $^2J_{C,P}$=5.4 Hz), 81.85, 78.60 (d, d, $^3J_{C,P}$=7.5 Hz), 78.01 (br-s), 76.36, 75.27, 74.72, 74.46, 74.27, 73.90, 73.26, 72.72, 72.16, 71.96, 71.16, 71.08, 70.58, 70.33 (d, $^3J_{C,P}$=5.3 Hz), 69.81, 69.75, 69.30, 63.20, 56.49, 56.45 (d, $^2J_{C,P}$=6.8 Hz), 55.36, 53.06, 30.57 (br-d), 23.08, 23.06, 21.35, 21.10, 20.83, 20.73, 20.58, 20.49, 18.25, 16.62; $^{31}$P NMR (162 MHz, CD$_3$OD): δ−0.97; LRMS (ESI) calcd for C$_{64}$H$_{90}$N$_5$O$_{43}$PNa [M+Na]$^+$ 1670.5. found 1670.5.

Example (I-d)

Characterization of Compound (5)

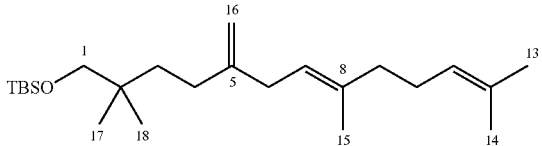

$^1$H NMR (CDCl$_3$, 500 MHz): δ 5.20-5.24 (m, H$_7$, 1H), 5.12-5.16 (m, H$_{11}$, 1H,), 4.74 (br. s, H$_{16}$, 2H), 3.28 (s, H$_1$, 2H,), 2.75 (d, J=7.0 Hz, H$_6$, 2H), 1.96-2.14 (m, H$_4$, H$_9$, H$_{10}$, 6H), 1.72 (s, H$_{15}$, 3H), 1.65 (s, H$_{13}$, 3H), 1.64 (s, H$_{14}$, 3H), 1.37-1.41 (m, H$_3$, 2H), 0.92 (s, 3×(CH$_3$)$_3$CSi, 9H,), 0.87 (s, H$_{17}$, H$_{18}$, 6H), 0.06 (s, (CH$_3$)$_2$Si, 6H); $^{13}$C NMR (CDCl$_3$, 125 MHz) δ 150.5, 136.6, 131.6, 124.6, 122.3, 108.6, 71.7, 40.0, 37.4, 35.4, 35.2, 30.9, 26.9, 26.2, 26.0, 24.3, 18.5, 17.9, 16.2, −5.3; HRFABMS calcd for C$_{24}$H$_{47}$OSi [M+H]$^+$ 379.3396. found 379.3396.

Example (I-e)

Synthesis of (R)-3-(3,4-Dimethoxybenzyloxy)-1-triisopropylsiloxy-2-propanol (7)

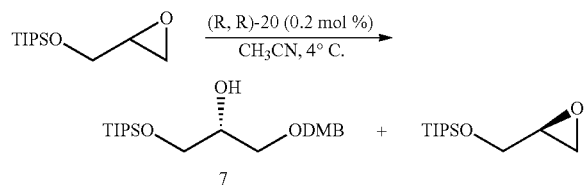

To a mixture of racemic 2,3-epoxy-1-[(triisopropylsilyl)oxy]propane prepared by literature method[1] (2.30 g, 10.0 mmol) and 3,4-dimethoxy benzyl alcohol (0.73 mL, 5.0 mmol) in CH$_3$CN (4 ml) at 4° C. was added (R,R)-20 (1.6 mg, 0.02 mmol) in one portion.

After being stirred 24 h at 4° C., the reaction mixture was concentrated in vacuo. The residue was purified by silica gel chromatography (hexane:ethyl acetate=4:1) to give (R)-3-(3,4-dimethoxybenzyloxy)-1-triisopropylsiloxy-2-propanol (7) (1.735 g, 4.35 mmol, 86%) as a colorless oil.

$^1$H NMR (500 MHz, CDCl$_3$): δ 6.80 (s, Ar—H, 1H), 6.87 (br-d, Ar—H, J=9.0 Hz, 1H), 6.82 (d, Ar—H, J=7.5 Hz, 1H), 4.49 (s, Benzylic-H, 2H), 3.88 (s, OMe, 3H), 3.87 (s, OMe, 3H), 3.86 (m, H-2, 1H), 3.74 (m, H-1, 2H), 3.53 (m, H-3, 2H), 2.53 (br-s, OH, 1H), 1.10 (septet, isopropyl-H, J=6.5 Hz, 3H), 1.05 (d, isopropyl-Me, J=6.0 Hz, 18H); $^{13}$C NMR (125 MHz, CDCl$_3$): δ 148.98, 148.62, 130.61, 120.38, 111.06, 110.83, 73.37, 70.79, 70.72, 64.28, 55.90, 55.78, 17.92, 11.85; HRMS (ESI) calcd for C$_{21}$H$_{42}$NO$_5$Si [M+NH$_4$]$^+$ 416.2832. found 416.2836; LRMS (ESI) calcd for C$_{21}$H$_{42}$NO$_5$Si [M+NH$_4$]$^+$ 416.3. found 416.5.

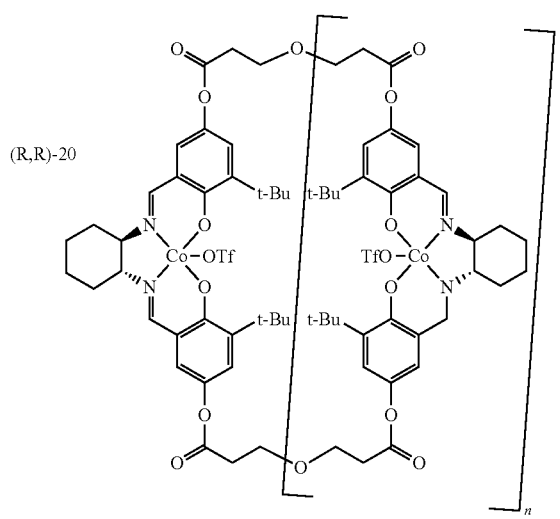

(R,R)-20 n=1-6

Example (I-f)

Synthesis of (R)-3-(3,4-Dimethoxybenzyloxy)-1-triisopropylsiloxy-2-[(2Z,6E,13E)-3,8,8,14,18-pentamethyl-11-methylene-nonadeca-2,6,13,17-tetraen-1-yloxy]-propane (8)

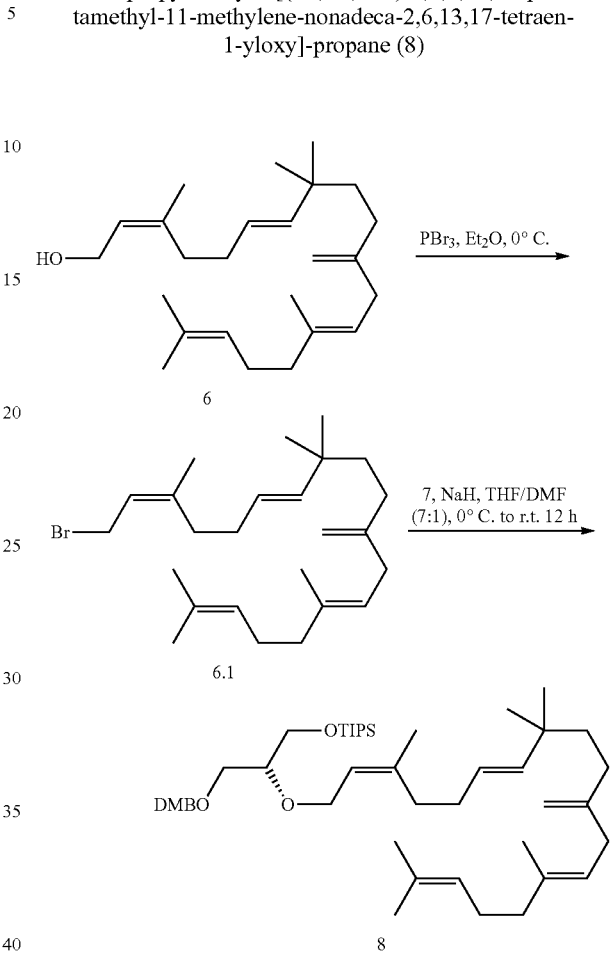

To a solution of moenocinol (6) (28.0 mg, 74.3 μmol, 1.00 eq.) in dry diethyl ether (3.00 mL) was added phosphorus tribromide (2.90 μL, 31.2 μmol, 0.42 eq.) at 0° C. After being stirred at the same temperature for 1 h, the reaction mixture was poured into ice-cooled water. The aqueous layer was extracted with two portions of diethyl ether:hexane (1:1). The combined extract was washed with water, dried over MgSO$_4$, filtered and concentrated in vacuo to give the crude bromide (6.1) (26.1 mg, 59.4 μmol, 80%). This unstable intermediate was used immediately without further purification.

To a suspension of 95% sodium hydride (13.5 mg, 53.4 μmol, 9.00 eq.), washed twice with dry hexane, in dry tetrahydrofuran (0.35 mL) and dry N,N-dimethylformamide (0.05 mL) was added a solution of (R)-3-(3,4-dimethoxybenzyloxy)-1-triisopropylsiloxy-2-propanol (7) (71.0 mg, 0.178 mmol, 3.00 eq.) in dry tetrahydrofuran (0.35 mL) and dry N,N-dimethylformamide (0.05 mL) at 0° C. The reaction mixture was stirred at the same temperature for 30 min. Then a solution of above bromide (6.1) (26.1 mg, 59.4 μmol, 1.00 eq.) in dry tetrahydrofuran (0.35 mL) and dry N,N-dimethylformamide (0.05 mL) was added to the reaction mixture at 0° C. After being stirred at room temperature for 12 h, the reaction mixture was poured into saturated aq. NH$_4$Cl at 0° C. The aqueous layer was extracted with two portions of diethyl ether. The combined extract was washed with brine, dried over Na$_2$SO$_4$, filtered and concentrated in vacuo. The residue was purified by silica gel chromatography (hexane:diethyl ether=91:9, 0.5% NEt$_3$) to give (R)-3-(3,4-dimethoxybenzyloxy)-1-triisopropylsiloxy-2-[(2Z,6E,13E)-3,8,8,14,18-pentamethyl-11-methylene-nonadeca-2,6,13,17-tetraen-1-yloxy]-propane (8) (28.5 mg, 39.3 μmol, 66%) as a colorless oil.

$^1$H NMR (500 MHz, CDCl$_3$): δ 6.89 (d, Ar—H, J=2.2 Hz, 1H), 6.86 (dd, Ar—H, J=8.0 Hz, J=1.5 Hz, 1H), 6.81 (d, Ar—H, J=8.5 Hz, 1H), 5.37 (t, I-2, $J_{1,2}$=7.0 Hz, 1H), 5.34 (d, I-7, $J_{6,7}$=15.5 Hz, 1H), 5.24 (dt, I-6, $J_{5,6}$=15.0 Hz, $J_{6,7}$=6.5 Hz, 1H), 5.17 (t, I-13, $J_{12,13}$=6.5 Hz, 1H), 5.10 (t, I-17, $J_{16,17}$=5.5 Hz, 1H), 4.68 (s, I-22, 2H), 4.52 (d, benzylic-H, $J_{gem}$=11.5 Hz, 1H), 4.46 (d, benzylic-H, $J_{gem}$=11.5 Hz, 1H), 4.15 (m, I-1, 2H), 3.88 (s, OMe, 3H), 3.87 (s, OMe, 3H), 3.74 (m, H-1, 2H), 3.62 (dd, H-3, $J_{2,3}$=4.0 Hz, $J_{3,3'}$=9.5 Hz, 1H), 3.56 (m, H-2, 1H), 3.50 (dd, H-3' $J_{2,3'}$=5.0 Hz, $J_{3,3'}$=9.5 Hz, 1H), 2.68 (d, I-12, $J_{12,13}$=7.5 Hz, 2H), 2.01-2.12 (m, I-4, I-4', I-5, I-5', I-15, I-15', I-16, I-16', 8H), 1.89 (m, I-10, 2H), 1.82 (s, I-25, 3H), 1.67 (s, I-19, 3H), 1.60 (s, I-20, I-21, 6H), 1.38 (m, I-9, 1H), 1.04-1.12 (isopropyl-H, isopropyl-Me, 21H), 0.95 (s, I-23, I-24, 6H); $^{13}$C NMR (125 MHz, CDCl$_3$): δ 150.02, 148.92, 148.44, 140.38, 139.61, 136.39, 131.37, 131.05, 125.44, 124.29, 122.47, 121.95, 120.17, 110.94, 110.77, 108.31, 78.79, 73.26, 70.08, 66.67, 63.28, 55.88, 55.74, 41.45, 39.78, 35.49, 34.93, 32.53, 31.46, 31.37, 27.27, 26.68, 25.71, 23.59, 17.97, 17.68, 15.93, 11.89; HRMS (ESI) calcd for C$_{46}$H$_{82}$NO$_5$Si [M+NH$_4$]$^+$ 756.5962. found 756.5993; LRMS (ESI) calcd for C$_{46}$H$_{82}$NO$_5$Si [M+NH$_4$]$^+$ 756.6. found 756.6.

Example (I-g)

Synthesis of (S)-3-(3,4-Dimethoxybenzyloxy)-2-[(2Z,6E,13E)-3,8,8,14,18-pentamethyl-11-methylene-nonadeca-2,6,13,17-tetraen-1-yloxy]-1-propanol (9)

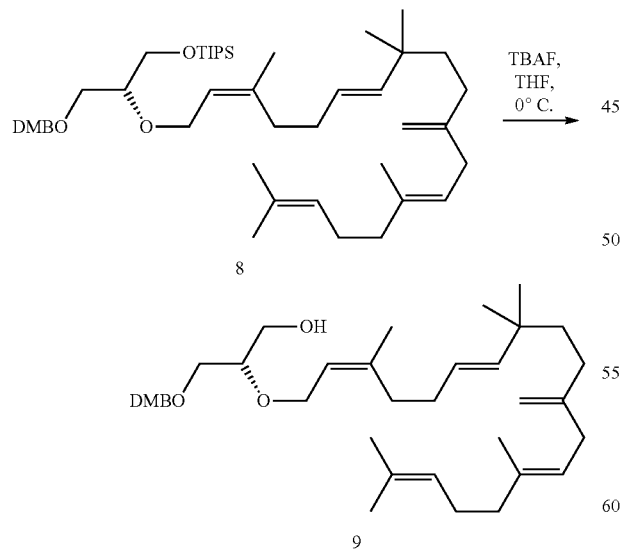

To a solution of (R)-3-(3,4-dimethoxybenzyloxy)-1-triisopropylsiloxy-2-[(2Z,6E,13E)-3,8,8,14,18-pentamethyl-11-methylene-nonadeca-2,6,13,17-tetraen-1-yloxy]-propane (8) (20.0 mg, 27.3 μmol, 1.00 eq.) in dry tetrahydrofuran (0.55 mL) was added 1 M tetrabutylammonium fluoride solution in tetrahydrofuran (41 μL, 40.9 μmol, 1.50 eq.) at 0° C. After being stirred at the same temperature for 1 h, the reaction mixture was poured into brine. The aqueous layer was extracted with two portions of ethyl acetate. The combined extract was washed with brine, dried over Na$_2$SO$_4$, filtered and concentrated in vacuo. The residue was purified by silica gel chromatography (hexane:ethyl acetate=55:45) to give (S)-3-(3,4-dimethoxybenzyloxy)-2-[(2Z,6E,13E)-3,8,8,14,18-pentamethyl-11-methylene-nonadeca-2,6,13,17-tetraen-1-yloxy]-1-propanol (9) (15.4 mg, 26.4 μmol, 97%) as a colorless oil.

$^1$H NMR (500 MHz, CDCl$_3$): δ 6.87 (s, Ar—H, 1H), 6.86 (dd, Ar—H, J=10.0 Hz, J=1.5 Hz, 1H), 5.34-5.37 (m, I-2, I-7, 2H), 5.23 (dt, I-6, $J_{5,6}$=15.5 Hz, $J_{6,7}$=6.5 Hz, 1H), 5.16 (t, I-13, $J_{12,13}$=6.0 Hz, 1H), 5.10 (t, I-17, $J_{16,17}$=7.0 Hz, 1H), 4.68 (br-s, I-22, 2H), 4.48 (s, benzylic-H, 2H), 4.29 (dd, I-1, $J_{1,1'}$=11.5 Hz, $J_{1,2}$=7.0 Hz, 1H), 4.07 (dd, I-1', $J_{1,1'}$=11.5 Hz, $J_{1',2}$=5.0 Hz, 1H), 3.88 (s, OMe, 3H), 3.87 (s, OMe, 3H), 3.73 (dd, H-1, $J_{1,1'}$=11.0 Hz, $J_{1,2}$=2.5 Hz, 1H), 3.63 (dd, H-1', $J_{1,1'}$=11.0 Hz, $J_{1',2}$=5.0 Hz, 1H), 3.51-3.60 (m, H-2, H-3, H-3', 3H), 2.68 (d, I-12, $J_{12,13}$=7.5 Hz, 2H), 2.00-2.10 (m, OH, I-4, I-4', I-5, I-5', I-15, I-15', I-16, I-16', 9H), 1.89 (m, I-10, 2H), 1.73 (s, I-25, 3H), 1.67 (s, I-19, 3H), 1.60 (s, I-20, I-21, 6H), 1.37 (m, I-9, 2H), 0.95 (s, I-23, I-24, 6H); $^{13}$C NMR (125 MHz, CDCl$_3$): δ 150.01, 149.00, 148.62, 140.56, 136.41, 131.37, 130.50, 125.24, 124.27, 121.92, 121.76, 120.24, 110.91, 110.83, 77.50, 73.42, 69.83, 66.27, 62.89, 55.88, 55.80, 41.43, 39.70, 35.52, 34.92, 32.49, 31.39, 31.36, 27.26, 26.56, 25.69, 23.55, 17.67, 15.92; HRMS (ESI) calcd for C$_{37}$H$_{62}$NO$_5$ [M+NH$_4$]$^+$ 600.4628. found 600.4631; LRMS (ESI) calcd for C$_{37}$H$_{62}$NO$_5$ [M+NH$_4$]$^+$ 600.5. found 600.5.

Example (I-h)

Methyl (R)-3-(3,4-Dimethoxybenzyloxy)-2-[(2Z,6E,13E)-3,8,8,14,18-pentamethyl-11-methylene-nonadeca-2,6,13,17-tetraen-1-yloxy]-propanoate (10)

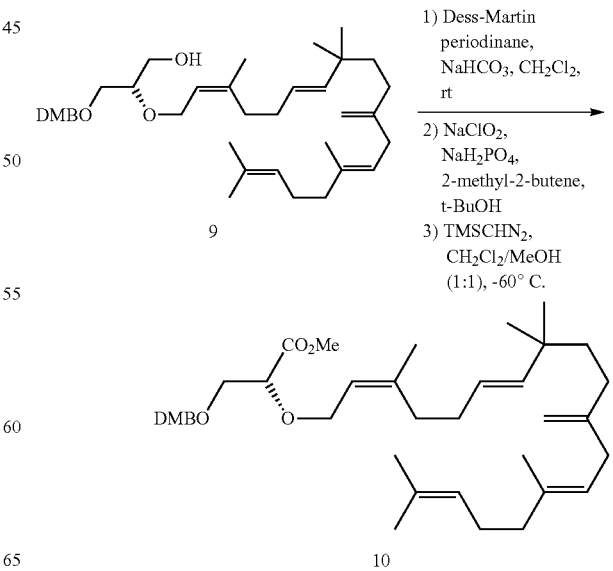

To a solution of (S)-3-(3,4-dimethoxybenzyloxy)-2-[(2Z,6E,13E)-3,8,8,14,18-pentamethyl-11-methylene-nonadeca-2,6,13,17-tetraen-1-yloxy]-1-propanol (9) (16.0 mg, 27.3 μmol, 1.00 eq.) in dry dichloromethane (0.82 mL) was added sodium bicarbonate (23.0 mg, 0.273 mmol, 10.0 eq.) and Dess-Martin periodinane (13.9 mg, 32.7 μmol, 1.20 eq.) at 0° C. After being stirred at the same temperature for 90 min, the reaction mixture was diluted with diethyl ether and treated with a mixture of saturated aq. $Na_2S_2O_3$ and saturated aq. $NaHCO_3$. After being stirred at 0° C. for 30 min, the reaction mixture was extracted with two portions of ethyl acetate. The combined extract was washed with brine, dried over $Na_2SO_4$, filtered and concentrated in vacuo. The residue was used for the next reaction without further purification.

To a solution of the residue in tert-butyl alcohol (190 μL) was added 2-methyl-2-butene (20 μL, 0.191 mmol, 7.00 eq.), a solution of $NaClO_2$ (6.20 mg, 54.6 μmol, 2.00 eq.) and $NaH_2PO_4$ (11.3 mg, 81.9 μmol, 3.00 eq.) in water (82.0 μL) at room temperature. After being stirred at the same temperature for 90 min, the reaction mixture was diluted with ethyl acetate and treated with 1N HCl at 0° C. The reaction mixture was extracted with two portions of ethyl acetate. The combined extract was washed with brine, dried over $Na_2SO_4$, filtered and concentrated in vacuo. The residue was used for the next reaction without further purification.

To a solution of the residue in dry methanol (250 μL) and dry dichloromethane (250 μL) was added 2 M (trimethylsilyl) diazomethane solution in hexane (20.5 μL, 41.0 μmol, 1.50 eq.) at −60° C. After being stirred at the same temperature for 30 min, the reaction mixture was quenched by addition of acetic acid (20 μL), allowed to warm to room temperature and treated with saturated aq. $NaHCO_3$ at 0° C. The reaction mixture was extracted with two portions of ethyl acetate. The combined extract was washed with brine, dried over $Na_2SO_4$, filtered and concentrated in vacuo. The residue was purified by silica gel chromatography (hexane:diethyl ether=70:30) to give methyl (R)-3-(3,4-dimethoxybenzyloxy)-2-[(2Z,6E,13E)-3,8,8,14,18-pentamethyl-11-methylene-nonadeca-2,6,13,17-tetraen-1-yloxy]-propanoate (10) (9.50 mg, 15.6 μmol, 57% in 3 steps) as a colorless oil.

$^1$H NMR (500 MHz, $CDCl_3$): δ 6.81-6.88 (m, Ar—H, 3H), 5.37 (t, I-2, $J_{1,2}$=6.5 Hz, 1H), 5.36 (d, I-7, $J_{6,7}$=15.5 Hz, 1H), 5.23 (dt, I-6, $J_{5,6}$=6.0 Hz, $J_{6,7}$=15.5 Hz, 1H), 5.16 (t, I-13, $J_{12,13}$=7.5 Hz, 1H), 5.10 (t, I-17, $J_{16,17}$=7.0 Hz, 1H), 4.68 (br-s, I-22, 2H), 4.53 (d, benzylic-H, $J_{gem}$=12.0 Hz, 1H), 4.49 (d, benzylic-H, $J_{gem}$=12.0 Hz, 1H), 4.16 (dd, I-1, $J_{1,1'}$=11.0 Hz, $J_{1,2}$=6.0 Hz, 1H), 4.12 (t, H-2, $J_{2,3}$=5.0 Hz, 1H), 4.01 (dd, I-1', $J_{1,1'}$=12.0 Hz, $J_{1',2}$=7.5 Hz, 1H), 3.88 (s, OMe, 3H), 3.87 (s, OMe, 3H), 3.74 (s, OMe, 3H), 3.71 (d, H-3, $J_{2,3}$=5.0 Hz, 2H), 2.68 (d, I-12, $J_{12,13}$=7.5 Hz, 2H), 2.00-2.10 (m, I-4, I-4', I-5, I-5', I-15, I-15', I-16, I-16', 8H), 1.88 (m, I-10, 2H), 1.73 (s, I-25, 3H), 1.67 (s, I-19, 3H), 1.60 (s, I-20, I-21, 6H), 1.36 (m, I-9, 2H), 0.95 (s, I-23, I-24, 6H); $^{13}$C NMR (125 MHz, $CDCl_3$): δ 171.46, 150.02, 148.98, 148.59, 141.33, 140.53, 136.42, 131.39, 130.42, 125.28, 124.29, 121.93, 121.03, 120.29, 111.03, 110.76, 108.32, 77.65, 73.34, 70.18, 66.88, 55.90, 55.80, 51.98, 41.43, 39.78, 35.52, 34.93, 32.45, 31.38, 27.26, 26.67, 25.71, 23.59, 17.68, 15.93; HRMS (ESI) calcd for $C_{38}H_{62}NO_6$ $[M+NH_4]^+$ 628.4577. found 628.4595; LRMS (ESI) calcd for $C_{38}H_{62}NO_6$ $[M+NH_4]^+$ 628.4. found 628.4.

Example (I-i)

Synthesis of Methyl (R)-3-hydroxy-2-[(2Z,6E,13E)-3,8,8,14,18-pentamethyl-11-methylene-nonadeca-2,6,13,17-tetraen-1-yloxy]-propanoate (11)

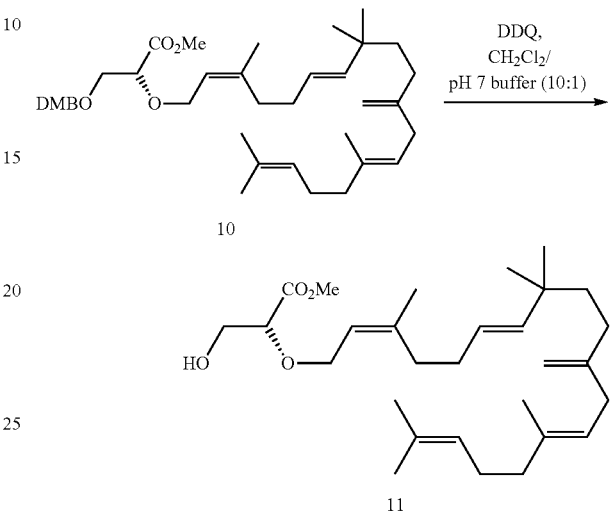

To a solution of methyl (R)-3-(3,4-dimethoxybenzyloxy)-2-[(2Z,6E,13E)-3,8,8,14,18-pentamethyl-11-methylene-nonadeca-2,6,13,17-tetraen-1-yloxy]-propanoate (10) (9.00 mg, 14.7 μmol, 1.00 eq.) in dichloromethane (2.00 mL) and phosphate buffer (0.20 mL, pH=7) was added 2,3-dichloro-5,6-dicyano-1,4-benzoquinone (5.00 mg, 22.1 μmol, 1.50 eq.) at 5° C. After being stirred at the same temperature for 1 h, the reaction mixture was diluted with dichloromethane and treated with saturated aq. $NaHCO_3$ at 0° C. The reaction mixture was extracted with two portions of dichloromethane. The combined extract was washed with saturated aq. $NaHCO_3$, brine, dried over $Na_2SO_4$, filtered and concentrated in vacuo. The residue was purified by silica gel chromatography (hexane:diethyl ether=89:11) to give methyl (R)-3-hydroxy-2-[(2Z,6E,13E)-3,8,8,14,18-pentamethyl-11-methylene-nonadeca-2,6,13,17-tetraen-1-yloxy]-propanoate (11) (4.10 mg, 8.89 μmol, 61%) as a colorless oil and recover (10) (3.10 mg, 5.12 μmol, 34%).

$^1$H NMR (500 MHz, $CDCl_3$): δ 5.38 (t, I-2, $J_{1,2}$=6.5 Hz, 1H), 5.36 (d, I-7, $J_{6,7}$=15.5 Hz, 1H), 5.24 (dt, I-6, $J_{5,6}$=6.5 Hz, $J_{6,7}$=15.5 Hz, 1H), 5.17 (t, I-13, $J_{12,13}$=7.5 Hz, 1H), 5.10 (t, I-17, $J_{16,17}$=7.5 Hz, 1H), 4.68 (br-s, I-22, 2H), 4.23 (dd, I-1, $J_{1,1'}$=12.0 Hz, $J_{1,2}$=7.5 Hz, 1H), 4.04 (m, H-2, 1H), 4.02 (dd, I-1', $J_{1,1'}$=11.0 Hz, $J_{1',2}$=7.5 Hz, 1H), 3.78-3.89 (m, H-3, 2H), 3.77 (s, OMe, 3H), 2.69 (d, I-12, $J_{12,13}$=7.5 Hz, 1H), 2.01-2.14 (m, OH, I-4, I-4', I-5, I-5', I-15, I-15', I-16, I-16', 9H), 1.89 (m, I-10, 2H), 1.76 (s, I-25, 3H), 1.68 (s, I-19, 3H), 1.60 (s, I-20, I-21, 6H), 1.38 (m, I-9, 2H), 0.96 (s, I-23, I-24, 6H); $^{13}$C NMR (125 MHz, $CDCl_3$): δ 171.30, 150.04, 141.98, 140.65, 136.44, 131.40, 125.18, 124.29, 121.34, 120.66, 108.34, 78.19, 66.95, 63.45, 52.10, 41.44, 39.78, 35.54, 34.94, 32.43, 31.37, 27.27, 26.66, 25.71, 23.59, 17.68, 15.94; HRMS (ESI) calcd for $C_{29}H_{52}NO_4$ $[M+NH_4]^+$ 478.3896. found 478.3877; LRMS (ESI) calcd for $C_{29}H_{52}NO_4$ $[M+NH_4]^+$ 478.4. found 478.5.

Example (I-j)

Synthesis of $N_1$-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl)-(1→2)-3-O-carbamoyl-1-O-(hydrogen phosphonate)-4-C-methyl-α-D-glucopyranuronamide, Ammonium Salt (12)

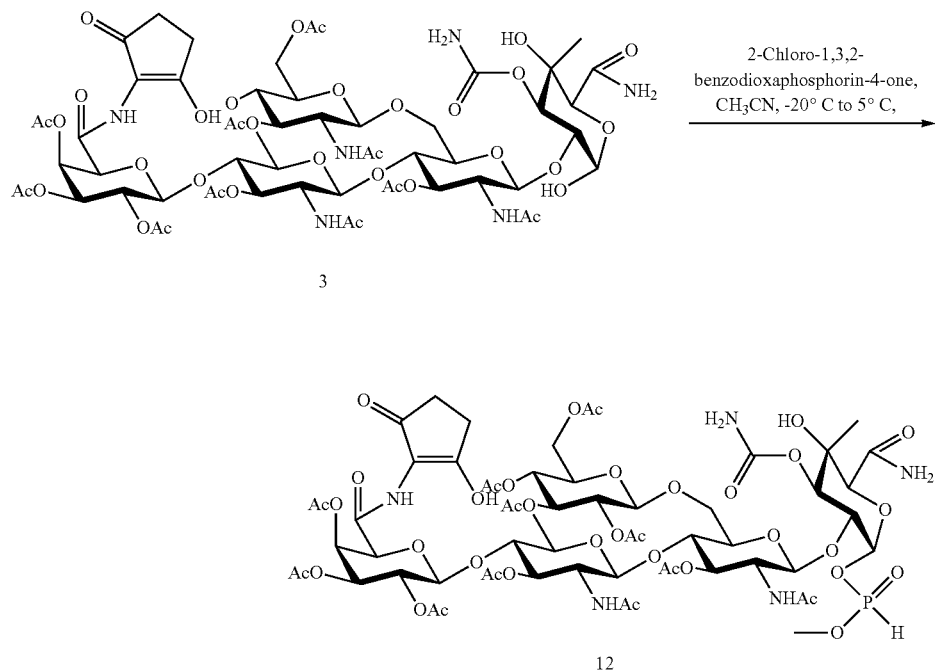

To a solution of nonaacetyl moenomycin A pentasaccharide lactol (3) (41.0 mg, 28.2 μmol, 1.00 eq.) in dry pyridine (3.00 mL) and dry acetonitrile (3.00 mL) was added 2 M 2-chloro-4H-1,3,2-benzodioxaphosphorin-4-one solution in dry acetonitrile (25 μL, 50.8 μmol, 1.80 eq.) at −20° C. After being stirred for 5 min, the reaction mixture was allowed to warm to −5° C. over 30 min. Then water was added to the reaction mixture at 0° C. After being stirred for 1 h at the same temperature, the reaction mixture was concentrated in vacuo. The residue was purified by reverse-phase HPLC (gradient 0-90% acetonitrile/water with 0.1% $NH_4HCO_3$ over 60 min) to give nonaacetyl moenomycin A pentasaccharide H-phosphonate (12) (36.7 mg, 24.0 μmol, 85%) as a white solid.

$^1$H NMR (500 MHz, $D_2O$): δ 6.90 (d, H-phosphonate, $J_{H,P}$=655 Hz, 1H), 5.78 (dd, F-1, $^3J_{1,P}$=9.0 Hz, $J_{1,2}$=3.5 Hz, 1H), 5.75 (dd, B-4, $J_{3,4}$=3.0 Hz, $J_{4,5}$=1.0 Hz, 1H), 5.36 (dd, D-3, $J_{2,3}$=9.0 Hz, $J_{3,4}$=9.5 Hz, 1H), 5.29 (dd, B-3, $J_{2,3}$=10.0 Hz, $J_{3,4}$=3.5 Hz, 1H), 5.15 (dd, E-3, $J_{2,3}$=9.5 Hz, $J_{3,4}$=9.5 Hz, 1H), 5.12 (dd, D-4, $J_{3,4}$=9.5 Hz, $J_{4,5}$=10.0 Hz, 1H), 5.04-5.09 (m, B-1, B-2, C-3, 3H), 5.03 (d, F-3, $J_{2,3}$=10.5 Hz, 1H), 4.97 (dd, D-2, $J_{1,2}$=8.0 Hz, $J_{2,3}$=9.0 Hz, 1H), 4.93 (d, D-1, $J_{1,2}$=8.0 Hz, 1H), 4.76 (d, E-1, $J_{1,2}$=9.0 Hz, 1H), 4.71 (d, C-1, $J_{1,2}$=7.0 Hz, 1H), 4.70 (s, B-5, 1H), 4.49 (s, F-5, 1H), 4.45 (dd, D-6, $J_{5,6}$=3.5 Hz, $J_{6,6'}$=12.5 Hz, 1H), 4.25 (dd, D-6', $J_{5,6'}$=1.0 Hz, $J_{6,6'}$=12.0 Hz, 1H), 4.10 (ddd, D-5, $J_{4,5}$=10.0 Hz, $J_{5,6}$=3.5 Hz, $J_{5,6'}$=1.0 Hz, 1H), 3.99 (br-d, E-6, $J_{6,6'}$=11.5 Hz, 1H), 3.92 (dd, E-6', $J_{5,6'}$=7.5 Hz, $J_{6,6'}$=12.0 Hz, 1H), 3.74-3.84 (m, C-2, C-4, E-2, E-4, F-2, 5H), 3.70 (ddd, E-5, $J_{4,5}$=9.5 Hz, $J_{5,6}$=7.0 Hz, $J_{5,6'}$=1.5 Hz, 1H), 3.62 (dq, C-5, $J_{4,5}$=9.5 Hz, $J_{5,6}$=6.0 Hz, 1H), 2.64 (s, A-4, A-4', A-5, A-5', 4H), 2.16 (s, Ac, 3H), 2.15 (s, Ac, 3H), 2.15 (s, Ac, 3H), 2.13 (s, Ac, 3H), 2.10 (s, Ac, 3H), 2.09 (s, Ac, 3H), 2.08 (s, Ac, 3H), 2.04 (s, Ac, 3H), 2.01 (s, Ac, 3H), 1.98 (s, Ac, 3H), 1.95 (s, Ac, 3H), 1.29 (d, C-6, $J_{5,6}$=6.0 Hz, 3H), 1.24 (s, F-4-Me, 3H); $^{13}$C NMR (125 MHz, $D_2O$): δ 198.38, 176.95, 176.50, 176.18, 175.82, 175.78, 175.67, 175.62, 175.57, 175.34, 169.83, 160.90, 113.89, 103.61, 103.35, 102.89, 102.49, 95.53 (br-s), 82.62, 79.28 (br-d, $^3J_{C,P}$=6.0 Hz), 79.00, 77.18, 76.75, 76.72, 76.07, 75.74, 75.48, 75.40, 75.32, 74.39, 73.71, 73.32, 73.09, 72.20, 70.75, 70.67, 64.26, 56.98, 56.55, 31.37, 24.46, 24.46, 24.39, 22.92, 22.66, 22.62, 22.59, 22.42, 22.37, 22.29, 22.23, 19.17, 17.18; $^{31}$P NMR (162 MHz, $CD_3OD$): δ 5.48; LRMS (ESI) calcd for $C_{59}H_{81}N_5O_{39}P$ [M−$NH_3$—H]$^-$ 1514.4. found 1514.4.

Example (I-k)

Synthesis of N₁-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-13-D-glucopyranosyl-(1→6)]-2-acetamido-3-O-acetyl-2-deoxy-β-D-glucopyranosyl)-(1→2)-3-O-carbamoyl-1-O-{[(R)-2-methoxycarbonyl-2-((2Z,6E,13E)-3,8,8,14,18-pentamethyl-11-methylene-nonadeca-2,6,13,17-tetraen-1-yloxy)-ethoxy]-hydroxyphosphoryl}-4-C-methyl-α-D-glucopyranuronamide, Ammonium Salt (12.1)

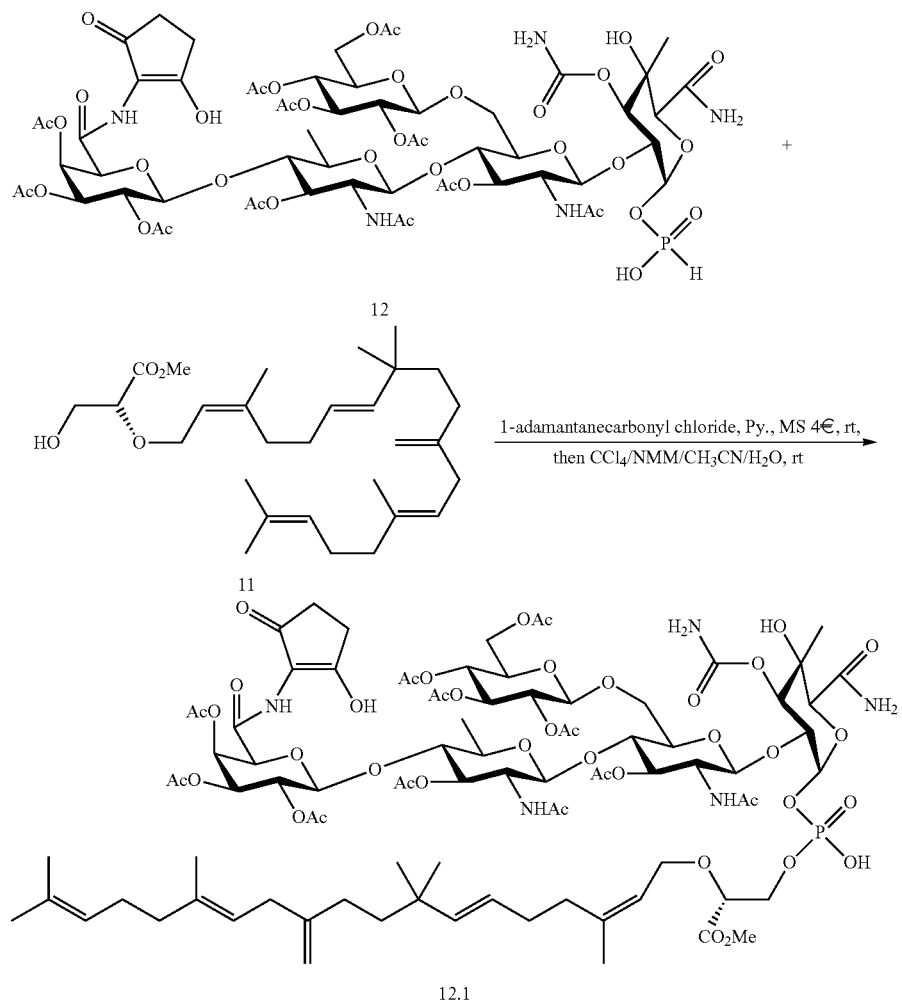

A mixture of nonaacetyl moenomycin A pentasaccharide H-phosphonate (12) (8.00 mg, 5.28 μmol, 1.20 eq.), methyl (R)-3-hydroxy-2-[(2Z,6E,13E)-3,8,8,14,18-pentamethyl-11-methylene-nonadeca-2,6,13,17-tetraen-1-yloxy]-propanoate (11) (2.10 mg, 4.40 μmol, 1.00 eq.) and pulverized activated MS-4 Å in dry pyridine (0.90 mL) was stirred at room temperature for 30 min to remove a trace of water. Then 1-adamantanecarbonyl chloride (5.30 mg, 26.4 μmol, 6.00 eq.) was added to the reaction mixture at the same temperature. After being stirred for 2 h, the reaction mixture was treated with carbon tetrachloride (0.50 mL), 4-methylmorpholine (0.20 mL), acetonitrile (0.20 mL) and water (0.20 mL) at the same temperature. After being stirred for 2 h, the reaction mixture was filtered and concentrated in vacuo. The residue was purified by reversed-phase HPLC (gradient 0-70% acetonitrile/water with 0.1% NH₄HCO₃ over 70 min) to give nonaacetyl moenomycin A pentasaccharide phosphonate diester (12.1) (5.40 mg, 2.71 μmol, 62%) as a white solid and lactol (2) (2.20 mg, 1.51 μmol, 34%).

Synthetic Compound: $^1$H NMR (500 MHz, CD$_3$OD): δ 5.79 (dd, F-1, $^3J_{1,P}$=7.0 Hz, $J_{1,2}$=3.5 Hz, 1H), 5.70 (dd, B-4, $J_{3,4}$=3.5 Hz, $J_{4,5}$=1.0 Hz, 1H), 5.40 (t, I-2, $J_{1,2}$=5.0 Hz, 1H), 5.38 (d, I-7, $J_{6,7}$=16.0 Hz, 1H), 5.33 (dd, D-3, $J_{2,3}$=9.0 Hz, $J_{3,4}$=9.5 Hz, 1H), 5.30 (dt, I-6, $J_{5,6}$=6.5 Hz, $J_{6,7}$=15.5 Hz, 1H), 5.08-5.20 (m, B-3, C-2, E-2, F-3, I-13, I-17, 6H), 5.05 (dd, B-2, $J_{1,2}$=8.0 Hz, $J_{2,3}$=10.5 Hz, 1H), 5.04 (dd, D-4, $J_{3,4}$=9.5 Hz, $J_{4,5}$=9.5 Hz, 1H), 4.94 (d, D-1, $J_{1,2}$=8.0 Hz, 1H), 4.90 (d, B-1, $J_{1,2}$=8.0 Hz, 1H), 4.87 (m, D-2, 1H), 4.67 (m, C-1 or E-1, I-22, I-22', 3H), 4.59 (d, C-1 or E-1, $J_{1,2}$=8.0 Hz, 1H), 4.53 (br-s, B-5, 1H), 4.48 (s, F-5, 1H), 4.39 (dd, D-6, $J_{5,6}$=4.0 Hz, $J_{6,6'}$=12.0 Hz, 1H), 4.15-4.25 (m, D-6', H-2, H-3, H-3', I-1, 5H), 4.10 (dd, I-1', $J_{1,1'}$=12.0 Hz, $J_{1,2}$=7.0 Hz, 1H), 4.07 (ddd, D-5, $J_{4,5}$=10.0 Hz, $J_{5,6}$=3.5 Hz, $J_{5,6'}$=2.0 Hz, 1H), 4.03 (br-d, E-6, $J_{6,6'}$=12.0 Hz, 1H), 3.85 (dd, E-6', $J_{5,6'}$=6.0 Hz, $J_{6,6'}$=11.5 Hz, 1H), 3.76-3.82 (m, OMe, C-2 or E-2, 4H), 3.55-3.68 (m, C-2 or E-2, C-4, E-4, E-5, F-2, 5H), 3.48 (dq, C-5, $J_{4,5}$=9.0 Hz, $J_{5,6}$=6.0 Hz, 1H), 2.69 (d, I-12, $J_{12,13}$=7.5 Hz, 1H), 2.38 (s, A-4, A-4', A-5, A-5', 4H), 2.00-2.14 (m, Ac x7, I-4, I-4', I-5, I-5', I-15, I-15', I-16, I-16', 29H), 1.89-1.94 (m, Ac x4, I-10, I-10', 14H), 1.76 (s, I-25, 3H), 1.66 (s, I-19, 3H), 1.61 (s, I-21, 3H), 1.60 (s, I-20, 3H), 1.38 (m, I-9, 2H), 1.34 (d, C-6, $J_{5,6}$=6.5 Hz, 1H), 1.24 (s, F-4-Me, 3H), 0.97 (s, I-23, I-24, 6H); $^{13}$C NMR (125 MHz, CD$_3$OD): δ 175.23, 173.94, 173.82, 173.28, 172.93, 172.84, 172.16, 172.00, 171.90, 171.73, 171.71, 171.65, 171.29, 167.81, 159.30, 151.42, 142.44, 141.88, 137.62, 132.45, 127.07, 125.61, 123.73, 122.85, 111.88, 109.42, 103.15, 102.16, 102.04, 101.70, 95.92 (br-s), 81.59, 78.72 (d, $^3J_{C,P}$=8.0 Hz), 78.57 (d, $^3J_{C,P}$=7.3 Hz), 77.69, 76.77, 76.12, 74.67, 74.59, 74.46, 74.37, 73.59, 73.40, 72.81, 72.41, 72.16, 70.82, 69.78, 69.39, 67.93, 67.24, 63.12, 56.58, 55.70, 52.80, 42.86, 40.87, 36.46, 35.93, 33.43, 32.57, 32.31, 31.15 (br-s), 27.81, 27.67, 25.88, 23.05, 23.00, 21.32, 21.13, 21.11, 20.80, 20.70, 20.56, 20.54, 20.50, 20.41, 18.20, 17.70, 16.63, 16.04; $^{31}$P NMR (162 MHz, CD$_3$OD): δ −1.16; LRMS (ESI) calcd for C$_{88}$H$_{128}$N$_5$O$_{43}$PNa [M−NH$_3$+Na]$^+$ 1996.7. found 1996.7.

Authentic Compound (by demethylation using PhSH). $^1$H NMR (500 MHz, CD$_3$OD): δ 5.79 (dd, F-1, $^3J_{1,P}$=7.0 Hz, $J_{1,2}$=3.5 Hz, 1H), 5.67 (dd, B-4, $J_{3,4}$=3.5 Hz, $J_{4,5}$=1.5 Hz, 1H), 5.39 (d, I-7, $J_{6,7}$=16.5 Hz, 1H), 5.33 (dd, D-3, $J_{2,3}$=9.5 Hz, $J_{3,4}$=9.5 Hz, 1H), 5.29 (dt, I-6, $J_{5,6}$=9.0 Hz, $J_{6,7}$=16.0 Hz, 1H), 5.20 (dd, B-3, $J_{2,3}$=10.0 Hz, $J_{3,4}$=3.5 Hz, 1H), 5.19 (m, C-2, E-2, 2H), 5.08-5.15 (m, F-3, I-13, I-17, 3H), 5.06 (dd, B-2, $J_{1,2}$=8.5 Hz, $J_{2,3}$=9.5 Hz, 1H), 5.04 (dd, D-4, $J_{3,4}$=9.5 Hz, $J_{4,5}$=10.5 Hz, 1H), 4.96 (d, D-1, $J_{1,2}$=10.5 Hz, 1H), 4.93 (d, B-1, $J_{1,2}$=8.5 Hz, 1H), 4.88 (m, D-2, 1H), 4.70 (d, C-1 or E-1, $J_{1,2}$=8.5 Hz, 1H), 4.67 (d, I-22, J=5.0 Hz, 2H), 4.62 (d, B-5, $J_{4,5}$=1.0 Hz, 1H), 4.58 (d, C-1 or E-1, $J_{1,2}$=8.0 Hz, 1H), 4.47 (s, F-5, 1H), 4.39 (dd, D-6, $J_{5,6}$=4.0 Hz, $J_{6,6'}$=12.5 Hz, 1H), 4.13-4.24 (m, D-6', H-2, H-3, H-3', I-1, 5H), 4.07-4.11 (m, D-5, I-1', 2H), 4.03 (br-d, E-6, $J_{6,6'}$=11.5 Hz, 1H), 3.86 (dd, E-6', $J_{5,6'}$=7.0 Hz, $J_{6,6'}$=12.0 Hz, 1H), 3.78 (s, OMe, 3H), 3.68-3.75 (m, C-2, E-2, 2H), 3.55-3.64 (m, C-4, E-4, E-5, F-2, 4H), 3.51 (dq, C-5, $J_{4,5}$=9.5 Hz, $J_{5,6}$=6.0 Hz, 1H), 2.69 (d, I-12, $J_{12,13}$=7.5 Hz, 1H), 2.55 (s, A-4, A-4', A-5, A-5', 4H), 2.00-2.15 (m, Ac x7, I-4, I-4', I-5, I-5', I-15, I-15', I-16, I-16', 29H), 1.91-1.94 (m, Ac x4, I-10, I-10', 14H), 1.75 (s, I-25, 3H), 1.66 (s, I-19, 3H), 1.61 (s, I-21, 3H), 1.60 (s, I-20, 3H), 1.38 (m, I-9, 2H), 1.32 (d, C-6, $J_{5,6}$=6.0 Hz, 1H), 1.25 (s, F-4-Me, 3H), 0.97 (s, I-23, I-24, 6H); $^{13}$C NMR (125 MHz, CD$_3$OD): δ 175.23, 173.99, 173.86, 173.21, 172.84, 172.80, 172.08, 171.92, 171.76, 171.70 x2, 171.61, 171.32, 168.21, 159.26, 151.42, 142.33, 141.87, 137.62, 132.45, 127.08, 125.61, 123.74, 122.88, 114.04, 109.43, 102.99, 102.17, 102.09, 101.91, 95.96 (br-s), 82.29, 78.89 (d, $^3J_{C,P}$=8.3 Hz), 78.43 (d, $^3J_{C,P}$=7.6 Hz), 77.93, 76.80, 76.19, 74.82, 74.61, 74.54, 74.49, 74.39, 73.63, 73.39, 72.78, 72.15, 71.95, 70.63, 69.83, 69.77, 69.37, 68.01, 67.19, 63.09, 56.48,

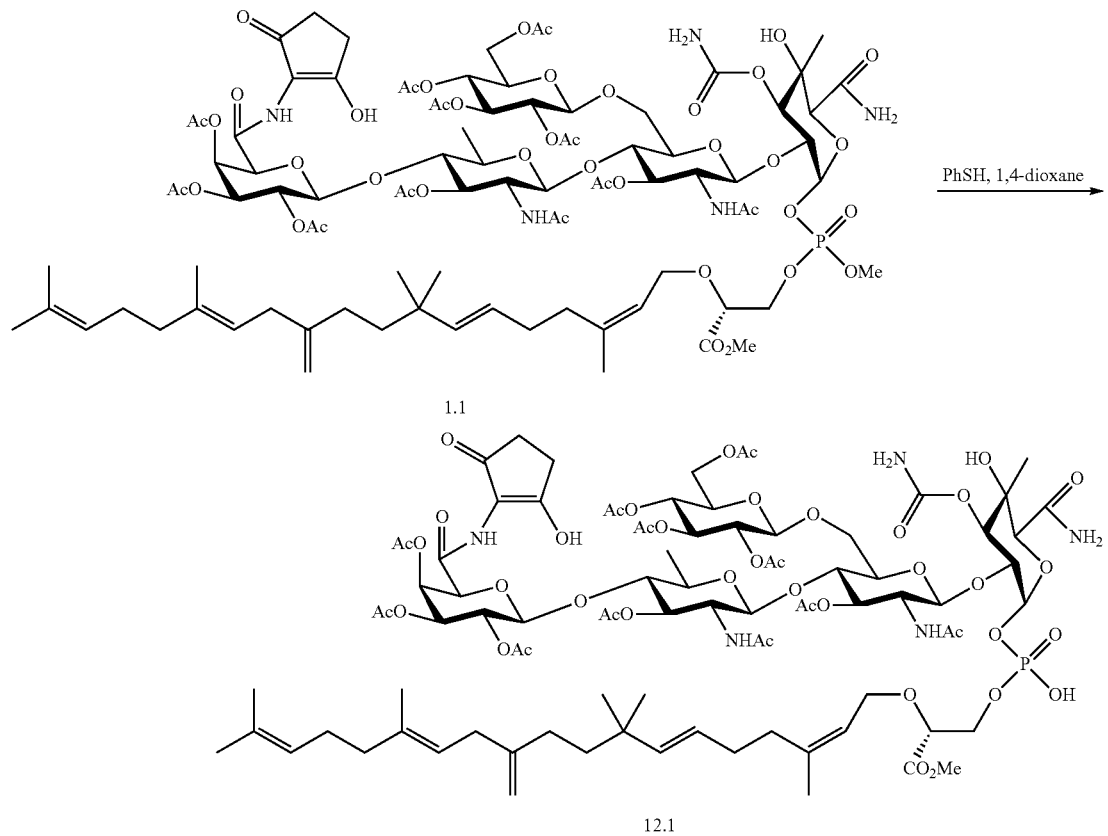

55.90, 52.78, 42.86, 40.87, 36.47, 35.93, 33.43, 32.54, 32.32, 29.92 (br-s), 27.83, 27.67, 25.89, 23.82, 23.09, 23.03, 21.33, 21.10, 20.98, 20.81, 20.71, 20.59, 20.51, 20.38, 18.31, 17.72, 16.67, 16.05; $^{31}$P NMR (162 MHz, CD$_3$OD): δ −1.17; LRMS (ESI) calcd for C$_{88}$H$_{128}$N$_5$O$_{43}$PNa [M−NH$_3$+Na]$^+$ 1996.7. found 1996.7.

Example (I-1)

Synthesis of Moenomycin A, Ammonium Salt (1)

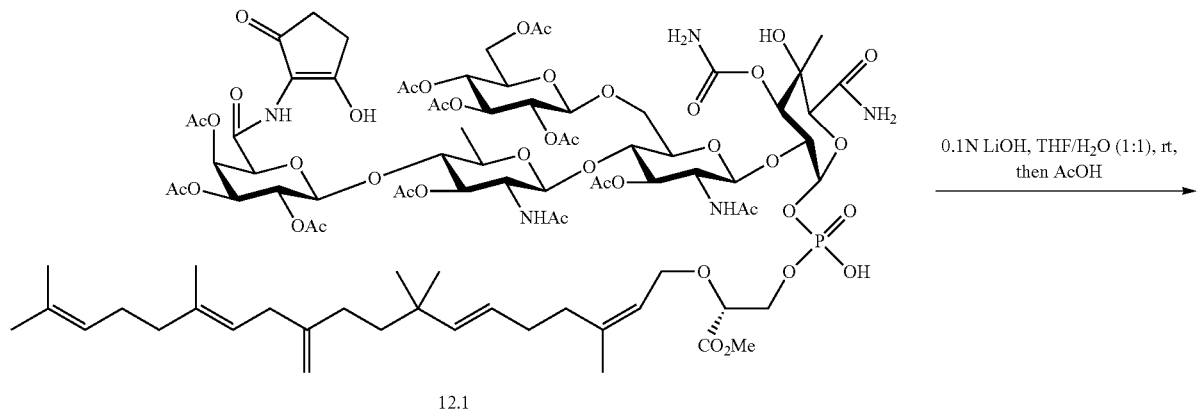

12.1

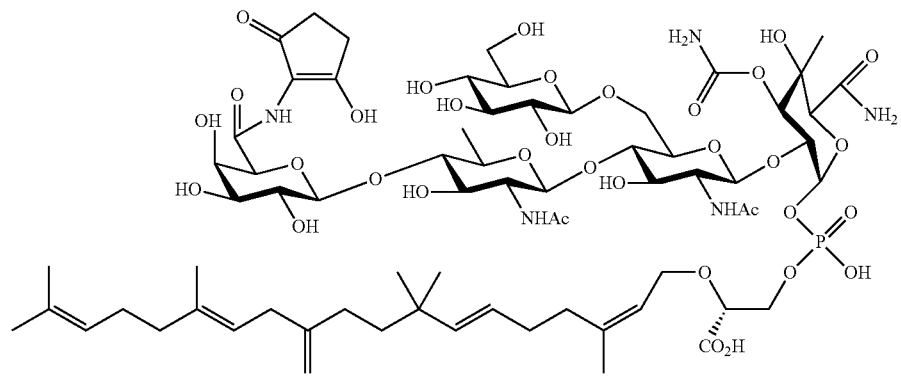

1

To a solution of nonaacetyl moenomycin A pentasaccharide phosphonate diester (19) (6.50 mg, 3.29 μmol, 1.00 eq.) in tetrahydrofuran (0.35 mL) and water (0.35 mL) was added 0.1N LiOH (0.35 mL) at room temperature. After being stirred at the same temperature for 7 hours, the reaction mixture was treated with acetic acid (0.70 mL) at 0° C. and concentrated in vacuo. The residue was purified by reversed-phase HPLC (gradient 0-60% acetonitrile/water with 0.1% NH$_4$HCO$_3$ over 70 min) to give moenomycin A (1) (2.71 mg, 1.68 μmol, 47%) as a white solid.

$^1$H NMR (500 MHz, CD$_3$OD): δ 5.87 (br-t, F-1, $^3$J$_{1,P}$=6.0 Hz, 1H), 5.43 (br-t, I-2, J$_{1,2}$=6.5 Hz, 1H), 5.37 (d, I-7, J$_{6,7}$=15.5 Hz, 1H), 5.29 (dt, I-6, J$_{5,6}$=6.0 Hz, J$_{6,7}$=15.5 Hz, 1H), 5.13 (t, I-13, J$_{12,13}$=7.5 Hz, 1H), 5.08-5.13 (m, F-3, I-17, 2H), 4.66 (d, I-22, J=4.0 Hz, 2H), 4.54 (d, C-1, E-1, J$_{1,2}$=8.0 Hz, 2H), 4.46-4.49 (m, B-1, D-1, F-5, 3H), 4.14-4.27 (m, B-4, B-5, I-1, I-1', H-2, H-3, H-3', 7H), 4.12 (br-d, E-6, J$_{6,6'}$=11.0 Hz, 1H), 3.91 (dd, D-6, J$_{5,6}$=2.0 Hz, J$_{6,6'}$=12.5 Hz, 1H), 3.74 (dd, C-2 or E-2, J$_{1,2}$=9.0 Hz, J$_{2,3}$=10.5 Hz, 1H), 3.53-3.71 (m, C-2 or E-2, B-2, B-3, C-3, C-5, D-6', E-3, E-5, E-6', F-2, 10H), 3.44-3.47 (m, 2H, D-3, E-4, 2H), 3.37 (dd, C-4, J$_{3,4}$=8.5 Hz, J$_{4,5}$=8.5 Hz, 1H), 3.35 (m, D-5, 1H), 3.26 (dd, D-4, J$_{3,4}$=9.5 Hz, J$_{4,5}$=9.0 Hz, 1H), 3.21 (dd, D-2, J$_{1,2}$=8.5 Hz, J$_{2,3}$=9.0 Hz, 1H), 2.69 (d, I-12, J$_{12,13}$=8.0 Hz, 2H), 2.45 (s, A-4, A-4', A-5, A-5', 4H), 2.00-2.14 (m, I-4, I-4', I-5, I-5', I-15, I-15', I-16, I-16', 8H), 2.03 (s, C-2-NAc, 3H), 1.99 (s, E-2-NAc, 3H), 1.90 (m, I-10, 2H), 1.76 (s, I-25, 3H), 1.66 (s, I-19, 3H), 1.61 (s, I-21, 3H), 1.60 (s, I-20, 3H), 1.42 (d, C-6, J$_{5,6}$=6.5 Hz, 3H), 1.37 (m, I-9, 2H), 1.24 (s, F-4-Me, 3H), 0.96 (s, I-23, I-24, 6H); $^{13}$C NMR (125 MHz, CD$_3$OD): δ 175.84, 175.39, 174.74 x2, 171.43, 159.88, 151.92, 142.71, 142.34, 138.10, 132.94, 127.61, 126.11, 124.25, 123.57, 114.15, 109.89, 105.48, 105.22, 104.48, 103.74, 101.93 (impurity), 96.72 (br-s), 85.80, 83.05, 79.43 (br-s), 78.72, 77.00, 76.55, 75.87, 75.80, 75.04, 74.87, 74.40, 74.20, 74.09, 73.31, 72.80, 72.44, 71.20, 70.20, 68.53, 68.05, 63.32, 58.00, 57.17, 43.38, 41.37, 36.94, 36.41, 33.95, 33.12, 32.81, 31.00 (br-s), 28.30 x2, 28.17, 26.38, 24.36, 23.85, 23.77, 18.47, 18.19, 16.96, 16.52; $^{31}$P NMR (162 MHz, CD$_3$OD): δ −1.11; LRMS (ESI) calcd for C$_{69}$H$_{107}$N$_5$O$_{34}$P [M−NH$_3$−H]$^-$ 1580.7. found 1580.6.

Example I-m

Characterization of (R)-3-(3,4-Dimethoxybenzyloxy)-1-triisopropylsiloxy-2-[2-(Z)-3,7-dimethyl-octa-2,6-dien-1-yloxy]-propane (12.2)

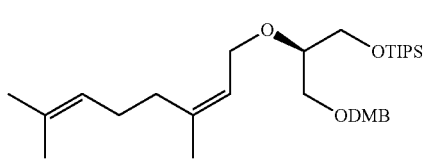

$^1$H NMR (500 MHz, CDCl$_3$): 6.80-6.89 (m, Ar—H, 3H), 5.36 (t, I-2, $J_{1,2}$=6.9 Hz, 1H), 5.06 (m, I-6, 1H), 4.51 (d, benzylic-H, $J_{gem}$=11.7 Hz, 1H), 4.46 (d, benzylic-H, $J_{gem}$=11.7 Hz, 1H), 4.15 (d, I-1, $J_{1,2}$=6.9 Hz, 2H), 3.87 (s, 2×OMe, 6H), 3.71-3.77 (m, H-1, 2H), 3.62 (dd, H-3, $J_{2,3}$=3.9 Hz, $J_{3,3'}$=9.8 Hz, 1H), 3.56-3.60 (m, H-2, 1H), 3.50 (dd, H-3' $J_{2,3'}$=5.3 Hz, $J_{3,3'}$=9.7 Hz, 1H), 2.02-2.08 (m, I-4, I-4', I-5, I-5', 4H), 1.72 (s, I-10, 3H), 1.66 (s, I-8, 3H), 1.58 (s, I-9, 3H), 1.04-1.10 (Si(i-Pr)$_3$, 21H); $^{13}$C NMR (125 MHz, CDCl$_3$): 148.91, 148.42, 139.83, 131.80, 131.06, 123.88, 122.41, 120.15, 110.93, 110.76, 78.77, 73.25, 70.12, 66.65, 63.26, 55.88, 55.72, 32.27, 26.73, 25.67, 23.49, 17.96, 17.63, 11.88; HRMS (ESI) calcd for C$_{31}$H$_{58}$NO$_5$Si [M+NH$_4$]$^+$ 552.4084. found 552.4095; LRMS (ESI) calcd for C$_{31}$H$_{54}$O$_5$SiNa [M+Na]$^+$ 557.4. found 557.3.

Example I-n

Characterization of (S)-3-(3,4-Dimethoxybenzyloxy)-2-[2-(Z)-3,7-dimethyl-octa-2,6-dien-1-yloxy]-1-propanol (13)

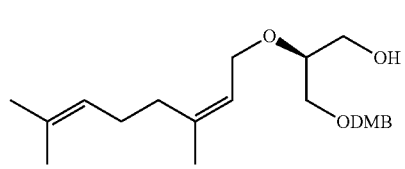

$^1$H NMR (500 MHz, CDCl$_3$): 6.81-6.87 (m, Ar—H, 3H), 5.35 (t, I-2, $J_{1,2}$=6.8 Hz, 1H), 5.06 (m, I-6, 1H), 4.49 (d, benzylic-H, $J_{gem}$=12.2 Hz, 1H), 4.46 (d, benzylic-H, $J_{gem}$=12.2 Hz, 1H), 4.14 (dd, I-1, $J_{1,1'}$=11.7 Hz, $J_{1,2}$=6.8 Hz, 1H), 4.07 (dd, I-1', $J_{1,1'}$=11.7 Hz, $J_{1,2}$=6.8 Hz, 1H), 3.88 (s, OMe, 3H), 3.87 (s, OMe, 3H), 3.73 (m, H-1, 1H), 3.55-3.65 (m, H-1', H-3, H-2, 3H), 3.51 (dd, H-3' $J_{2,3'}$=5.3 Hz, $J_{3,3'}$=9.7 Hz, 1H), 2.12 (br-s, OH, 1H), 2.02-2.08 (m, I-4, I-4', I-5, I-5', 4H), 1.74 (s, I-10, 3H), 1.67 (s, I-8, 3H), 1.58 (s, I-9, 3H); $^{13}$C NMR (125 MHz, CDCl$_3$): 148.99, 148.61, 140.77, 132.02, 130.49, 123.65, 121.68, 120.23, 110.90, 110.81, 77.47, 73.40, 69.83, 66.23, 62.89, 55.87, 55.78, 32.21, 26.73, 25.66, 23.46, 17.96, 17.63; LRMS (ESI) calcd for C$_{22}$H$_{34}$O$_5$Na [M+Na]$^+$ 401.5. found 401.5.

Example I-o

Characterization of Methyl (R)-3-(3,4-Dimethoxybenzyloxy)-2-[2-(Z)-3,7-dimethyl-octa-2,6-dien-1-yloxy]-propanoate (13.1)

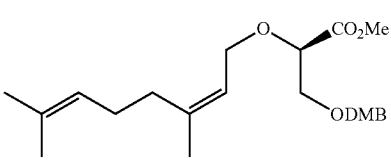

$^1$H NMR (500 MHz, CDCl$_3$): 6.80-6.88 (m, Ar—H, 3H), 5.36 (t, 1-2, $J_{1,2}$=6.8 Hz, 1H), 5.05 (m, I-7,1H), 4.53 (d, benzylic-H, $J_{gem}$=12.2 Hz, 1H), 4.49 (d, benzylic-H, $J_{gem}$=12.2 Hz, 1H), 4.15 (dd, I-1, $J_{1,1'}$=11.3 Hz, $J_{1,2}$=6.4 Hz, 1H), 4.12 (t, H-2, $J_{2,3}$=4.9 Hz, 1H), 4.02 (dd, I-1, $J_{1,1'}$=11.3 Hz, $J_{1,2}$=6.4 Hz, 1H), 3.88 (s, OMe, 3H), 3.86 (s, OMe, 3H), 3.74 (s, OMe, 3H), 3.71 (d, H-3, $J_{2,3}$=4.9 Hz, 1H), 2.02-2.08 (m, I-4, I-4', I-5, I-5', 4H), 1.74 (s, I-10, 3H), 1.66 (s, I-8, 3H), 1.58 (s, I-9, 3H); $^{13}$C NMR (125 MHz, CDCl$_3$): 171.43, 148.94, 148.55, 141.45, 131.97, 130.39, 123.67, 120.98, 120.24, 110.99, 110.71, 77.59, 73.29, 70.15, 66.83, 55.86, 55.76, 51.94, 32.16, 26.61, 25.64, 23.47, 17.61; LRMS (ESI) calcd for C$_{23}$H$_{34}$O$_6$Na [M+Na]$^+$ 429.2. found 429.2.

Example I-p

Characterization of Methyl (R)-3-(3,4-Dimethoxybenzyloxy)-2-[2-(Z)-3,7-dimethyl-octa-2,6-dien-1-yloxy]-propanoate (14)

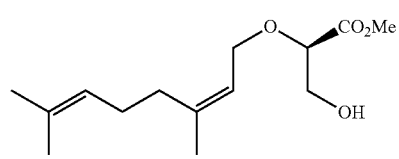

$^1$H NMR (500 MHz, CDCl$_3$): 5.37 (t, I-2, $J_{1,2}$=6.8 Hz, 1H), 5.07 (m, I-7,1H), 4.23 (dd, I-1, $J_{1,1'}$=11.2 Hz, $J_{1,2}$=6.8 Hz, 1H), 4.02-4.04 (m, I-1', H-2, 2H), 3.83-3.90 (m, H-3, 1H), 3.78-3.82 (m, H-3', 1H), 3.77 (s, OMe, 3H), 2.17 (br-s, OH, 1H), 2.03-2.11 (m, I-4, I-4', I-5, I-5', 4H), 1.76 (s, I-10, 3H), 1.67 (s, I-8, 3H), 1.59 (s, I-9, 3H); $^{13}$C NMR (125 MHz, CDCl$_3$): 171.30, 142.17, 132.915, 123.58, 120.62, 120.24, 78.16, 66.91, 63.43, 52.07, 32.16, 26.61, 25.66, 23.48, 17.65; LRMS (ESI) calcd for C$_{14}$H$_{24}$NO$_4$Na [M+Na]$^+$ 279.2. found 279.1; HRMS (ESI) calcd for C$_{14}$H$_{28}$NO$_4$ [M+NH$_4$]$^+$ 274.2018. found 274.2018.

Example I-q

Characterization of $N_1$-[(2-hydroxy-5-oxo-cyclopenten-1-yl)-2,3,4-tri-O-acetyl-(5S)-β-D-galactopyranuronamide]-(1→4)-2-acetamide-3-O-acetyl-2,6-dideoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl)-(1→2)-3-O-carbamoyl-1-O-{[(R)-2-methoxycarbonyl-2-(2-(Z)-3,7-dimethyl-octa-2,6-dien-1-yloxy)-ethoxy]-hydroxyphosphoryl}-4-C-methyl-α-D-glucopyranuronamide, Ammonium Salt (14.1)

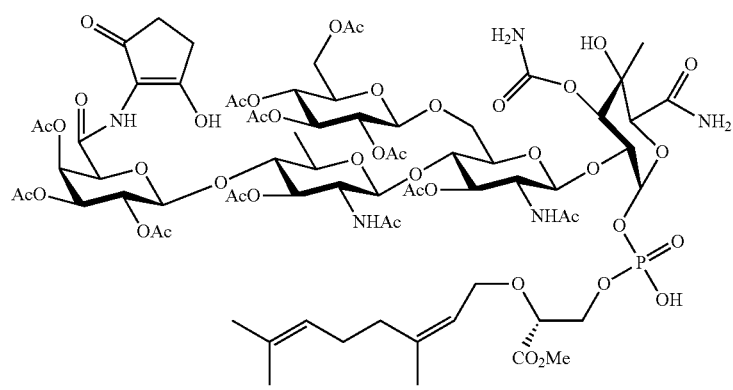

14.1

$^1$H NMR (500 MHz, D$_2$O): 5.68-5.70 (m, B-4, 1H), 5.64 (dd, F-1, $^3J_{1,P}$=6.9 Hz, $J_{1,2}$=3.5 Hz, 1H), 5.38 (t, I-2, $J_{1,2}$=6.8 Hz, 1H), 5.31 (dd, J=9.8, 9.3 Hz, 1H), 5.24 (dd, J=9.3, 3.4 Hz, 1H), 5.05-5.13 (m, 4H), 4.99-5.02 (m, 3H), 4.95 (dd, J=9.3, 9.3 Hz, 1H), 4.90 (d, J=8.3 Hz, 1H), 4.83 (d, J=8.3 Hz, 1H), 4.62 (s, 1H), 4.59 (d, J=8.3 Hz, 1H), 4.39-4.42 (m, 2H), 4.31 (d, J=4.9 Hz, 1H), 4.14-4.22 (m, 4H), 4.06-4.11 (m, 2H), 3.98 (br-d, J=11.7 Hz, 1H), 3.87 (dd, J=5.9 Hz, J=11.7 Hz, 1H), 3.80 (s, OMe, 3H), 3.60-3.69 (m, 3H), 3.47-3.50 (m, 1H), 2.31-2.33 (s, A-4, A-4', A-5, A-5', 4H), 2.03-2.13 (m, Ac x7, I-4, I-5, 25H), 2.00, 1.95, 1.92, 1.90 (s, Ac, 3H), 1.74 (s, I-10, 3H), 1.64 (s, I-8, 3H), 1.61 (s, I-9, 3H), 1.26-1.29 (m, 3H), 1.19 (s, F-4-Me, 3H); $^{31}$P NMR (162 MHz, CD$_3$OD): −1.37; LRMS (ESI) calcd for C$_{73}$H$_{103}$N$_5$O$_{43}$PNa [M−NH$_3$+Na]$^+$ 1768.6. found 1768.5.

Example I-r

Characterization of $N_1$-[(2-hydroxy-5-oxo-cyclopenten-1-yl)-(5S)-β-D-galactopyranuronamide]-(1→4)-2-acetamide-2,6-dideoxy-β-D-glucopyranosyl-(1→4)-[β-D-glucopyranosyl-(1→6)]-2-acetamido-2-deoxy-β-D-glucopyranosyl)-(1→2)-3-O-carbamoyl-1-O-{[(R)-2-carboxy-2-(2-(Z)-3,7-dimethyl-octa-2,6-dien-1-yloxy)-ethoxy]-hydroxyphosphoryl}-4-C-methyl-α-D-glucopyranuronamide, Ammonium Salt (15)

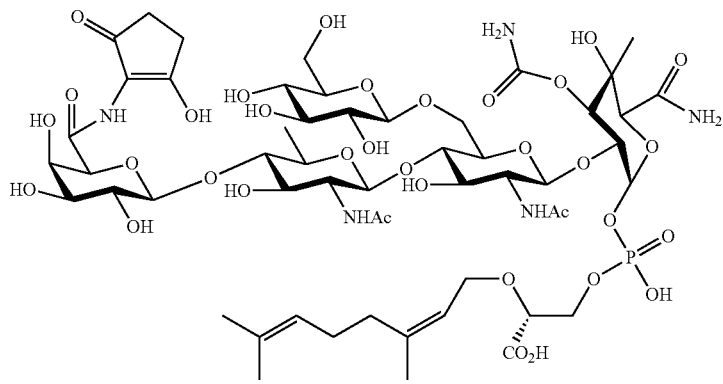

15

¹H NMR (500 MHz, CD$_3$OD): 5.72-5.74 (m, F-1, 1H), 5.36 (t, I-2, $J_{1,2}$=5.9 Hz, 1H), 5.14 (m, I-6, 1H), 4.99 (d, F-3, $J_{2,3}$=10.3 Hz, 1H), 4.55-4.49 (m, 3H), 4.47 (d, J=7.3 Hz, 1H), 4.40 (br-s, 1H), 4.26 (br-s, 1H), 4.22 (d, J=3.4 Hz, 1H), 3.88-4.09 (m, 8H), 3.80-3.82 (m, 1H), 3.48-3.74 (m, 14H), 3.43-3.46 (m, 1H), 3.34 (dd, J=9.7, 9.3 Hz, 1H), 3.30-3.32 (m, 1H), 3.25 (dd, J=8.3, 8.3 Hz, 1H), 2.35 (s, A-4, A-4', A-5, A-5', 4H), 2.06-2.11 (m, I-4, I-5, 4H), 2.03 (s, C-2-NAc, 3H), 1.99 (s, E-2-NAc, 3H), 1.72 (s, I-10, 3H), 1.64 (s, I-8, 3H), 1.57 (s, I-9, 3H), 1.35 (d, J=5.9 Hz, 3H), 1.17 (s, F-4-Me, 3H); $^{31}$P NMR (162 MHz, CD$_3$OD): −1.00; LRMS (ESI) calcd for C$_{54}$H$_{84}$N$_5$O$_{34}$P [M−NH$_3$−H]⁻ 1376.5. found 1376.4.

IC$_{50}$ Values for PBP2:

*S. aureus* PBP2 was over-expressed and purified as described[4,5]. The IC$_{50}$s for moenomycin and neryl compounds were carried out using the following reaction condition: (0-50 μM) and PBP2 (final concentration 30 nM) were incubated in Eppendorf tubes containing 9 μL of buffer [(50 mM HEPES buffer, 50 mM MOPS, 50 mM MES, 50 mM AcOH) at pH 5.0, 10 mM CaCl$_2$, 20% DMSO (v/v), 250 unit/mL penicillin G] for 30 min. The reaction was initiated by adding 4 μM [$^{14}$C]-GlcNAc-labeled lipid II analogue[4] (specific activity=101 cpm/pmol) and quenched after 80 min with 10 μL of ice-cold 10 mM Tris (pH=8.0) containing 0.2% Triton X-100. The reaction mixture was immediately spotted on cellulose chromatography paper (3MM Whatmann). Products and starting material were separated using chromatography (isobutryic acid:1 N NH$_4$OH=5:3) and quantitated by scintillation counting. The data were fit using Prism, as described[3,4].

Overexpression and Purification of PBP2a from *E. faecalis.*

Figure 1:
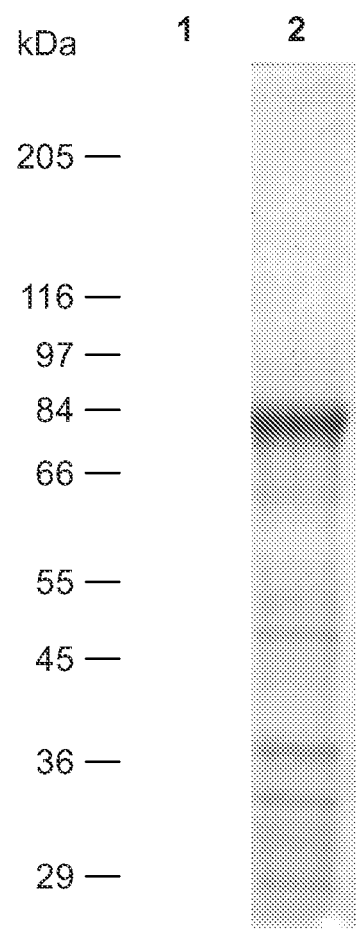
FIG. 1. SDS-PAGE (12%) analysis of purified C-terminal $His_8$-tagged PBP2a (lane 2) along with molecular weight markers (lane 1).

The pbp2a gene was PCR-amplified from *E. faecalis* (CL4877) purified genomic DNA using the following primer pair: 5'-GAGCATGTCCATATGGAATCCATGGAC AATCTTAAACAATTTTTT-3' (SEQ ID NO: 1) and 5'ACT-GCAGTGCTCGAGATTTCCTAATAAGCCTCCGAA-3' (SEQ ID NO: 2). The first primer introduced a NdeI restriction site (underlined), and the second primer introduced a XhoI site into the PCR product. The PCR product was subcloned into pET42 (Novagen) for expression in *E. coli* BL21 (DE3) (Novagen) as a C-terminal His$_8$ fusion. PBP2a was expressed after induction of a log phase culture grown at 37° C. with 1 mM IPTG and grown at 15° C. for an additional 20 h. The cells were harvested by centrifugation, and the cell pellets were resuspended in buffer A (20 mM Tris-HCl, 150 mM NaCl, pH 7.4) supplemented with 360 kU of rLysozyme (Novagen). The cells were lysed using a French pressure cell at 16,000 psi in buffer A. Freely soluble proteins were decanted and the pellet resuspended in buffer A containing 0.5% Sarkosyl to release membrane-anchored PBP2a. The solubilized fusion protein was then loaded onto a Ni$^{2+}$ column, which was washed with an imidazole gradient (5-60 mM) using detergent-free buffer B [20 mM Tris-HCl, 500 mM NaCl, pH 7.9] and then eluted with buffer B containing 100-200 mM imidazole and 0.1% Sarkosyl. Fractions were analyzed by 12% SDS-PAGE, pooled and concentrated using a Amicon Ultra Centrifuga Filter Device (50K MW cutoff). The concentrated protein was washed 2×5 (mL) of buffer A. The protein was more than 80% pure (FIG. 1) and the yield was estimated to be 2.0 mg/L.

IC$_{50}$ Values for PBP2a. *E. faecalis* PBP2a was over-expressed and purified as described above. The IC$_{50}$s for moenomycin and neryl compounds were carried out using the following reaction condition: (0-50 μM) and PBP2a (final concentration 52 nM) were incubated in Eppendorf tubes containing 9 μL of buffer [50 mM HEPES buffer at pH 7.5, 10 mM CaCl$_2$, 20% DMSO (v/v), 250 unit/mL penicillin G] for 30 min. The reaction was initiated by adding 4 μM [$^{14}$C]-GlcNAc-labeled lipid II analogue[4] (specific activity=101 cpm/pmol) and quenched after 45 min with 10 μL of ice-cold 10 mM Tris (pH=8.0) containing 0.2% Triton X-100. The reaction mixture was immediately spotted on cellulose chromatography paper (3MM Whatmann). Products and starting material were separated using chromatography (isobutryic acid:1 N NH$_4$OH=5:3) and quantitated by scintillation counting. The data were fit using Prism, as described[3,4].

MIC Values:

MIC values (μg/mL) were obtained using a standard microdilution assay. The MIC is defined as the lowest antibiotic concentration that resulted in no visible growth after incubation at 35° C. for 22 h.

TABLE 1

| | IC$_{50}$ (μg/ml) | | MIC (μg/ml) | |
| --- | --- | --- | --- | --- |
| | S. aureus PBP2 | E. faecalis PBP2a | S. aureus[a] | E. faecalis[b] |
| 1 | 0.035 | 0.042 | 0.016 | 0.063 |
| 15 | 0.057 | 0.022 | >250 | >250 |

[a]Baterial strain 29213;
[b]Bacterial strain 29212.

REFERENCES

1. Tirado, R.; Prieto, J. A., *J. Org. Chem.* 1993, 58, 5666-5673.
2. Chen, L.; Walker, D.; Sun, B.; Hu, Y.; Walker, S.; Kahne, D., *P. Natl. Acad. Sci. USA* 2003, 100, 5658-5663.
3. Ye, X. Y.; Lo, M. C.; Brunner, L.; Walker, D.; Kahne, D.; Walker, S., *J. Am. Chem. Soc.* 2001, 123, 3155-3156.
4. Leimkuhler, C.; Chen, L.; Barrett, D.; Panzone, G.; Sun, B. Y.; Falcone, B.; Obertür, M.; Donadio, S.; Walker, S.; Kahne, D., *J. Am. Chem. Soc.* 2005, 127, 3250-3251.
5. Barrett, D.; Leimkuhler, C.; Chen, L.; Walker, D.; Kahne, D.; Walker, S., *J. Bacteriol.* 2005, 187, 2215-2217.

Example 2

Total Synthesis of Moenomycin A

Moenomycin A is the only known natural antibiotic that inhibits bacterial cell wall synthesis by binding to the transglycosylases that catalyze formation of the carbohydrate chains of peptidoglycan. This example reports the total synthesis of moenomycin A using the sulfoxide glycosylation method. A newly discovered byproduct of sulfoxide reactions was isolated that resulted in substantial loss of the glycosyl acceptor. A general method to suppress this byproduct was introduced, which enabled the glycosylations to proceed efficiently. The inverse addition protocol for sulfoxide glycosylations also proved important in constructing some of the glycosidic linkages. The synthetic route is flexible and allows for derivatives to be prepared to further analyze moenomycin A's mechanism of action.

One synthetic approach involved constructing the BCEF tetrasaccharide from the BC and EF disaccharide fragments, followed by attachment of the D ring. The synthesis of the protected BCEF tetrasaccharide 10 is shown in Scheme 4. Because preliminary investigations into the synthesis of the BC disaccharide revealed that the A ring would not survive the glycosylation conditions, the C6 position of the B ring 2 was protected as an ester to allow for late stage attachment of the A ring. The C2 amine of the C ring acceptor 3 was protected with a tetrachlorophthaloyl (TCP) group[7] as reports have demonstrated that this bulky protecting group enables regioselective glycosylation at C4 in the presence of an unprotected C3 hydroxyl.[8] In addition, the TCP protecting group allows for neighboring group participation at C2, providing—stereochemical control during formation of the subsequent CE glycosidic linkage. The glycosylation of 2 with 3 afforded BC disaccharide 6 regioselectively and stereoselectively in 75% yield using the standard sulfoxide glycosylation protocol, which involves adding triflic anhydride to the glycosyl sulfoxide prior to adding the acceptor.[9] Disaccharide 6 was then oxidized to sulfoxide 7.

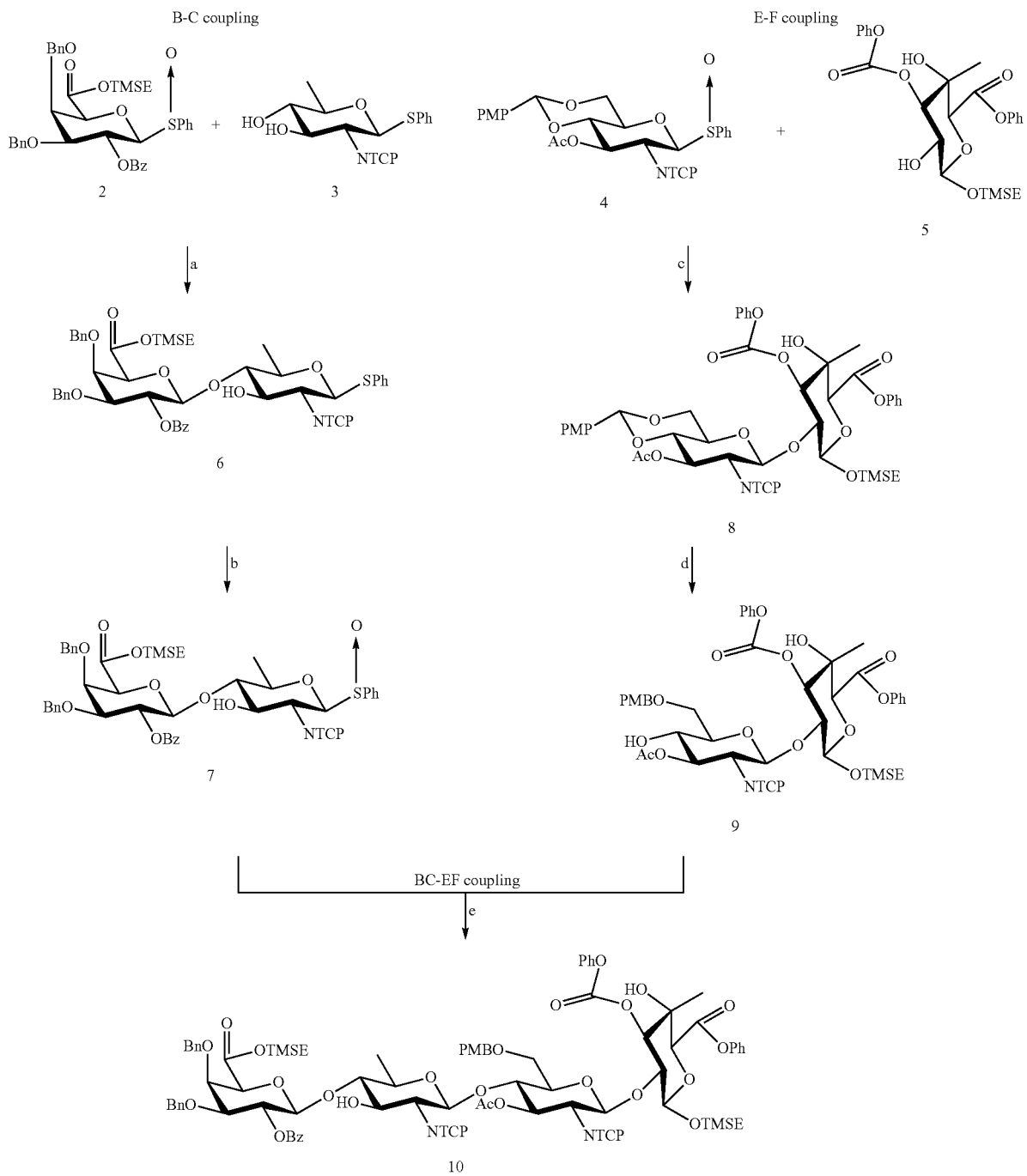

Scheme 4.

Conditions: (a) Tf2O, DTBMP, ADMB, CH2Cl2, -78 to 0 C, 75%; (b) mCPBA, CH2Cl2, -78 to 0 C, 70%; (c) Tf2O, DTBMP, ADMB, CH2Cl2, -42 C, 84%; (d) Bu2BOTf, BH3•THF, THF, -60 C, 83%; (e) Tf2O, DTBMP, ADMB, CH2Cl2, -60 C, 50%. DTBMP = 2,6-di-tert-butyl-4-methylpyridine, ADMB = 4-allyl-1,2-dimethoxybenzene Unlike the BC linkage, none of the other glycosidic bonds were formed using the standard glycosylation conditions. In the case of the EF-1,2 linkage, we observed that benzenesulfinic ester formation on the C2 hydroxyl of F ring 5 led to significant loss of the glycosyl acceptor.[10] PhSOTf is generated during sulfoxide glycosylations and is known to activate glycosyl sulfoxides.[11] Benzenesulfinic ester formation was presumed to be a downstream byproduct resulting from the reaction of PhSOTf with glycosyl sulfoxides. Using 4-allyl-1,2-dimethoxybenzene (ADMB) to scavenge PhSOTf[12] and changing the order of reagent addition during the reaction (inverse addition)[13] suppressed benzenesulfinic ester formation, and the EF disaccharide 8 was obtained in 84% yield.

The 4,6-(p-methoxylbenzylidene) group was then regioselectively opened[14] to afford 9.

Coupling of the EF and BC disaccharide fragments also required the inverse addition protocol because the BC glycosyl donor decomposed under the standard activation conditions. Inverse addition decreases decomposition because the oxacarbenium ion is generated slowly in the presence of the acceptor alcohol, which traps the reactive intermediate before it reacts with other species.[13] Thus, when donor 7 was added to a solution containing triflic anhydride and acceptor 9, tetrasaccharide 10 was obtained stereoselectively in 50% yield. The free hydroxyl on the C ring was then acetylated followed by removal of the PMB ether with DDQ to give 11 (Scheme 5).

Scheme 5.
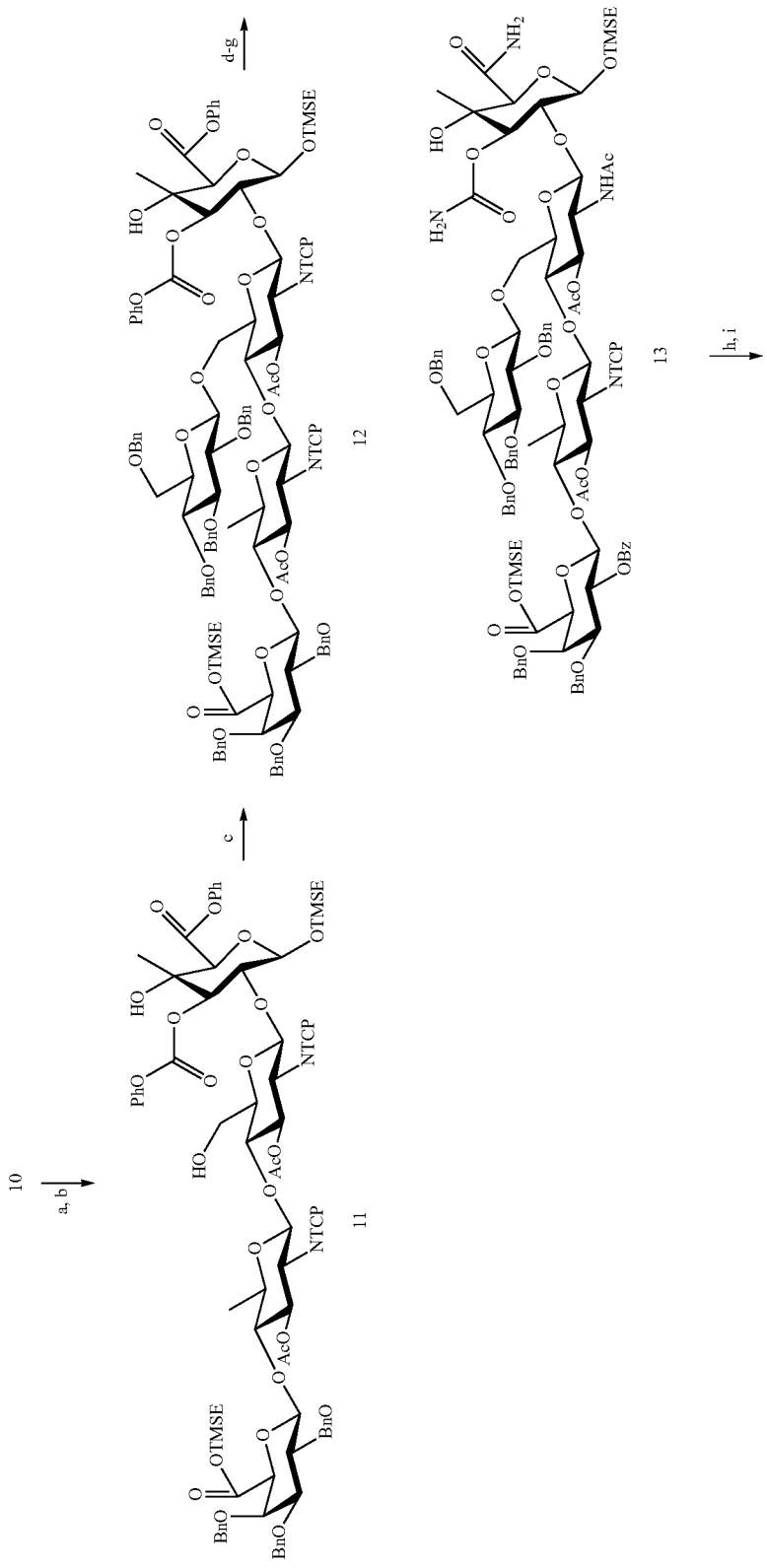

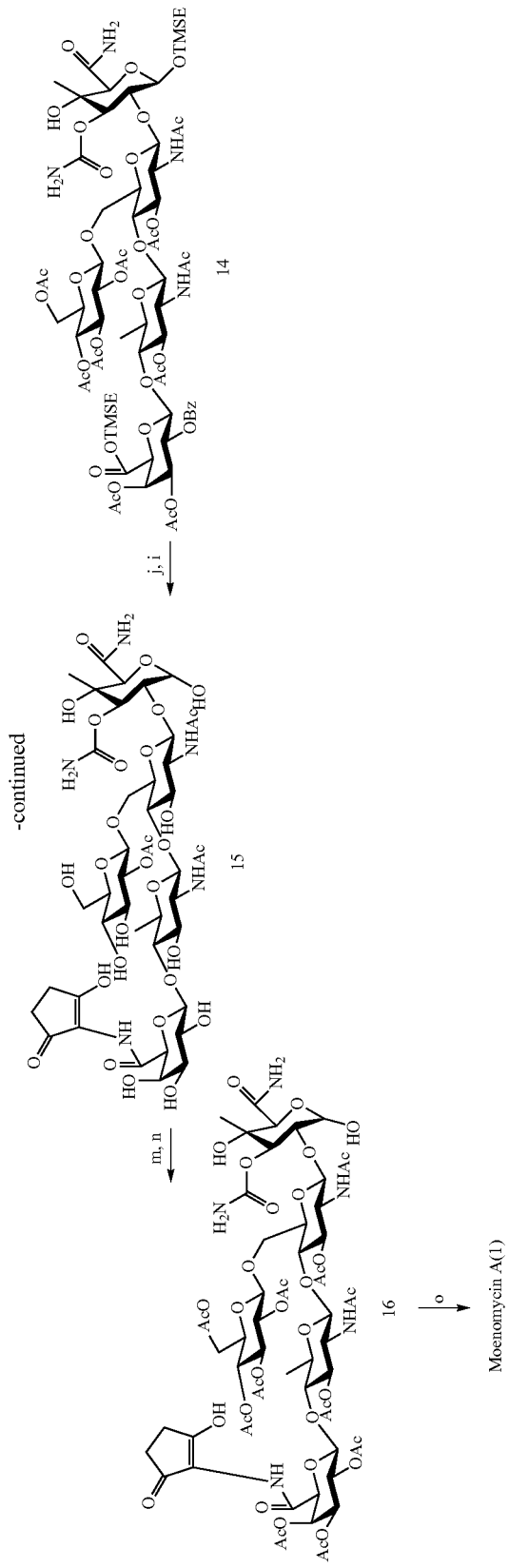

Conditions:
(a) Ac₂O, Py, 93%;
(b) DDQ, CH2Cl2/pH 7 buffer, 79%;
(c) Phenyl 2,3,4,6-tetra-O-benzyl-1-thio-D-glucopyranoside S-oxide, Tf2O, DTBMP, ADMB, propionitrile, -78 C., 76%;
(d) NH3 in IPA/CH2Cl2;
(e) ethylenediamine, EtOH, 60 C.;
(f) Ac2O, EtOH;
(g) Ac2O, Py, 66% four steps;
(h) H2, Pd(OH)2/C, MeOH;
(i) BF3·Et2O, CH2Cl2, 97%;
(j) Ac2O, Py, 63% two steps;
(k) 2-amino-3-hydroxy-2-cyclopenten-1-one hydrochloride, HATU, DIPEA, CH2Cl2/DMF, 55%;
(l) NaOH, THF, 80%;
(m) Ac2O, Py, 78%;
(n) H2NNH2·HOAc, 75%;
(1) 2-Chloro-1,3,2-benzodioxaphosphorin-4-one, CH3CN, 85%;
(2) Py, 4 Å MS, methyl (R)-3-hydroxy-2-[(2Z, 6E, 13E)-3,8,8,14,18-pentamethyl-11-methylene-nonadeca-2,6,13,17-tetraen-1-yloxy]]propanoate, 1-adamantanecarbonyl chloride, then NMM/CCl4/Py/CH3CN/H2O (1:2.5:6:1:1), 62%;
(3) 0.1N LiOH, THF/H2O (1:1), then AcOH, 47%

The final glycosylation involved forming a -1,6 linkage between a D ring sulfoxide and tetrasaccharide 11. To avoid introducing a hindered, electron-withdrawing ester group on the C2 position of the D ring donor, this glycosidic linkage was formed with solvent control using propionitrile, which is known to give high-stereoselectivity in glycosylations.[9,15] As before, benzenesulfinic ester byproducts dominated the reaction in the absence of a PhSOTf scavenger. When the reaction was carried out using the scavenger ADMB and inverse addition, pentasaccharide 12 was obtained in 76% yield with complete—stereoselectivity.

Completion of the moenomycin pentasaccharide synthesis required protecting group removal and installation of the 2-amino-3-hydroxy-2-cyclopenten-1-one (A ring) chromophore and F ring amide and carbamate. Selective conversion of the phenyl ester and phenyl carbonate of 12 into the desired carboxamide and carbamate, respectively, was accomplished using NH3 in IPA/CH2Cl2. The TCP protecting groups were then removed with ethylenediamine and the liberated amines were acylated in situ to give 13. Hydrogenation of the benzyl groups using Pd(OH)$_2$/C in MeOH and acetylation of the hydroxyls gave 14. Removal of the TMSE groups with BF3,[16] followed by coupling of the A ring[17] using HATU, and global deprotection with NaOH afforded the fully deprotected pentasaccharide 15. The identity of 15 was confirmed by correlation with the natural pentasaccharide obtained through degradation of moenomycin A. Peracetylation of 15 followed by selective deprotection of the anomeric acetate with H2NNH2.HOAc gave 16. Coupling of 16 to the moenocinyl glycerate unit and deprotection, using our published procedure,[18] afforded moenomycin A (1).

This synthesis of moenomycin A is both efficient and flexible, allowing for variants of the antibiotic to be constructed in order to probe its mechanism of action. Each glycosidic linkage was synthesized stereoselectively using the sulfoxide glycosylation reaction. Two sets of reaction conditions were employed depending on the reactivity of the donor-acceptor pair. The sulfoxide activation conditions described here, along with those described previously,[19] should enable the construction of most glycosidic linkages.

REFERENCES 1. van Heijenoort, J. Glycobiology 2001, 11, 25R-36R and references therein.
2. For a review of previous synthetic efforts toward moenomycin A see Welzel, P. Chem. Rev. 2005, 105, 4610-4660.
3. Müller, T.; Schneider, R.; Schmidt, R. R. Tetrahedron Lett. 1994, 35, 4763-4766.
4. (a) Paulsen, H. Angew. Chem., Int. Ed. Engl. 1982, 21, 155-173. [CrossRef] (b) Crich, D.; Dudkin, V. J. Am. Chem. Soc. 2001, 123, 6819-6825.
5. Welzel, P.; Kunisch, F.; Kruggel, F.; Stein, H.; Scherkenbeck, J.; Hiltmann, A.; Duddeck, H.; Müller, D.; Maggio, J. E.; Fehlhaber, H. W.; Seibert, G.; van Heijenoort, Y.; van Heijenoort, J. Tetrahedron 1987, 43, 585-598.
6. Marzian, S.; Happel, M.; Wagner, U.; Müller, D.; Welzel, P.; Fehlhaber, H. W.; Stark, A.; Schütz, H. J.; Markus, A.; Limbert, M.; van Heijenoort, Y.; van Heijenoort, J. Tetrahedron 1994, 50, 5299-5308.
7. (a) Debenham, J. S.; Madsen, R.; Roberts, C.; Fraser-Reid, B. J. Am. Chem. Soc. 1995, 117, 3302-3303. (b) Castro-Palomino, J. C.; Schmidt, R. R. Tetrahedron Lett. 1995, 36, 5343-5346.
8. (a) Lay, L.; Manzoni, L.; Schmidt, R. R. Carbohyd. Res. 1998, 310, 157-171. (b) Ellervik, U.; Magnusson, G. J. Org. Chem. 1998, 63, 9314-9322.
9. Kahne, D.; Walker, S.; Cheng, Y.; Van Engen, D. J. Am. Chem. Soc. 1989, 111, 6881-6882.
10. For a discussion of benzenesulfinic ester formation see Taylor, J. G. Ph.D. Thesis, Harvard University, 2006.
11. Crich, D.; Sun, S. J. Am. Chem. Soc. 1997, 119, 11217-11223.
12. Gildersleeve, J.; Smith, A.; Sakurai, K.; Raghavan, S.; Kahne, D. J. Am. Chem. Soc. 1999, 121, 6176-6182.
13. Gildersleeve, J.; Pascal, R. A. J.; Kahne, D. J. Am. Chem. Soc. 1998, 120, 5961-5969.
14. Hernndez-Torres, J. M.; Achkar, J.; Wei, A. J. Org. Chem. 2004, 69, 7206-7211.
15. Schmidt, R. R.; Behrendt, M.; Toepfer, A. Synlett 1990, 11, 694-696.
16. Jansson, K.; Ahlfors, S.; Frejd, T.; Kihlberg, J.; Magnusson, G.; Dahmén, J.; Noori, G.; Stenvall, K. J. Org. Chem. 1988, 53, 5629-5647.
17. Ebenezer, W. J. Synth. Commun 1991, 21, 351-358.
18. Adachi, M.; Zhang, Y.; Leimkuhler, C.; Sun, B.; LaTour, J., Kahne, D. D. J. Am. Chem. Soc. 2006, 128, 14012-14013.
19. Crich, D.; Lim, L. B. L. Org. React. 2004, 64, 115-251.

General Methods.

Unless otherwise noted, all reactions were conducted under an argon atmosphere using anhydrous solvents (either distilled or passed through an activated alumina column) Commercially available reagents were used without further purification. Thin layer chromatography (TLC) was performed using glass plates coated with silica gel (250 μm, Sorbent Technologies), with detection by UV and p-anisaldehyde. Flash chromatography was carried out on silica gel (60 Å, 32-63 μm) purchased from Sorbent Technologies. Analytical HPLC was performed on a Hewlett-Packard 1100 series instrument using a Phenomenex Luna 5 μm C18 column (250 mm×4.6 mm) Preparative HPLC was performed on a Hitachi L6200 instrument using a Phenomenex Luna 5 μm C18 column (250×21.2 mm)

NMR spectra were recorded on a Varian Inova 400 (400 MHz for $^1$H, 100 MHz for $^{13}$C), Varian Inova 500 (500 MHz for $^1$H, 125 MHz for $^{13}$C), Varian Inova 600 (600 MHz for $^1$H), or Bruker DMX 500 (500 MHz for $^1$H, 125 MHz for $^{13}$C) spectrometer. Proton chemical shifts are reported in parts per million (ppm) on the δ scale from an internal standard of residual protium in the NMR solvents (CHCl$_3$: δ 7.26, D$_2$HCOD 3.30). Data for $^{13}$C NMR are reported in terms of chemical shift from the carbon resonances of the solvent (CDCl$_3$: δ 77.16, CD$_3$OD 49.0). Data are reported as follows: chemical shift, multiplicity (s=singlet, d=doublet, t=triplet, q=quartet, m=multiplet, br=broad), coupling constant in Hz, integration, and assignment. A peak designated as "ABq" in the $^1$H NMR spectrum indicates it was one partner in an AB quartet. Low resolution mass spectra (LRMS) were obtained on an Agilent Technologies LC/MSD instrument (Model #G1956B) using electrospray ionization (ESI), while high resolution mass spectra (HRMS), ESI mode, were obtained at the Harvard University Mass Spectrometry Facilities.

Example 2-a

Synthesis of Compound 2

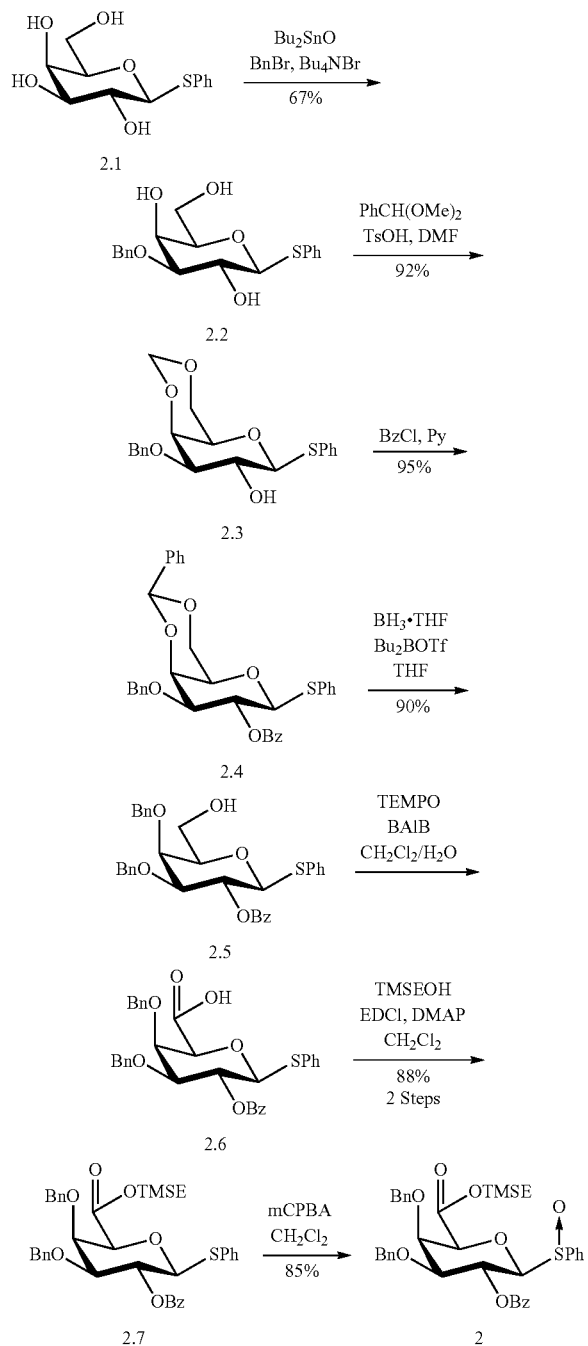

Synthesis of Phenyl 3-O-benzyl-1-thio-β-D-galactopyranoside (2.2)

A solution of phenyl 1-thio-β-D-galactopyranoside (2.1) (3.00 g, 11.0 mmol) and dibutyltin oxide (3.00 g, 12.1 mmol) in dry methanol (80 ml) was refluxed for 2 hours to produce a clear mixture. The solvent was then evaporated under reduced pressure. The resultant residue was dissolved in dry benzene (80 mL) followed by the addition of Bu$_4$NBr (3.90 g, 12.11 mmol) and BnBr (1.3 ml, 12.1 mmol). The mixture was refluxed overnight. After cooling to room temperature, the mixture was concentrated and the residue was purified by silica gel chromatography (50% EtOAc/petroleum ether) to afford the title compound (2.71 g, 7.48 mmol, 67%). $^1$H NMR (400 MHz, CDCl$_3$): δ 7.60-7.20 (m, 10H, PhH), 4.77, 4.68 (ABq, J=11.7 Hz, 1H each, OCH$_2$Ph), 4.59 (d, J=9.5 Hz, 1H, H-1), 4.08 (d, J=2.6 Hz, 1H, H-4), 3.76 (dd, J=9.5, 9.5 Hz, 1H, H-2), 3.75 (dd, J=11.4, 5.8 Hz, 1H, H-6), 3.70 (dd, J=11.4, 5.8 Hz, 1H, H-6), 3.50 (dd, J=5.8, 5.8 Hz, 1H, H-5), 3.41 (dd, J=9.5, 2.6 Hz, 1H, H-3); $^{13}$C NMR (100 MHz, CDCl$_3$): δ 131.0, 128.6, 128.1, 127.8, 127.4, 126.8, 89.1, 82.5, 79.2, 71.5, 69.0, 66.2, 61.4; HRMS calcd for C$_{19}$H$_{26}$O$_5$SN [M+NH$_4$]$^+$: 380.1532. found 380.1527.

Synthesis of Phenyl 3-O-benzyl-4,6-O-benzylidene-1-thio-β-D-galactopyranoside (2.3)

To a solution of 2.2 (2.71 g, 7.48 mmol) in dry CH$_3$CN was successively added benzaldehyde dimethylacetal (1.35 ml, 9.72 mmol) and TsOH.H$_2$O (0.42 g, 1.49 mmol). After 3 h, the reaction was cooled to 0° C. and triethylamine (2 ml) was added to neutralize the reaction mixture at 0° C. After evaporation of the solvent, the crude residue was purified by silica gel chromatography (20% EtOAc/toluene) to afford the title compound (3.10 g, 6.88 mmol, 92%). $^1$H NMR (500 MHz, CDCl$_3$): δ 7.70-7.20 (m, 15H, PhH), 5.42 (s, 1H, CHPh), 4.73, 4.69 (ABq, J=12.2 Hz, 1H each, OCH$_2$Ph), 4.51 (d, J=9.8 Hz, 1H, H-1), 4.33 (d, J=12.2 Hz, 1H, H-6), 4.13 (d, J=3.0 Hz, 1H, H-4), 3.96 (d, J=12.2 Hz, 1H, H-6), 3.84 (dd, J=9.8, 9.8 Hz, 1H, H-2), 3.49 (dd, J=9.8, 3.0 Hz, 1H, H-3), 3.41 (s, 1H, H-5); $^{13}$C NMR (125 MHz, CDCl$_3$): δ 133.9, 129.3, 129.1, 128.7, 128.4, 128.3, 128.1, 126.7, 101.4, 87.3, 80.5, 73.5, 71.8, 70.3, 69.6, 67.4; HRMS calcd for C$_{26}$H$_{30}$O$_5$SN [M+NH$_4$]$^+$: 468.1835. found 468.1845.

Synthesis of Phenyl 2-O-benzoyl-3-O-benzyl-4,6-O-benzylidene-1-thio-β-D-galactopyranoside (2.4)

To a solution of 2.3 (1.85 g, 4.11 mmol) in dry pyridine (10 ml) was added benzoyl chloride (0.95 ml, 4.22 mmol). The mixture was stirred at room temperature overnight then diluted with EtOAc and washed sequentially with water and brine, then the organic phase dried over Na$_2$SO$_4$. After evaporation of the solvent, the crude residue was purified by silica gel chromatography (20% EtOAc/toluene) to afford the title compound (2.16 g, 3.89 mmol, 95%). $^1$H NMR (400 MHz, CDCl$_3$): δ 8.20-7.20 (m, 20H, PhH), 5.70 (dd, J=9.9, 9.9 Hz, 1H, H-2), 5.52 (s, 1H, CHPh), 4.87 (d, J=9.9 Hz, 1H, H-1), 4.71, 4.60 (ABq, J=12.8 Hz, 1H each, OCH$_2$Ph), 4.36 (d, J=11.5 Hz, 1H, H-6), 4.32 (d, J=2.9 Hz, 1H, H-4), 4.04 (d, J=11.5 Hz, 1H, H-6), 3.84 (dd, J=9.9, 2.9 Hz, 1H, H-3), 3.48 (s, 1H, H-5); $^{13}$C NMR (100 MHz, CDCl$_3$): δ 165.4, 138.2, 138.0, 133.6, 132.4, 130.1, 129.4, 129.1, 128.7, 128.4, 128.0, 126.9, 101.4, 85.9, 78.5, 73.2, 71.1, 70.3, 69.5, 69.4; HRMS calcd for C$_{33}$H$_{34}$O$_6$SN [M+NH$_4$]$^-$: 572.2107. found, 572.2089.

Synthesis of Phenyl 2-O-benzoyl-3,4-di-O-benzyl-1-thio-β-D-galactopyranoside (2.5)

A solution of 1 M BH$_3$.THF (30 ml, 30.00 mmol) was added to compound 2.4 (1.61 g, 2.90 mmol), at 0° C., and then a solution of 1 M Bu$_2$BOTf in CH$_2$Cl$_2$ (3.0 ml, 3.00 mmol) was added to the reaction slowly. After 1 hour at 0° C., triethylamine was added followed by careful addition of methanol until the evolution of H$_2$ ceased. The crude mixture was then concentrated and purified by silica gel chromatography (25% EtOAc/petroleum ether) to afford the title compound (1.45 g, 2.60 mmol, 90%). $^1$H NMR (400 MHz, CDCl$_3$): δ 8.10-7.20 (m, 20H, PhH), 5.71 (dd, J=9.9, 9.9 Hz, 1H, H-2), 5.00, 4.64 (ABq, J=12.0 Hz, 1H each, OCH$_2$Ph), 4.79 (d, J=9.9 Hz, 1H, H-1), 4.68, 4.55 (ABq, J=12.0 Hz, 1H each, OCH$_2$Ph), 4.93 (d, J=2.5 Hz, 1H, H-4), 3.85 (m, 1H, H-6), 3.72 (dd, J=9.9, 2.5 Hz, 1H, H-3), 3.60-3.53 (m, 2H, H-5,6); $^{13}$C NMR (100 MHz, CDCl$_3$): δ 165.5, 138.3, 133.6, 133.3, 132.2, 129.0, 128.6, 128.0, 127.8, 87.1, 81.5, 79.2, 74.3, 72.4, 70.6, 62.4; LRMS calcd for C$_{33}$H$_{33}$O$_6$S [M+H]$^+$: 557.2. found, 557.2.

Synthesis of Phenyl 3,4-di-O-benzyl-2-O-benzoyl-1-thio-β-D-galactopyranosiduronic acid (2.6)

To a vigorously stirred solution of compound 2.5 (1.40 g, 2.51 mmol) in 10 ml CH$_2$Cl$_2$ and 5 ml H$_2$O was added TEMPO (78 mg, 0.50 mmol) and BAIB (2.00 g, 6.21 mmol). The reaction mixture was stirred for 1 h then quenched by the addition of 10% Na$_2$S$_2$O$_3$ solution and extracted twice with EtOAc. The combined organic layers were washed with brine and then dried over Na$_2$SO$_4$. After evaporation of the solvent, the crude residue was subjected to the next step without further purification. (500 MHz, CDCl$_3$): δ 8.10-7.20 (m, 20H, PhH), 5.71 (dd, J=9.7, 9.7 Hz, 1H, H-2), 4.94, 4.65 (ABq, J=12.0 Hz, 1H each, OCH$_2$Ph), 4.83 (d, J=9.7 Hz, 1H, H-1), 4.65, 4.50 (ABq, J=12.0 Hz, 1H each, OCH$_2$Ph), 4.44 (s, 1H, H-4), 4.18 (s, 1H, H-5), 3.78 (br d, J=9.7 Hz, 1H, H-3). HRMS calcd for C$_{33}$H$_{34}$O$_7$SN [M+NH$_4$]$^+$: 588.2056. found 588.2034.

Synthesis of 2-(Trimethylsilyl)ethyl (phenyl 3,4-di-O-benzyl-2-O-benzoyl-1-thio-β-D-galactopyrosid) uronate (2.7)

A solution of the above residue, EDCI (0.58 g, 3.02 mmol), DMAP (46 mg, 0.38 mmol) and 2-(trimethylsilyl)ethanol (0.89 ml, 6.25 mmol) in CH$_2$Cl$_2$ (10 ml) was stirred at room temperature for 2 hours. The reaction mixture was then diluted with CH$_2$Cl$_2$, washed with water and brine, then the organic phase was dried over Na$_2$SO$_4$. After evaporation of the solvent, the residue was purified by silica gel chromatography (20% EtOAc/petroleum ether) to afford the title compound (1.48 g, 2.21 mmol, 88% over 2 steps). $^1$H NMR (400 MHz, CDCl$_3$): δ 8.10-7.10 (m, 20H, PhH), 5.71 (dd, J=10.0, 10.0 Hz, 1H, H-2), 4.98, 4.64 (ABq, J=11.7 Hz, 1H each, OCH$_2$Ph), 4.77 (d, J=10.0 Hz, 1H, H-1), 4.67, 4.53 (ABq, J=12.2 Hz, 1H each, OCH$_2$Ph), 4.42 (dd, J=2.6, 1.1 Hz, 1H, H-4), 4.30-4.16 (m, 2H, OCH$_2$CH$_2$SiMe$_3$), 4.13 (d, J=1.1 Hz, H-5), 3.78 (dd, J=10.0, 2.6 Hz, 1H, H-3), 1.00 (m, 2H, OCH$_2$CH$_2$SiMe$_3$), 0.02 (s, 9H, SiMe$_3$); $^{13}$C NMR (100 MHz, CDCl$_3$): δ 168.1, 165.4, 138.4, 137.5, 133.4, 133.3, 130.3, 128.9, 128.6, 128.1, 128.0, 127.7, 87.0, 80.6, 77.8, 74.7, 72.1, 70.0, 64.4, 60.4, 22.4, 17.6, −1.1, −1.3; HRMS calcd for C$_{38}$H$_{46}$O$_7$SSiN [M+NH$_4$]$^+$: 688.2764. found 688.2798.

Synthesis of 2-(Trimethylsilyl)ethyl (phenyl 3,4-di-O-benzyl-2-O-benzoyl-1-thio-β-D-galactopyrosid) uronate S-Oxide (2)

To a solution of 2.7 (850 mg, 1.24 mmol) in CH$_2$Cl$_2$ (5 ml) was added mCPBA (307 mg of 75% dispersion, 1.33 mmol) at −78° C. The suspension was gradually warmed to 0° C. over 2 h then quenched with saturated NaHCO$_3$ and extracted with CH$_2$Cl$_2$. The organic layer was washed with brine then dried over Na$_2$SO$_4$. After evaporation of the solvent, the crude residue was purified by silica gel chromatography (30% EtOAc/petroleum ether) to afford the title compound (723 mg, 1.05 mmol, 85%). $^1$H NMR (400 MHz, CDCl$_3$): δ 8.00-7.00 (m, 20H, PhH), 5.74 (dd, J=9.6, 9.6 Hz, 1H, H-2), 4.85, 4.46 (ABq, J=11.7 Hz, 1H each, OCH$_2$Ph), 4.66, 4.52 (ABq, J=12.2 Hz, 1H each, OCH$_2$Ph), 4.56 (d, J=9.6 Hz, 1H, H-1), 4.32 (dd, J=2.6, 1.5 Hz, 1H, H-4), 4.13 (d, J=1.5 Hz, 1H, H-5), 4.14-4.02 (m, 2H, OCH$_2$CH$_2$SiMe$_3$), 3.82 (dd, J=9.6, 2.6 Hz, 1H, H-3), 0.96 (m, 2H, OCH$_2$CH$_2$SiMe$_3$), 0.02 (s, 9H, SiMe$_3$); $^{13}$C NMR (100 MHz, CDCl$_3$): δ 167.6, 165.5, 138.8, 138.2, 137.2, 133.6, 131.7, 130.2, 129.6, 128.7, 128.3, 127.9, 127.5, 127.2, 92.8, 79.8, 77.8, 74.6, 74.5, 72.1, 67.7, 64.3, 17.7, −1.3. HRMS calcd for C$_{38}$H$_{43}$O$_8$SSi [M+H]$^+$: 687.2448. found 687.2457.

Example 2-b

Synthesis of Compound 3

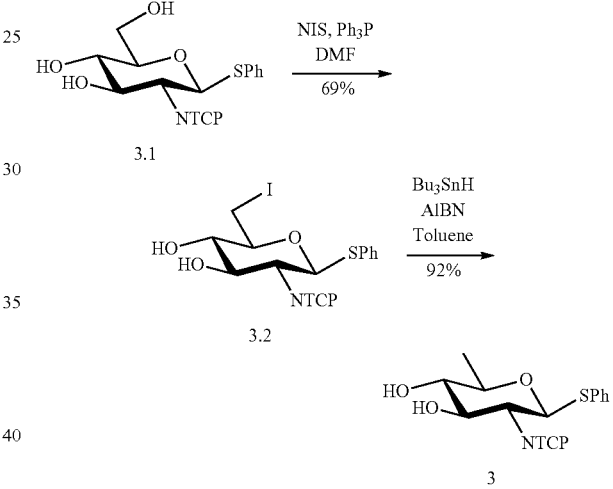

Synthesis of Phenyl 6-Iodo-2-deoxy-2-tetrachlorophthalimido-1-thio-β-D-glucopyranoside (3.2)

To a stirred solution of phenyl 2-deoxy-2-tetrachlorophthalimido-1-thio-β-D-glucopyranoside[1] (3.1) (440 mg, 0.816 mmol) in DMF (7 mL) at 0° C. was added N-iodosuccinimide (404 mg, 1.80 mmol). Triphenylphosphine (471 mg, 1.80 mmol) in DMF (5 mL) was then added dropwise over 30 min followed by heating of the reaction mixture to 50° C. for an additional 30 min.[2] After concentration in vacuo, the crude mixture was purified by silica gel chromatography (30% EtOAc/petroleum ether) to afford the title compound (367 mg, 0.565 mmol, 69%). $^1$H NMR (500 MHz, 10% CD$_3$OD/CDCl$_3$) δ ppm 7.45 (dd, J=6.6, 3.2 Hz, 2H, PhH), 7.23-7.19 (m, 3H, PhH), 5.50 (d, J=10.3 Hz, 1H, H-1), 4.19-4.13 (m, 1H, H-3), 4.08 (dd, J=10.3, 10.3 Hz, 1H, H-2), 3.61 (d, J=10.3 Hz, 1H, H-6), 3.36-3.30 (m, 1H, H-4), 3.26-3.30 (m, 2H, H-5,6); $^{13}$C NMR (125 MHz, 10% CD$_3$OD/CDCl$_3$): δ ppm 163.58, 163.01, 140.36, 132.85, 131.48, 130.04, 129.68, 128.92, 128.11, 127.28, 127.22, 82.98, 79.01, 74.82, 71.78, 56.30, 5.81; HRMS calcd for C$_{20}$H$_{18}$Cl$_4$IN$_2$O$_5$S [M+NH$_4$]$^+$: 664.8735. found 664.8713.

Synthesis of Phenyl 2,6-Dideoxy-2-tetrachlorophthalimido-1-thio-β-D-glucopyranoside (3)

Compound 3.2 (367 mg, 0.565 mmol) was dried by azeotropic distillation with toluene (3×10mL) then suspended in toluene and heated to 70° C. 2,2'-Azobis(2-methylpropionitrile) (70 mg, 0.426 mmol) was added followed by tributyltin hydride (941 µL, 3.40 mmol) and the reaction stirred for 1 h.[2] After cooling to room temperature, the mixture was concentrated in vacuo then separated by silica gel chromatography (40% EtOAc/petroleum ether) to afford the title compound (271 mg, 0.518 mmol, 92% yield). $^1$H NMR (600 MHz, CDCl$_3$): δ ppm 7.35 (dd, J=7.8, 1.6 Hz, 2H, PhH), 7.26-7.21 (m, 3H, PhH), 5.49 (d, J=10.3 Hz, 1H, H-1), 4.19 (dd, J=9.5, 9.5 Hz, 1H, H-3), 4.10 (dd, J=10.4, 10.4 Hz, 1H, H-2), 3.56-3.50 (m, 1H, H-5), 3.16 (dd, J=8.9, 8.9 Hz, 1H, H-4), 1.35 (d, J=6.2 Hz, 3H, H-6); $^{13}$C NMR (125 MHz, CDCl$_3$): δ ppm 163.76, 163.25, 140.52, 140.34, 132.25, 131.79, 130.50, 129.56, 129.00, 127.78, 127.38, 127.13, 82.62, 76.89, 76.16, 71.79, 56.66, 17.93; HRMS calcd for C$_{20}$H$_{19}$Cl$_4$N$_2$O$_5$S [M+NH$_4$]$^+$: 538.9769. found 538.9786.

Synthesis of Phenyl 2-Deoxy-4,6-O-p-methoxybenzylidene-2-tetrachlorophthalimido-1-thio-β-D-glucopyranoside (4.1)

To a solution of phenyl 2-deoxy-2-tetrachlorophthalimido-1-thio-β-D-glucopyranoside[1] (3.1) (3.70 g, 6.86 mmol) in DMF (20 mL) was added anisaldehyde dimethyl acetal (2.34 mL, 13.7 mmol) and p-toluenesulfonic acid monohydrate (131 mg, 0.689 mmol) and the reaction mixture was heated at 35° C. under reduced pressure (to remove methanol as it was generated) for 3 h. The reaction mixture was then cooled to room temperature, quenched with solid NaHCO$_3$ (500 mg), and concentrated in vacuo. The residue was redissolved in CH$_2$Cl$_2$ and washed with saturated aqueous NaHCO$_3$, H$_2$O, and brine. The organic layer was dried over Na$_2$SO$_4$, decanted, and then concentrated in vacuo. Purification of the crude residue by silica gel chromatography (2% EtOAc/CH$_2$Cl$_2$) afforded the title compound (4.50 g, 6.85 mmol, 100%). $^1$H NMR (400 MHz, CDCl$_3$): δ ppm 7.39-7.33 (m, 2H, ArH), 7.29 (d, J=8.4 Hz, 2H, ArH), 7.27-7.22 (m, 3H, ArH), 6.81 (d, J=8.8 Hz, 2H, ArH), 5.59 (d, J=10.6 Hz, 1H, H-1), 5.44 (s, 1H, CHPMP), 4.57 (ddd, J=9.6, 9.6, 3.5 Hz, 1H, H-3), 4.34 (dd, J=10.4, 4.9 Hz, 1H, H-6), 4.25 (dd, J=10.4, 10.4 Hz, 1H, H-2), 3.79 (s, 3H, OMe), 3.75 (dd, J=10.4, 10.4 Hz, 1H, H-6), 3.61 (ddd, J=9.6, 9.6, 4.9 Hz, 1H, H-5), 3.49 (dd, J=9.1, 9.1 Hz, 1H, H-4), 3.10 (d, J=3.3 Hz, 1H, OH); $^{13}$C NMR (100 MHz, CDCl$_3$): δ ppm 163.68, 162.68, 160.34, 140.48, 140.36, 132.48, 131.67, 130.25, 129.83, 129.19, 128.26, 127.49, 127.17, 127.08, 113.77, 101.84, 83.78, 81.73, 70.47, 69.24, 68.57, 56.37, 55.43; HRMS calcd for C$_{28}$H$_{22}$Cl$_4$NO$_7$S [M+H]$^+$: 655.9871. found 655.9843.

Example 2-c

Synthesis of Compound 4

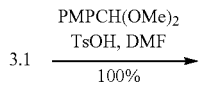

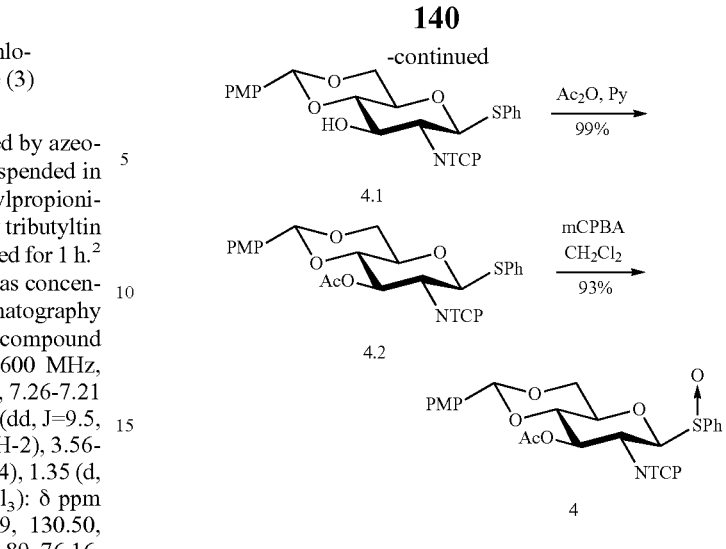

Synthesis of Phenyl 3-O-Acetyl-2-deoxy-4,6-O-p-methoxybenzylidene-2-tetrachlorophthalimido-1-thio-β-D-glucopyranoside (4.2)

To a solution of 4.1 (3.62 g, 5.51 mmol) in pyridine (30 mL) was added acetic anhydride (1.56 mL, 16.5 mmol). After stirring overnight at room temperature, the reaction was concentrated and separated by silica gel chromatography (CH$_2$Cl$_2$) to afford the title compound (3.81 g, 5.45 mmol, 99%). $^1$H NMR (500 MHz, CDCl$_3$): δ ppm 7.41-7.38 (m, 2H, ArH), 7.36 (d, J=8.8 Hz, 2H, ArH), 7.31-7.28 (m, 3H, ArH), 6.87 (d, J=9.3 Hz, 2H, ArH), 5.82-5.78 (m, 1H, H-3), 5.79 (d, J=10.7 Hz, 1H, H-1), 5.49 (s, 1H, CHPMP), 4.41 (dd, J=9.8, 3.4 Hz, 1H, H-6), 4.34 (dd, J=10.3, 10.3 Hz, 1H, H-2), 3.79 (s, 3H, OMe), 3.84-3.74 (m, 3H, H-4,5,6), 1.90 (s, 3H, OAc); $^{13}$C NMR (126 MHz, CDCl$_3$): δ ppm 170.87, 163.41, 162.59, 160.34, 140.88, 140.56, 133.15, 130.76, 130.23, 130.04, 129.32, 129.19, 128.59, 127.71, 127.25, 126.90, 113.73, 101.82, 83.14, 78.64, 70.83, 70.67, 68.55, 55.39, 55.20, 20.72; HRMS calcd for C$_{30}$H$_{24}$Cl$_4$NO$_8$S [M+H]$^+$: 697.9976. found 697.9971.

Synthesis of Phenyl 3-O-Acetyl-2-deoxy-4,6-O-p-methoxybenzylidene-2-tetrachlorophthalimido-1-thio-β-D-glucopyranoside S-Oxide (4)

The sulfide 4 (1.57 g, 2.25 mmol) in CH$_2$Cl$_2$ (50 mL) was chilled to −78° C. and 3-chloroperoxybenzoic acid (517 mg of 75% dispersion, 2.25 mmol) was added. After 1 h, the reaction was slowly warmed to −30° C. then diluted with CH$_2$Cl$_2$ and extracted from saturated aqueous NaHCO$_3$ and brine. The organic layer was dried over Na$_2$SO$_4$, decanted, and concentrated in vacuo. Purification of the crude residue by silica gel chromatography (5% EtOAc/CH$_2$Cl$_2$) afforded a mixture of sulfoxide diastereomers (1.51 g, 2.10 mmol, 93%). Less polar diastereomer: (1.29 g) $^1$H NMR (500 MHz, CDCl$_3$): δ ppm 7.44 (d, J=8.3 Hz, 2H, ArH), 7.35 (d, J=8.8 Hz, 2H, ArH), 7.20 (t, J=7.8 Hz, 2H, ArH), 7.00 (t, J=7.3 Hz, 1H, ArH), 6.86 (d, J=8.8 Hz, 2H, ArH), 5.73 (dd, J=9.3, 9.3 Hz, 1H, H-3), 5.52 (d, J=9.8 Hz, 1H, H-1), 5.50 (s, 1H, CHPMP), 4.98 (dd, J=9.8, 9.8 Hz, 1H, H-2), 4.45-4.38 (m, 1H, H-6), 3.88-3.80 (m, 3H, H-4,5,6), 3.78 (s, 3H, OMe), 1.89 (s, 3H, OAc); $^{13}$C NMR (125 MHz, CDCl$_3$): δ ppm 171.13 (s), 163.24, 161.64, 160.36, 140.29, 140.18, 139.43, 130.11, 129.68, 129.60, 129.13, 128.94, 127.68, 126.81, 126.73, 123.94, 113.71, 101.80, 90.12, 77.61, 71.09, 70.89, 68.13, 55.38, 47.32, 20.66. More polar diastereomer: (0.22 g) $^1$H NMR (500 MHz, CDCl$_3$): δ ppm 7.59 (d, J=6.8 Hz, 2H, ArH), 7.54-7.47 (m, 3H, ArH), 7.32 (d, J=8.8 Hz, 2H, ArH), 6.86 (d, J=8.8 Hz, 2H, ArH), 5.75 (dd, J=9.3, 9.3 Hz, 1H, H-3), 5.46 (d, J=10.3 Hz, 1H, H-1), 5.44 (s, 1H, CHPMP), 4.69 (dd, J=10.0, 10.0 Hz, 1H, H-2), 4.23 (dd, J=10.0, 3.2 Hz, 1H, H-6), 3.78 (s, 3H, OMe), 3.80-3.67 (m, 3H, H-4,5,6), 1.90 (s, 3H, OAc); $^{13}$C NMR (125 MHz, CDCl$_3$): δ ppm 171.14, 163.89, 162.23, 160.40, 140.98, 140.76, 131.91, 130.23, 129.16, 129.07, 127.70, 127.26, 126.86, 125.88, 113.74, 101.90, 87.06, 78.00, 71.07, 70.90, 68.03, 55.40, 50.79, 20.68; HRMS calcd for C$_{30}$H$_{27}$Cl$_4$N$_2$O$_9$S [M+NH$_4$]$^+$: 731.0191, found 731.0214.
Example 2-d
Synthesis of Compound 5
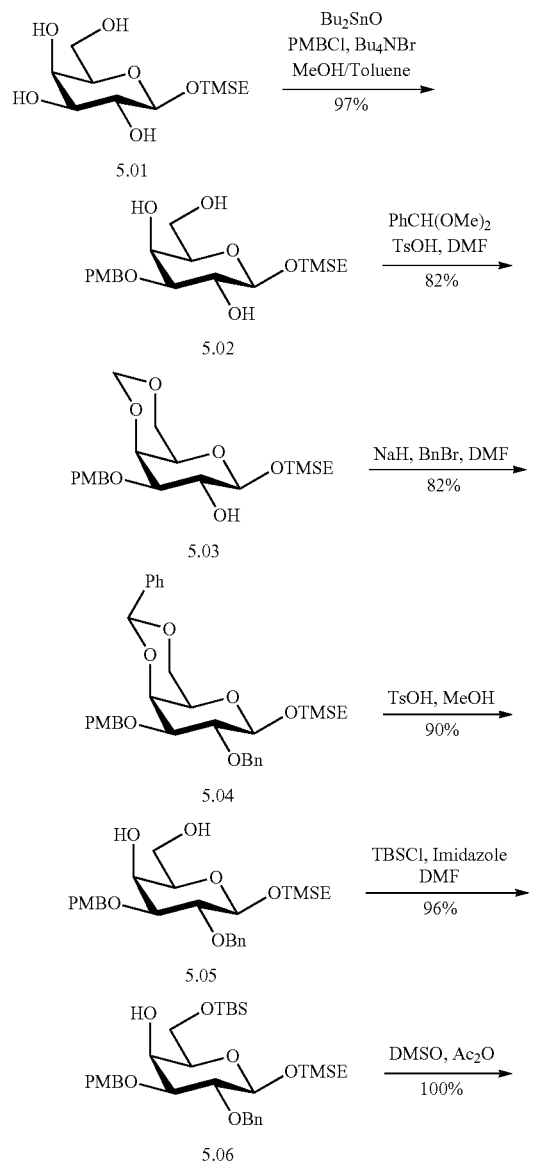
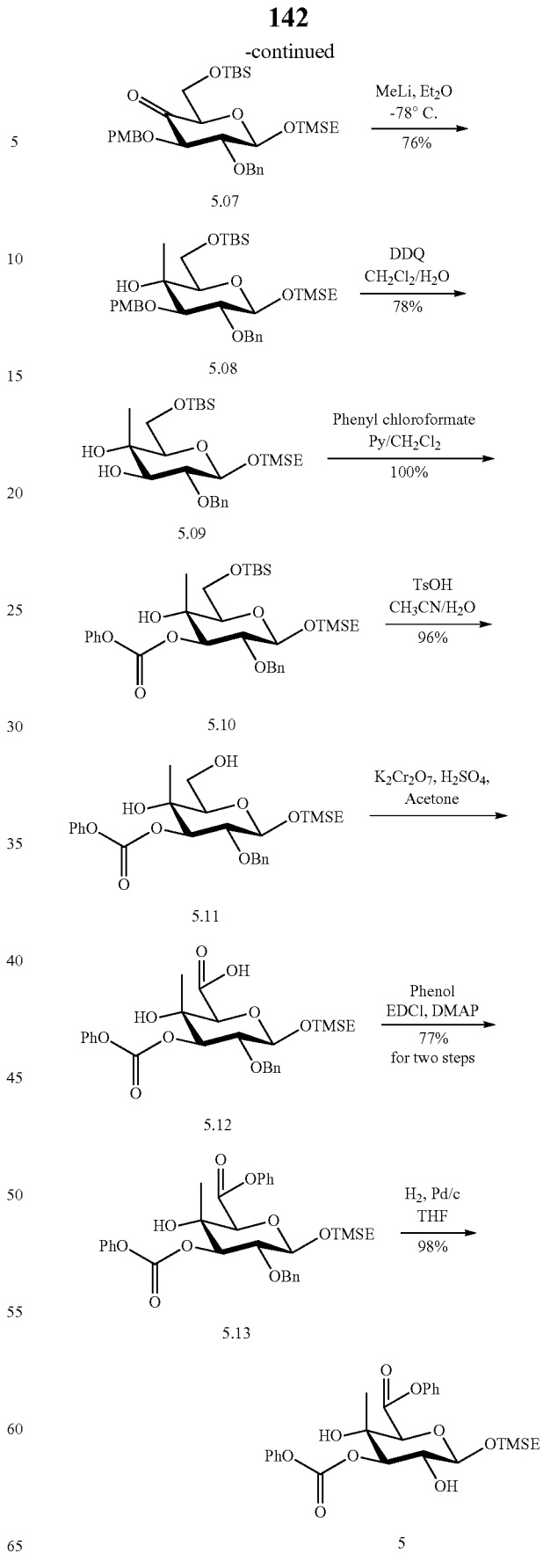

Synthesis of 2-(Trimethylsilyl)ethyl 3-O-p-Methoxybenzyl-β-D-galactopyranoside (5.02)

To a suspension of 2-(trimethylsilyl)ethyl β-D-galactopyranoside[3,4] (5.01) (42.3 g, 151 mmol) in 350 mL of methanol was added dibutyltin oxide (56.3 g, 227 mmol) and the mixture was heated at reflux until the material completely dissolved (3.5 h). The clear reaction mixture was then concentrated and azeotroped 3× from toluene. Benzene (500 mL), p-methoxybenzyl chloride (61.5 mL, 453 mmol), tetrabutylammonium bromide (24.3 g, 75.5 mmol) and 4 Å molecular sieves (10 g) were then added and the mixture was refluxed for 1 h. The mixture was then cooled to 0° C., quenched with 30 mL diethylamine, filtered through a pad of celite, and the filtrate was concentrated in vacuo. The crude residue was purified by silica gel chromatography (gradient 50-66% EtOAc/petroleum ether) to give the title compound (59.0 g, 147 mmol, 97%). $^1$H NMR (600 MHz, CDCl$_3$): δ ppm 7.30 (d, J=8.5 Hz, 2H, PMPH), 6.88 (d, J=8.5 Hz, 2H, PMPH), 4.67, 4.65 (ABq, J=11.7 Hz, 1H each, OCH$_2$PMP), 4.25 (d, J=7.9 Hz, 1H, H-1), 4.01 (ddd, J=11.7, 9.7, 5.6 Hz, 1H, OCHHCH$_2$SiMe$_3$), 3.98 (d, J=2.9 Hz, 1H, H-4), 3.94 (dd, J=11.4, 6.4 Hz, 1H, H-6), 3.82 (dd, J=11.7, 5.0 Hz, 1H, H-6), 3.80 (s, 3H, OMe), 3.74 (dd, J=8.2, 8.2 Hz, 1H, H-2), 3.57 (ddd, J=11.3, 9.6, 6.0 Hz, 1H, OCHHCH$_2$SiMe$_3$), 3.47 (dd, J=5.6, 5.6 Hz, 1H, H-5), 3.41 (dd, J=9.4, 3.2 Hz, 1H, H-3), 2.74 (br s, 1H, OH), 2.53 (br s, 1H, OH), 2.42 (br s, 1H, OH), 1.08-0.92 (m, 2H, OCH$_2$CH$_2$SiMe$_3$), 0.01 (s, 9H, SiMe$_3$); $^{13}$C NMR (100 MHz, CDCl$_3$): δ ppm 159.46, 129.74, 129.66, 114.00, 102.66, 79.84, 74.21, 71.62, 70.85, 67.39, 66.74, 62.02, 55.29, 18.25, −1.37; HRMS calcd for C$_{19}$H$_{36}$NO$_7$Si [M+NH$_4$]$^+$: 418.2261. found 418.2269.

Synthesis of 2-(Trimethylsilyl)ethyl 4,6-O-Benzylidene-3-O-p-methoxybenzyl-β-D-galactopyranoside (5.03)

To a solution of 5.02 (3.06 g, 7.64 mmol) in 10 mL DMF was added benzaldehyde dimethyl acetal (1.5 mL, 9.93 mmol) and p-toluenesulfonic acid monohydrate (145 mg, 0.76 mmol) and the reaction mixture was heated at 55° C. under reduced pressure (to remove generated methanol) for 3 h. The reaction mixture was then cooled to room temperature, quenched with solid sodium bicarbonate (500 mg), and concentrated in vacuo. The residue was redissolved in CH$_2$Cl$_2$ and washed with saturated aqueous NaHCO$_3$, H$_2$O, and brine. The organic layer was dried over Na$_2$SO$_4$, decanted, and then concentrated in vacuo. The residue was purified by silica gel chromatography (30% EtOAc/petroleum ether) to afford the title compound (3.05 g, 6.24 mmol, 82%). $^1$H NMR (500 MHz, CDCl$_3$): δ ppm 7.53 (dd, J=7.6, 1.7 Hz, 2H, PhH), 7.38-7.30 (m, 5H, PhH, PMPH), 6.86 (d, J=8.3 Hz, 2H, PMPH), 5.46 (s, 1H, CHPh), 4.71, 4.67 (ABq, J=11.7 Hz, 1H each, OCH$_2$PMP), 4.29-4.28 (m, 1H, H-6), 4.10 (d, J=2.9 Hz, 1H, H-4), 4.06 (ddd, J=9.6, 5.7, 5.6 Hz, 1H, OCHHCH$_2$SiMe$_3$), 4.02 (dd, J=12.7, 2.0 Hz, 1H, H-6), 3.97 (dd, J=9.3, 9.3 Hz, 1H, H-2), 3.79 (s, 3H, OMe), 3.58 (ddd, J=11.2, 9.5, 6.1 Hz, 1H, OCHHCH$_2$SiMe$_3$), 3.47 (dd, J=9.8, 3.4 Hz, 1H, H-3), 3.33 (s, 1H, H-5), 2.54 (s, 1H, OH), 1.11-0.98 (m, 2H, OCH$_2$CH$_2$SiMe$_3$), 0.03 (s, 9H, SiMe$_3$); $^{13}$C NMR (125 MHz, CDCl$_3$): δ ppm 159.36, 137.90, 130.23, 129.51, 128.90, 128.11, 126.47, 113.87, 102.49, 101.16, 78.81, 73.24, 71.09, 70.07, 69.34, 67.05, 66.65, 55.31, 18.22, −1.34; HRMS calcd for C$_{26}$H$_{40}$NO$_7$Si [M+NH$_4$]$^+$: 506.2574. found 506.2570.

Synthesis of 2-(Trimethylsilyl)ethyl 2-O-Benzyl-4,6-O-benzylidene-3-O-p-methoxybenzyl-β-D-galactopyranoside (5.04)

A solution of 5.03 (3.05 g, 6.24 mmol) in DMF (10 mL) was chilled to 0° C. then NaH (315 mg, 12.5 mmol) was added. The reaction mixture was stirred for 30 minutes then treated with benzyl bromide (2.1 mL, 12.5 mmol) and stirred for an additional 1 h at 0° C. After being quenched with methanol (5 mL), the mixture was concentrated in vacuo. The crude residue was redissolved in CH$_2$Cl$_2$ and washed with saturated aqueous NaHCO$_3$, H$_2$O, and brine. The organic layer was dried over Na$_2$SO$_4$, decanted, and concentrated in vacuo. The residue was purified by silica gel chromatography (20% EtOAc/petroleum ether) to afford the title compound (2.96 g, 5.11 mmol, 82%). $^1$H NMR (600 MHz, CDCl$_3$): δ ppm 7.57 (d, J=6.4 Hz, 2H, PhH), 7.41 (d, J=7.3 Hz, 2H, PhH), 7.39-7.32 (m, 5H, PhH), 7.32-7.27 (m, 3H, PhH, PMPH), 6.84 (d, J=8.8 Hz, 2H, PMPH), 5.50 (s, 1H, CHPh), 4.95, 4.79 (ABq, J=10.8 Hz, 1H each, OCH$_2$Ph), 4.72, 4.69 (ABq, J=12.0 Hz, 1H each, OCH$_2$PMP), 4.40 (d, J=7.6 Hz, 1H, H-1), 4.31 (d, J=12.3 Hz, 1H, H-6), 4.08 (d, J=3.2 Hz, 1H, H-4), 4.10-4.04 (m, 1H, OCHHCH$_2$SiMe$_3$), 4.01 (dd, J=12.2, 1.3 Hz, 1H, H-6), 3.83 (dd, J=9.7, 7.9 Hz, 1H, H-2), 3.80 (s, 3H, OMe), 3.62-3.56 (m, 1H, OCHHCH$_2$SiMe$_3$), 3.54 (dd, J=9.7, 3.5 Hz, 1H, H-3), 3.31 (br s, 1H, H-5), 1.11-1.02 (m, 2H, OCH$_2$CH$_2$SiMe$_3$), 0.04 (s, 9H, SiMe$_3$); $^{13}$C NMR (100 MHz, CDCl$_3$): δ ppm 159.30, 139.16, 138.03, 130.62, 129.49, 129.01, 128.36, 128.20, 128.17, 127.60, 126.70, 113.82, 103.36, 101.51, 78.90, 78.73, 75.36, 74.22, 71.74, 69.39, 67.47, 66.47, 55.38, 18.61, −1.27; HRMS calcd for C$_{33}$H$_{46}$NO$_7$Si [M+NH$_4$]$^+$: 596.3044. found 596.3034.

Synthesis of 2-(Trimethylsilyl)ethyl 2-O-Benzyl-3-O-p-methoxybenzyl-β-D-galactopyranoside (5.05)

To a stirred suspension of 5.04 (3.17 g, 5.48 mmol) in methanol (40 mL) was added p-toluenesulfonic acid monohydrate (104 mg, 0.55 mmol). After stirring for 2 h the mixture became clear and then a portion of solid NaHCO$_3$ (500 mg) was added to quench the reaction. After concentration, the residue was redissolved in CH$_2$Cl$_2$ then washed with saturated aqueous NaHCO$_3$ and H$_2$O. The organic layer was dried over Na$_2$SO$_4$, then concentrated in vacuo. The residue was purified by silica gel chromatography (40% EtOAc/petroleum ether) to afford the title compound (2.42 g, 6.24 mmol, 90%). $^1$H NMR (600 MHz, CDCl$_3$): δ ppm 7.38 (d, J=7.3 Hz, 2H, PhH), 7.34 (t, J=7.5 Hz, 2H, PhH), 7.29 (t, J=7.3 Hz, 1H, PhH), 7.25 (d, J=8.5 Hz, 2H, PMPH), 6.85 (d, J=8.2 Hz, 2H, PMPH), 4.93, 4.73 (ABq, J=11.0 Hz, 1H each, OCH$_2$Ph), 4.66, 4.64 (ABq, J=11.2 Hz, 1H each, OCH$_2$PMP), 4.38 (d, J=7.6 Hz, 1H, H-1), 4.06-4.00 (m, 1H, OCHHCH$_2$SiMe$_3$), 4.02-3.94 (m, 2H, H-4,6), 3.83 (dd, J=8.6, 4.5 Hz, 1H, H-6), 3.80 (s, 3H, OMe), 3.64-3.57 (m, 2H, H-2, OCHHCH$_2$SiMe$_3$), 3.49 (dd, J=9.4, 3.5 Hz, 1H, H-3), 3.45 (t, J=5.4 Hz, 1H, H-5), 2.64 (s, 1H, OH), 2.20 (dd, J=8.5, 4.1 Hz, 1H, OH), 1.04 (t, J=8.5 Hz, 2H, OCH$_2$CH$_2$SiMe$_3$), 0.02 (s, 9H, SiMe$_3$); $^{13}$C NMR (100 MHz, CDCl$_3$): δ ppm 159.52, 138.82, 129.97, 129.65, 128.42, 128.17, 127.73, 114.01, 103.43, 80.17, 79.13, 75.31, 73.98, 72.30, 67.67, 67.60, 62.72, 55.40, 18.68, −1.29; HRMS calcd for C$_{26}$H$_{42}$NO$_7$Si [M+NH$_4$]$^+$: 508.2731. found 508.2715.

Synthesis of 2-(Trimethylsilyl)ethyl 2-O-Benzyl-6-O-tert-butyldimethylsilyl-3-O-p-methoxybenzyl-β-D-galactopyranoside (5.06)

A solution of 5.05 (8.90 g, 18 mmol) in DMF (60 mL) was treated with tert-butyldimethylsilyl chloride (6.8 g, 45.2 mmol) and imidazole (3.1 g, 45.2 mmol). After stirring for 8 h, the reaction was concentrated in vacuo. The residue was redissolved in CH$_2$Cl$_2$ then washed with H$_2$O. The organic layer was dried over Na$_2$SO$_4$, decanted, and concentrated in vacuo. The residue was purified by silica gel chromatography (10% EtOAc/petroleum ether) to afford the title compound (10.5 g, 17.4 mmol, 96%). $^1$H NMR (600 MHz, CDCl$_3$): δ ppm 7.38 (d, J=7.0 Hz, 2H, PhH), 7.33 (t, J=7.6 Hz, 2H, PhH), 7.30-7.26 (m, 3H, PhH, PMPH), 6.85 (d, J=8.2 Hz, 2H, PMPH), 4.92, 4.73 (ABq, J=11.1 Hz, 1H each, OCH$_2$Ph), 4.68, 4.64 (ABq, J=11.4 Hz, 1H each, OCH$_2$PMP), 4.34 (d, J=7.9 Hz, 1H, H-1), 4.04-3.98 (m, 1H, OCHHCH$_2$SiMe$_3$), 3.94 (br s, 1H, H-4), 3.89 (dd, J=10.3, 6.2 Hz, 1H, H-6), 3.82 (dd, J=10.4, 5.7 Hz, 1H, H-6), 3.80 (s, 3H, OMe), 3.64-3.54 (m, 2H, H-2, OCHHCH$_2$SiMe$_3$), 3.45 (dd, J=9.4, 3.2 Hz, 1H, H-3), 3.38 (t, J=6.0 Hz, 1H, H-5), 2.50 (br s, 1H, OH), 1.03 (t, J=8.5 Hz, 2H, OCH$_2$CH$_2$SiMe$_3$), 0.90 (s, 9H, SiCMe$_3$), 0.082, 0.078 (s, 3H each, SiMe$_2$), 0.02 (s, 9H, SiMe$_3$); $^{13}$C NMR (125 MHz, CDCl$_3$): δ ppm 159.41, 138.99, 130.26, 129.56, 128.35, 128.14, 127.62, 113.93, 103.33, 80.55, 79.34, 75.23, 74.56, 72.18, 67.24, 66.75, 62.50, 55.33, 25.97, 18.59, 18.41, −1.32, −5.23, −5.28; HRMS calcd for C$_{32}$H$_{56}$NO$_7$Si$_2$ [M+NH$_4$]$^+$: 622.3595. found 622.3580.

Synthesis of 2-(Trimethylsilyl)ethyl 2-O-Benzyl-6-O-tert-butyldimethylsilyl-3-O-p-methoxybenzyl-β-D-xylo-hexopyranoside-4-ulose (5.07)

Compound 5.06 (10.5 g, 17.4 mmol) in DMSO (80 mL) and acetic anhydride (60 mL) was heated to 65° C. for 3 h then cooled to room temperature. The reaction mixture was poured into a separatory funnel, diluted with ethyl ether, and washed with H$_2$O. The aqueous layer was back-extracted with additional ethyl ether (5×). The organic layers were combined, dried over Na$_2$SO$_4$, and concentrated in vacuo. The resulting oil was purified by silica gel column chromatography (8% EtOAc/petroleum ether) to afford the title compound (10.4 g, 17.4 mmol, 100%). $^1$H NMR (500 MHz, CDCl$_3$): δ ppm 7.40-7.34 (m, 6H), 7.32 (d, J=8.3 Hz, 2H), 6.85 (d, J=8.3 Hz, 2H), 4.88 (d, J=7.8 Hz, 1H), 4.86 (d, J=7.8 Hz, 1H), 4.79-4.74 (m, 2H), 4.58 (d, J=11.2 Hz, 1H), 4.15-4.08 (m, 3H), 4.05 (t, J=8.5 Hz, 1H), 3.98 (dd, J=7.1, 3.7 Hz, 1H), 3.85-3.81 (m, 1H), 3.80 (s, 3H), 3.74-3.61 (m, 2H), 1.09-1.02 (m, 2H), 0.93 (s, 9H), 0.11 (s, 6H), 0.06 (s, 9H); $^{13}$C NMR (125 MHz, CDCl$_3$): δ ppm 202.00, 159.50, 138.34, 129.89, 129.72, 128.41, 128.12, 127.81, 113.86, 102.52, 83.74, 83.10, 74.75, 73.50, 67.53, 61.74, 55.31, 25.97, 18.46, 18.42, −1.29, −5.17, −5.25; HRMS calcd for C$_{32}$H$_{54}$NO$_7$Si$_2$ [M+NH$_4$]$^+$: 620.3439. found 620.3423.

Synthesis of 2-(Trimethylsilyl)ethyl 2-O-Benzyl-6-O-tert-butyldimethylsilyl-3-O-p-methoxybenzyl-4-C-methyl-β-D-glucopyranoside (5.08)

A stirred solution of 5.07 (9.2 g, 15 mmol) in ethyl ether (250 mL) was chilled to −78° C. then methyl lithium (48 mL of 1.6 M solution in diethyl ether, 76 mmol) was added dropwise over 20 minutes. The reaction was kept at −78° C. for an additional 4 h then warmed to room temperature and carefully quenched with saturated NH$_4$Cl and transferred to a separatory funnel containing diethyl ether. The organic phase collected then washed with H$_2$O and brine, dried over over Na$_2$SO$_4$, decanted, and concentrated in vacuo. The resulting oil was purified by silica gel chromatography (8-12% EtOAc/petroleum ether) to give the desired glucopyranoside product 5.08 (7.2 g, 11.6 mmol, 76%) and its galactopyranoside diastereomer (2.1 g, 3.4 mmol, 22%). Desired glucopyranoside product 5.08: $^1$H NMR (500 MHz, CDCl$_3$): δ ppm 7.38-7.27 (m, 7H, ArH), 6.86 (d, J=8.8 Hz, 2H, PMPH), 4.89, 4,71 (ABq, J=10.7 Hz, 1H each, OCH$_2$Ar), 4.84, 4.79 (ABq, J=11.0 Hz, 1H each, OCH$_2$Ar), 4.44 (d, J=7.8 Hz, 1H, H-1), 4.04-3.97 (m, 1H, OCHHCH$_2$SiMe$_3$), 3.92-3.81 (m, 2H, H-6), 3.80 (s, 3H, OMe), 3.57-3.65 (m, 1H, OCHHCH$_2$SiMe$_3$), 3.49 (d, J=9.8 Hz, 1H, H-3), 3.42 (t, J=6.8 Hz, 1H, H-5), 3.27 (dd, J=9.8, 7.8 Hz, 1H, H-2), 1.30 (s, 3H, Me$_2$), 1.05 (t, J=8.3 Hz, 2H, OCH$_2$CH$_2$SiMe$_3$), 0.93 (s, 9H, SiCMe$_3$), 0.13, 0.12 (s, 3H each, SiMe), 0.04 (s, 9H, SiMe$_3$); $^{13}$C NMR (125 MHz, CDCl$_3$): δ ppm 159.21, 138.96, 131.46, 129.60, 128.41, 128.14, 127.66, 113.85, 103.85, 86.30, 81.41, 75.78, 75.32, 75.16, 75.10, 67.85, 62.73, 55.36, 25.99, 18.71, 18.31, 16.37, −1.29, −5.32, −5.48; HRMS calcd for C$_{33}$H$_{58}$NO$_7$Si$_2$ [M+NH$_4$]$^+$: 636.3752. found 636.3726.

Synthesis of 2-(Trimethylsilyl)ethyl 2-O-Benzyl-6-O-tert-butyldimethylsilyl-4-C-methyl-β-D-glucopyranoside (5.09)

To a stirred solution of 5.08 (7.2 g, 11.6 mmol) in CH$_2$Cl$_2$ (137 mL) and H$_2$O (8 mL) at 0° C. was added 2,3-dichloro-5,6-dicyano-1,4-benzoquinone (3.4 g, 15.0 mmol). The reaction mixture was stirred for 1 h then diluted with CH$_2$Cl$_2$ and sequentially washed with saturated aqueous NaHCO$_3$, H$_2$O, and brine. After concentration of the organic phase in vacuo, the crude residue was purified by silica gel chromatography (25% EtOAc/petroleum ether) to afford the title compound (4.5 g, 9.0 mmol, 78%). $^1$H NMR (500 MHz, CDCl$_3$): δ ppm 7.39-7.32 (m, 4H, PhH), 7.29 (t, J=6.8 Hz, 1H, PhH), 4.95, 4.68 (ABq, J=11.2 Hz, 1H each, OCH$_2$Ph), 4.42 (d, J=7.8 Hz, 1H, H-1), 4.01-3.94 (m, 1H, OCHHCH$_2$SiMe$_3$), 3.90-3.80 (m, 2H, H-6), 3.60 (d, J=9.8 Hz, 1H, H-3), 3.60-3.54 (m, 1H, OCHHCH$_2$SiMe$_3$), 3.51 (br s, 1H, OH), 3.41 (t, J=6.8 Hz, 1H, H-5), 3.16 (dd, J=9.8, 7.8 Hz, 1H, H-3), 2.48 (br s, 1H, OH), 1.25 (s, 3H, Me), 1.05-0.99 (m, 2H, OCH$_2$CH$_2$SiMe$_3$), 0.90 (s, 9H, SiCMe$_3$), 0.11, 0.11 (s, 3H each, SiME$_2$), 0.02 (s, 9H, SiMe$_3$); $^{13}$C NMR (125 MHz, CDCl$_3$): δ ppm 138.73, 128.56, 128.03, 127.86, 103.70, 80.62, 78.29, 75.77, 74.63, 73.80, 67.81, 62.57, 25.91, 18.68, 18.21, 15.31, −1.31, −5.39, −5.52; HRMS calcd for C$_{25}$H$_{50}$NO$_6$Si$_2$ [M+NH$_4$]$^+$: 516.3177. found 516.3165.

Synthesis of 2-(Trimethylsilyl)ethyl 2-O-Benzyl-6-O-tert-butyldimethylsilyl-4-C-methyl-3-O-phenoxycarbonyl-β-D-glucopyranoside (5.10)

Compound 5.09 (4.0 g, 8.0 mmol) was dissolved in CH$_2$Cl$_2$ (80 mL) and pyridine (2.6 mL, 32 mmol) then chilled to 0° C. Phenyl chloroformate (1.1 mL, 8.8 mmol) was added and the reaction was stirred for 20 min then quenched with 20 mL MeOH and concentrated in vacuo. The residue was dissolved in CH$_2$Cl$_2$ then washed with H$_2$O and brine. The organic layer was concentrated in vacuo and the residue was purified by silica gel chromatography (10% EtOAc/petroleum ether) to afford the title compound (5.0 g, 8.0 mmol, 100%). $^1$H NMR (500 MHz, CDCl$_3$): δ ppm 7.36-7.25 (m, 7H, PhH), 7.22 (t, J=7.3 Hz, 1H, PhH), 7.10 (d, J=8.8 Hz, 2H, PhH), 4.97 (d, J=10.3 Hz, 1H, H-3), 4.95, 4.67 (ABq, J=11.2 Hz, OCH$_2$Ph1H each,), 4.53 (d, J=7.8 Hz, 1H, H-1), 4.04-3.96 (m, 1H, OCHHCH$_2$SiMe$_3$), 3.89 (d, J=7.3 Hz, 2H, H-6), 3.64 (s, 1H, OH), 3.63-3.58 (m, 1H, OCHHCH$_2$SiMe$_3$), 3.54 (t, J=7.1 Hz, 1H, H-5), 3.38 (dd, J=10.3, 7.8 Hz, 1H, H-2), 1.36 (s, 3H, Me), 1.04 (t, J=8.8 Hz, 2H, OCH$_2$CH$_2$SiMe$_3$), 0.91 (s, 9H, SiCMe$_3$), 0.13, 0.12 (s, 3H each, SiMe$_2$), 0.04 (s, 9H, SiMe$_3$); $^{13}$C NMR (125 MHz, CDCl$_3$): δ ppm 153.72, 151.34, 138.51, 129.43, 128.44, 127.66, 127.64, 125.97, 121.18, 103.63, 83.26, 79.14, 75.22, 74.80, 73.57, 68.06, 62.56, 25.94, 18.69, 18.26, 16.13, −1.29, −5.38, −5.55; HRMS calcd for $C_{32}H_{54}NO_8Si_2$ $[M+NH_4]^+$: 618.3044. found 618.9056.

Synthesis of 2-(Trimethylsilyl)ethyl 2-O-Benzyl-4-C-methyl-3-O-phenoxycarbonyl-β-D-glucopyranoside (5.11)

To a stirred solution of 5.10 (4.7 g, 7.6 mmol) in $CH_3CN$ (30 mL) and $H_2O$ (30 mL) was added p-toluenesulfonic acid monohydrate (115 mg, 0.76 mmol). The reaction was stirred for 3 h then diluted with EtOAc and washed sequentially with saturated aqueous $NaHCO_3$, $H_2O$, and brine. After concentration of the organic phase in vacuo, the crude residue was purified by silica gel chromatography (50% EtOAc/petroleum ether) to afford the title compound (3.7 g, 7.3 mmol, 96%). $^1H$ NMR (500 MHz, $CDCl_3$): δ ppm 7.39-7.22 (m, 8H, PhH), 7.10 (d, J=7.3 Hz, 2H, PhH), 4.94, 4.67 (ABq, J=11.2 Hz, 1H each, $OCH_2Ph$), 4.88 (d, J=9.8 Hz, 1H, H-3), 4.53 (d, J=7.8 Hz, 1H, H-1), 4.04-3.96 (m, 1H, $OCHHCH_2SiMe_3$), 3.91 (dd, J=11.7, 4.9 Hz, 1H, H-6), 3.78 (dd, J=11.7, 6.8 Hz, 1H, H-6), 3.67-3.59 (m, 1H, $OCHHCH_2SiMe_3$), 3.46 (dd, J=6.8, 5.4 Hz, 1H, H-5), 3.39 (dd, J=10.0, 7.6 Hz, 1H, H-2), 1.29 (s, 3H, Me), 1.04 (t, J=8.5 Hz, 2H, $OCH_2CH_2SiMe_3$), 0.04 (s, 9H, $SiMe_3$); $^{13}C$ NMR (125 MHz, $CDCl_3$): δ ppm 154.43, 151.15, 138.34, 129.61, 128.50, 127.81, 127.73, 126.31, 121.06, 103.64, 84.03, 79.21, 77.45, 74.92, 73.40, 68.21, 61.05, 18.73, 15.90, −1.27; HRMS calcd for $C_{26}H_{40}NO_8Si$ $[M+NH_4]^+$: 522.2523. found 522.2501.

Synthesis of 2-(Trimethylsilyl)ethyl 2-O-Benzyl-4-C-methyl-3-O-phenoxycarbonyl-β-D-glucopyranuronic acid (5.12)

Compound 5.11 (3.6 g, 7.1 mmol) was dissolved in acetone (50 mL) then treated with a solution of potassium dichromate (4.2 g, 14.2 mmol) in 3 M $H_2SO_4$ (20 mL). The reaction mixture was heated at 70° C. for 1 h then cooled to room temperature. Dilution with EtOAc was followed by washing with $H_2O$. The aqueous phase was back-extracted with EtOAc (3×) and the combined organic extracts were washed with $H_2O$. The aqueous layer was back-extracted with EtOAc then the organic phases were combined, dried over $Na_2SO_4$, and concentrated in vacuo to afford the crude acid (3.7 g, 7.1 mmol), which was utilized in the next reaction without further purification. $^1H$ NMR (500 MHz, $CDCl_3$): δ ppm 7.38-7.27 (m, 7H, PhH), 7.24 (t, J=7.3 Hz, 1H, PhH), 7.09 (d, J=7.8 Hz, 2H, PhH), 5.05 (d, J=9.8 Hz, 1H, H-3), 4.94, 4.68 (ABq, J=11.5 Hz, 1H each, $OCH_2Ph$), 4.60 (d, J=7.8 Hz, 1H, H-1), 4.05 (s, 1H, H-5), 4.09-4.02 (m, 1H, $OCHHCH_2SiMe_3$), 3.71-3.62 (m, 1H, $OCHHCH_2SiMe_3$), 3.44 (dd, J=10.3, 7.8 Hz, 1H, H-2), 1.36 (s, 3H, Me), 1.06 (t, J=8.5 Hz, 2H, $OCH_2CH_2SiMe_3$), 0.05 (s, 9H, $SiMe_3$); $^{13}C$ NMR (125 MHz, $CDCl_3$): δ ppm 170.22, 153.72, 151.18, 138.01, 129.57, 128.53, 127.92, 127.75, 126.26, 121.06, 103.45, 81.87, 78.50, 77.41, 76.91, 75.83, 75.00, 72.96, 68.80, 18.66, 16.93, −1.27; HRMS calcd for $C_{26}H_{38}NO_9Si$ $[M+NH_4]^+$: 536.2316. found 536.2292.

Synthesis of Phenyl [2-(Trimethylsilyl)ethyl 2-O-benzyl-4-C-methyl-3-O-phenoxycarbonyl-β-D-glucopyranosid]uronate (5.13)

The acid 5.12 (555 mg, 1.07 mmol) was dissolved in $CH_2Cl_2$ (12 mL) and the mixture was cooled to 0° C. Phenol (504 mg, 5.35 mmol) and 4-dimethylaminopyridine (13 mg, 0.11 mmol) were added followed by N-(3-dimethylaminopropyl)-N'-ethylcarbodiimide hydrochloride (246 mg, 1.28 mmol). After being stirred overnight, the reaction mixture was diluted with $CH_2Cl_2$ and washed with $H_2O$ and brine. The organic phase was then dried over $Na_2SO_4$ followed by concentration in vacuo. The crude residue was then purified by silica gel chromatography (20% EtOAc/petroleum ether) to afford the title compound (489 mg, 0.822 mmol, 77%). $^1H$ NMR (600 MHz, $CDCl_3$): δ ppm 7.42 (t, J=7.8 Hz, 2H, PhH), 7.37 (d, J=6.7 Hz, 2H, PhH), 7.36-7.27 (m, 6H, PhH), 7.22 (t, J=7.5 Hz, 1H, PhH), 7.14 (d, J=7.6 Hz, 2H, PhH), 7.13 (d, J=7.6 Hz, 2H, PhH), 5.12 (d, J=10.0 Hz, 1H, H-3), 4.99, 4.72 (ABq, J=11.4 Hz, 1H each, $OCH_2Ph$), 4.64 (d, J=7.9 Hz, 1H, H-1), 4.25 (s, 1H, H-5), 4.11 (ddd, J=10.2, 10.2, 6.6 Hz, 1H, $OCHHCH_2SiMe_3$), 3.69 (ddd, J=10.1, 10.1, 6.2 Hz, 1H, $OCHHCH_2SiMe_3$), 3.51 (dd, J=10.1, 7.8 Hz, 1H, H-2), 3.27 (s, 1H, OH), 1.49 (s, 3H, Me), 1.14-1.04 (m, 2H, $OCH_2CH_2SiMe_3$), 0.06 (s, 9H, $SiMe_3$); $^{13}C$ NMR (100 MHz, $CDCl_3$); δ ppm 167.47, 153.68, 151.22, 150.09, 138.22, 129.73, 129.51, 128.49, 127.82, 127.73, 126.60, 126.13, 121.49, 121.06, 103.47, 82.23, 78.71, 76.75, 74.88, 73.41, 68.35, 18.61, 17.11, −1.26; HRMS calcd for $C_{32}H_{42}NO_9Si$ $[M+NH_4]^+$: 612.2629. found 612.2616.

Synthesis of Phenyl [2-(Trimethylsilyl)ethyl 4-C-methyl-3-O-phenoxycarbonyl-β-D-glucopyranosid]uronate (5)

To a stirred solution of 5.13 (460 mg, 0.773 mmol) in degassed THF (10 mL) under an atmosphere of argon was added Pd/C (100 mg). The suspension was degassed and backfilled with $H_2$ three times then stirred under $H_2$ (1 atm) overnight. The reaction mixture was then filtered through a pad of celite and concentrated in vacuo. Silica gel chromatography (25% EtOAc/petroleum ether) afforded the title compound (381 mg, 0.755 mmol, 98%). $^1H$ NMR (600 MHz, $CDCl_3$): δ ppm 7.41 (t, J=7.9 Hz, 2H, PhH), 7.37 (dd, J=8.5, 7.3 Hz, 2H, PhH), 7.28 (t, J=7.5 Hz, 1H, PhH), 7.26-7.21 (m, 3H, PhH), 7.14 (d, J=7.6 Hz, 2H, PhH), 5.04 (d, J=10.3 Hz, 1H, H-3), 4.49 (d, J=7.9 Hz, 1H, H-1), 4.27 (s, 1H, H-5), 4.10 (ddd, J=10.3, 10.3, 5.9 Hz, 1H, $OCHHCH_2SiMe_3$), 3.70-3.62 (m, 2H, H-2, $OCHHCH_2SiMe_3$), 3.29 (s, 1H, OH), 1H, OH), 1.48 (s, 3H, Me), 1.10-0.99 (m, 2H, $OCH_2CH_2SiMe_3$), 0.04 (s, 9H, $SiMe_3$); $^{13}C$ NMR (125 MHz, $CDCl_3$): δ ppm 167.43, 153.91, 151.26, 150.04, 129.76, 129.55, 126.64, 126.19, 121.47, 121.11, 102.91, 82.44, 76.91, 73.40, 71.20, 68.39, 18.30, 17.21, −1.26; HRMS calcd for $C_{25}H_{36}NO_9Si$ $[M+NH_4]^+$: 522.2159. found 522.2167.

Example 2-e

Synthesis of Phenyl [2-(Trimethylsilyl)ethyl 3,4-di-O-benzyl-2-O-benzoyl-β-D-galactopyrosyl-uronate]-(1→4)-2-deoxy-2-tetrachlorophthalimido-1-thio-β-D-glucopyranoside (6)

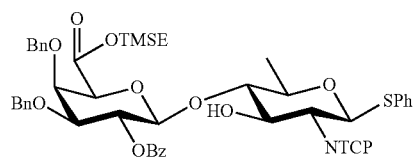

A solution of sulfoxide 2 (187 mg, 0.27 mmol), 4 Å molecular sieves and 4-allyl-1,2-dimethoxybenzene (81 µL, 0.54 mmol) in methylene chloride (2.5 ml) was stirred at room temperature for 1 h then cooled to −78° C. and triflic anhydride (44 μl, 1.1, 0.27 mmol) was slowly added. A solution of acceptor 3 (119 mg, 0.22 mmol) and 2,6-di-tert-butyl-4-methylpyridine (145 mg, 0.70 mmol) in methylene chloride (2 ml) was added dropwise via syringe over 10 min. The reaction mixture was warmed to 0° C. over 1 hour and then quenched with a saturated aqueous NaHCO$_3$ solution. The crude mixture was then diluted with CH$_2$Cl$_2$ and washed with H$_2$O and brine. The organic phase was then dried over Na$_2$SO$_4$ and concentrated in vacuo. The crude residue was purified by silica gel chromatography (20% EtOAc/petroleum ether) to afford the title compound (184 mg, 0.20 mmol, 75%). $^1$H NMR (400 MHz, CDCl$_3$): δ 8.00-7.04 (m, 20H, PhH), 5.70 (dd, J=10.2, 8.1 Hz, 1H, H-2$^B$), 5.50 (d, J=10.6 Hz, 1H, H-1$^C$), 4.98, 4.64 (ABq, J=11.7 Hz, 1H each, OCH$_2$Ph), 4.68, 4.49 (ABq, J=12.4 Hz, 1H each, OCH$_2$Ph), 4.59 (d, J=8.1 Hz, 1H, H-1$^B$), 4.44 (dd, J=10.6, 8.4 Hz, 1H, H-3$^C$), 4.38 (br s, 1H, H-4$^B$), 4.19 (dd, J=10.6, 10.6 Hz, 1H, H-2$^C$), 4.14 (m, 1H, OCHHCH$_2$SiMe$_3$), 4.09 (s, 1H, H-5$^B$), 4.01 (m, 1H, OCHHCH$_2$SiMe$_3$,), 3.72 (dd, J=2.5, 10.2 Hz, 1H, H-3$^B$), 3.51 (m, 1H, H-5$^C$), 3.18 (dd, J=8.4, 8.4 Hz, 1H, H-4$^C$), 1.05 (d, J=5.8 Hz, 3H, H-6$^C$), 0.72 (m, 2H, OCH$_2$CH$_2$SiMe$_3$), −0.90 (s, 9H, SiMe$_3$); $^{13}$C NMR (100 MHz, CDCl$_3$): δ 167.2, 165.2, 163.3, 162.8, 140.3, 138.0, 137.2, 133.6, 132.4, 130.1, 129.9, 129.1, 128.7, 128.2, 127.9, 127.6, 102.2, 88.9, 83.0, 78.9, 74.9, 74.6, 74.1, 73.8, 72.1, 71.3, 70.7, 64.8, 56.3, 17.8, 17.4, −1.5; LRMS calcd for C$_{52}$H$_{51}$Cl$_4$NO$_{12}$SSiNa [M+Na]:$^+$: 1104.2. found 1104.2.

Example 2-f

Synthesis of Phenyl [2-(Trimethylsilyl)ethyl 3,4-di-O-benzyl-2-O-benzoyl-β-D-galactopyrosyluronate]-(1→4)-2-deoxy-2-tetrachlorophthalimido-1-thio-β-D-glucopyranoside S-Oxide (7)

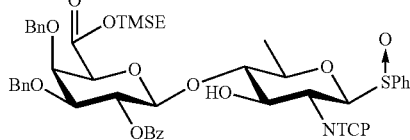

To a solution of sulfide 6 (500 mg, 0.46 mmol) in CH$_2$Cl$_2$ was added mCPBA (100 mg, ~75%, 0.43 mmol) at −78° C. The reaction mixture was warmed to 0° C. over 2 h and quenched with saturated aqueous NaHCO$_3$. The mixture was then extracted with CH$_2$Cl$_2$. The organic layer was washed with brine and dried over Na$_2$SO$_4$. After concentration of the organic phase in vacuo, the product was purified by silica gel chromatography (30% EtOAc/petroleum ether) to afford the title compound as a mixture of diastereomeric sulfoxides (350 mg, 0.32 mmol, 70%). Major: $^1$H NMR (400 MHz, CDCl$_3$): δ 8.00-7.04 (m, 20H, PhH), 5.68 (dd, J=9.2, 8.0 Hz, 1H, H-2$^B$), 5.06 (d, J=10.2 Hz, 1H, H-1$^C$), 4.96, 4.62 (ABq, J=11.7 Hz, 1H each, CH$_2$Ph), 4.72 (dd, J=10.2, 10.2 Hz, 1H, H-2$^C$), 4.68, 4.48 (ABq, J=12.4 Hz, 1H each, CH$_2$Ph), 4.59 (d, J=8.0 Hz, 1H, H-1$^B$), 4.40 (dd, J=10.2, 8.0 Hz, 1H, H-3$^C$), 4.38 (br s, 1H, H-4$^B$), 4.34 (m, 1H, OCHHCH$_2$SiMe$_3$), 4.12 (s, 1H, H-5$^B$), 4.02 (m, 1H, OCHHCH$_2$SiMe$_3$,), 4.75 (dd, J=2.5, 9.2 Hz, 1H, H-3$^B$), 3.41 (dd, J=6.2, 8.0 Hz, 1H, H-5$^C$), 3.17 (dd, J=8.0, 8.0 Hz, 1H, H-4$^C$), 1.00 (d, J=6.2 Hz, 3H, H-6$^C$), 0.80 (m, 2H, OCH$_2$CH$_2$SiMe$_3$), −0.90 (s, 9H, SiMe$_3$); $^{13}$C NMR (100 MHz, CDCl$_3$): δ 167.2, 165.2, 163.3, 162.3, 140.3, 139.9, 138.0, 137.2, 133.6, 130.6, 130.0, 129.8, 128.8, 128.6, 128.2, 128.0, 127.9, 127.3, 124.6, 102.2, 89.2, 88.1, 79.0, 75.3, 74.9, 74.1, 73.8, 72.1, 71.3, 70.6, 64.8, 50.7, 17.4, −1.5. Minor: $^1$H NMR (400 MHz, CDCl$_3$): δ 8.00-7.04 (m, 20H, PhH), 5.66 (dd, J=7.7, 9.9 Hz, 1H, H-2$^B$), 5.08 (d, J=10.6 Hz, 1H, H-1$^C$), 4.95, 4.62 (ABq, J=11.7 Hz, 1H each, CH$_2$Ph), 4.66, 4.45 (ABq, J=12.5 Hz, 1H each, CH$_2$Ph), 4.53 (d, J=7.7 Hz, 1H, H-1$^B$), 4.50 (dd, J=10.7, 10.7 Hz, 1H, H-2$^C$), 4.35 (dd, J=10.8, 8.1 Hz, 1H, H-3$^C$), 4.34 (br s, 1H, H-4$^B$), 4.38-4.18 (m, 1H, OCHHCH$_2$SiMe$_3$), 4.06 (s, 1H, H-5$^B$), 4.03-3.90 (m, 1H, OCHHCH$_2$SiMe$_3$), 3.70 (dd, J=9.9, 2.2 Hz, 1H, H-3$^B$), 3.40 (m, 1H, H-5$^C$), 3.11 (dd, J=8.1, 8.1 Hz, 1H, H_4$^C$), 0.90 (d, J=6.2 Hz, 3H, H-6$^C$), 0.82-0.75 (m, 2H, OCH$_2$CH$_2$SiMe$_3$), −0.90 (s, 9H, SiMe$_3$); $^{13}$C NMR (100 MHz, CDCl$_3$); δ 167.2, 165.1, 163.9, 162.3, 140.4, 139.2, 138.0, 137.2, 133.6, 131.5, 130.3, 130.0, 129.9, 129.6, 128.9, 128.5, 128.3, 127.6, 127.4, 125.9, 124.6, 102.2, 88.4, 87.4, 78.8, 75.6, 75.0, 74.2, 73.7, 72.1, 71.3, 70.9, 64.8, 52.1, 94.7, 88.8, 82.3, 78.9, 75.8, 75.2, 74.8, 74.0, 73.6, 73.5, 73.2, 72.1, 71.2, 70.3, 69.0, 68.4, 64.8, 57.6, 56.3, 55.5, 55.3, 42.7, 20.9, 18.4, 17.4, 17.3, 16.7, −1.35, −1.54; LRMS calcd for C$_{52}$H$_{51}$Cl$_4$NO$_{13}$SSiNa [M+Na]$^+$: 1120.2. found 1120.2.

Example 2-g

Synthesis of Phenyl {3-O-Acetyl-2-deoxy-4,6-O-p-methoxybenzylidene-2-tetrachlorophthalimido-β-D-glucopyranosyl-(1→2)-[2-(trimethylsilyl)ethyl 4-C-methyl-3-O-phenoxycarbonyl-β-D-glucopyranosid]}uronate (8)

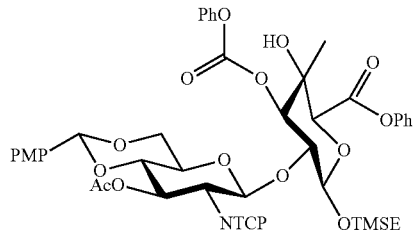

To a flame dried flask was added acceptor 5 (216 mg, 0.428 mmol) and 4-allyl-1,2-dimethoxybenzene (736 μL, 0.428 mmol). In a second flame dried flask was added sulfoxide 4 (612 mg, 0.855 mmol) and 2,6-di-tert-butyl-4-methylpyridine (264 mg, 1.29 mmol). Both flasks were placed under vacuum for 2 h then switched to an atmosphere of argon. To the acceptor flask was added CH$_2$Cl$_2$ (8 mL) and 4 Å molecular sieves then the suspension was stirred at room temperature for 1 h. The suspension was cooled to −42° C. and treated with triflic anhydride (180 μL, 0.302 mmol). The sulfoxide in CH$_2$Cl$_2$ (4 mL) was then added to the acceptor solution by syringe pump over 1 h at −42° C. After addition of sulfoxide, the reaction mixture was stirred for 1 h at −42° C. then quenched with triethylamine (200 μL) and poured into a separatory funnel containing H$_2$O and CH$_2$Cl$_2$. The organic phase was collected, extracted from brine, dried over Na$_2$SO$_4$, and concentrated in vacuo. The crude residue was purified by silica gel chromatography (4% EtOAc/toluene) to afford the title compound (392 mg, 0.358 mmol, 84%). $^1$H NMR (600 MHz, CDCl$_3$): δ ppm 7.42-7.35 (m, 6H, ArH), 7.29-7.22 (m, 2H, ArH), 7.17 (d, J=8.8 Hz, 2H, ArH), 7.10 (d, J=8.8 Hz, 2H, ArH), 6.89 (d, J=8.5 Hz, 2H, ArH), 5.79 (d, J=8.5 Hz, 1H, H-1$^E$), 5.71 (dd, J=9.7, 9.7 Hz, 1H, H-3$^E$), 5.51 (s, 1H, CHPMP), 4.91 (d, J=10.0 Hz, 1H, H-3$^F$), 4.53 (d, J=7.6 Hz, 1H, H-1$^F$), 4.38 (dd, J=10.5, 5.0 Hz, 1H, H-6$^E$), 4.30 (dd, J=10.1, 8.3 Hz, 1H, H-2$^E$), 4.13 (s, 1H, H-5$^F$), 4.07 (ddd, J=9.9, 9.9, 6.3 Hz, 1H, OCHHCH$_2$SiMe$_3$), 3.85 (dd, J=10.3, 10.3 Hz, 1H, H-4$^E$), 3.80 (s, 3H, OMe), 3.82-3.76 (m, 1H, H-6$^E$), 3.76-3.67 (m, 3H, OCHHCH$_2$SiMe$_3$, H-2$^F$,E$^5$), 3.12 (s, 1H, OH), 1.90 (s, 3H, OAc), 1.32 (s, 3H, Me), 1.12-1.00 (m, 2H, OCH$_2$CH$_2$SiMe$_3$), 0.09 (s, 9H, SiMe$_3$); $^{13}$C NMR (100 MHz, CDCl$_3$): δ ppm 170.89, 167.24, 164.02, 163.18, 160.39, 153.07, 151.07, 150.00, 140.52, 140.21, 130.14, 129.74, 129.39, 129.34, 127.75, 127.38, 127.10, 126.64, 126.25, 121.36, 121.15, 121.05, 113.78, 101.96, 101.92, 98.42, 81.91, 78.96, 77.02, 76.27, 73.74, 70.39, 68.79, 68.18, 66.58, 56.74, 55.42, 20.72, 18.35, 16.88, −1.11; HRMS calcd for C$_{49}$H$_{49}$Cl$_4$NO$_{17}$SiNa [M+Na]$^+$: 1114.1422. found 1114.1392.

Example 2-h

Synthesis of Phenyl {3-O-Acetyl-2-deoxy-6-O-p-methoxybenzyl-2-tetrachlorophthalimido-β-D-glucopyranosyl-(1→2)-[2-(trimethylsilyl)ethyl 4-C-methyl-3-O-phenoxycarbonyl-β-D-glucopyranosid]}uronate (9)

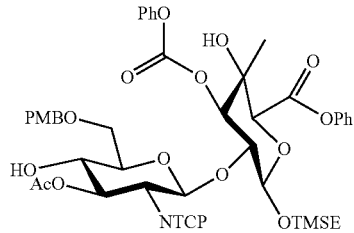

Disaccharide 8 (522 mg, 0.477 mmol) was dissolved in THF (10 mL) then cooled to −65° C. A solution of 1 M BH$_3$.THF (2.38 mL, 2.38 mmol) was then added and the mixture was stirred for 5 min then treated with dibutylboron triflate (1.19 mL of a 1 M complex in CH$_2$Cl$_2$, 1.19 mmol).[5] The reaction mixture was kept at −65° C. for 6 h then quenched with triethylamine (1 mL) and slowly poured into a separatory funnel containing saturated aqueous NaHCO$_3$ and CH$_2$Cl$_2$. The separatory funnel was carefully shaken and vented (H$_2$ gas is produced as the borane is quenched) then the organic phase was collected. The organic phase was washed with H$_2$O and brine, dried over Na$_2$SO$_4$, and concentrated in vacuo. The crude residue was purified by silica gel chromatography (30% EtOAc/petroleum ether) to afford the title compound (432 mg, 0.394 mmol, 83%). $^1$H NMR (600 MHz, CDCl$_3$): δ ppm 7.39 (dd, J=8.5, 7.6 Hz, 2H, ArH), 7.35 (dd, J=8.5, 7.6 Hz, 2H, ArH), 7.29-7.25 (m, 3H, ArH), 7.23 (t, J=7.3 Hz, 1H, ArH), 7.12-7.08 (m, 4H, ArH), 6.90 (d, J=8.8 Hz, 2H, ArH), 5.72 (d, J=8.5 Hz, 1H, H-1$^E$), 5.45 (dd, J=10.8, 8.8 Hz, 1H, H-3$^E$), 4.88 (d, J=10.0 Hz, 1H, H-3$^F$), 4.59, 4.52 (ABq, J=11.4 Hz, 1H each, OCH$_2$PMP), 4.55 (d, J=7.6 Hz, 1H, H-1$^F$), 4.22 (dd, J=10.8, 8.5 Hz, 1H, H-2$^E$), 4.12 (s, 1H, H-5$^F$), 4.03 (ddd, J=11.2, 9.2, 6 Hz, 1H, OCHHCH$_2$SiMe$_3$), 3.91 (ddd, J=8.5, 8.5, 1.5 Hz, 1H, H-4$^E$), 3.87 (dd, J=9.4, 3.5 Hz, 1H, H-6$^E$), 3.81 (s, 3H, OMe), 3.76-3.66 (m, 4H, OCHHCH$_2$SiMe$_3$, H-2$^F$,5$^E$,6$^E$), 3.08 (s, 1H, OH), 2.99 (d, J=2.6 Hz, 1H, OH), 1.93 (s, 3H, OAc), 1.33 (s, 3H, Me), 1.07-1.01 (m, 1H, OCH$_2$CHHSiMe$_3$), 0.99-0.94 (m, 1H, OCH$_2$CHHSiMe$_3$), 0.04 (s, 9H, SiMe$_3$); $^{13}$C NMR (100 MHz, CDCl$_3$): δ ppm 171.32, 167.20, 163.94, 163.21, 159.57, 153.13, 150.95, 150.00, 140.35, 140.12, 129.72, 129.69, 129.47, 129.39, 127.38, 127.20, 126.60, 126.24, 121.37, 121.17, 114.07, 102.05, 97.99, 81.81, 76.77, 76.30, 73.97, 73.89, 73.75, 73.71, 71.40, 69.97, 68.05, 55.93, 55.39, 20.77, 18.39, 16.80, −1.19; HRMS calcd for C$_{49}$H$_{55}$Cl$_4$N$_2$O$_{17}$Si [M+NH$_4$]$^+$: 1111.2024. found 1111.1980.

Example 2-i

Synthesis of Phenyl {[2-(Trimethylsilyl)ethyl 2-O-benzoyl-3,4-di-O-benzyl-β-D-galactopyranosyluronate]-(1→4)-2,6-dideoxy-2-tetrachlorophthalimido-β-D-glucopyranosyl-(1→4)-3-O-acetyl-2-deoxy-6-O-p-methoxybenzyl-2-tetrachlorophthalimido-β-D-glucopyranosyl-(1→2)-[2-(Trimethylsilyl)ethyl 4-C-methyl-3-O-phenoxycarbonyl-β-D-glucopyranosid]}uronate (10)

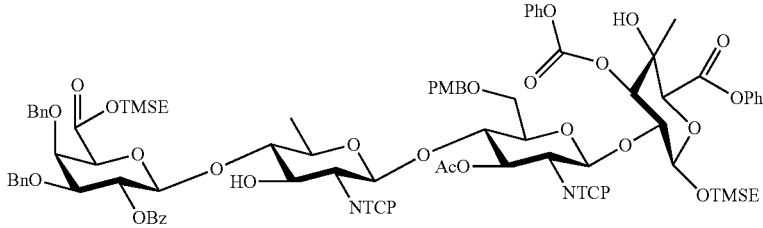

To a flame dried flask was added acceptor 9 (95 mg, 0.087 mmol), 4-allyl-1,2-dimethoxybenzene (149 µL, 0.87 mmol), and 2,6-di-tert-butyl-4-methylpyridine (53 mg, 0.26 mmol). The flask was placed under vacuum for 2 h then switched to an argon atmosphere. After addition of CH$_2$Cl$_2$ (2 mL) and 4 Å molecular sieves, the suspension was stirred at room temperature for 1 h then chilled to −65° C. and treated with triflic anhydride (74 µL, 0.46 mmol). A solution of sulfoxide 9 (97 mg, 0.088 mmol) in CH$_2$Cl$_2$ (1 mL) was added dropwise by syringe pump over 1 h. The reaction mixture was then allowed to slowly warm to −30° C. over an additional 1 h, then was quenched with triethylamine (50 µL) and poured into a separatory funnel containing H$_2$O and CH$_2$Cl$_2$. The organic phase was collected then extracted from brine, dried over Na$_2$SO$_4$, and concentrated in vacuo. The crude residue was purified by silica gel chromatography (gradient 2-4% EtOAc/CH$_2$Cl$_2$) to afford the title compound (90 mg, 0.043 mmol, 50%) along with recovered acceptor (24 mg, 0.022, 25%). $^1$H NMR (600 MHz, CDCl$_3$): δ ppm 7.95 (dd, J=7.3, 1.2 Hz, 2H, BzH), 7.57 (t, J=7.5 Hz, 1H, BzH), 7.41 (t, J=7.9 Hz, 2H, BzH), 7.36 (t, J=7.9 Hz, 2H, PhH), 7.34 (t, J=7.9 Hz, 2H, PhH), 7.28-7.16 (m, 8H, PhH), 7.13-7.12 (m, 6H, PhH), 7.06 (d, J=8.8 Hz, 2H, PhH), 6.85 (d, J=8.5 Hz, 2H, PMPH), 6.76 (d, J=8.5 Hz, 2H, PMPH), 5.66 (dd, J=8.8, 8.8 Hz, 1H, H-2$^B$), 5.57 (dd, J=10.3, 8.5 Hz, 1H, H-3$^E$), 5.55 (d, J=8.5 Hz, 1H, H-1$^E$), 5.30 (d, J=8.5 Hz, 1H, H-1$^C$), 4.97, 4.63 (ABq, J=11.7 Hz, 1H each, OCH$_2$Ph), 4.81 (d, J=10.0 Hz, 1H, H-3$^F$), 4.67 (br s, 1H, OH-3$^C$), 4.66, 4.47 (ABq, J=12.3 Hz, 1H each, OCH$_2$Ph), 4.54 (d, J=7.6 Hz, 1H, H-1$^B$), 4.42 (d, J=7.6 Hz, 1H, H-1$^F$), 4.39-4.35 (m, 1H, H-3$^C$), 4.37, 4.20 (ABq, J=11.5 Hz, 1H each, OCH$_2$PMP), 4.34 (br s, 1H, H-4$^B$), 4.09 (dd, J=10.5, 8.5 Hz, 1H, H-2$^E$), 4.15-4.07 (m, 1H, OCHHCH$_2$SiMe$_3$), 4.06 (s, 1H, H-5$^F$), 4.05 (s, 1H, H-5$^B$), 4.06-3.96 (m, 3H, H-2$^C$,4$^E$, OCHHCH$_2$SiMe$_3$), 3.89-3.83 (m, 1H, OCHHCH$_2$SiMe$_3$), 3.82 (s, 3H, OMe), 3.73 (dd, J=12.0, 2.3 Hz, 1H, H-6$^E$), 3.70-3.68 (m, 1H, H-2$^E$), 3.66 (dd, J=10.0, 7.6 Hz, 1H, H-2$^F$), 3.54-3.46 (m, 3H, H-5$^E$,H-6$^E$, OCHHCH$_2$SiMe$_3$), 3.33 (dd, J=9.1, 5.9 Hz, 1H, H-5$^C$), 3.06 (s, 1H, OH-4$^C$), 3.05 (ee, J=9.1, 9.1 Hz, 1H, H-4$^C$), 1.81 (s, 3H, OAc), 1.29 (s, 3H, Me), 0.86 (d, J=5.9 Hz, 3H, H-6$^C$), 0.70-0.69 (m, 4H, 2×OCH$_2$CH$_2$SiMe$_3$), −0.103, −0.105 (s, 9H each, SiMe$_3$); $^{13}$C NMR (125 MHz, CDCl$_3$): δ ppm 170.46, 167.28, 167.10, 165.16, 163.98, 163.70, 163.37, 163.29, 158.94, 153.01, 151.03, 150.02, 140.38, 139.97, 139.73, 139.68, 137.91, 137.04, 133.56, 130.12, 129.96, 129.84, 129.72, 129.58, 129.53, 129.37, 128.59, 128.35, 128.17, 128.09, 127.97, 127.86, 127.69, 127.49, 127.35, 127.16, 126.62, 126.22, 121.37, 121.27, 113.68, 102.25, 101.89, 97.85, 97.82, 88.85, 82.25, 78.90, 76.26, 76.11, 75.17, 75.07, 74.79, 74.01, 73.74, 73.58, 73.53, 72.02, 71.20, 70.22, 68.91, 67.99, 67.58, 64.74, 57.54, 56.32, 55.23, 20.85, 18.25, 17.29, 17.25, 16.91, −1.36, −1.63; LRMS calcd for C$_{95}$H$_{96}$Cl$_8$N$_2$O$_{29}$Si$_2$Na [M+Na]$^+$: 2087.3. found 2087.4.

Example 2-j

Synthesis of Phenyl {[2-(Trimethylsilyl)ethyl 2-O-benzoyl-3,4-di-O-benzyl-β-D-galactopyranosyluronate]-(1→4)-3-O-acetyl-2,6-dideoxy-2-tetrachlorophthalimido-β-D-glucopyranosyl-(1→4)-3-O-acetyl-2-deoxy-6-O-p-methoxybenzyl-2-tetrachlorophthalimido-β-D-glucopyranosyl-(1→2)-[2-(trimethylsilyl)ethyl 4-C-methyl-3-O-phenoxycarbonyl-β-D-glucopyranosid]}uronate To a solution of 10 (118 mg, 0.057 mmol) in pyridine (5 mL) was added acetic anhydride (81 μL, 0.857 mmol) and the reaction was stirred at room temperature overnight. After concentration in vacuo, the crude residue was purified by silica gel chromatography (30% EtOAc/petroleum ether) to afford the title compound (112 mg, 0.053 mmol, 93%). $^1$H NMR (600 MHz, CDCl$_3$): δ ppm 7.95 (d, J=7.3 Hz, 2H, BzH), 7.56 (t, J=7.3 Hz, 1H, BzH), 7.42 (t, J=7.8 Hz, 2H, BzH), 7.37 (t, J=7.8 Hz, 2H, PhH), 7.35 (t, J=7.8 Hz, 2H, PhH), 7.29-7.17 (m, 8H, PhH), 7.14 (d, J=4.4 Hz, 6H, PhH), 7.06 (d, J=8.5 Hz, 2H, PhH), 6.85 (d, J=8.2 Hz, 2H, PMPH), 6.76 (d, J=8.5 Hz, 2H, PMPH), 5.60-5.54 (m, 3H, H-2$^B$,3$^C$, 3$^E$), 5.55 (d, J=8.5 Hz, 1H, H-1$^E$), 5.42 (d, J=8.2 Hz, 1H, H-1$^C$), 4.94, 4.59 (ABq, J=11.7 Hz, 1H each, OCH$_2$Ph), 4.81 (d, J=10.0 Hz, 1H, H-3$^E$), 4.65, 4.46 (ABq, J=12.3 Hz, 1H each, OCH$_2$Ph), 4.57 (d, J=7.0 Hz, 1H, H-1$^B$), 4.41 (d, J=7.6 Hz, 1H, H-1$^F$), 4.36, 4.22 (ABq, J=11.8 Hz, 1H each, OCH$_2$PMP), 4.30 (s, 1H, H-4$^B$), 4.17 (ddd, J=11.5, 11.5, 5.7 Hz, 1H, OCHHCH$_2$SiMe$_3$), 4.09 (dd, J=10.3, 8.8 Hz, 1H, H-2$^E$), 4.06 (s, 1H, H-5$^F$), 4.08-3.97 (m, 4H, H-2$^C$,2$^E$,4$^E$, OCHHCH$_2$SiMe$_3$), 3.95 (s, 1H, H-5$^B$), 3.88-3.82 (m, 1H, OCHHCH$_2$SiMe$_3$), 3.81 (s, 3H, OMe), 3.69-3.64 (m, 3H, H-3$^B$,6$^E$,2$^F$), 3.52-3.45 (m, 3H, H-5$^E$,6$^E$, OCHHCH$_2$SiMe$_3$), 3.42 (dd, J=9.1, 9.1 Hz, 1H, H$_4^C$), 3.38-3.32 (m, 1H, H-5$^C$), 3.06 (s, 1H, OH), 1.84, 1.72 (s, 3H each, OAc), 1.29 (s, 3H, Me), 1.01 (d, J=6.2 Hz, 3H, H-6$^C$), 0.92 (ddd, J=13.2, 5.9 Hz, 1H, OCH$_2$CHHSiMe$_3$), 0.88-0.76 (m, 2H, OCH$_2$CH$_2$SiMe$_3$), 0.74-0.67 (m, 1H, OCH$_2$CHHSiMe$_3$), −0.00, −0.10 (s, 9H each, SiMe$_3$); $^{13}$C NMR (125 MHz, CDCl$_3$): δ ppm 170.58, 170.37, 167.38, 167.22, 164.94, 163.93, 163.67, 163.22, 163.19, 158.93, 152.97, 151.01, 149.98, 140.39, 140.11, 139.98, 139.69, 138.11, 137.26, 133.32, 130.13, 129.85, 129.81, 129.69, 129.56, 129.34, 129.16, 128.51, 128.24, 128.06, 127.99, 127.84, 127.68, 127.46, 127.43, 127.27, 127.10, 126.59, 126.20, 121.33, 121.25, 113.66, 101.82, 101.57, 97.71, 97.60, 82.25, 81.76, 78.92, 76.23, 75.96, 75.13, 75.06, 74.55, 74.33, 74.10, 73.71, 73.50, 73.40, 71.78, 71.71, 71.35, 70.80, 67.96, 67.43, 64.18, 56.71, 56.23, 55.18, 20.60, 20.52, 18.22, 17.70, 17.41, 16.87, −1.41, −1.47; LRMS calcd for C$_{92}$H$_{98}$Cl$_8$N$_2$O$_{30}$Si$_2$Na [M+Na]$^+$: 2129.3. found 2129.4.

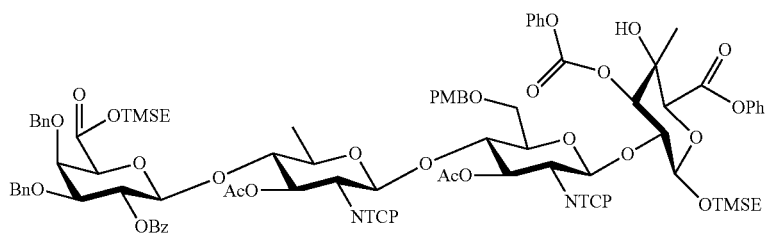

Example 2-k

Synthesis of Phenyl {[2-(Trimethylsilyl)ethyl 2-O-benzoyl-3,4-di-O-benzyl-β-D-galactopyranosyluronate]-(1→4)-3-O-acetyl-2,6-dideoxy-2-tetrachlorophthalimido-β-D-glucopyranosyl-(1→4)-3-O-acetyl-2-deoxy-2-tetrachlorophthalimido-β-D-glucopyranosyl-(1→2)-[2-(trimethylsilyl)ethyl 4-C-methyl-3-O-phenoxycarbonyl-β-D-glucopyranosid]}uronate (11)

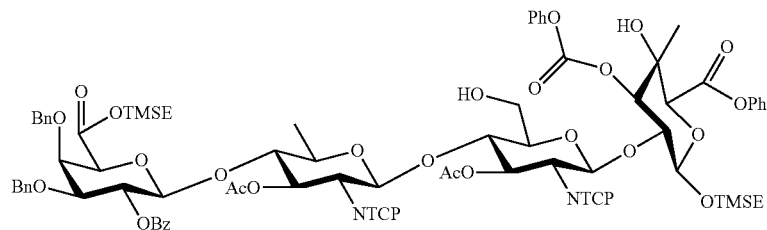

The above compound (112 mg, 0.053 mmol) was dissolved in $CH_2Cl_2$ (2 mL) and phosphate buffer (pH 7.0, 200 μL) then 2,3-dichloro-5,6-dicyano-1,4-benzoquinone (36 mg, 0.16 mmol) was added and the reaction was stirred at room temperature for 2 h. The reaction was then diluted with $CH_2Cl_2$ and washed with saturated aqueous $NaHCO_3$, $H_2O$, and brine. The organic phase was then dried over $Na_2SO_4$, concentrated in vacuo, then separated by silica gel chromatography (30% EtOAc/petroleum ether) to afford the title compound (83 mg, 0.042 mmol, 79%). $^1$H NMR (600 MHz, $CDCl_3$): δ ppm 7.95 (d, J=8.2 Hz, 2H, BzH), 7.55 (t, J=7.6 Hz, 1H, BzH), 7.41 (t, J=7.8 Hz, 2H, BzH), 7.37 (d, J=7.9 Hz, 2H, PhH), 7.33 (t, J=7.9 Hz, 2H, PhH), 7.27-7.19 (m, 8H, PhH), 7.14 (d, J=7.6 Hz, 4H, PhH), 7.09 (d, J=7.6 Hz, 2H, PhH), 7.07 (d, J=7.6 Hz, 2H, PhH), 5.57 (dd, J=10.2, 8.2 Hz, 1H, H-2$^B$), 5.55-5.52 (m, 3H, H-3$^C$,1$^E$,3$^E$), 5.44 (d, J=1 Hz, 1H, H-1$^C$), 4.93, 4.58 (ABq, J=12.0 Hz, 1H each, OCH$_2$Ph), 4.83 (d, J=9.9 Hz, 1H, H-3$^F$), 4.64, 4.46 (ABq, J=12.3 Hz, 1H each, OCH$_2$Ph), 4.56 (d, J=7.9 Hz, 1H, H-1$^B$), 4.45 (d, J=7.6 Hz, 1H, H-1$^F$), 4.30 (d, J=1.5 Hz, 1H, H_4$^B$), 4.20-4.15 (m, 1H, OCHHCH$_2$SiMe$_3$), 4.07 (s, 1H, H-5$^F$), 4.08-3.94 (m, 4H, H-2$^C$,E$^2$, OCH$_2$CH$_2$SiMe$_3$), 3.95 (d, J=1.1 Hz, 1H, H-5$^B$), 3.92 (dd, J=9.1, 9.1 Hz, 1H, H-4$^E$), 3.66 (dd, J=9.3, 2.9 Hz, 1H, H-3$^B$), 3.60-3.55 (m, 3H, H-6$^E$, 2$^F$, OCHHCH$_2$SiMe$_3$), 3.45-3.42 (m, 2H, H-5$^E$,6$^E$), 3.38-3.34 (dd, J=9.7, 6.2 Hz, 1H, H-5$^C$), 3.33-3.29 (m, 1H, H-4$^C$), 3.05 (s, 1H, OH), 1.87, 1.66 (s, 3H each, OAc), 1.26 (s, 3H, Me), 1.03 (d, J=6.2 Hz, 3H, H-6$^C$), 1.00-0.81 (m, 4H, 2×OCH$_2$CH$_2$SiMe$_3$), 0.00, −0.02 (s, 9H each, SiMe$_3$); $^{13}$C NMR (125 MHz, $CDCl_3$): δ ppm 170.75, 170.42, 167.40, 167.21, 164.95, 164.01, 163.76, 163.34, 163.12, 152.95, 150.98, 149.99, 140.44, 140.10, 139.98, 138.16, 137.31, 133.38, 130.08, 129.88, 129.81, 129.77, 129.57, 129.41, 128.57, 128.30, 128.04, 127.88, 127.78, 127.74, 127.42, 127.16, 127.10, 126.67, 126.27, 121.37, 121.00, 101.69, 101.54, 97.78, 97.61, 81.70, 81.82, 78.94, 76.72, 76.33, 74.96, 74.59, 74.37, 74.29, 74.13, 73.72, 73.04, 71.76, 71.43, 71.17, 68.06, 64.23, 60.87, 56.50, 56.19, 20.60, 20.56, 18.32, 17.89, 17.48, 16.85, −1.27, −1.42; LRMS calcd for $C_{89}H_{90}Cl_8N_2O_{29}Si_2Na$ [M+Na]$^+$: 2009.3. found 2009.3.

Example 2-l

Synthesis of Phenyl {[2-(Trimethylsilyl)ethyl 2-O-benzoyl-3,4-di-O-benzyl-β-D-galactopyranosyluronate]-(1→4)-3-O-acetyl-2,6-dideoxy-2-tetrachlorophthalimido-β-D-glucopyranosyl-(1→4)-[2,3,4,6-tetra-O-benzyl-β-D-glucopyranosyl-(1→6)]-3-O-acetyl-2-deoxy-2-tetrachlorophthalimido-β-D-glucopyranosyl-(1→2)-[2-(trimethylsilyl)ethyl 4-C-methyl-3-O-phenoxycarbonyl-β-D-glucopyranosid]}uronate (12)

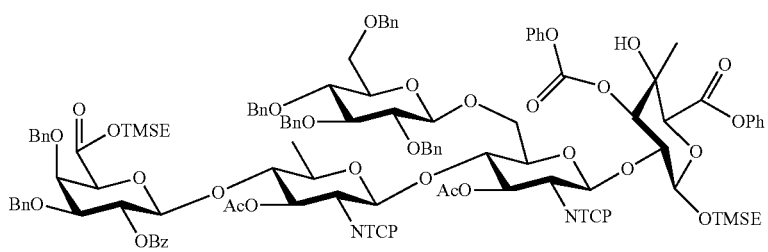

To a flame dried flask was added acceptor 11 (83 mg, 0.042 mmol), 4-allyl-1,2-dimethoxybenzene (144 μL, 0.87 mmol), and 2,6-di-tert-butyl-4-methylpyridine (17 mg, 0.083 mmol). The flask was placed under vacuum for 2 h, switched to an argon atmosphere and 4 Å molecular sieves were added followed by propionitrile (5 mL). The suspension was stirred at room temperature for 1 h then chilled to −78° C. and treated with triflic anhydride (10.5 mL, 0.063 mmol). A solution of phenyl 2,3,4,6-tetra-O-benzyl-1-thio-β-D-glucopyranoside S-Oxide (41 mg, 0.063 mmol) in propionitrile (1 mL) was added dropwise by syringe pump over 15 min. The reaction mixture was kept at −78° C. for an additional 15 minutes then 17.44, 16.83, −1.32, −1.44; LRMS calcd for $C_{123}H_{124}Cl_8N_2O_{34}Si_2Na$ [M+Na]$^+$: 2531.5. found 2531.4.

Example 2-m

[2-(Trimethylsilyl)ethyl 2-O-Benzoyl-3,4-di-O-benzyl-β-D-galactopyranosyluronate]-(1→4)-2-acetamido-2,6-dideoxy-β-D-glucopyranosyl-(1→4)-[2,3,4,6-tetra-O-benzyl-β-D-glucopyranosyl-(1→6)]-2-acetamido-3-O-acetyl-2-deoxy-β-D-glucopyranosyl-(1→2)-2-(trimethylsilyl)ethyl 3-O-carbamoyl-4-C-methyl-β-D-glucopyranuronamide (13)

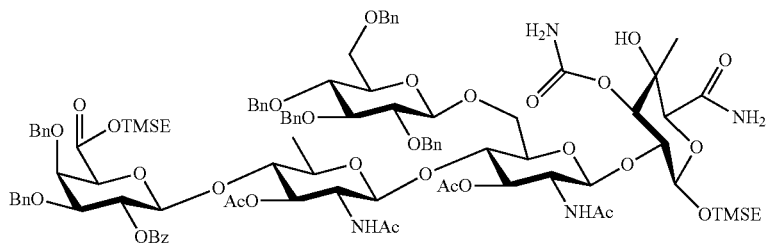

was quenched with triethylamine (50 μL) and poured into a separatory funnel containing H$_2$O and CH$_2$Cl$_2$. The organic phase then extracted from brine, dried over Na$_2$SO$_4$, and concentrated in vacuo. The crude residue was purified by silica gel chromatography (20% EtOAc/petroleum ether) to afford the title compound (80 mg, 0.032 mmol, 76%). $^1$H NMR (600 MHz, CDCl$_3$): δ ppm 7.99 (dd, J=8.2, 1.2 Hz, 2H, BzH), 7.58 (t, J=7.3 Hz, 1H, BzH), 7.46-7.20 (m, 31H, ArH), 7.17 (d, J=4.4 Hz, 4H, ArH), 7.17-7.14 (m, 5H, ArH), 7.04 (dd, J=8.6, 1.0 Hz, 2H, ArH), 5.66-5.56 (m, 4H, H-2$^B$,3$^C$,1$^E$, 3$^E$), 5.41 (d, J=8.2 Hz, 1H, H-1$^C$), 4.98 (d, J=11.7 Hz, 1H, OCHHPh), 4.87 (d, J=11.1 Hz, 1H, OCHHPh), 4.84 (d, J=10.3 Hz, 1H, H-3$^F$), 4.81-4.74 (m, 3H, OCHHPh), 4.69 (d, J=12.3 Hz, 1H, OCHHPh), 4.65-4.60 (m, 4H, H-1$^B$, OCHHPh), 4.57-4.52 (m, 3H, H-1$^D$, OCHHPh), 4.52-4.47 (m, 2H, H-1$^F$, OCHHPh), 4.34 (d, J=1.2 Hz, 1H, H_4$^B$), 4.26-4.18 (m, 3H, H-2$^E$,4$^E$, OCHHCH$_2$SiMe$_3$), 4.11 (dd, J=10.4, 8.3 Hz, 1H, H-2$^C$), 4.07 (s, 1H, H-5$^F$), 4.08-4.02 (m, 1H, OCHHCH$_2$SiMe$_3$), 3.98 (d, J=1.2 Hz, 1H, H-5$^B$), 3.98-3.91 (m, 2H, H-6, OCHHCH$_2$SiMe$_3$), 3.80-3.59 (m, 8H, H-3$^B$,3$^B$,4$^D$,5$^E$, 6, OCHHCH$_2$SiMe$_3$), 3.52-3.45 (m, 3H, H-4$^C$, 5$^D$, 6, 3.44-3.38 (m, 1H, H-5$^C$), 3.09 (s, 1H, OH), 2.93 (dd, J=8.5, 8.5 Hz, 1H, H-2$^D$), 1.90, 1.68 (s, 3H each, OAc), 1.28 (s, 3H, Me), 1.01 (d, J=5.9 Hz, 3H, H-6$^C$), 1.03-0.83 (m, 4H, 2×OCH$_2$CH$_2$SiMe$_3$), 0.04-0.06 (s, 9H each, SiMe$_3$); $^{13}$C NMR (125 MHz, CDCl$_3$): δ ppm 170.69, 170.49, 167.41, 167.28, 164.96, 163.74, 163.46, 163.09, 163.06, 153.10, 151.02, 149.97, 140.67, 140.35, 140.25, 139.96, 138.95, 138.63, 138.44, 138.29, 138.11, 137.26, 133.34, 130.13, 130.10, 129.84, 129.82, 129.72, 129.67, 129.56, 129.34, 128.61, 128.53, 128.50, 128.46, 128.35, 128.27, 128.20, 128.08, 128.02, 127.97, 127.93, 127.87, 127.78, 127.71, 127.60, 127.47, 127.36, 127.13, 126.53, 126.19, 121.35, 121.24, 103.46, 101.85, 101.64, 97.66, 96.35, 84.84, 82.29, 82.01, 81.91, 78.95, 78.11, 76.21, 75.51, 74.92, 74.83, 74.76, 74.56, 74.33, 74.07, 73.74, 73.59, 72.16, 71.81, 71.68, 70.86, 69.11, 67.86, 67.67, 64.24, 56.56, 56.22, 20.57, 18.48, 17.69, To a solution of 12 (80 mg, 0.032 mmol) in CH$_2$Cl$_2$ (1 mL) was added NH$_3$ (5 mL of 2N NH$_3$ in isopropanol) and the reaction was stirred at room temperature for 1 h. After concentration in vacuo, the crude residue was suspended in ethanol (5 mL) and ethylenediamine (10.7 μL, 0.160 mmol) was added.[6] The reaction mixture was heated at 50° C. for 8.5 h then cooled to room temperature. An excess of acetic anhydride (100 μL) was then added and the reaction was stirred for 15 min at room temperature before being concentrated in vacuo. The residue was then dissolved in pyridine (3 mL) and treated with acetic anhydride (200 μL). After stirring at room temperature for 9 h, the reaction was concentrated in vacuo then purified by silica gel chromatography (5% methanol/CH$_2$Cl$_2$) to afford the title compound (40 mg, 0.021 mmol, 66%). $^1$H NMR (600 MHz, CDCl$_3$): δ ppm 7.98 (d, J=7.0 Hz, 2H), 7.58 (t, J=7.5 Hz, 1H), 7.44 (t, J=7.8 Hz, 2H), 7.35-7.18 (m, 24H), 7.15 (d, J=4.4 Hz, 4H), 7.13-7.08 (m, 2H), 6.47 (br s, 1H), 6.31 (br s, 1H), 5.65 (br s, 1H), 5.62 (d, J=9.1 Hz, 1H), 5.58 (dd, J=10.0, 7.9 Hz, 1H), 4.97 (d, J=11.7 Hz, 1H), 4.87 (d, J=11.1 Hz, 1H), 4.82 (d, J=11.7 Hz, 1H), 4.77 (d, J=10.8 Hz, 1H), 4.75-4.71 (m, 3H), 4.68 (d, J=5.9 Hz, 1H), 4.66 (d, J=6.7 Hz, 1H), 4.62-4.56 (m, 3H), 4.54-4.46 (m, 5H), 4.32 (br s, 1H), 4.30 (d, J=7.9 Hz, 1H), 4.21 (ddd, J=11.6, 11.6, 5.6 Hz, 1H), 4.10 (dd, J=10.1, 3.1 Hz, 1H), 4.09-4.01 (m, 2H), 3.99-3.95 (m, 2H), 3.92-3.80 (m, 2H), 3.75-3.71 (m, 2H), 3.70-3.59 (m, 6H), 3.59-3.52 (m, 3H), 3.51-3.47 (m, 1H), 3.38 (t, J=8.5 Hz, 1H), 3.33 (dd, J=8.8, 8.8 Hz, 1H), 3.03-2.96 (m, 1H), 2.06 (s, 3H), 1.94 (s, 3H), 1.90 (s, 3H), 1.86 (s, 3H), 1.08 (s, 3H), 1.03 (d, J=6.2 Hz, 3H), 1.01-0.85 (m, 4H), 0.02 (s, 9H), −0.00 (s, 9H); $^{13}$C NMR (100 MHz, CDCl$_3$); δ ppm 171.72, 171.55, 170.97, 170.78, 170.32, 167.42, 164.98, 157.20, 138.65, 138.22, 138.19, 138.01, 137.28, 133.45, 129.84, 129.77, 128.72, 128.64, 128.55, 128.50, 128.29, 128.20, 128.01, 128.00, 127.96, 127.86, 127.82, 127.77, 127.73, 103.51, 102.10, 101.53, 100.93, 100.80, 84.77, 82.29, 80.88, 79.88, 78.97, 77.99, 75.89, 75.68, 75.57, 75.07, 74.85, 74.69, 74.60, 74.31, 74.26, 73.50, 73.40, 72.78, 71.80, 71.73, 70.89, 68.95, 68.49, 68.31, 64.14, 54.55, 53.06, 23.57, 23.26, 21.02, 20.92, 18.58, 17.80, 17.56, 16.88, −1.19, −1.42; LRMS calcd for $C_{99}H_{126}N_4O_{30}Si_2$ [M+H]$^+$: 1907.8. found 1907.7.

Example 2-n

Synthesis of [2-(Trimethylsilyl)ethyl 3,4-Di-O-acetyl-2-O-benzoyl-β-D-galactopyranosyluronate]-(1→4)-2-acetamido-3-O-acetyl-2,6-dideoxy-β-D-glucopyranosyl-(1→4)-[2,3,4,6-tetra-O-acetyl-β-D-glucopyranosyl)-(1→6)]-2-acetamido-3-O-acetyl-2-deoxy-β-D-glucopyranosyl-(1→2)-2-(trimethylsilyl) ethyl 3-O-carbamoyl-4-C-methyl-β-D-glucopyranuronamide (14)

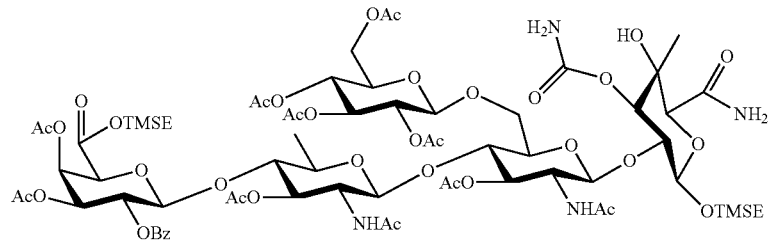

To a stirred solution of 13 (51 mg, 0.027 mmol) in degassed methanol (25 mL) under an atmosphere of argon was added Pd(OH)$_2$/C (20 mg). The suspension was degassed and backfilled with H$_2$ three times then stirred under H$_2$ (1 atm) for 11 h. The reaction was then filtered through a pad of celite and concentrated in vacuo. The crude residue was then dissolved in pyridine (2 mL) and treated with acetic anhydride (200 μL). After stirring at room temperature for 9 h, the reaction mixture was concentrated the separated by silica gel chromatography (7% methanol/CH$_2$Cl$_2$) to afford the title compound (28 mg, 0.017 mmol, 63%). $^1$H NMR (500 MHz, CDCl$_3$): δ ppm 7.97 (d, J=6.8 Hz, 2H, PhH), 7.59 (t, J=7.3 Hz, 1H, PhH), 7.46 (t, J=7.8 Hz, 2H, PhH), 6.95, 5.90 (br s, 1H each, NHH), 6.28 (d, J=8.8 Hz, 1H, NHAc$^E$), 5.98 (d, J=8.8 Hz, 1H, NHAc$^C$), 5.70 (d, J=2.0 Hz, 1H, H-4$^B$), 5.43 (dd, J=10.3, 7.8 Hz, 1H, H-2$^B$), 5.31 (dd, J=9.3, 9.3 Hz, 1H, H-3$^D$), 5.25 (dd, J=10.3, 3.4 Hz, 1H, H-3$^B$), 5.00-5.07 (m, 2H, H-3$^C$,4$^D$), 4.95 (dd, J=9.3, 7.8 Hz, 1H, H-2$^D$), 4.90-4.80 (m, 3H, H-1$^D$, E$^3$, F$^3$), 4.76 (br s, 1H), 4.72 (d, J=7.8 Hz, 1H, H-1$^B$), 4.55 (d, J=7.3 Hz, 1H, H-1$^E$), 4.46 (d, J=7.3 Hz, 1H, H-1$^F$), 4.29 (s, 1H, H-5$^B$), 4.28-4.23 (m, 2H, H-1$^C$, OCHHCH$_2$SiMe$_3$), 4.23-4.18 (m, 2H, H-6$^D$, OCHHCH$_2$SiMe$_3$), 4.15 (d, J=10.7 Hz, 1H, H-6$^D$), 4.06-3.99 (m, 1H, H-2$^E$), 3.94 (ddd, J=16.4, 5.9, 5.6 Hz, 1H, OCHHCH$_2$SiMe$_3$), 3.86 (s, 1H, H-5$^F$), 3.90-3.81 (m, 2H, H-2$^C$,6$^E$), 3.76-3.68 (m, 3H, H-5$^D$,6$^E$, OCHHCH$_2$SiMe$_3$), 3.59-3.52 (m, 3H, H-4$^E$,5$^E$,2$^F$), 3.42 (dd, J=9.0, 9.0 Hz, 1H, H-4$^C$), 3.29 (dd, J=8.8, 6.2 Hz, 1H, H-5$^C$), 2.12, 2.11, 2.07, 2.06, 2.01, 1.97, 1.95, 1.92, 1.89, 1.87, (s, 3H each, 2×NHAc, 8×OAc) 1.17 (s, 3H, Me), 1.09 (d, J=6.3 Hz, 3H, H-6$^C$), 1.06-0.91 (m, 4H, 2×OCH$_2$CH$_2$SiMe$_3$), 0.04, 0.03 (s, 9H each, SiMe$_3$); $^{13}$C NMR (125 MHz, CD$_3$OD): δ ppm 173.86, 173.79, 173.59, 172.82, 172.29, 171.91, 171.63, 171.46, 171.33, 171.21, 167.78, 166.52, 158.98, 135.01, 130.90, 130.65, 129.98, 103.02, 102.27, 102.24, 102.05, 101.64, 82.99, 81.09, 78.03, 77.77, 77.36, 75.40, 74.19, 74.14, 74.08, 73.65, 73.03, 72.70, 72.15, 72.07, 71.20, 70.70, 70.32, 69.33, 68.81, 65.21, 63.29, 56.21, 55.70, 23.19, 23.15, 21.44, 21.35, 21.27, 20.89, 20.85, 20.70, 20.62, 20.54, 19.60, 18.55, 18.39, 17.40, −1.10, −1.43; LRMS calcd for C$_{69}$H$_{104}$N$_4$O$_{36}$Si$_2$ [M+H]$^+$: 1619.6. found 1619.5.

Example 2-o

Synthesis of 3,4-Di-O-acetyl-2-O-benzoyl-β-D-galactopyranuronic acid-(1→4)-2-acetamido-3-O-acetyl-2-deoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl)-(1→2)-3-carbamoyl-4-C-methyl-α/β-D-glucopyranuronamide

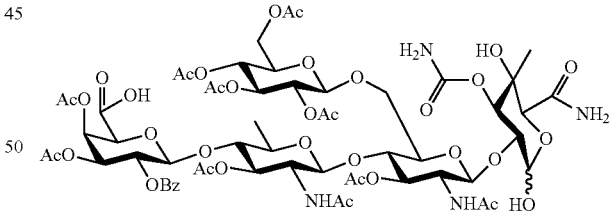

To a solution of compound 14 (20.2 mg, 12.5 μmol) in CH$_2$Cl$_2$ (1 ml), BF$_3$.OEt$_2$ (20 μl) was added dropwise at room temperature.$^3$ After stirring for 1 h, the mixture was directly applied onto a short silica column. The product was eluted with CHCl$_3$/MeOH/H$_2$O (18/12/2.7) to afford the title compound (17.0 mg, 12.0 μmol, 97%). $^1$H NMR (600 MHz, D$_2$O) δ 8.00-7.42 (m, 5H, PhH), 5.59 (m, 1H), 5.38-5.28 (m, 2H), 5.22-5.14 (m, 2H), 4.99-4.78 (m, 6H), 4.54-4.50 (m, 1H), 4.44 (t, J=8.5 Hz, 1H), 4.30-4.24 (m, 1H), 4.20 (s, 1H), 3.92 (s, 1H), 3.87-3.84 (m, 1H), 3.80-3.48 (m, 8H), 3.25 (m, 1H) 2.09-1.70 (m, 30H), 1.09 (s, 3H), 0.91-0.88 (m, 3H); LRMS calcd for C$_{59}$H$_{79}$N$_4$O$_{36}$ [M+H]$^+$: 1419.4. found 1419.4.

Example

Synthesis of 5-N-(3-hydroxy-1-oxocyclopenten-2-yl)-3,4-di-O-acetyl-2-O-benzoyl-β-D-galactopyranuronamide-(1→4)-2-acetamido-3-O-acetyl-2-deoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl-(1→2)-3-carbamoyl-4-C-methyl-α/β-D-glucopyranuronamide

Example

Synthesis of 5-N-(3-hydroxy-1-oxocyclopenten-2-yl)-β-D-galactopyranuronamide-(1→4)-2-acetamido-2-deoxy-β-D-glucopyranosyl-(1→4)-[β-D-glucopyranosyl-(1→6)]-2-acetamido-2-deoxy-β-D-glucopyranosyl-(1→2)-3-carbamoyl-4-C-methyl-α-D-glucopyranuronamide (15)

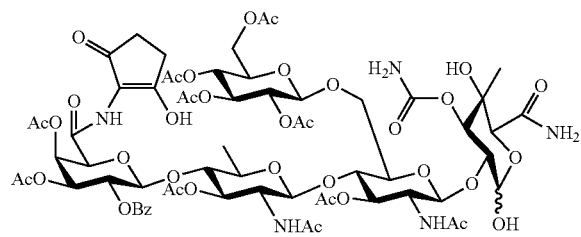

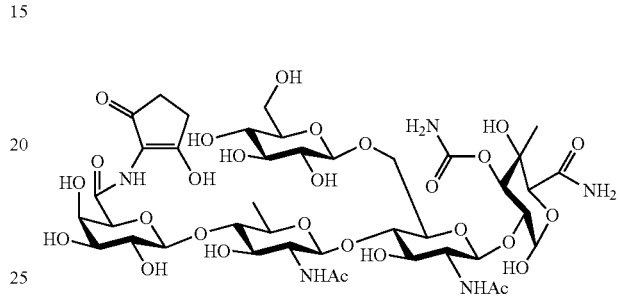

To a solution of the above compound (9.0 mg, 6.3 μmol) and HATU (9.9 mg, 26.0 μmol) in CH$_2$Cl$_2$/DMF (2/1, 0.5 ml), a solution of DIPEA (1.1 μL in 40 μL CH$_2$Cl$_2$, 6.3 μmol) was added dropwise. After the mixture was stirred for 10 min, a solution of 2-amino-3-hydroxy-2-cyclopenten-1-one hydrochloride (4.8 mg, 32.0 μmol) in DMF (0.5 ml) was added followed by the slow addition of a solution of DIPEA (4.4 μL in 160 μL CH$_2$Cl$_2$, 25.2 μmol)) over 3 h. After concentration in vacuo, the black mixture was purified by silica gel chromatography CHCl$_3$/MeOH/H$_2$O (18/12/2.7) to give a semi-pure product. Further purification by semi-prep HPLC, using a 0-100% gradient of CH$_3$CN/H$_2$O with 0.1% TFA, afforded the title compound (5.2 mg, 55%) as a mixture (α:β, 2:1 initial ratio becomes 5:1 after 40 h of sitting in D$_2$O solution). $^1$H NMR (600 MHz, D$_2$O) δ 8.10-7.60 (PhH, 5H), 5.80 (br d, J=2.3 Hz, 1H, H-4$^B$), 5.53 (dd, J=3.5, 10.6 Hz, 1H), 5.49 (d, J=3.8 Hz, 1H, H-1$^F$), 5.43 (t, J=8.6 Hz, 0.2H), 5.35 (dd, J=7.9, 9.7 Hz, 1H), 5.33 (t, J=9.4 Hz, 1H), 5.25 (m, 1H), 5.13-5.08 (m, 2.2H), 5.04 (dd, J=8.5, 10.2 Hz, 1H), 5.01 (d, J=10.8 Hz, 1H, H-3$^F$), 4.93 (dd, J=7.9, 9.3 Hz, 1H), 4.84 (d, J=7.7 Hz, 1H), 4.77 (s, 1H, H-5$^B$), 4.67-4.65 (m, 1.6H), 4.60-4.59 (m, 1.2H), 4.44 (s, 1H, H-5$^F$), 4.40-4.38 (m, 1.2H), 4.22 (br d, J=10.8 Hz, 1H), 4.05 (s, 0.2H), 4.00-3.97 (m, 2H), 3.86-3.63 (m, 10.2H), 3.35 (m, 1H), 2.65 (s, 4H, H$^A$), 2.19-1.87 (m, 36.8H), 1.22 (s, 3H), 1.09 and 1.07 (2 d, J=6.2 Hz, 3H, H-6$^C$); $^{13}$C NMR (125 MHz, D$_2$O) δ 197.5, 177.1, 176.9, 176.5, 176.1, 176.0, 175.8, 175.7, 176.6, 175.5, 175.3, 175.2, 170.0, 169.8, 160.9, 137.4. 132.5, 131.7, 130.7, 114.3, 104.0, 103.0, 102.7, 102.6, 94.2, 82.7, 80.2, 78.2, 77.2, 76.6, 76.0, 75.9, 75.7, 75.6, 75.5, 74.4, 64.3, 74.2, 73.8, 73.1, 72.7, 70.9, 70.6, 64.3, 56.9, 56.2, 31.2, 24.4, 24.3, 22.7, 22.6, 22.5, 22.4, 22.3, 22.2, 19.3, 19.2, 17.0; LRMS calcd for C$_{64}$H$_{83}$N$_5$O$_{37}$Na [M+Na]$^+$: 1536.4. found 1536.4.

Method 1: To a solution of the above compound (10.6 mg, 7.0 μmol) in MeOH (0 μl) was added a solution of 1 N NaOH (70 μL, 70.0 μmol). After stirring for 1 h, the mixture was directly injected onto a semi-prep reversed-phase HPLC, using a 0-100% gradient of CH$_3$CN/H$_2$O with 0.1% TFA, to afford the title compound (6.0 mg, 5.6 μmol, 80%). Apparently, treatment of the α:β (5:1) starting material mixture with NaOH facilitated conversion of the minor β isomer to the α product, affording only the α isomer after purification; HRMS calcd for C$_{41}$H$_{64}$N$_5$O$_{28}$[M+H]$^+$: 1074.3738. found 1074.3723.

Method 2: To a solution of 16 (5.0 mg, 3.4 μmol), obtained from the degradation of moenomycin A$^7$, in MeOH (700 μl), was added a solution of 1N NaOH (70 μL). The mixture was stirred for 45 min then directly injected onto a semi-prep reversed-phase HPLC, using a 0-100% gradient of CH$_3$CN/H$_2$O with 0.1% TFA to afford the title compound as the α product (2.6 mg, 2.4 μmol, 70%). LRMS calcd for C$_{41}$H$_{64}$N$_5$O$_{28}$[M+H]$^+$: 1074.4. found 1074.3. NMR spectra of product identical for both methods: $^1$H NMR (600 MHz, D$_2$O) δ 5.54 (d, J=3.8 Hz, 1H, H-1$^F$), 5.01 (d, J=10.5 Hz, 1H, H-3$^F$), 4.65 (d, J=7.9 Hz, 1H, H-1$^B$), 4.59 (d, J=8.5 Hz, 1H, H-1$^E$), 4.55 (d, J=8.5 H, H-1$^C$), 4.46 (d, J=8.0 Hz, 1H, H-1$^D$), 4.45 (s, 1H, H-5$^B$), 4.38 (s, 1H, H-5$^F$), 4.28 (br d, J=3.5 Hz, 1H, H-4$^B$), 4.17 (d, J=10.5 Hz, 1H), 3.98 (dd, J=12.3, 2.1 Hz, 1H), 3.79-3.41 (m, 16H), 3.33 (dd, J=9.4, 8.0 Hz, 1H, H-2$^D$), 2.63 (s, 4H, H-3$^A$), 1.07, 1.05 (s, 3H each, NHAc), 1.39 (d, J=5.8 Hz, 3H, H-6$^C$), 1.21 (s, 3H, CH$_3$); $^{13}$C NMR (125 MHz, D$_2$O) δ 197.2, 177.4, 176.0, 172.5, 165.9, 165.6, 105.6, 105.4, 104.8, 103.7, 94.3 (C-1$^F$), 94.3, 85.7, 79.7, 78.6, 78.3, 77.5, 77.0, 75.6, 75.5, 74.8, 74.6, 74.4, 74.2, 73.6, 73.1, 72.0, 71.4, 70.6, 63.2, 58.1, 57.4, 31.1, 24.7, 24.6, 19.0, 16.9.

Example 2-r

Synthesis of 5-N-(3-hydroxy-1-oxocyclopenten-2-yl)-3,4-di-O-acetyl-2-O-benzoyl-β-D-galactopyranuronamide-(1→4)-2-acetamido-3-O-acetyl-2-deoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl-(1→2)-1-O-acetyl-3-carbamoyl-4-C-methyl-α-D-glucopyranuronamide

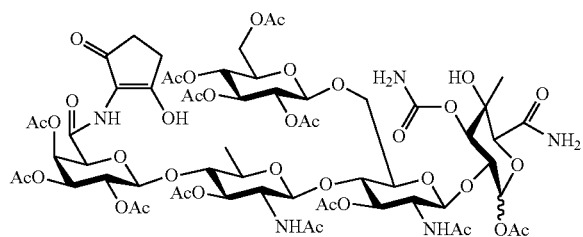

Compound 15 (4.5 mg, 4.19 μmol) in Ac$_2$O/pyridine (1 ml/1 ml) was stirred overnight. After evaporation of solvents and coevaporation with MeOH twice, the product was purified by gradient reversed-phase chromatography, using a 0-100% gradient of CH$_3$CN/H$_2$O, to afford the title compound (4.8 mg, 3.27 μmol, 78%). $^1$H NMR (600 MHz, D$_2$O) δ 6.45 (d, J=3.8 Hz, 1H, H-1$^F$), 4.72 (br s, 1H, H__4$^B$), 5.45 (t, J=9.7 Hz, 1H, H-3$^D$), 5.30 (dd, J=3.3, 11.0 Hz, 1H, H-3$^B$), 5.15-5.03 (m, 6H), 4.98 (t, J=8.2 Hz, 1H), 4.88 (d, J=7.9 Hz, 1H, H-1$^D$), 4.75 (d, J=8.8 Hz, 1H, H-1$^C$), 4.70 (s, 1H, H-5$^B$), 4.69 (d, J=8.0 Hz, 1H, H-1$^E$), 4.41 (dd, J=11.8, 3.0 Hz, 1H), 4.39 (s, 1H, H-5$^F$), 4.27 (br d, J=11.8 Hz, 1H), 4.01-3.92 (m, 3H), 3.84-3.76 (m, 5H), 3.70 (m, 1H), 3.61 (m, 1H), 2.64 (s, 4H, H$^A$), 2.25-1.96 (m, 36H, 12×Ac), 1.28 (d, J=6.6 Hz, 3H, H-6$^C$), 1.25 (s, 3H, Me); $^{13}$C NMR (125 MHz, D$_2$O) δ 197.5, 179.5, 177.0, 176.5, 176.2, 175.8, 175.7, 175.6, 175.4, 175.1, 169.8, 166.1, 165.8, 160.9, 114.3, 104.3, 103.3, 103.2, 102.5, 93.0, 82.6, 78.8, 77.0, 76.6, 76.2, 76.1, 75.9, 75.6, 75.4, 75.3, 74.5, 73.9, 73.3, 73.2, 72.3, 71.5, 70.8, 64.5, 57.1, 56.3, 31.2, 24.5, 22.9, 22.8, 22.6, 22.4, 22.3, 22.2, 19.3, 17.2; LRMS calcd for C$_{61}$H$_{84}$N$_5$O$_{38}$ [M+H]$^+$: 1494.4. found 1494.4.

Example 2-s

Synthesis of 5-N-(3-hydroxy-1-oxocyclopenten-2-yl)-2,3,4-tri-O-acetyl-β-D-galactopyranuronamide-(1→4)-2-acetamido-3-O-acetyl-2-deoxy-β-D-glucopyranosyl-(1→4)-[2,3,4,6-tetra-O-acetyl-β-D-glucopyranosyl-(1→6)]-2-acetamido-3-O-acetyl-2-deoxy-β-D-glucopyranosyl-(1→2)-3-carbamoyl-4-C-methyl-α-D-glucopyranuronamide (16)

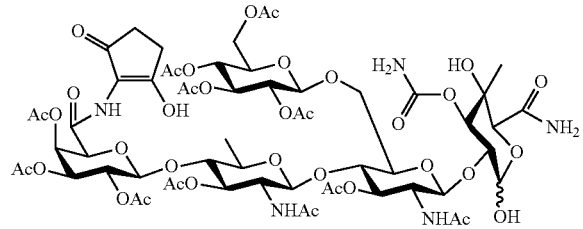

To a mixture of the above compound (7.5 mg, 5.01 μmol) in DMF (1 ml) was added H$_2$NNH$_2$·HOAc (0.94 mg, 10.0 μmol). After stirring for 1 h, the solvent was evaporated and then the crude residue was purified by gradient reversed-phase chromatography, using a 0-100% gradient of CH$_3$CN/H$_2$O, to afford the title compound (5.5 mg, 3.78 μmol, 75%) as a mixture (α:β, 3:1). $^1$H NMR (600 MHz, D$_2$O) δ 5.74 (br d, J=2.1 Hz, 1H, H-4$^B$), 5.52 (d, J=3.5 Hz, 1H, H-1$^F$), 5.36 (t, J=9.4 Hz, 1H, H-3$^D$), 5.31 (dd, J=3.6, 10.0 Hz, 1H, H-3$^B$), 5.15-4.97 (m, 6H, H-3$^E$,4$^D$,3$^C$,2$^B$,1$^B$,3$^F$), 4.87 (d, J=7.9 Hz, 1H, H-1$^D$), 4.73-4.69 (m, 3H, H-1$^C$,1$^E$, 5$^B$), 4.61-4.44 (m, 2H, H-5$^F$, 6$^D$), 4.27 (m, 1H, H-6$^D$), 4.07-4.01 (m, 2H, H-5$^D$,6$^E$), 3.90-3.62 (m, 8H, H-2$^C$,4$^C$,2$^E$,6$^E$,4$^E$,2$^F$,5$^E$,5$^C$), 2.64 (s, 4H, H$^A$), 2.16-1.97 (m, 33H, 11×Ac), 1.30 (d, J=6.2 Hz, 3H, H-6$^C$), 1.24 (s, 3H, Me); LRMS calcd for C$_{59}$H$_{82}$N$_5$O$_{37}$ [M+H]$^+$: 1452.4. found 1452.4.

REFERENCES

1. Lay, L.; Manzoni, L.; Schmidt, R. R. *Carbohyd. Res.* 1998, 310, 157-171.
2. Srivastava, G.; Alton, G.; Hindsgaul, O. *Carbohyd. Res.* 1990, 207, 259-276.
3. Jansson, K.; Ahlfors, S.; Frejd, T.; Kihlberg, J.; Magnusson, G.; Dahmén, J.; Noori, G.; Stenvall, K. *J. Org. Chem.* 1988, 53, 5629-5647.
4. Kartha, K. P. R.; Aloui, M.; Field, R. A. *Tetrahedron Lett.* 1996, 37, 8807-8810.
5. Hernández-Torres, J. M.; Achkar, J.; Wei, A. *J. Org. Chem.* 2004, 69, 7206-7211.
6. Debenham, J. S.; Madsen, R.; Roberts, C.; Fraser-Reid, B. *J. Am. Chem. Soc.* 1995, 117, 3302-3303.
7. Adachi, M.; Zhang, Y.; Leimkuhler, C.; Sun, B.; LaTour, J.; Kahne, D. *J. Am. Chem. Soc.* 2006, 128, 14012-14013.

Example 3

Biosynthesis of Moenomycin Analogs

We recently cloned and sequenced the biosynthetic genes for moenomycin production.[4-6] Functions for each gene were proposed based on sequence analysis, but the order of assembly could not be established. In order to enable biosynthetic and chemoenzymatic approaches to the synthesis of PGT inhibitors based on the moenomycin scaffold, we have here characterized the biosynthetic pathway and identified the subsets of genes involved in the production of bioactive analogs.[3,5]

Figure 2:
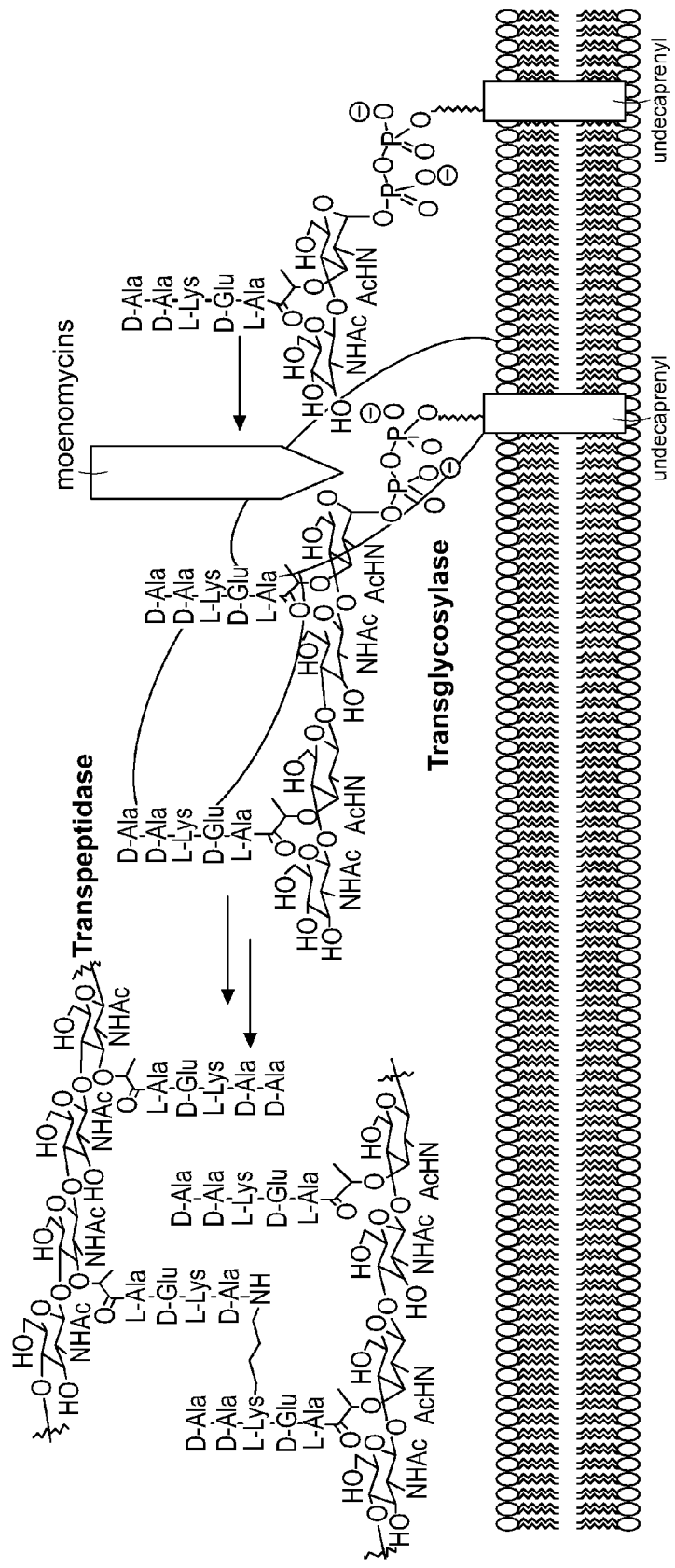
FIG. 2. Interaction of moenomycin A with various targets on a cell membrane.
Figure 3A:
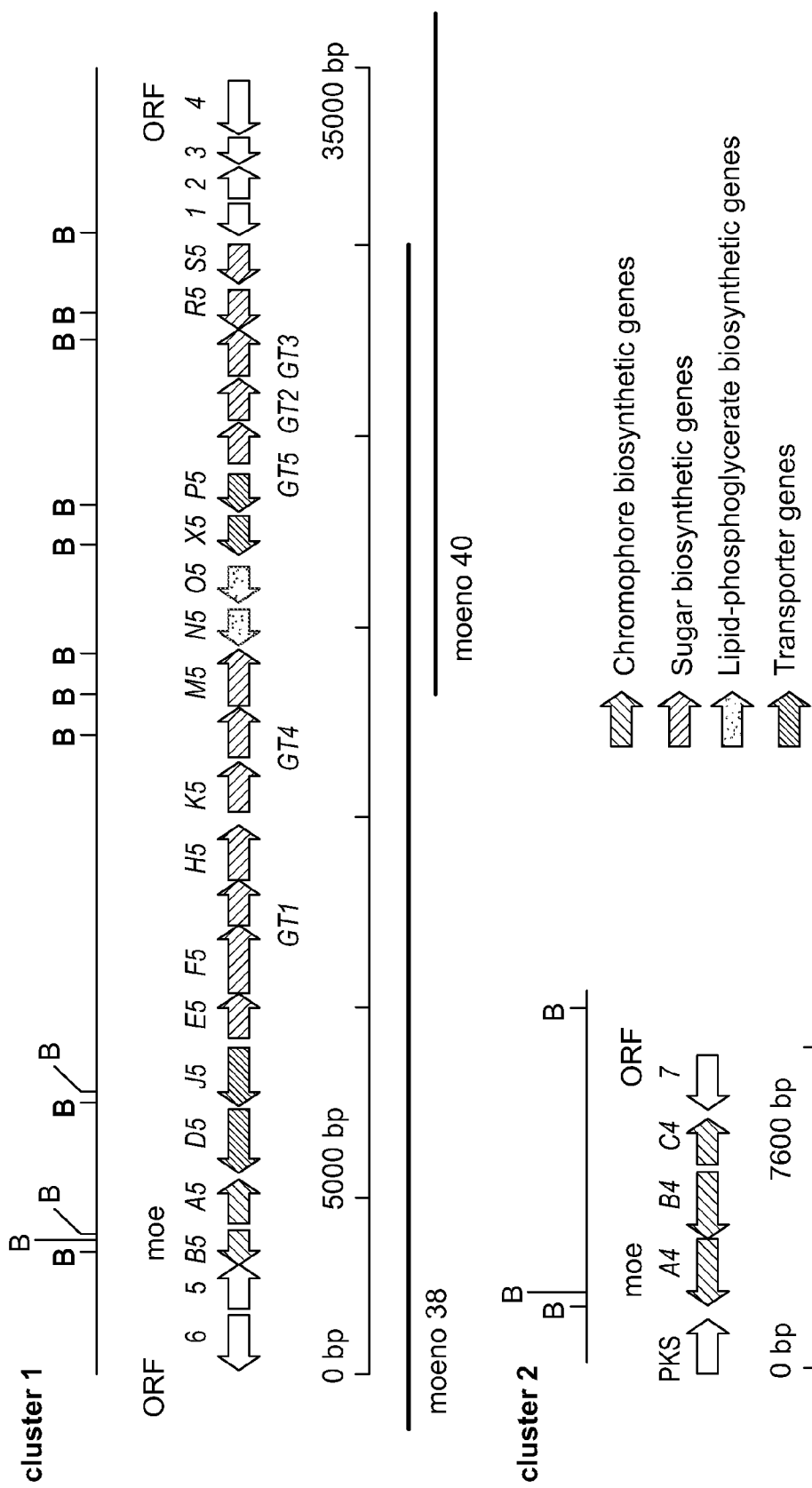
FIGS. 3A-3B.
Figure 3B:
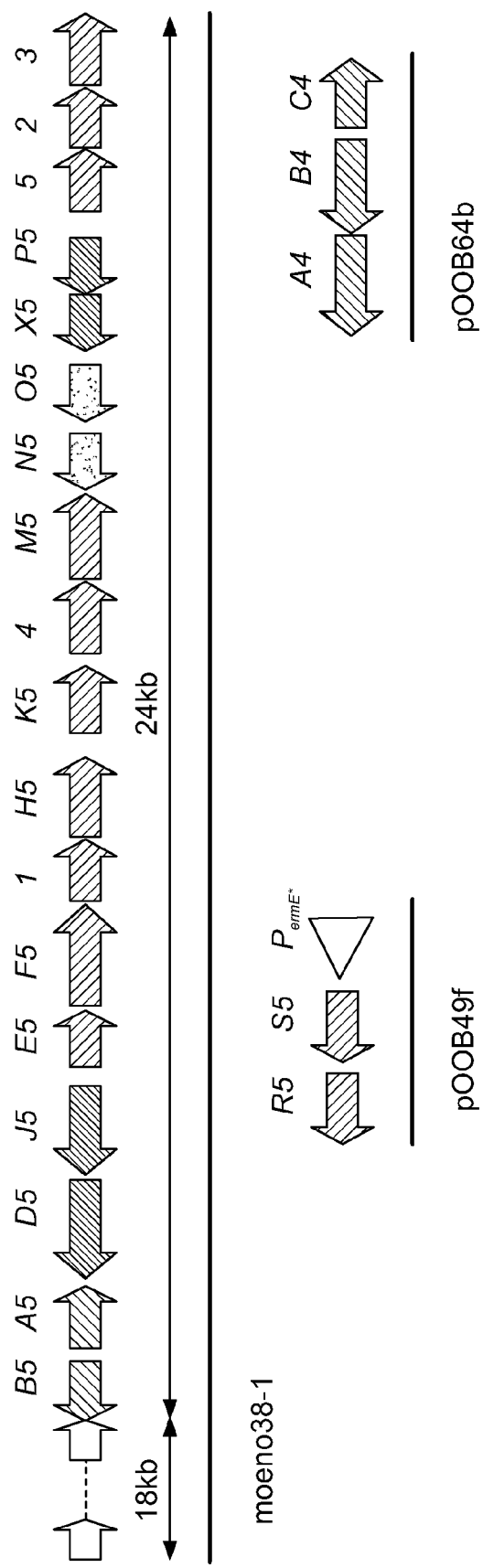

An approach to the genetic analysis of MmA biosynthesis. The MmA biosynthetic genes are located in two clusters on the *S. ghanaensis* chromosome: a three gene operon involved in A ring assembly and a larger cluster containing most of the genes involved in the assembly of the lipid-phosphoglycerate-pentasaccharide scaffold (FIG. 2). We have previously shown that the hygromycin resistant cosmid moeno38-1 (FIG. 3A-3B) contains the major moe cluster minus the moeR5moeS5 genes and directs the production of MmA derivative 19 in *S. lividans* TK24.[5] To illuminate the functions of individual moe genes in moeno38-1, we have constructed a set of moeno38-1 derivatives carrying λ-Red-induced gene deletions.[9,10] Genes moeR5moeS5 were cloned both individually and as a pair into the pKC1139-based plasmid pMKI9 (FIG. 3A); the three genes in moe cluster 2 are on plasmid pOOB64b, which is based on vector pSOK804 and carries an apramycin resistance marker and an actinophage VWB attP-int fragment.[11] The derivatives of moeno38-1 were integrated into the *S. lividans* attP$^{ΦC31}$ site and then certain strains were further supplemented with either pOOB49f or pOOB64b, or their truncated versions. The names of the recombinant strains are abbreviated. For example, the *S. lividans* strain carrying the moeno38-1 derivative with a deleted moeF5 is referred to as ΔmoeF5; the strain having a deleted moeH5 but supplemented with a plasmid expressing moeR5 is denoted as moeR5+ ΔmoeH5; strains carrying the parental cosmid, moeno38-1, are denoted as 38-1+ strains. The mutations in individual moe genes were complemented with exact copies of the genes, thus ruling out polar effects. Moenomycin analogs produced in recombinant strains were isolated from cell extracts in purified yields of approximately 0.1 mg/L depending on the compound, and structures were assigned based on exact masses and MS$^2$ fragmentation patterns using extensive published data on the fragmentation of moenomycins isolated from feed stocks. NMR was used to confirm the structure of some compounds.

Functions of the Two Prenyltransferases in Moe Gene Cluster 1.

The phosphoglycerate-moenocinol chain of moenomycin is unusual in containing a cis-allylic ether linkage and an irregular isoprenoid chain. Two putative prenyltransferases, moeO5 and moeN5, were previously identified in moe cluster 1 via in silico analysis of the genes.[5] MoeO5, which is similar to enzymes involved in transferring geranylgeraniol to glycerol phosphate in the first step of archaeal membrane lipid biosynthesis, was proposed to form an ether linkage between 3-R-phosphoglycerate and an activated moenocinol chain; MoeN5 was proposed to couple two isoprene-derived precursors to produce the activated moenocinol chain. To establish the function of MoeO5, we cloned the moeO5 gene into the pAF/urdR thiostrepton-resistant plasmid and expressed it as a His-tag fusion in *S. lividans* TK24. After purification, MoeO5 was tested for activity with geranyl, neryl, farnesyl, geranylgeranyl, and moenocinol pyrophosphate. Under the conditions tested, MoeO5 was found to react only with farnesyl pyrophosphate. This finding suggested that MoeN5 couples a C10 lipid to a farnesylated moenomycin precursor to produce the moenocinol chain found in the natural product. Consistent with this, disruption of moeN5 in moeno38-1 yielded a recombinant *S. lividans* TK24 strain (ΔmoeN5) that accumulated two compounds, differing by one mass unit, which have similar fragmentation patterns as compound 19 but molecular weights consistent with a C-15 rather than a C-25 chain (Note: refers to total number of carbons in the chain). The compounds were assigned as 22 and 23, and they differ in the structure of unit B (MmA numbering; see FIG. 2), which contains either a carboxyl group (22) or a carboxamide (23) at carbon 5. Heterogeneity at this position has been reported for other moenomycins,[12] and results below suggest that it reflects incomplete conversion of the acid to the amide by the amidotransferase MoeH5.

Functions of the Glycosyltransferases in Moe Gene Cluster 1 and Order of Assembly of the Phosphoglycolipid.

Figure 4:
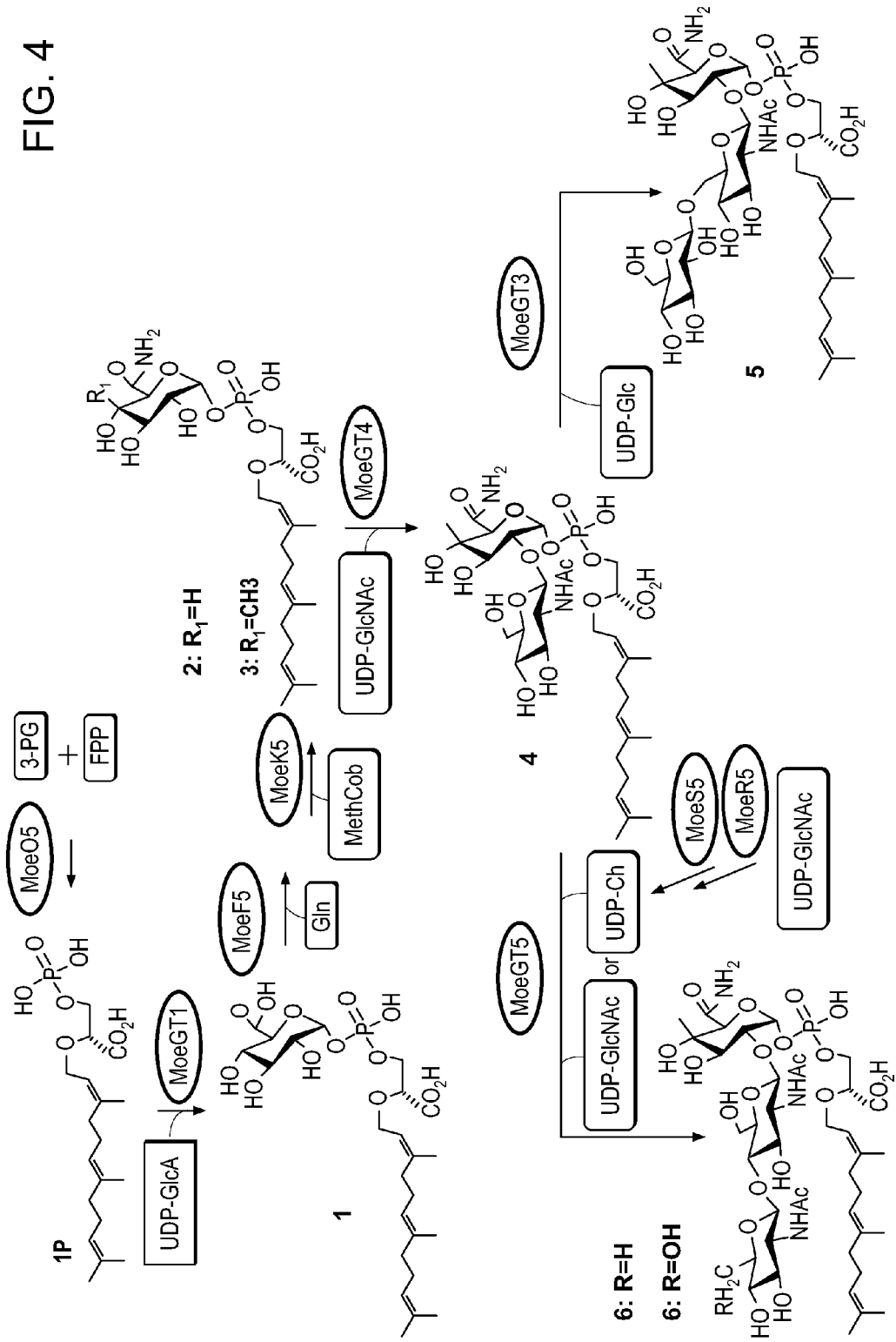
FIG. 4. Moenomycin A (MnA) biosynthetic pathway. Dotted arrow line represents multiple biosynthetic steps (omitted on the scheme) leading from compound 8 to 22/23.
Figure 4:
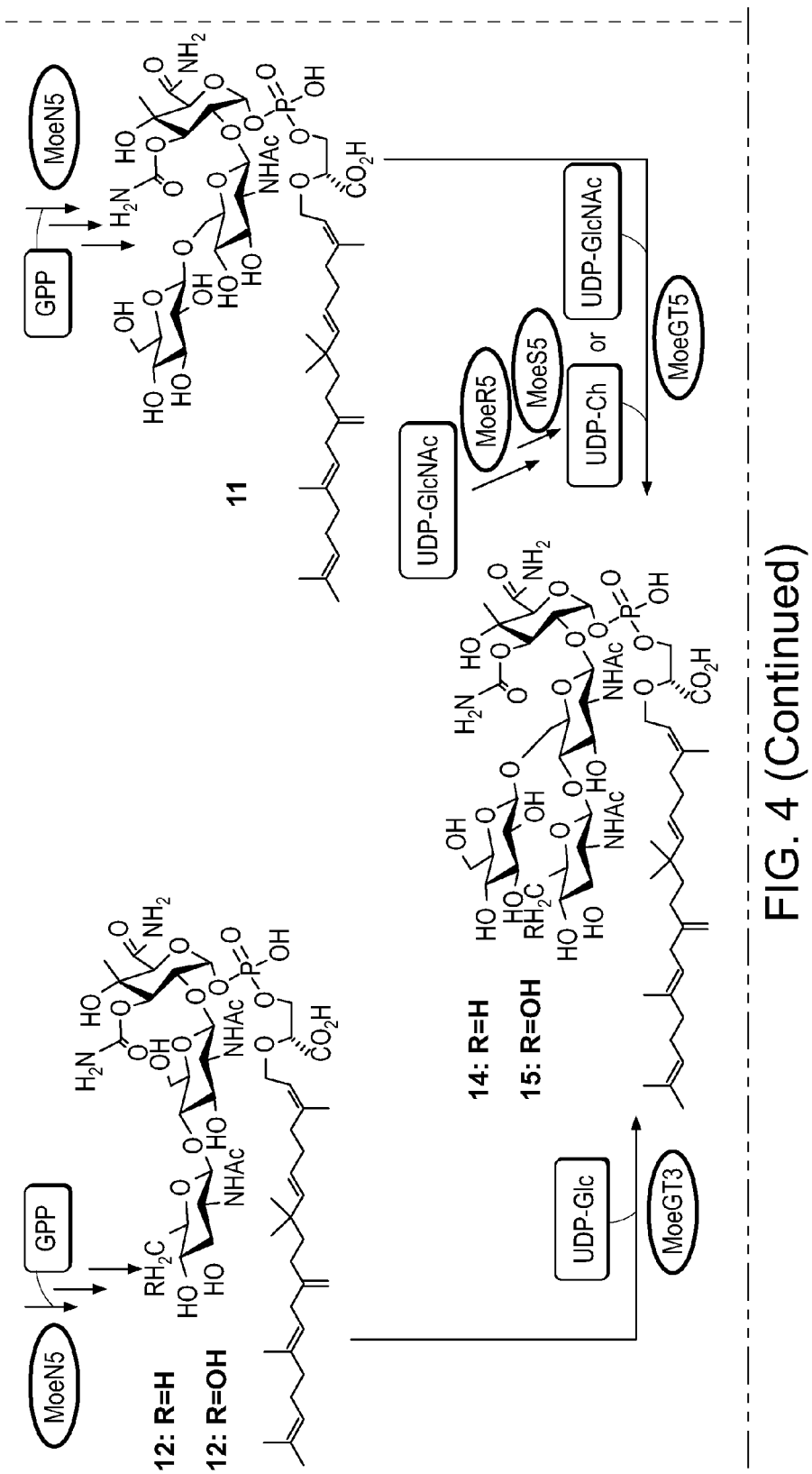
Figure 4:
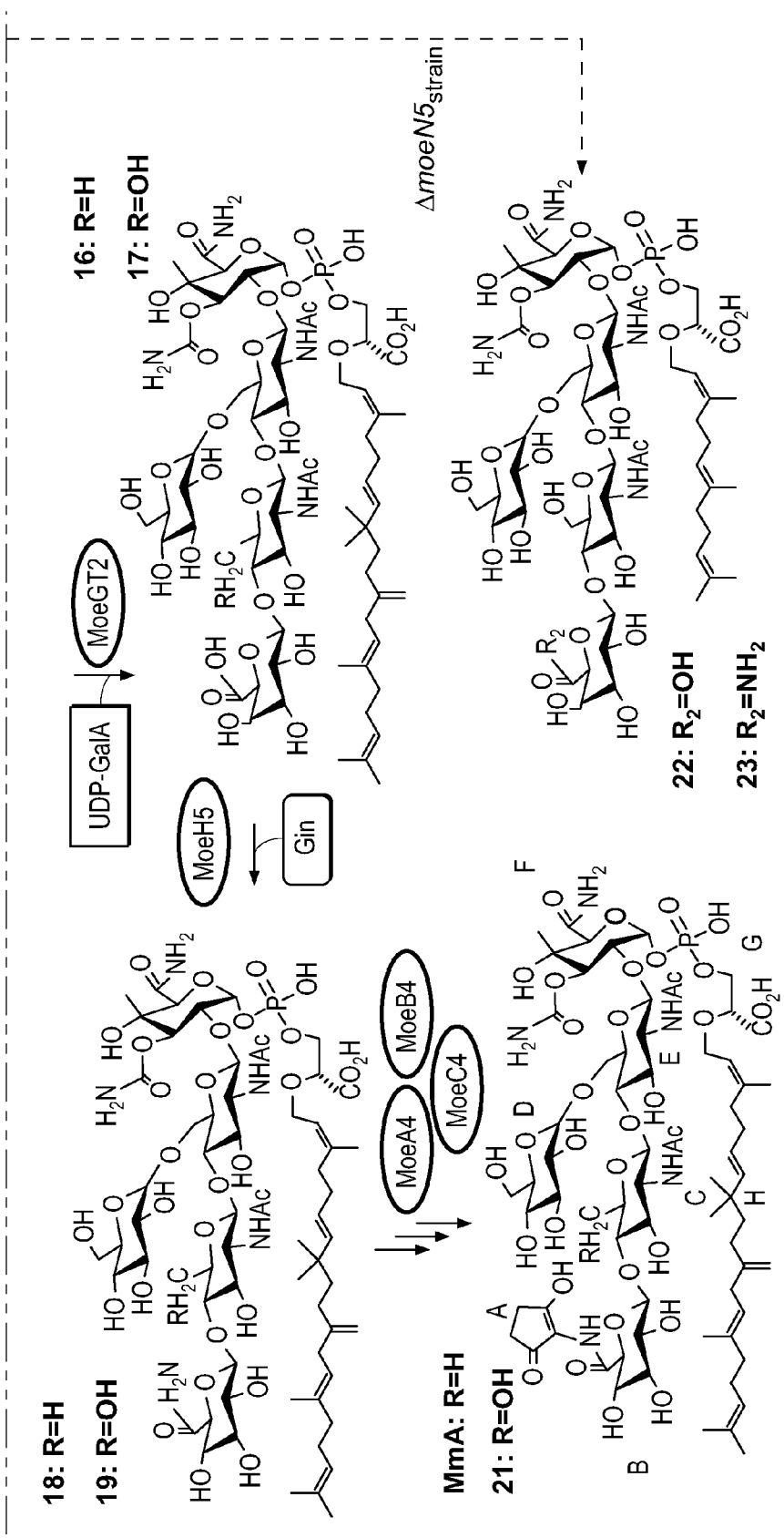
Figure 5:
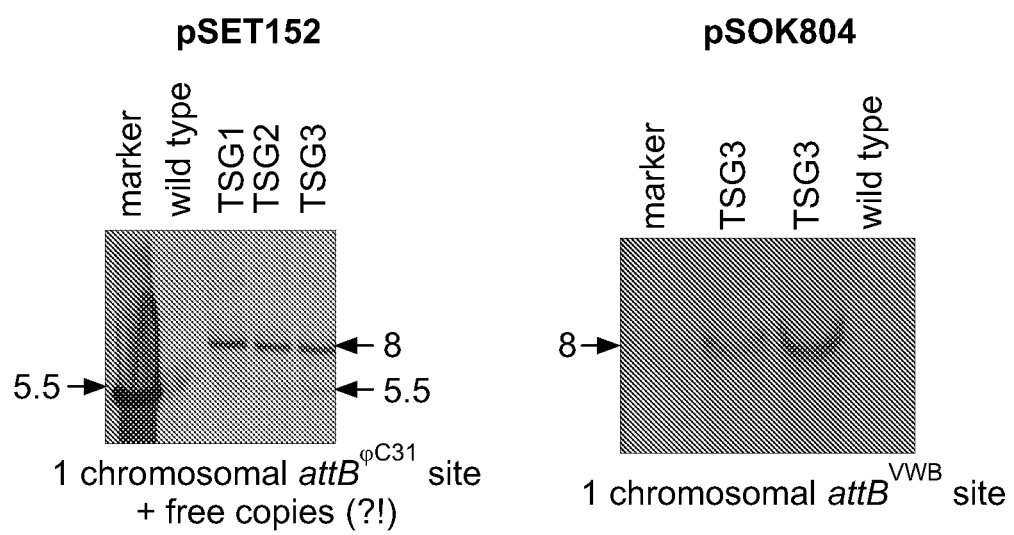
FIG. 5. A Southern blot demonstrating the integration of vectors pSET152 and pSOK804 in the *S. ghanaensis* genome.
Figure 6:
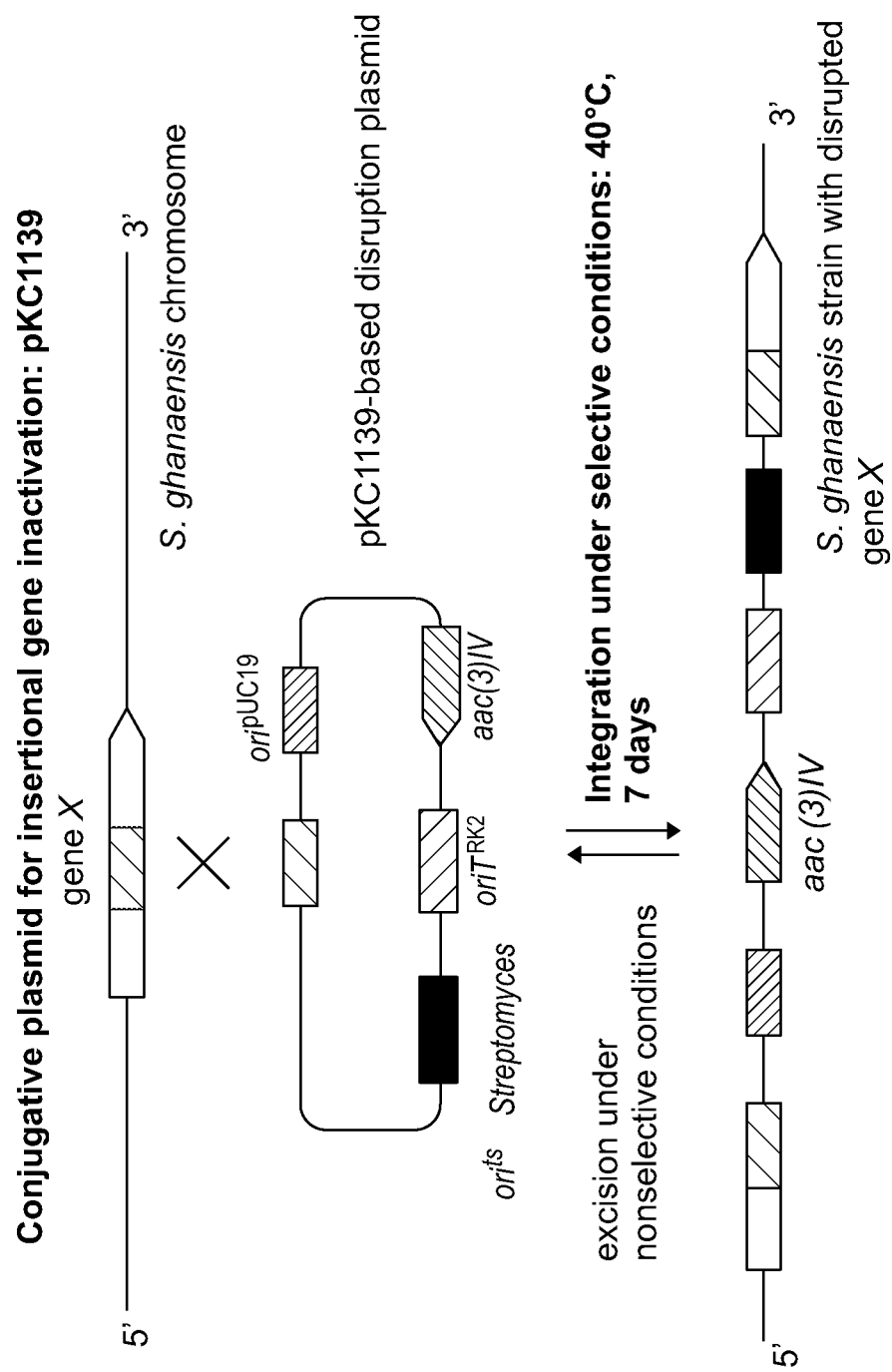
FIG. 6. A schematic for the generation of a conjugative plasmid that may be used for insertional gene inactivation.
Figure 7:
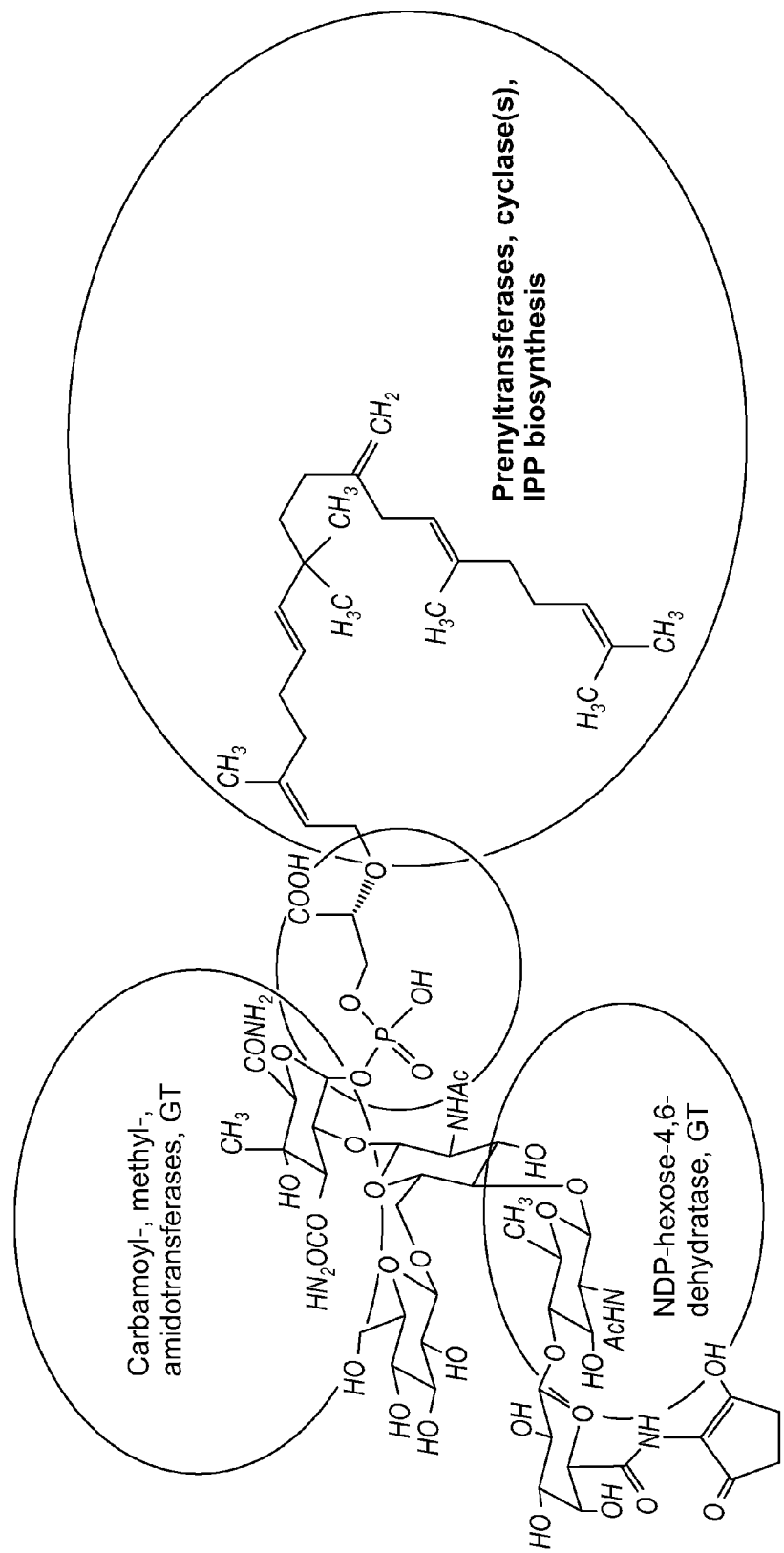
FIG. 7. A schematic describing an approach for in silico screening involving classes of enzymes directed to producing different domains of moes.
Figure 9:
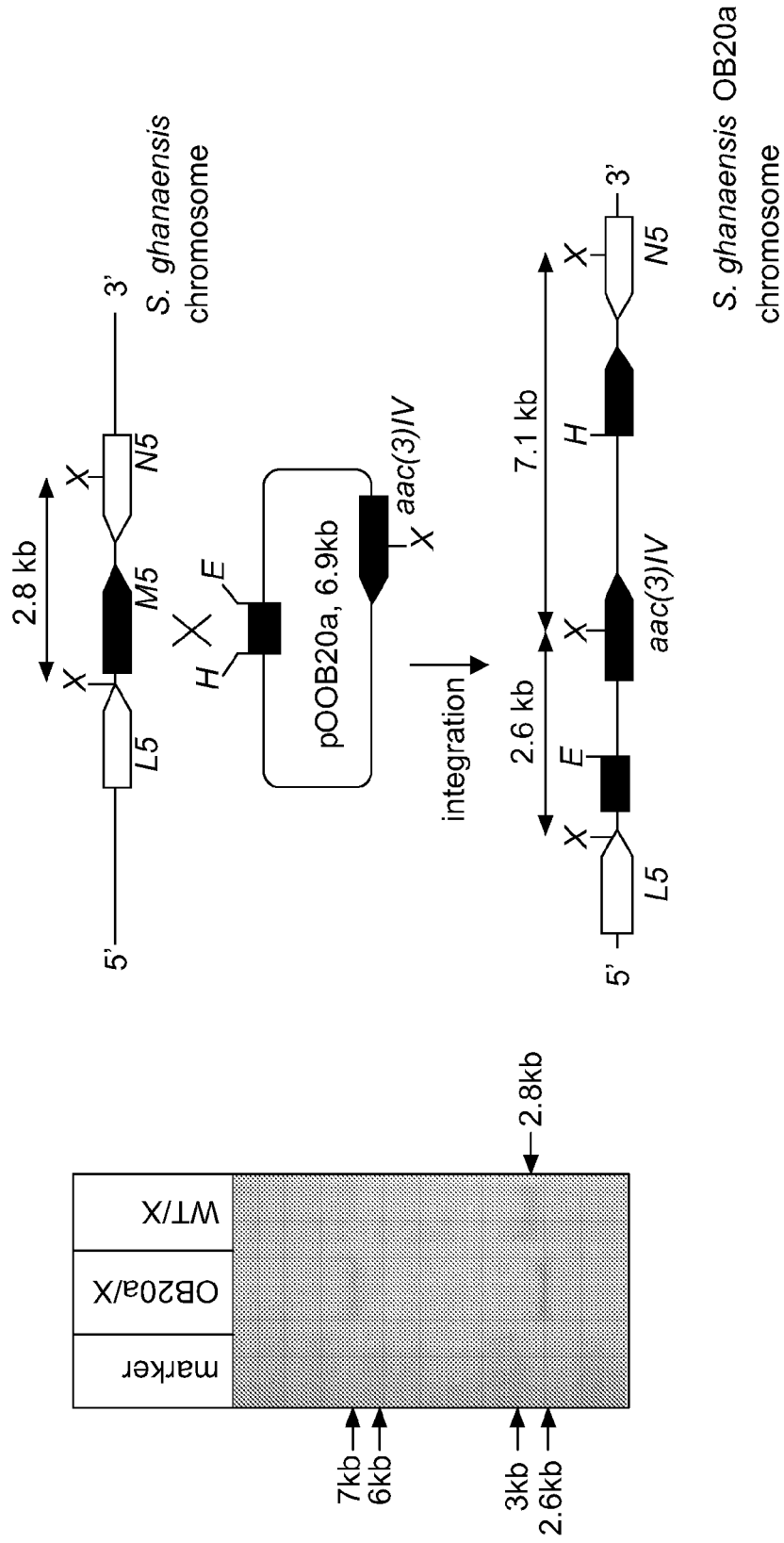
FIG. 9. A schematic for the insertional inactivation of the moeM5 gene.
Figure 10:
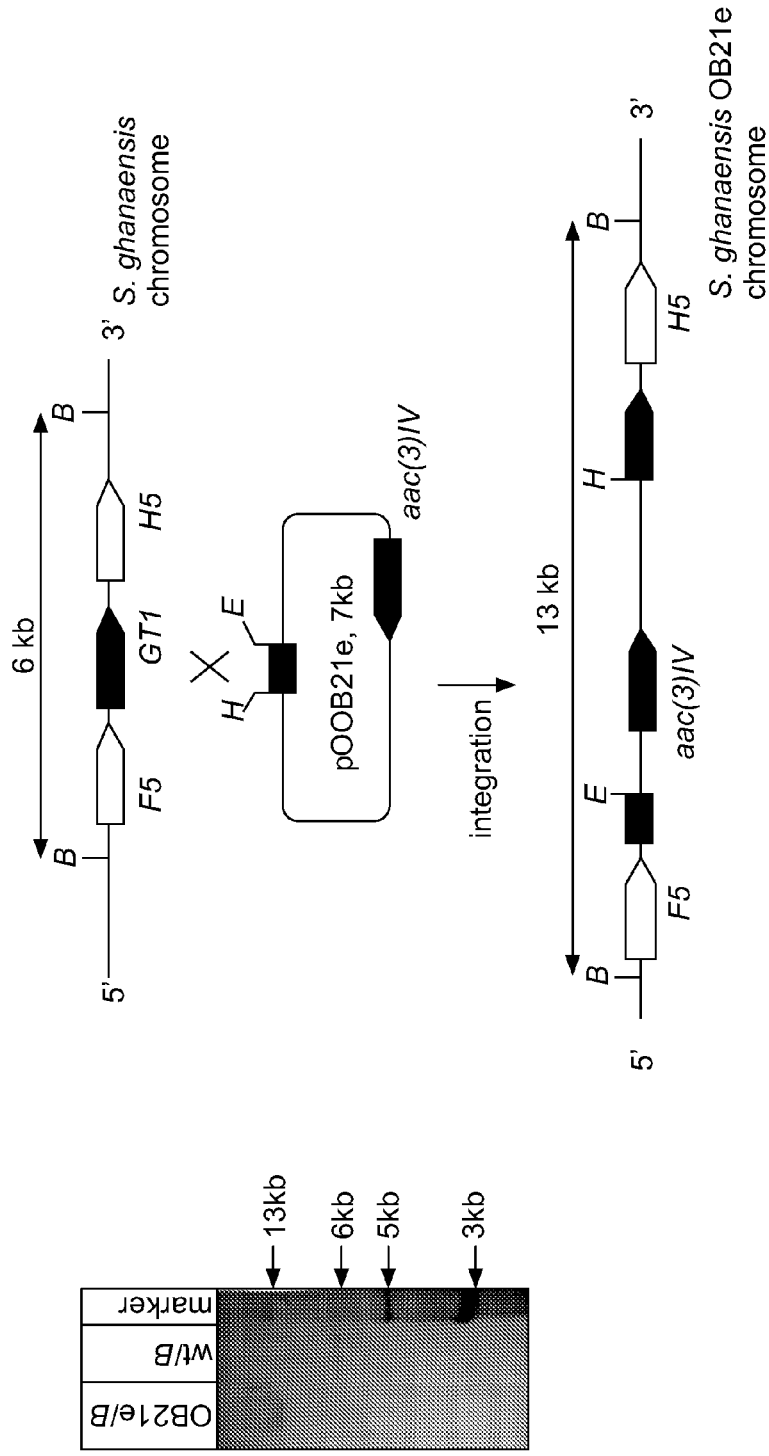
FIG. 10. A schematic of the insertional inactivation of the moeGT1 gene.
Figure 11:
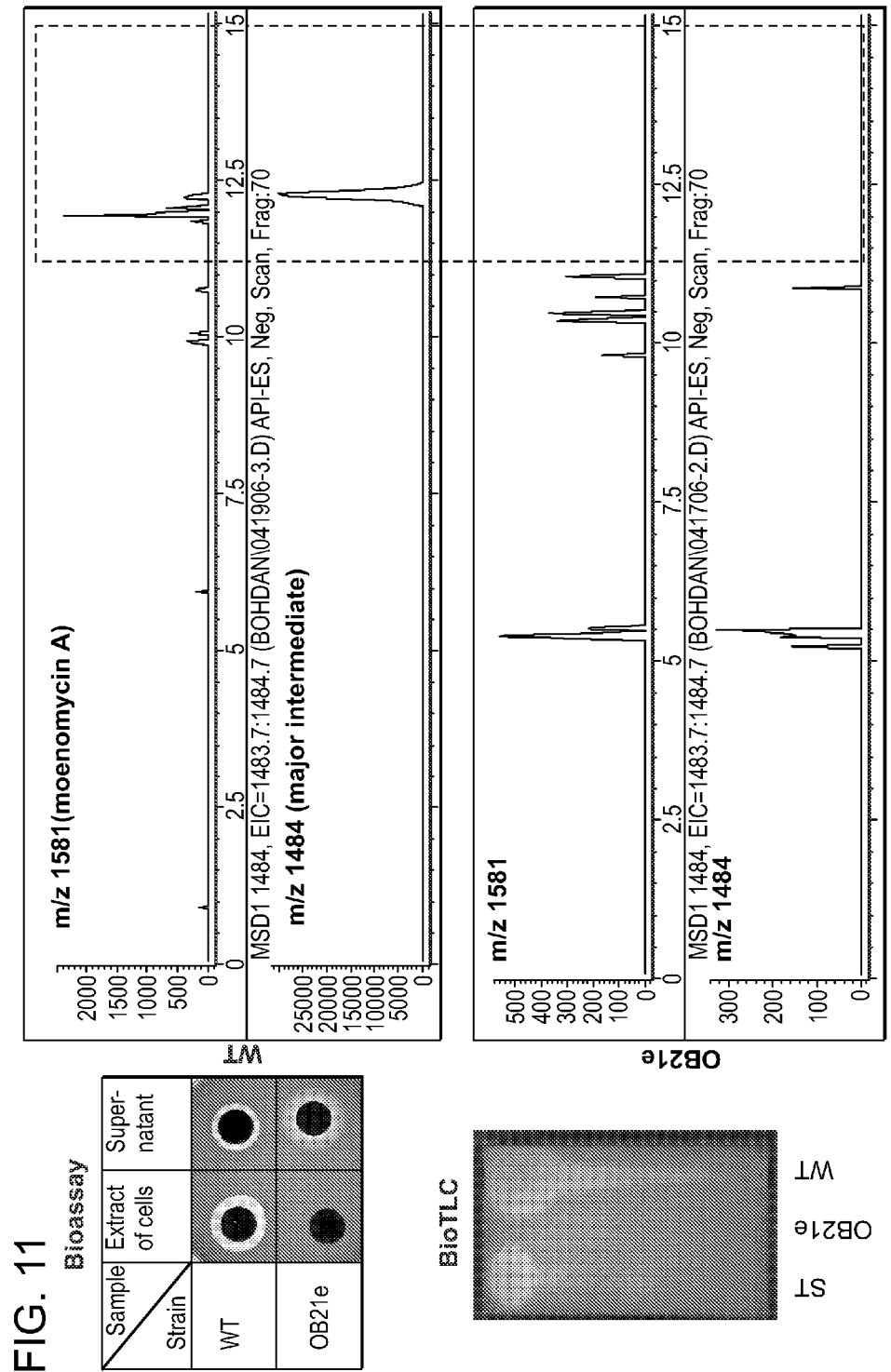
FIG. 11. Bioassay and liquid chromatography and mass spectrometry ("LC-MS") data indicating that in the moeGT1 mutant, moe A production appears to be reduced or abolished.
Figure 12:
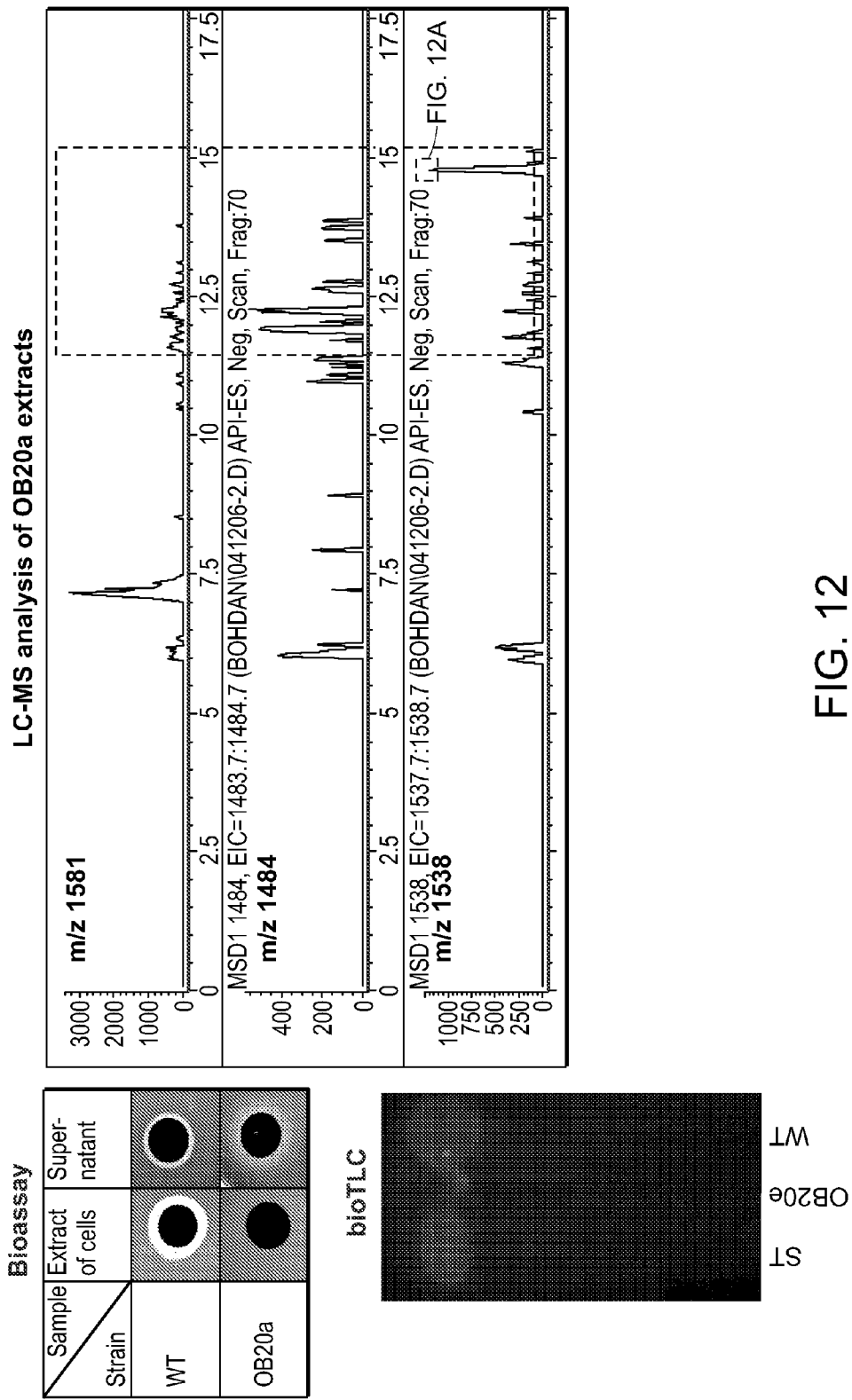
FIG. 12. Bioassay and LC-MS data of the moe A analog in the moeM5 mutant.
Figure 12A:
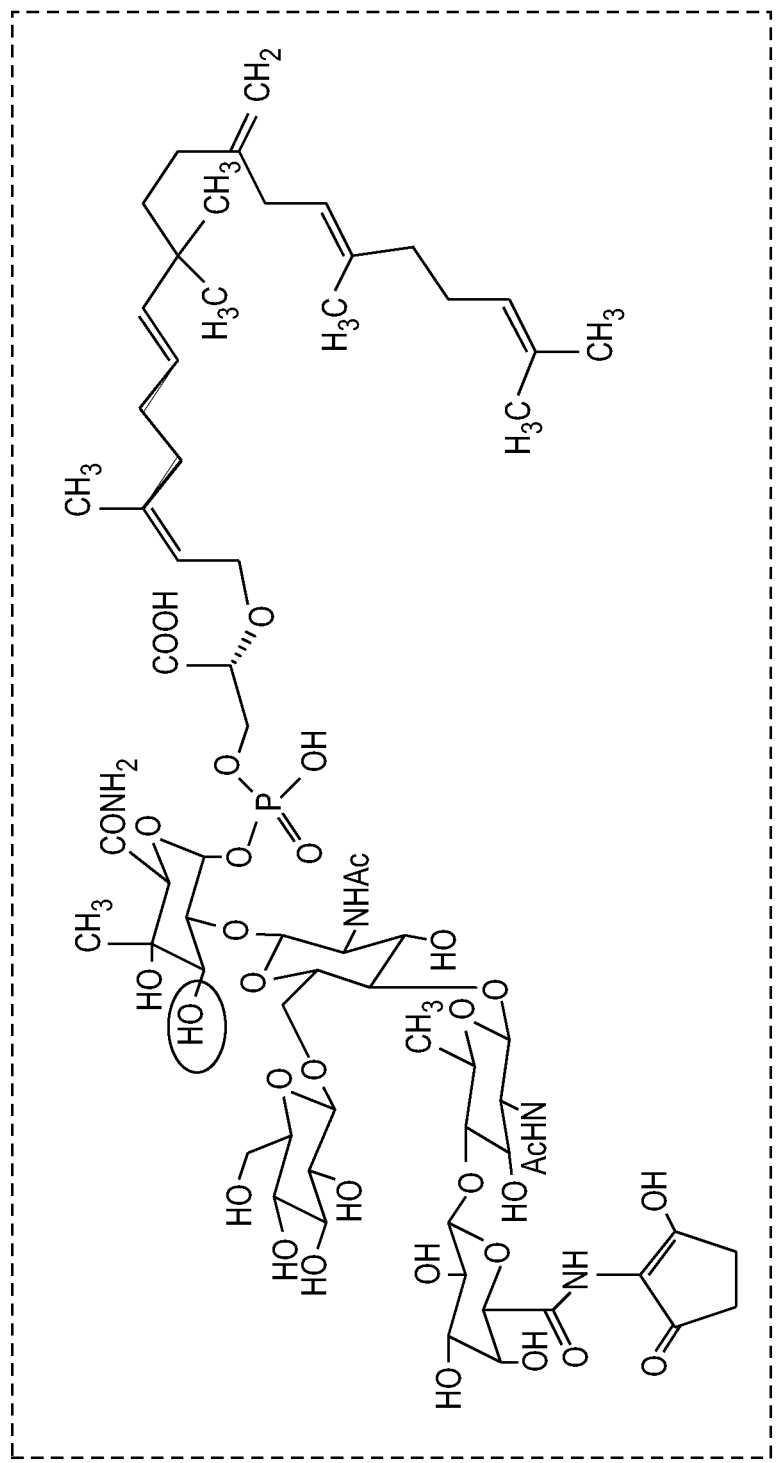
Figure 13A:
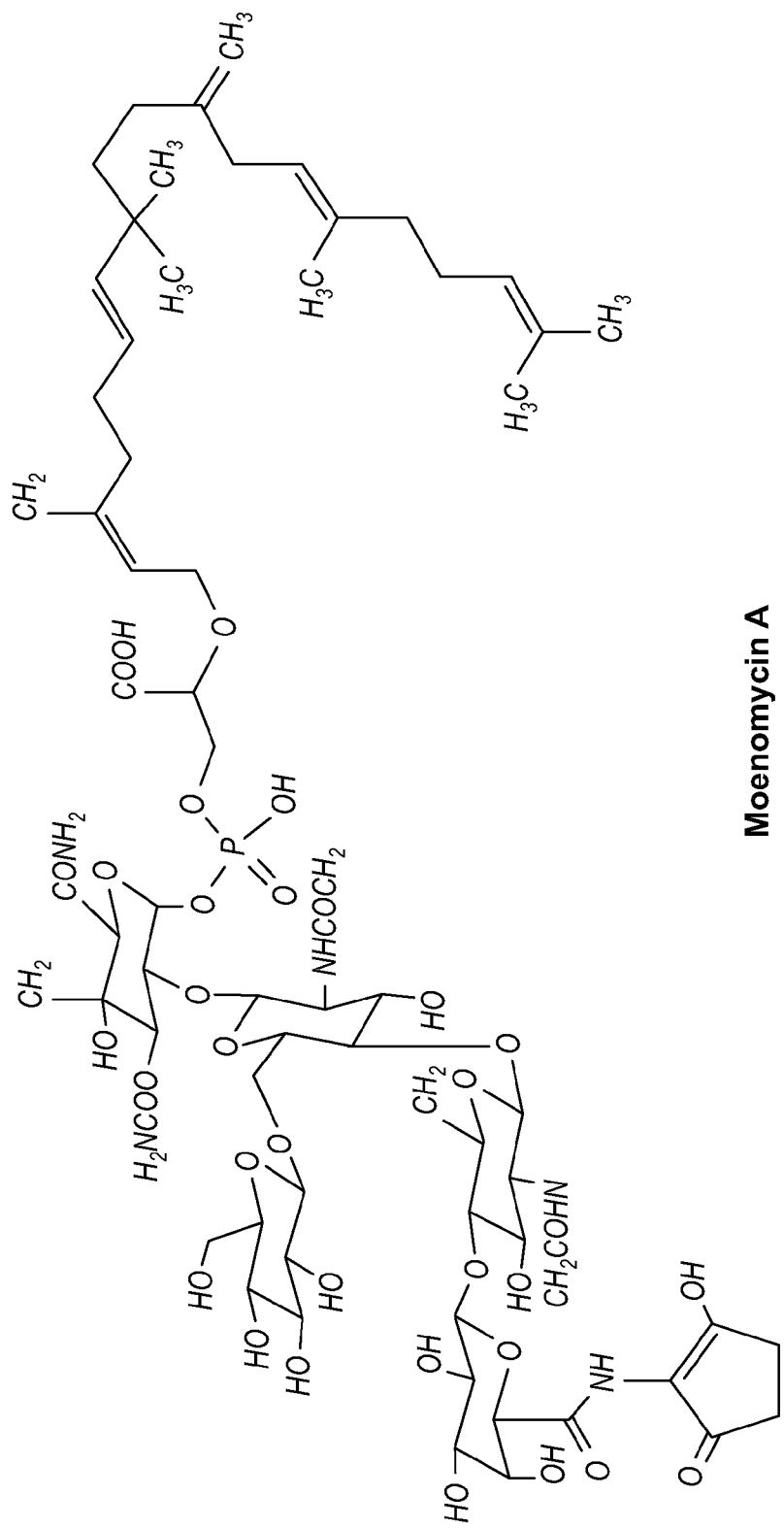
Figure 13B:
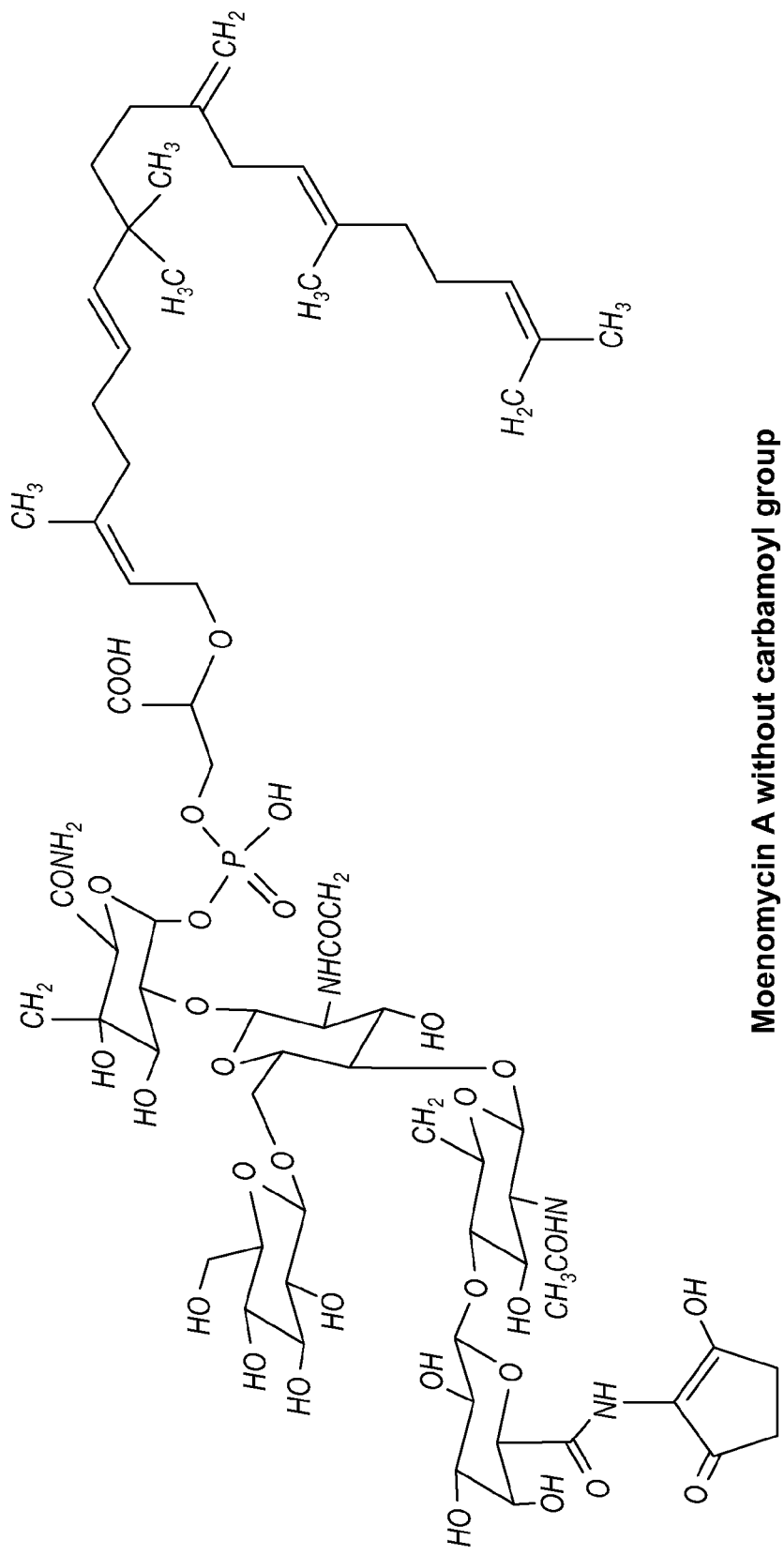
Figure 14:
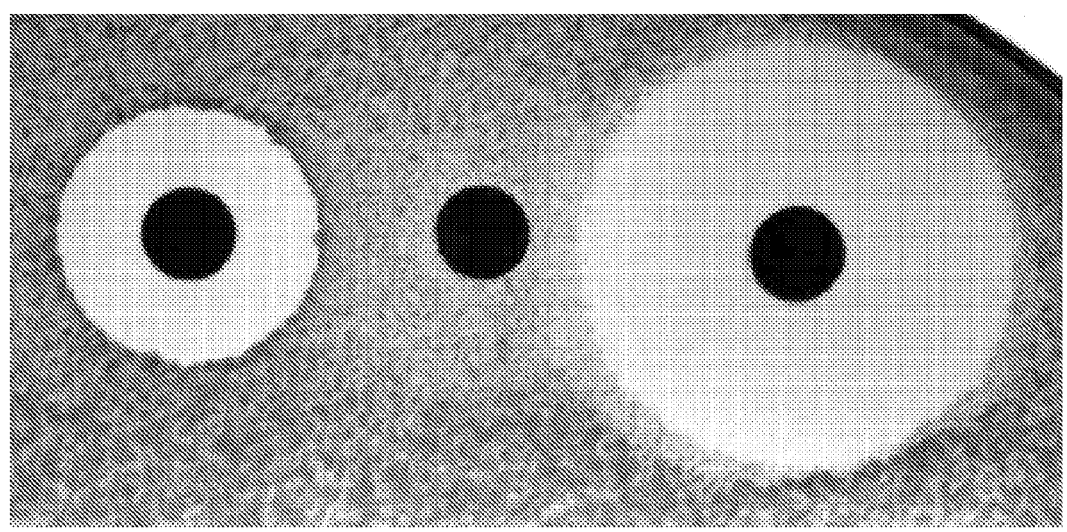
FIG. 14. Bioassay of methanol extracts from 2 g of mycelia of strains *S. lividans* J1725 38-1$^+$ (2) and *S. lividans* J1725 38-1$^+$ pIJ584$^+$ (3). (1)—standard (moe A, 4 mcg).
Figures 15A, 15B, 15C:
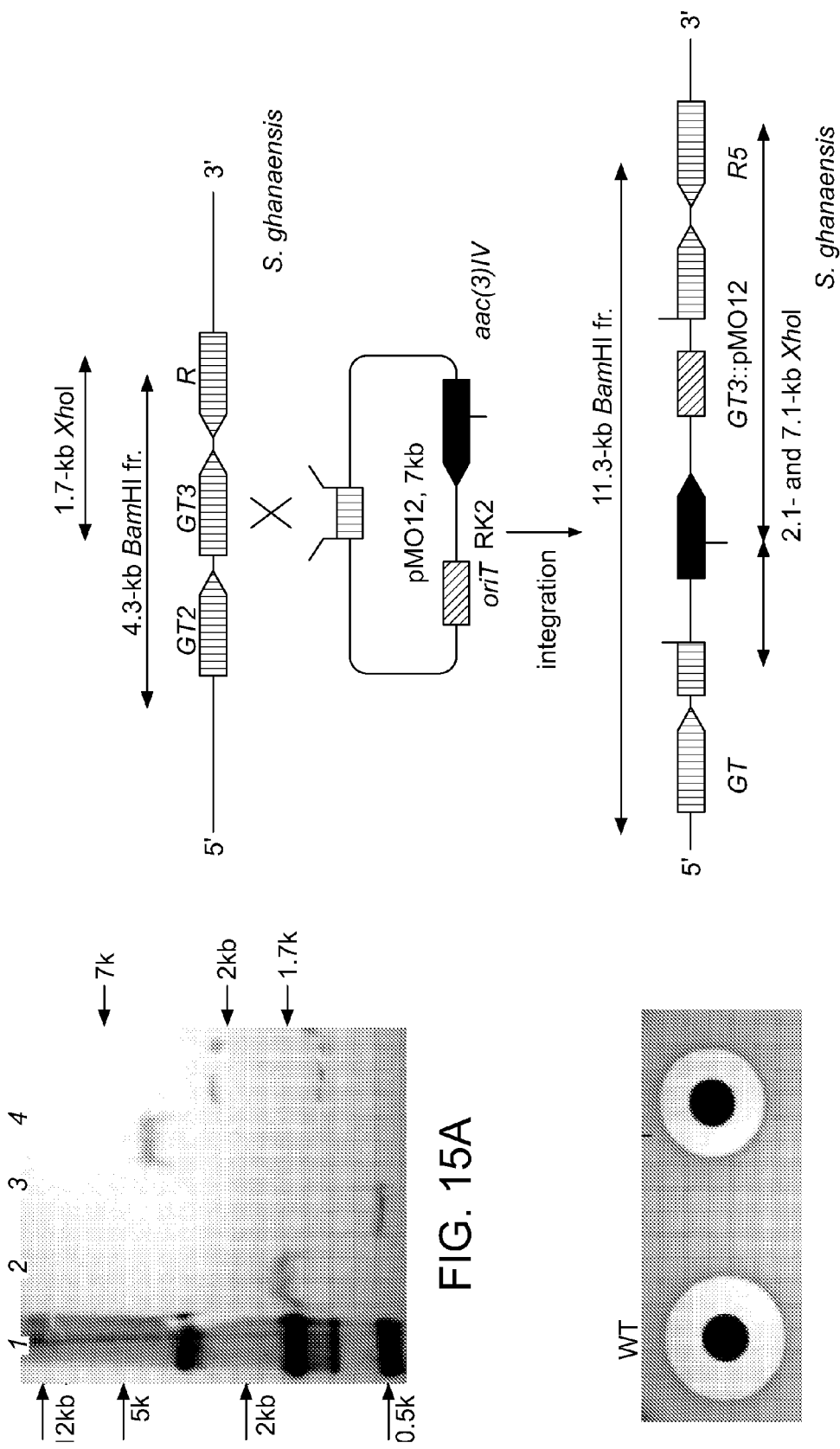
FIGS. 15A-15C.
Figures 16, 16A:
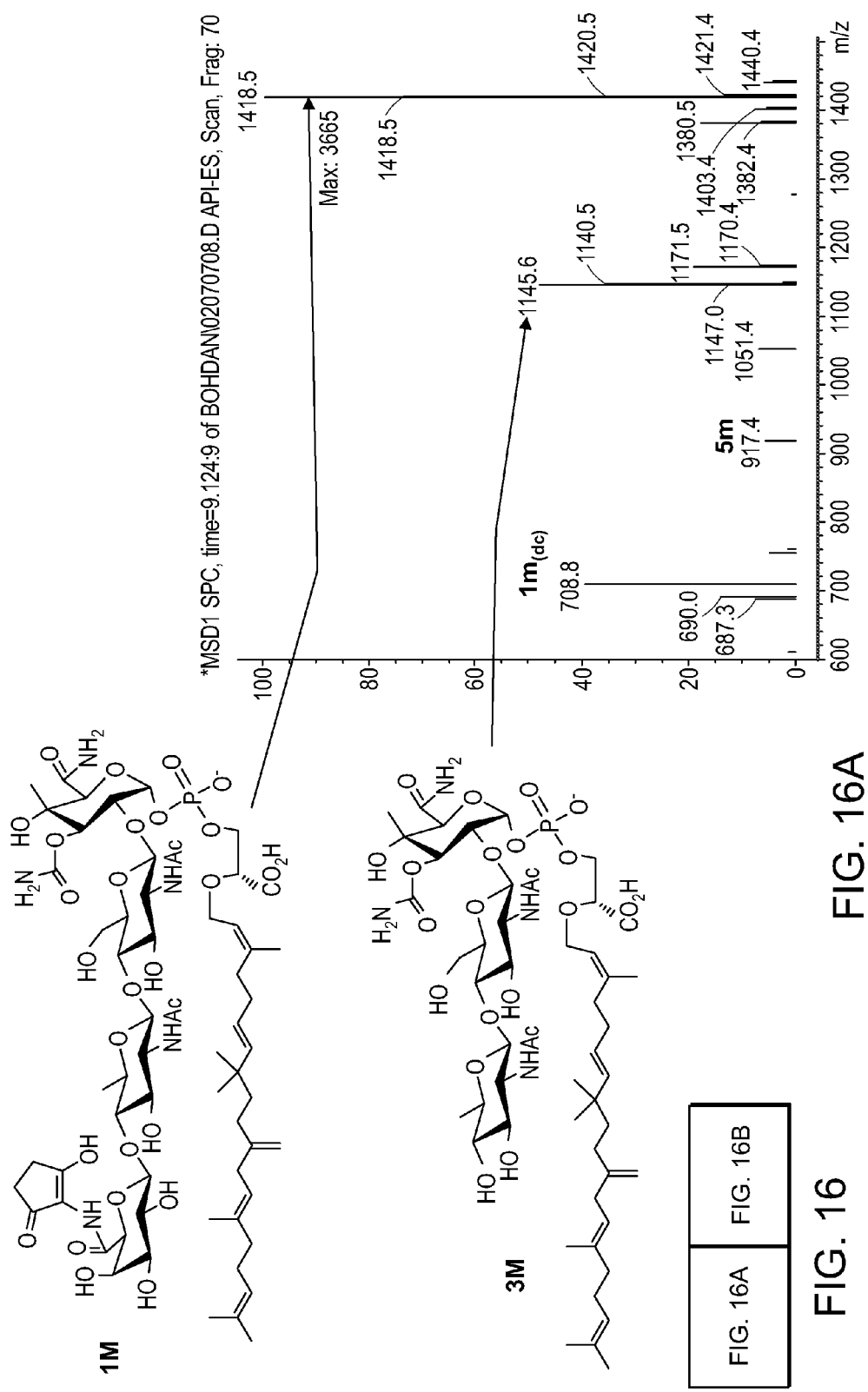
FIG. 16. Graph of LC-MS analysis of moenomycin metabolites accumulated by *S. ghanaensis* MO12 strain. The final product is moenomycin C4 (1m) having Rt 9.2 min. The strain also accumulates its precursor lacking chromophore unit (2m; Rt 10.0 min) Peaks corresponding to trisaccharide and disaccharide precursors of moenomycin C4 (3m and 4m, respectively) are observed. 5m is decarbamoylated derivative of 4m. 2m(dc) and 1m(dc) are doubly charged ions of 2m and 1m, respectively.
Figure 16B:
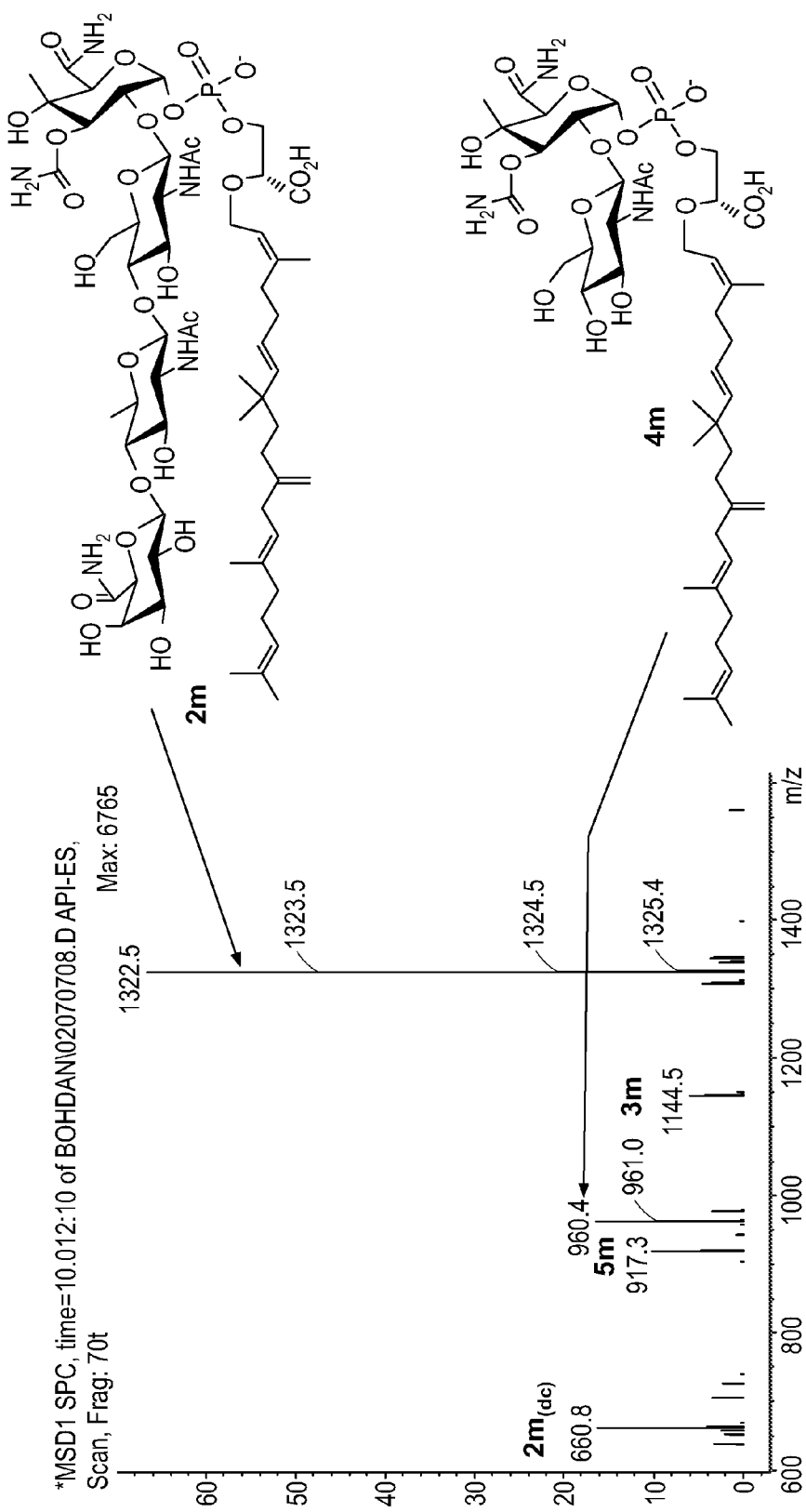
Figure 17A:
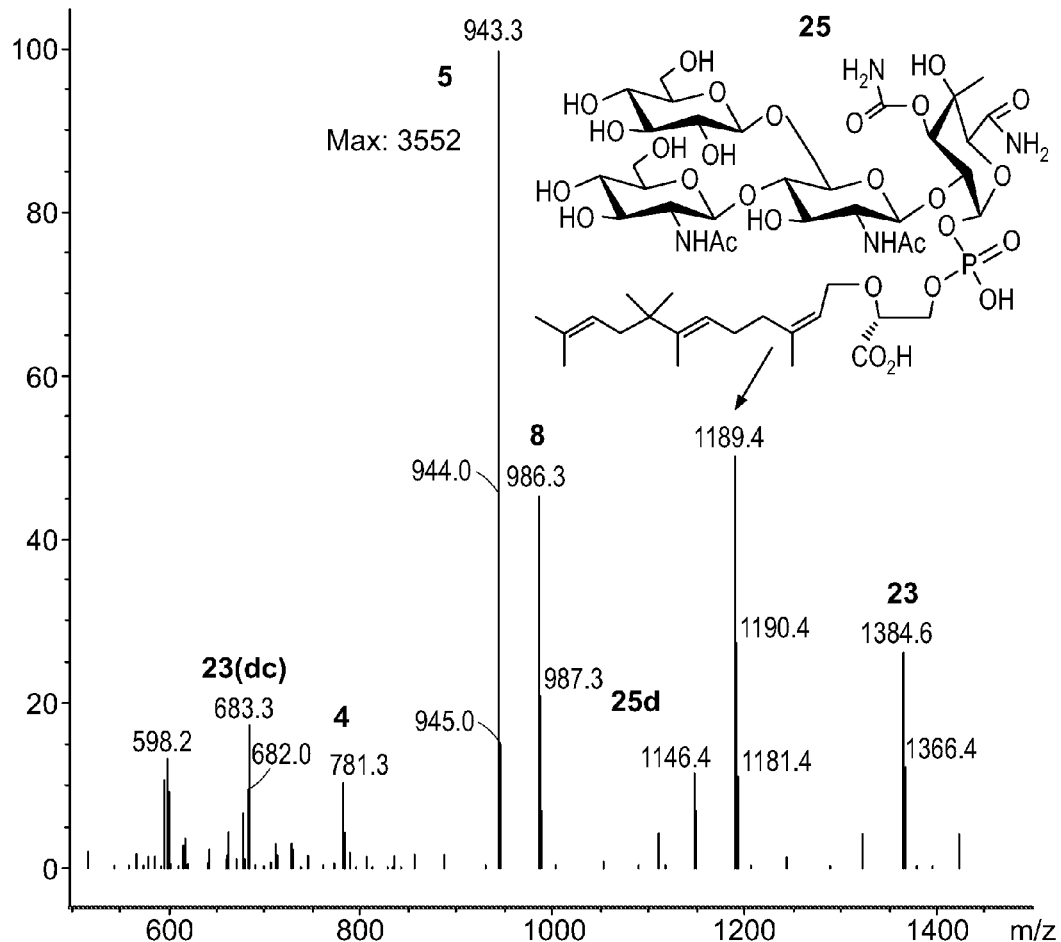
FIGS. 17A-17B. Graph of LC-MS analysis of moenomycin metabolites accumulated by *S. lividans* TK24 ΔmoeN5 strain. Panel A. The final product is compound 23 having Rt 4.2 min. Panel B. The strain also accumulates its monosaccharide precursors 2 and 3 (Rt 4.7-4.8 min) Structures of compounds 2, 3, 4, 8 and 23 are shown in FIG. 4. Compounds 5 and 25d are decarbamoylated derivatives of 8 and 25, respectively. 23(dc) is doubly charged ion of 23.
Figure 17B:
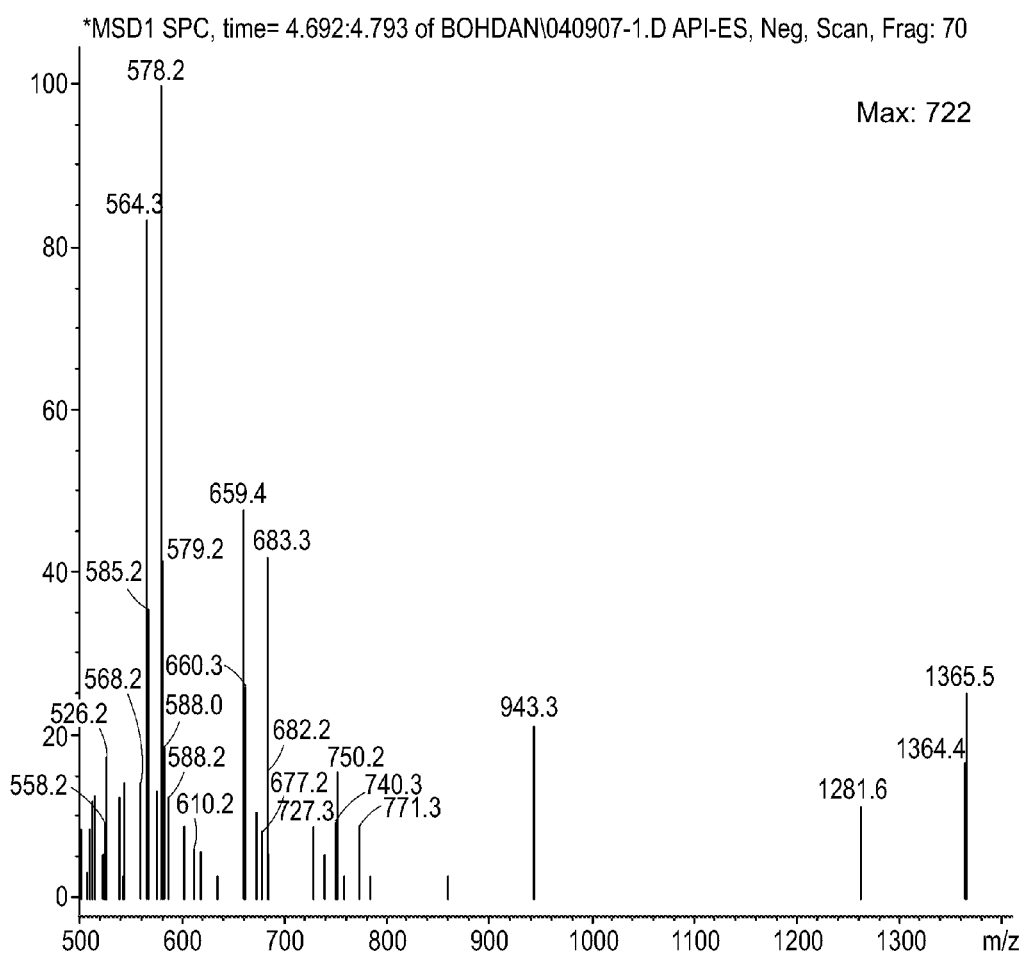
Figure 18A:
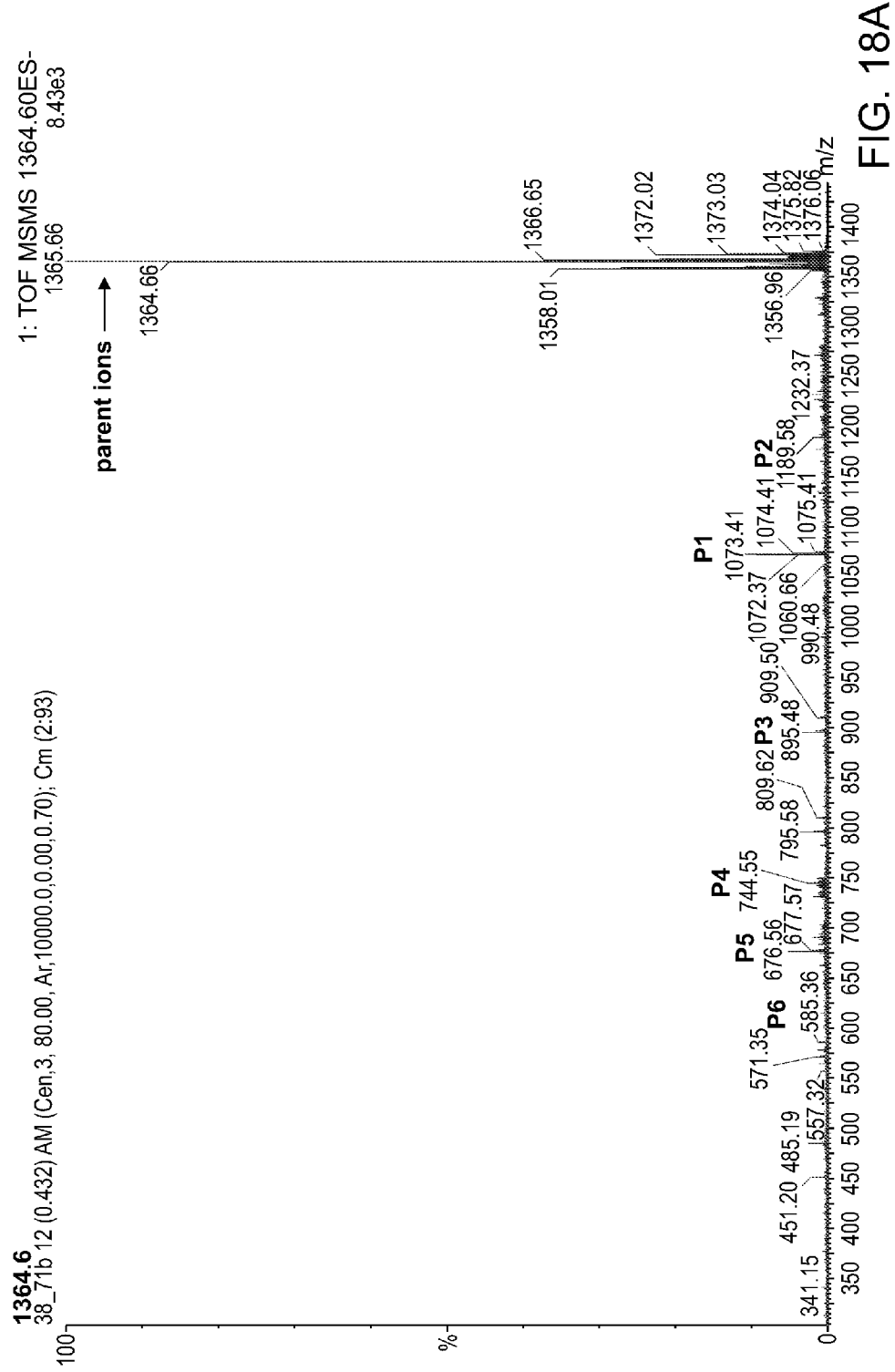
FIGS. 18A-18B. LC-MS spectrum of (A) Mixed (−)-ESI-MS2 spectrum of compounds 22 and 23 (FIG. 4) produced by the *S. lividans* ΔmoeN5 strain and (B) the proposed fragmentation pathway of the compounds.
Figure 18B:
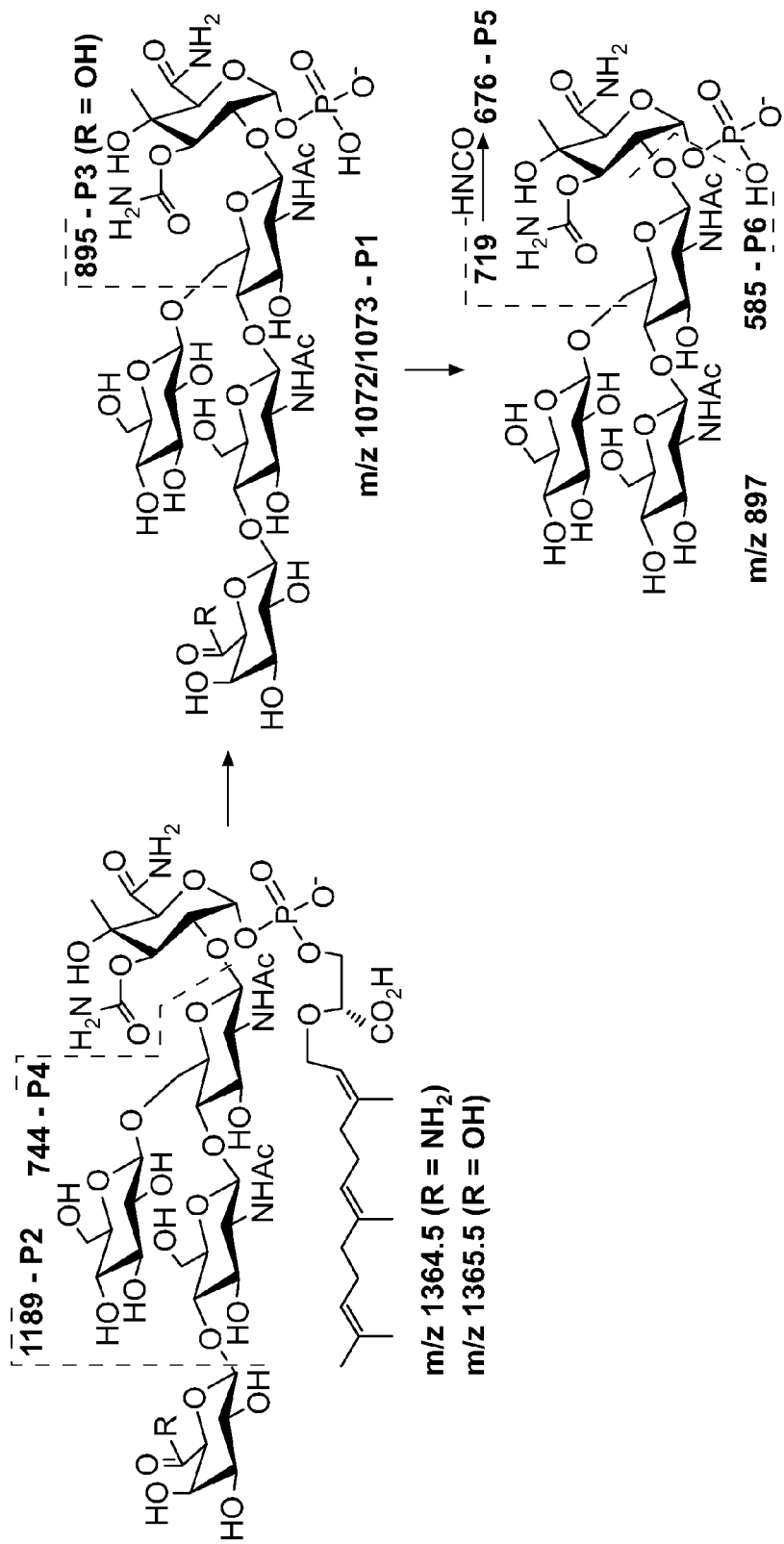
Figure 19:
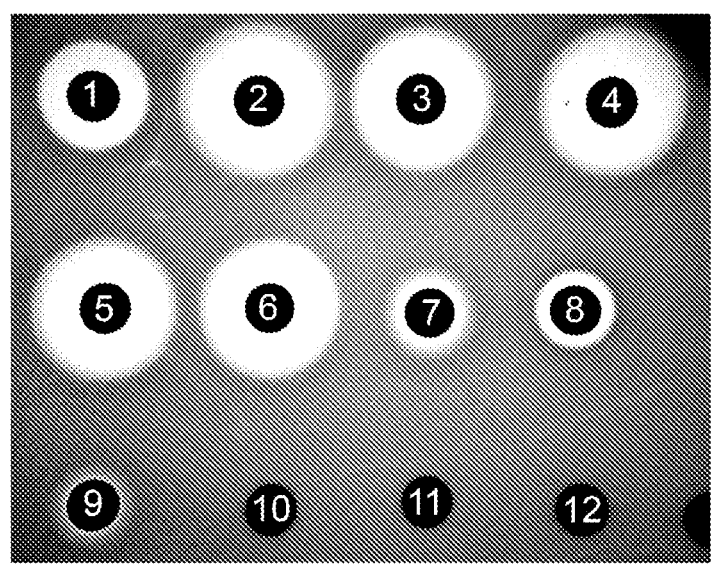
FIG. 19. Results of a disc diffusion assay of antibacterial activity of moe a intermediates (FIG. 4) against *B. cereus*. Spots 1 and 2—moe A (100 and 10 nM per disc, respectively); 3—compound 15 (100 nM); 4—compound 16 (100 nM), 5—compound 17 (100 nM), 6—compound 24 (100 nM), 7—mixture of compounds 22 and 23 (200 nM), 8—compound 11 (100 nM), 9—mixture of compounds 22 and 23 (50 nM), 10—mixture of compounds 2 and 3 (200 nM), 11—compound 1 (200 nM), 12—extract from 5 g *S. lividans* TK24 mycelial cake.

The preceding experiments established that MoeO5 and MoeN5 are prenyltransferases involved in the assembly of the moenocinol chain, but they but did not provide any information about whether the lipid-phosphoglycerate is attached to the saccharide scaffold early or late in the biosynthesis of moenomycin. To probe the order of assembly of moenomycin, we disrupted either singly or in combination each of the 5 putative glycosyltransferase (GT) genes proposed to govern the synthesis of the MmA pentasaccharide moiety (FIG. 4). We were unable to isolate any glycosylated MmA intermediates from an *S. ghanaensis* strain deficient in MoeGT1. However, the recombinant ΔmoeGT4 *S. lividans* TK24 strain was found to accumulate two new compounds having exact masses consistent with monosaccharide intermediates 2 and 3. 2 and 3 contain C15 chains and we were unable to detect any monosaccharides having C-25 chains. Strains ΔmoeGT5 and ΔmoeGT2 were found to produce trisaccharide 11 and tetrasaccharide 15, respectively, both of which contain the complete C25 chain; the double mutant strain ΔmoeGT5ΔmoeGT3 accumulated a disaccharide, 4, having a C15 chain (Table 2, FIG. 4, SD). Based on the preceding results, we propose that MmA biosynthesis begins with the formation of a farnesylphosphoglycerate starter unit, which serves as the acceptor for the GT that attaches the F ring precursor. Because recombinant strains containing gene disruptions in moeGT2, moeGT3, moeGT4, and moeGT5 produce glycosylated moenomycin intermediates, but a moeGT1-deficient strain does not,[5] we have identified the F-ring glycosyltransferase as MoeGT1. MoeGT4 is the E ring glycosyltransferase and produces disaccharide precursor 4. Since moenomycin analogs lacking the branching glucose (the D ring) are naturally produced in *S. ghanaensis*[3] and also accumulate when moeGT3 is disrupted in this strain, we propose that MmA biosynthesis can follow two branches from precursor 4, depicted in FIG. 4, which merge at the stage of the tetrasaccharide 14/15. In one branch, MoeGT3 attaches the D ring glucose; in the other, MoeGT5 attaches the C ring, which can be either chinovosamine or GlcNAc (see below). Trisaccharides 8 and 9/10 from both branches of the biosynthetic pathway serve as acceptor substrates for MoeN5-catalyzed lipid chain elongation. Following chain elongation, MoeGT2 attaches the B ring sugar to the C ring to produce the tetrasaccharide precursor 15.

Functions of the Sugar Biosynthesis and Tailoring Enzymes.

The prenyltransferase and GT gene disruption experiments established the order of assembly of the moenomycin scaffold, but did not reveal the function or timing of the genes that appear to be involved in sugar biosynthesis or tailoring. Appropriate recombinant strains were constructed to address the functions of these genes. MoeR5moeS5, which are missing from the moeno 38-1 cosmid, encode a 4,6-dehydratase/ketoreductase pair that we have proposed controls the conversion of UDP-GlcNAc into UDP-chinovosamine[5] (FIG. 4) based on the observation that the 38-1+ strain accumulates a MmA derivative containing GlcNAc in place of chinovosamine (19). Consistent with this, the moeR5+moeS5+ 38-1+ strain accumulates compound 18 (FIG. 4).[5] While this result was expected, we were surprised to find that the moeR5+38-1+ strain also produces 18 (Table 2). There is a close moeS5 homolog in the *S. coelicolor* genome,[5] and it is probable that a similar homolog exists in the *S. lividans* genome and complements the loss of moeS5 function in the moeR5+38-1+ strain. However, we cannot rule out the possibility that MoeR5 catalyzes both reactions. Co-expression of moeS5 and moeno38-1 yielded no new products (data not shown).

Gene moeK5 encodes a protein homologous to a family of putative SAM-radical, methyl-cobalamin-dependent methyl transferases involved in the biosynthesis of fosfomycin and a handful of other secondary metabolites. Therefore, we have proposed that moeK5 controls the methylation of the first sugar (unit F).[5] Indeed, strain ΔmoeK5 accumulated a compound having a mass 14 Da less than that of compound 19 from the parental 38-1+ strain (Table 2, SD), indicative of the loss of a methyl group. The fragmentation patterns for the compound were consistent with loss of the methyl group from the F ring, and the structure of the compound was assigned as 24, with the C4 hydroxyl stereochemistry axial. Methylation of unit F most likely takes place after its attachment to farnesyl-phosphoglycerate since we detected a mixture of nonmethylated and methylated monosaccharide-phosphoglycerate lipids (compounds 2 and 3, respectively; Table 2) in the ΔmoeGT4 strain. To our knowledge, MoeK5 is the first example of a sugar methyltransferase that does not use an anionic mechanism in catalyzing methyl transfer.

The moeF5 and moeH5 genes share significant homology at the nucleotide sequence level, suggesting that the pair arose via a gene duplication event. The proteins encoded by these genes resemble a large family of ATP-dependent amidotransferases that form amides from carboxylic acids. Because neither gene appears fully functional based on sequence analysis, we had previously speculated that a MoeF5MoeH5 heterodimer is involved in carboxamidation of unit F, with MoeF5 generating ammonia from glutamine in an ATP-dependent manner and MoeH5 acting as the transferase.[5] The gene disruptions of moeF5 and moeH5 have led us to revise this proposal. Strain ΔmoeF5 accumulated compound 1 (Table 2), which has a mass 1 Da higher than that of the monosaccharide MmA precursor 2 accumulated by the ΔmoeGT4 strain, consistent with the presence of a carboxyl moiety at C6 instead of the carboxamide group (as found in 2/3; see FIG. 4). These data show that moeF5 is involved in F ring carboxamidation, as speculated. We could not detect the formation of methylated monosaccharide precursors or of any larger MmA intermediates, implying that the absence of the carboxamide moiety abolishes unit F methylation and subsequent glycosylations. Therefore, MoeF5-catalyzed carboxamidation occurs prior to, and is required for, other modifications of 1 (FIG. 4)

Gene moeH5 proved not to be involved in F ring carboxamidation, but instead controls the carboxamidation of unit B (see compound 19), as determined from the accumulation of the MmA precursor 17 (Table 2, FIG. 4, SD) in the ΔmoeH5 strain. Expression of moeR5 in the ΔmoeH5 strain led to the accumulation of the previously described compound 16,[12] supporting the structure assignment for 17 (FIG. 4). Thus, despite having high sequence homology, moeF5 and moeH5 have been shown via gene disruptions to play quite different roles in MmA biosynthesis, and they cannot substitute for one another functionally in cross-complementation experiments.

The finding that MoeH5 amidates the B ring carboxyl group was unexpected because the unit A chromophore is attached to the B ring via an amide linkage that was speculated to form via the coupling of an amino cyclopentadione moiety to a carboxylic acid, such as 16/17.[5] The presence of a gene dedicated to the conversion of the acid MmA precursor 16/17 into the amide precursor 18/19 (FIG. 4) raised questions about this scheme. To determine whether the moeH5-controlled reaction is a branch of MmA metabolism or an essential biosynthetic step prior to attachment of the unit A chromophore moiety, we coexpressed the genes for unit A biosynthesis (pOOB64b) in the 38-1+ recombinant strain, which directs the production of 19, and in its ΔmoeH5 derivative, which produces 17. Expression of pOOB64b in ΔmoeH5 yielded no new products, while the pOOB64b+38-1+ strain produced the known compound pholipomycin 21 (Table 2, FIG. 4), which contains the Unit A chromophore.[3] The inability of pOOB64b+ΔmoeH5 strain to produce pholipomycin 21 implies that either 17 is not a precursor to 21 or that moeH5 is essential for MmA chromophore attachment for other reasons.[5,13,14] At the moment, we propose that carboxamide 19 serves as a necessary intermediate to MmA (FIG. 4).

Moe clusters 1 and 2 carry redundant copies of genes proposed to be involved in A ring biogenesis (moeA5B5 and moeA4B4C4, respectively; FIG. 2).[5] Coexpression of different truncated variants of moe clusters 1 and 2 has revealed that the putative aminolevulinate synthase gene moeA5 in cluster 1 is nonfunctional and that the three moe cluster 2 genes are necessary and sufficient to convert the precursor 19 into pholipomycin 21. It is likely that moe cluster 2 arose via duplication of a subset of genes in cluster 1, which then lost function. Based on these results, we have concluded that moe cluster 1 contains fourteen functional structural genes while moe cluster contains 3. Of these seventeen structural genes, fewer than half are required to produce bioactive intermediates (see below).

Antibacterial Activity of Moenomycins produced in Recombinant Strains.

The results described above show that it is possible to obtain a wide range of moenomycin analogs by manipulating the biosynthetic genes for moenomycin production. For example, disruption of selected glycosyltransferase genes produces mono-, di-, tri-, tetra- or pentasaccharide analogs. The tri-, tetra- and pentasaccharide analogs can be obtained with either a C15 or a C25 lipid chain, depending on whether moeN5 is present, while the mono- and disaccharide analogs can be obtained with a C15 chain. The chemical composition of these analogs can be further varied by manipulating genes involved in sugar biosynthesis or tailoring. For example, analogs lacking the F ring methyl can be produced by disrupting moeK5. Analogs containing GlcNAc rather than chinovosamine as the C ring can be produced by deleting moeR5moeS5. Analogs containing a carboxyl group in place of the carboxamide at C6 of the B ring can be produced by deleting moeH5. Opportunities to make a more diverse array of moenomycin analogs exist through in vitro chemoenzymatic synthesis (e.g., glycorandomization), but rational exploitation of these opportunities requires knowing which enzymes are required for the production of bioactive analogs. Extensive studies on moenomycin degradation products and synthetic derivatives have suggested that the minimal moenomycin pharmacophore comprises the CEF trisaccharide linked to the moenocinol-phosphoglycerate moiety. To gain further insight into the structural requirements for activity, we assessed the activity of selected moenomycin analogs isolated from recombinant S. lividans strains on a B. cereus reporter strain using a disk diffusion assay. The assay is not quantitative, but relative compound potencies can be assessed by comparing the antibiotic concentrations required to achieve clear zones of inhibition. The results show that the monosaccharide compounds are not active, as expected, whereas the moenocinol-linked penta- and tetrasaccharide compounds X and Y are approximately as active as MmA itself, consistent with previous reports that the A and B rings play at best a modest role in biological activity. The moenomycin analog lacking the C4 methyl group is also active, consistent with other reports that the methyl group is not required for biological activity. Compounds 22/23, which feature a $C_{15}$ isoprenoid chain, are less active than similar compounds containing the full C-25 chain, but nevertheless show a clear zone of inhibition. Since neryl-moenomycin was recently shown to be biologically inactive, the results with 22/23 establish that a minimum of three isoprene units in the prenyl chain is required for biological activity. Unexpectedly, trisaccharide 11, which contains the DEF sugars attached to moenocinol-phosphoglycerate, was also found to have biological activity,[3] implying that the C ring, previously thought to be essential for biological activity, is not. We note that other studies have shown that the smallest degradation product required for enzyme inhibition is the EF disaccharide. Moreover, a cocomplex of a moenomycin derivative with the PGT domain of A. aeolicus PBP1A has established that most of the contacts that anchor moenomycin in the active site are to the EF sugars, indicating that the most important part of the molecule is the disaccharide. It should be possible to produce both the CEF and DEF moenomycin trisaccharide scaffolds in vitro using a relatively small number of enzymes, including MoeO5, MoeGT1, MoeGT4, and either MoeGT3 or MoeGT5, enabling wide-ranging explorations of the potential of chemoenzymatic synthesis for the production of other analogs.

The integration of the results reported here with sequence data[5] has allowed us to outline the biosynthetic pathway leading to MmA, a prototypical member of the phosphoglycolipid family of antibiotics. The phosphoglycolipids are the only known inhibitors of the peptidoglycan glycosyltransferases and thus provide a starting point for the production of clinically useful antibiotics that target these enzymes. The biosynthesis of MmA begins with the coupling of farnesyl pyrophosphate and phosphoglycerate. Sugars are then transferred to the phosphoglycerate-lipid starter unit 1P one by one, beginning with the transfer of a uronic acid sugar, presumed to be galacturonic acid (unit F). In vitro analysis of the MoeGT1 reaction will be required to establish the identify of the natural donor with certainty. Before additional sugars are attached, the uronic acid must be tailored by MoeF5, which converts the C6 carboxylic acid to a carboxamide. Methylation at the C4 position, which is catalyzed by MoeK5, can occur prior to the second glycosylation but is not required for the assembly of a complete MmA pentasaccharide. After MoeGT4 transfers N-acetylglucosamine (unit E) to the growing scaffold, the biosynthetic pathway splits. MoeGT5 and MoeGT3 catalyze the addition of the C and D units respectively (FIG. 4). Carbamoylation of the first sugar appears to happen only after the attachment of three sugars since we could not detect any mass-peaks corresponding to carbamoylated disaccharide precursors (FIG. 4). Extension of the lipid chain by MoeN5 to form the "mature" $C_{25}$ isoprenoid chain also appears to occur only after the attachment of three sugars. The sequence of carbamoyltransferase and prenyltransferase reactions shown in FIG. 2 is speculative and the reverse order cannot be excluded. However, it is evident from the production of des-carbamoylated MmA pentasaccharides in a ΔmoeM5 strain and $C_{15}$ MmA pentasaccharides in a ΔmoeN5 strain that carbamoylation is not required for prenylation and prenylation is not required for carbamoylation. The attachment of the two remaining sugars and the chromophore completes MmA biosynthesis.

It has been suggested by others that the biosynthesis of the moenomycins must be complex because a complex mixture of compounds is typically isolated from the producing organisms.[14] In fact, as shown here, the biosynthetic pathway is relatively simple, with fewer than ten structural genes required to produce an active antibiotic. The complex mixture of related compounds arises because the moenomycin biosynthetic machinery is flexible. Except for unit F carboxamidation, all the sugar tailoring reactions can be bypassed without adverse effects on the assembly of the prenyl-phosphoglycerate-oligosaccharide scaffold. Prenyl transfer to form the C25 lipid from the C15 precursor can also be bypassed. Moreover, both MoeGT4 and MoeGT5 can accept either UDP-GlcNAc or UDP-chinovosamine as donor substrates, as evidenced by the production of pholipomycin and moenomycin $C_3$ as well as moenomycin A in both producing organisms and the heterologous expression host, *S. lividans*.[3] The promiscuity of some of the Moe biosynthetic enzymes, perhaps in combination with the unbalanced expression of certain moe genes, leads to an interesting phenomenon where a relatively simple pathway yields not one compound but a complex mixture of related ones that have antibiotic activity.[12] It should be possible to simplify the spectrum of moenomycin metabolites for commercial production of compounds by judicious deletion or overexpression of certain genes.

Other types of genetic manipulations of the MmA pathway may facilitate the discovery of compounds that have better properties than the natural moenomycins for clinical use. The investigations reported here have already yielded previously undescribed bioactive compounds that provide new opportunities for exploration. For example, the farnesylated MmA analog 23 or other bioactive C15 derivatives could have better pharmacokinetic properties than the parent compounds, which may compensate for the decrease in potency evident from the disk diffusion assay.[4,22] Furthermore, trisaccharide 5 provides a previously undescribed alternative carbohydrate scaffold for the combinatorial biosynthesis of analogs.[3]

Antibiotics.

Pure MmA was provided by M. Adachi (Dept. of Chemistry and Chemical Biology, Harvard University). For recombinant strains selection following commercially available antibiotics were used (mcg/mL): ampicillin (100), chloramphenicol (35), kanamycin (50), apramycin (50), hygromycin (100), spectinomycin (200), streptomycin (100), thiostrepton (50), nalidixic acid (50).

Strains and Vector DNAs.

*Streptomyces ghanaensis* ATCC14672 and *Bacillus cereus* ATCC19637 were obtained from ATCC. *S. lividans* TK24 was kindly provided by M. Kobayashi (University of Tsukuba, Japan). The methylation-deficient conjugative strain *E. coli* ET12567 (pUB307)[23] was obtained from Prof. C. P. Smith (Manchester University, UK). *E. coli* BW25113 (pIJ790) was from John Innes Center (Norwich, UK). *S. lividans* J1725 (bldA mutant) and pIJ584 plasmid harboring intact bldA gene were donated by B. Leskiw (University of Alberta, Canada). Strain *S. ghanaensis* MO12 with disrupted moeGT3 gene and *S. lividans* strains expressing various subsets of moe genes were constructed in this work. Vectors pKC1139, pSET152, pMKI9, pOOB40 were obtained as described previously.[5] Integrative vector pSOK804[11] was from S. Zotchev (Norwegian University of Science and Technology, Trondheim, Norway). Expression vector pAF1 (ori$^{pIJ101}$ bla tsr, PermE*, 6His tag) was provided by A. Bechthold (Freiburg University, Germany). Plasmids pKD4 and pCP20[9] were obtained from J. Beckwith (Harvard Medical School, USA). Spectinomycin resistance cassette pHP45[24] was from J.-L. Pernodet (Université Paris-Sud, France).

DNA Manipulations and Analysis.

Standard molecular biology procedures were used throughout the work.[25,26] We followed the same scheme for all λ-RED-assisted deletions of moe genes within cosmid moeno38-1 (except for moeGT3). That is, the entire open reading frame(s) was replaced with a kanamycin resistance cassette (pKD4) and then the mutated cosmid was introduced into strain DH5α (pCP20) to evict kanR as described.[9] The presence of expected deletions within the cosmids was checked by PCR. λ-RED recombination was used to replace moeGT3 with the disrupted allele moeGT3::aadA in the ΔmoeGT5 derivative of moeno38-1 (see SD). Generation of plasmids for moe gene expression/complementation studies is described in SD.

Generation of Recombinant *S. ghanaensis* and *S. lividans* Strains.

Gene moeGT3 was insertionally inactivated in the *S. ghanaensis* genome according to an established procedure.[5] All constructs carrying moe genes were transferred into *S. lividans* via intergeneric conjugation. Plasmids pIJ584 and pMoeO5 extra were introduced via protoplast transformation. Integration of moeno38-1 and its derivatives into the *S. lividans* genome was checked as described.[5] Verifications of the recombinant strains are described in SD.

Moenomycin Production Analysis.

Small-scale fermentation and purification of moenomycins was performed as described.[5] To obtain pure moenomycin intermediates (>90% as judged by TLC) from recombinant S. lividans strains, the following procedure was used. TSB medium (30 mL in a 250 mL flask containing 70 glass beads (Ø 5 mm)) was inoculated with 100 µL (approx. $10^4$-$10^5$ cfu) of stock culture (kept in 10.3% sucrose at −20° C.). The flask was incubated on an orbital shaker (240 rpm) for 2 days at 37° C. and then used as a preculture to start the fermentation. R5 medium[25] in a slightly modified form (sucrose: 6% instead of 10.3%; 1 mg/L $CoCl_2$ was added after autoclaving) was used as a fermentation medium. 8.4 L flasks (500 mL of medium per each one) containing beads were grown for 6 days at 37° C. The mycelium was harvested by centrifugation and extracted exhaustively with methanol-water (9:1) at 37° C. (when necessary, the pH of extraction mixture was adjusted to 7-7.5 with Tris-HCl). The extract was concentrated, reconstituted in water and extracted with dichloromethane. The aqueous phase was loaded on a XAD-16 column (30×400 mm), washed with water (300 mL) and eluted with methanol (500 mL). Methanol fractions containing the desired compound were combined, concentrated and purified on a Sep-Pak $C_{18}$ SPE cartridge (Waters) as described.[27] Further silica gel flash chromatography or preparative TLC of the obtained extract according to Adachi et al. (REF) yielded pure compound (0.1-0.4 mg/4 L, depending on strain). Antibiotic disc diffusion assays, LC-MS, MS/MS and determination of accurate mass spectra of moenomycins were carried out as described in previously.[5] $^1$H NMR spectra of compound 11 were recorded on a Varian Inova 500 (500 MHz) instrument in $D_2O$ (4.80 ppm). Chemical shifts are reported in parts per million (ppm) units.

TABLE 2

Moeno38-1 pathway products found in S. lividans TK24 strains carrying subsets of moe genes

| Mutation(s) in moeno38-1/ coexpression type | Mt. | Min[1] | Mass ((M-H)$^-$) Calcd | Mass ((M-H)$^-$) Obsvd |
|---|---|---|---|---|
| ΔmoeN5 | 23 | 4.2 | 1364.5026 | 1364.5023 |
|  | 22 | 4.1 | 1365.4867 | 1365.4884 |
| ΔmoeGT4 | 2 | 4.7 | 564.2215 | 564.2210 |
|  | 3 | 4.8 | 578.2372 | 578.2374 |
| ΔmoeF5 | 1 | 3.9 | 565.2056 | 565.2054 |
| ΔmoeGT5GT3 | 4 | 4.8 | 781.3166 | 781.3143 |
| ΔmoeGT5 | 11 | 10.4 | 1122.5004 | 1122.5004 |
| ΔmoeGT2 | 15 | 10 | 1325.5797 | 1325.5789 |
| ΔmoeH5 | 17 | 9.3 | 1501.6118 | 1501.6115 |
| ΔmoeK5 | 24[2] | 9.6 | 1486.6122 | 1486.6116 |
| ΔmoeB5A5 | 19 | 9.9 | 1500.6278 | 1500.6273 |
| 5-1$^+$ ΔmoeB5A5 | 21 | 9.3 | 1596.6490 | 1596.6492 |
| 5-1$^+$ ΔmoeH5 | 17 | 9.7 | 1501.6118 | 1501.6122 |
| moeR5$^+$ ΔmoeB5A5 | 18 | 10.0 | 1484.6329 | 1484.6326 |
| moeR5$^+$ ΔmoeH5 | 16 | 9.4 | 1485.6169 | 1485.6195 |

[1]250 × 4.6 mm Agilent $C_{18}$ column, under LC conditions used for accurate mass determination

REFERENCES

1. Goldman, R. C.; Gange, D, Inhibition of transglycosylation involved in bacterial peptidoglycan synthesis. Curr Med Chem 2000, 7, (8), 801-20.
2. Ostash, B.; Walker, S., Bacterial transglycosylase inhibitors. Current Opinion In Chemical Biology 2005, 9, (5), 459-466.
3. Welzel, P., Syntheses around the transglycosylation step in peptidoglycan biosynthesis. Chemical Reviews 2005, 105, (12), 4610-4660.
4. Adachi, M.; Zhang, Y.; Leimkuhler, C.; Sun, B.; LaTour, J. V.; Kahne, D. E., Degradation and reconstruction of moenomycin A and derivatives: dissecting the function of the isoprenoid chain. J Am Chem Soc 2006, 128, (43), 14012-3.
5. Ostash, B.; Saghatelian, A.; Walker, S., A streamlined metabolic pathway for the biosynthesis of moenomycin A. Chemistry & Biology 2007, 14, (3), 257-267.
6. Taylor, J. G.; Li, X.; Oberthur, M.; Zhu, W.; Kahne, D. E., The total synthesis of moenomycin A. J Am Chem Soc 2006, 128, (47), 15084-5.
7. Lovering, A. L.; de Castro, L. H.; Lim, D.; Strynadka, N. C., Structural insight into the transglycosylation step of bacterial cell-wall biosynthesis. Science 2007, 315, (5817), 1402-5.
8. Yuan, Y.; Barrett, D.; Zhang, Y.; Kahne, D.; Sliz, P.; Walker, S., Crystal structure of a peptidoglycan glycosyltransferase suggests a model for processive glycan chain synthesis. Proc Natl Acad Sci USA 2007, 104, (13), 5348-53.
9. Datsenko, K. A.; Wanner, B. L., One-step inactivation of chromosomal genes in Escherichia coli K-12 using PCR products. Proceedings Of The National Academy Of Sciences Of The United States Of America 2000, 97, (12), 6640-6645.
10. Gust, B.; Challis, G. L.; Fowler, K.; Kieser, T.; Chater, K. F., PCR-targeted Streptomyces gene replacement identifies a protein domain needed for biosynthesis of the sesquiterpene soil odor geosmin. Proceedings Of The National Academy Of Sciences Of The United States Of America 2003, 100, (4), 1541-1546.
11. Sekurova, O. N.; Brautaset, T.; Sletta, H.; Borgos, S. E. F.; Jakobsen, O. M.; Ellingsen, T. E.; Strom, A. R.; Valla, S.; Zotchev, S. B., In vivo analysis of the regulatory genes in the nystatin biosynthetic gene cluster of Streptomyces noursei ATCC 11455 reveals their differential control over antibiotic biosynthesis. Journal Of Bacteriology 2004, 186, (5), 1345-1354.
12. Zehl, M.; Pittenauer, E.; Rizzi, A.; Allmaier, G., Characterization of moenomycin antibiotic complex by multistage MALDI-IT/RTOF-MS and ESI-IT-MS. J Am Soc Mass Spectrom 2006, 17, (8), 1081-90.
13. Petricek, M.; Petrickova, K.; Havlicek, L.; Felsberg, J., Occurrence of two 5-aminolevulinate biosynthetic pathways in Streptomyces nodosus subsp asukaensis is linked with the production of asukamycin. Journal Of Bacteriology 2006, 188, (14), 5113-5123.
14. Schuricht, U.; Endler, K.; Hennig, L.; Findeisen, M.; Welzel, P., Studies on the biosynthesis of the antibiotic moenomycin A. Journal Fur Praktische Chemie-Practical Applications And Applied Chemistry 2000, 342, (8), 761-772.
15. Chater, K. F., Streptomyces inside-out: a new perspective on the bacteria that provide us with antibiotics. Philosophical Transactions Of The Royal Society B-Biological Sciences 2006, 361, (1469), 761-768.
16. Hodgson, D. A., Primary metabolism and its control in streptomycetes: A most unusual group of bacteria. In Advances In Microbial Physiology, Vol 42, 2000; Vol. 42, pp 47-238.
17. Trepanier, N. K.; Jensen, S. E.; Alexander, D. C.; Leskiw, B. K., The positive activator of cephamycin C and clavulanic acid production in Streptomyces clavuligerus is mistranslated in a bldA mutant. Microbiology-Sgm 2002, 148, 643-656.
18. Leskiw, B. K.; Lawlor, E. J.; Fernandezabalos, J. M.; Chater, K. F., Tta Codons In Some Genes Prevent Their Expression In A Class Of Developmental, Antibiotic- 19. El-Abadla, N.; Lampilas, M.; Hennig, L.; Findeisen, M.; Welzel, P.; Muller, D.; Markus, A.; van Heijenoort, J., Moenomycin A: The role of the methyl group in the moenuronamide unit and a general discussion of structure-activity relationships. *Tetrahedron* 1999, 55, (3), 699-722.
20. Fehlhaber, H. W.; Girg, M.; Seibert, G.; Hobert, K.; Welzel, P.; Vanheijenoort, Y.; Vanheijenoort, J., Moenomycin-A—A Structural Revision And New Structure-Activity Relations. *Tetrahedron* 1990, 46, (5), 1557-1568.
21. Ritzeler, O.; Hennig, L.; Findeisen, M.; Welzel, P.; Muller, D., Search for new moenomycin structure-activity relationships. Synthesis of a trisaccharide precursor of a moenomycin analogue. *Tetrahedron* 1997, 53, (15), 5357-5357.
22. Goldman, R. C.; Baizman, E. R.; Branstrom, A. A.; Longley, C. B., Differential antibacterial activity of moenomycin analogues on gram-positive bacteria. *Bioorg Med Chem Lett* 2000, 10, (20), 2251-4.
23. Flett, F.; Mersinias, V.; Smith, C. P., High efficiency intergeneric conjugal transfer of plasmid DNA from Escherichia coli to methyl DNA-restricting streptomycetes. *Fems Microbiology Letters* 1997, 155, (2), 223-229.
24. BlondeletRouault, M. H.; Weiser, J.; Lebrihi, A.; Branny, P.; Pernodet, J. L., Antibiotic resistance gene cassettes derived from the Omega interposon for use in *E-coli* and *Streptomyces*. *Gene* 1997, 190, (2), 315-317.
25. Kieser, T.; Bibb, M. J.; Buttner, M. J.; Chater, K. F.; Hopwood, D. A., *Practical Streptomyces Genetics*. The John Innes Foundation: Norwich, UK, 2000.
26. Sambrook, J.; Russel, D. W., *Molecular Cloning: A Laboratory Manual*. 3 ed.; Cold Spring Harbor Lab. Press: Cold Springs Harbor, N.Y., 2001.
27. Eichhorn, P.; Aga, D. S., Characterization of moenomycin antibiotics from medicated chicken feed by ion-trap mass spectrometry with electrospray ionization. *Rapid Communications In Mass Spectrometry* 2005, 19, (15), 2179-2186.

Example 4

Biosynthesis of Moenomycin Analogys

Cloning.

MoeO5 was PCR amplified from Cosmid 38-1 with the oligonucleotides MoeO5HinDIIIup (AAAAAGCT-TCGGGGCGTGCCTTCTTC (SEQ ID NO: 3) and MoeO5XbaIrp (AAATCTAGACCGCCCGCTC-CCCG-GAC (SEQ ID NO: 4)) using KOD Hot Start DNA polymerase. The PCR product was digested with HindIII and XbaI and cloned into vector pAF. The ligated gene product encoded a protein product with a C-terminal $His_6$-tag. MoeGT1 was PCR amplified from Cosmid 38-201 with the oligonucleotides MoeGT1NdeI (AAACATATGGCTGC-CCCCGACCGAC (SEQ ID NO: 5)) and MoeGT1NotI (ATAAAGCGGCCGCTCGGGCGTC (SEQ ID NO: 6)) by using KOD Hot Start DNA polymerase. The PCR product was digested with NdeI and NotI and cloned into vector pET24b. The ligated gene product encoded a protein product with a C-terminal $His_6$-tag. MoeF5 was cloned in an identical fashion using the oligonucleotides MoeF5NdeI (AAAAA-CATATGTGCGGCTT-CGTCGGATTCAGTG (SEQ ID NO: 7)) and MoeF5NotI (AAAAAGCGGCCGCG-GAGAGGGC (SEQ ID NO: 8)). MoeGT5 was cloned into vector pET24b in a similar fashion using NdeI and XhoI digestion sites and oligonucleotides MoeGT5NdeI (AAAA-CATATGGTGCTGCGCCGTCTGGC (SEQ ID NO: 9)) and MoeGT5XhoI (AAAAACTCG-AGGCGCCCGGCG (SEQ ID NO: 10)). MoeGT3 was cloned into vector pET24b using NdeI and NotI digestion sites and oligonucleotides MoeGT3NdeI (AAAACATATGGTGGCCGTCCTCCGCG (SEQ ID NO: 11)) and MoeGT3NotI (AAA AAGCGGC-CGCCAAACCAGGAAAC (SEQ ID NO: 12)).The final gene constructs of MoeF5, MoeGT5, and MoeGT3 encoded proteins with a C-terminal $His_6$-tag. MoeE5 was PCR amplified from Cosmid 38-7 with the oligonucleotides MoeE5BamHI (AAAAAGGATCCGGTGTCGAGCGATA-CACACGG (SEQ ID NO: 13)) and MoeE5XhoI (AAAAACTCGAGCTAC-AGCCGCGGCACGGAC (SEQ ID NO: 14)) by using KOD Hot Start DNA polymerase. The PCR product was digested with BamHI and XhoI and cloned into vector pET48b. The final gene product encoded a protein product with an N-terminal thioredoxin protein tag and an N-terminal $His_6$-tag. MoeGT4 was cloned into vector pET48b in a similar fashion using KpnI and XhoI digestion sites and oligonucleotides MoeGT4 KpnI (AAAAAGGTAC-CAGGTGACTTCTGAGCCCGC (SEQ ID NO: 15)) and MoeGT4XhoI (AAAAACTC GAGTCAGCTCTCCT-GACGCGTG (SEQ ID NO: 16)). MoeM5 was PCR amplified from Cosmid 38-1 with the oligonucleotides MoeM5NdeI (GGCGCGCCCATATGAAGGTACT-GTCGCTCCACTCCGCCGG (SEQ ID NO: 17)) and MoeM5EcoR1 (AAAATAAAGAATTCTCAGTGGTG-GTGGTGGTGGTGGTGGTGCCGCGC GGCGGCGCCC (SEQ ID NO: 18)). The PCR product was digested with NdeI and EcoR1 and cloned into vector pET24b and subcloned into a *Streptomyces-E. coli* shuttle vector pJVD53 using XbaI and EcoR1 restriction sites. The ligated gene product encoded a protein product with a C-terminal $His_8$-tag.

Expression.

Purified pAF1-MoeO5 was transferred to *Streptomyces lividans* TK24 via protoplast transformation. A single colony was inoculated into 30 ml TSB $Thio^{50}$ media and grown at 30° C. in a baffled flask. After 2 days, an 100 ul aliquot was used to start a 50 ml culture in R5 media. The cells were grown at 30° C. for 4 days before harvesting by centrifugation.

Purified pET24b-MoeGT1, pET24b-MoeF5, pET24b-MoeGT5, pET24b-MoeGT3, pET48b-MoeE5, and pET48b-MoeGT4 were transformed into Rosetta2(DE3)pLysS competent *Escherichia coli* cells. Starting from a 10 mL overnight culture, MoeGT1, MoeF5, MoeGT3, MoeE5, and MoeGT4 were grown at 37° C. in Luria-Bertani (LB) medium to an $OD_{600}$ of 0.6. The temperature was reduced to 16° C. and the cells were induced by the addition of 1 mM IPTG. After 10 h, the cells were harvested by centrifugation and frozen at −80° C. Purified pET24b-MoeGT5 was transformed into Arctic Express(DE3)RP competent *E. coli* cells and grown at 30° C. in LB medium to an $OD_{600}$ of 0.6. At that point, the cells were induced with 1 mM IPTG and grown for an additional 24 h at 10° C. before the culture was harvested by centrifugation.

Purified pJVD53-MoeM5 was transformed into *E. coli* donor strain WM6026. Intergenic conjugation between the *E. coli* donor strain and the *Streptomyces lividans* TK24 recipient was carried out, and *S. lividans* spores were obtained by spreading MYG-grown cultures to ISP2 medium. Mycelia was grown on ISP2 $Thio^{50}$ plates and were used to inoculate 15 ml MYG $Thio^{25}$ medium as a starter culture. After 72 hours of growth, 100 ul of the starter culture was used to inoculate 1 L YEME (0.5% glycine) $Thio^{25}$ in a 4 L baffled flask. The culture was grown for 72 hours at 30° C. and the cells were induced with 8.8 mM (final concentration) of ε-caprolactam. After 24 hours of growth, the cells were harvested by centrifugation and frozen at −80 C.

Purification. Cell pellets containing Trx-MoeE5, MoeGT1, moeGT3 and MoeF5 were lysed by freeze-thaw in Buffer A (20 mM Tris-HCl/pH 8, 200 mM NaCl, 5 mM imidazole, 5% glycerol, 0.5% CHAPS) supplemented with rLysozyme, Benzonase, and protease inhibitor cocktail. Cellular debris and membrane components were pelleted by centrifugation at 38,724×g for 45 minutes. The clarified cell lysate was loaded onto a column containing Ni-NTA resin equilibrated with Buffer A. The columns were washed with 8 column volumes of Buffer W (20 mM Tris-HCl/pH 8, 200 mM NaCl, 5 mM imidazole) followed by 6 column volumes of Buffer W containing 30 mM imidazole. The proteins were eluted with a step gradient of imidazole in Buffer W (75-500 mM imidazole). Purified MoeE5 and MoeGT1 were dialyzed twice against 4 L of 20 mM Tris-HCl/pH 7. Purified MoeF5 was dialyzed twice against 3 L of 20 mM Tris-HCl/pH 7, 4 mM dithiothreitol (DTT), and 10% glycerol.

Cells from expression cultures of Trx-MoeGT4 were lysed by freeze-thaw in Buffer B (20 mM Tris-HCl/pH 8, 10% glycerol, 0.5% CHAPS) supplemented with rLysozyme, Benzonase, and protease inhibitor cocktail. After centrifugation at 16,000×g for 40 min to remove cellular debris and membrane components, the supernatant was rocked with Ni-NTA resin for 6 hours. The resin/lysate was loaded onto a column and washed with 18 column volumes of Buffer V (20 mM Tris-HCl/pH 8, 5 mM imidazole) followed by 12 column volumes of Buffer V containing 30 mM imidazole. The purified protein was eluted with 500 mM imidazole in Buffer V, and dialyzed against 3 L of 20 mM Tris-HCl/pH 7, 5 mM $MnCl_2$, and 10% glycerol.

Cell pellets containing MoeGT5 were lysed by freeze-thaw in Buffer C (20 mM Tris-HCl/pH 8, 200 mM NaCl, 5 mM imidazole, 1% n-octyl-β-D-glucopyranoside) supplemented with rLysozyme, Benzonase, and protease inhibitor cocktail. After clarification of the cell lysate at 38,724×g for 30 min, the supernatant was loaded onto a column containing Ni-NTA resin. The protein was washed and eluted in a manner identical to the MoeGT1/MoeE5/MoeF5 purification.

Cell pellets containing MoeM5 and MoeO5 were lysed by passage through a cell disrupter (10,000 psi) and the lysate was cleared via centrifugation for 30 minutes at 13,000×g. Cleared supernatant was loaded onto a column containing Ni-NTA resin. The protein was washed and eluted in a manner identical to the MoeGT1/MoeE5/MoeF5 purification.

$C_{15}$-farnesyl-EF-disaccharide 5 biosynthesis. The $C_{15}$-farnesyl-phosphoglycerate 1 was prepared by adding 3-phosphoglycerate (500 uM final concentration) and farnesyl pyrophosphate (40 uM final concentration) to Buffer O (20 mM Tris-HCl/pH 7.5, 5 mM $MgCl_2$). The reaction was initiated by addition of purified MoeO5, and allowed to incubate at 30° C. for 2 h. The reaction was stopped by immersing in an 85° C. water bath for 5 min followed by centrifugation at 14,000×g for 10 min. Analytical HPLC was carried out on a Gemini C18 column (50×4.6 mm) using solvent A (95 water: 5 methanol+ 0.1% ammonium hydroxide) and solvent B (60 isopropanol: 35 methanol: 5 water+0.1% ammonium hydroxide). A gradient of 0-75% solvent B over 17 minutes was used at a flow rate of 1 ml/min. Product peaks were detected using absorbance at 210 nm, collected, and characterized with HRMS: 389.1729 $[M-H]^-$ calculated, 389.1737 observed.

To synthesize $C_{15}$-farnesyl-F-monosaccharide 2, purified MoeGT1 was incubated with 0.1 mg $C_{15}$-farnesyl-phosphoglycerate 1 and 2 mM of UDP-galacturonic acid (UDP-GalUA) at 30° C. with mild shaking for 10 h. The reaction was stopped by passage through a Microcon filtration unit [10K molecular weight cutoff]. Analytical HPLC was carried out as described above. Product peaks were detected using absorbance at 210 nm, collected, and characterized with high-resolution mass spectrometry: 565.2056 $[M-H]^-$ calculated, 565.2066 observed.

The $C_{15}$-farnesyl-F-amido-monosaccharide 3 was synthesized by adding Buffer F (20 mM Tris-HCl, 10 mM $MgCl_2$, 10 mM ATP) to a tube containing dried $C_{15}$-farnesyl-monosaccharide 2 and glutamine/pH 9 (10 mM final concentration) or ammonium acetate/pH 7 (100 mM final concentration). The reaction was initiated by addition of purified MoeF5, and allowed to incubate at 30° C. with mild shaking for 10 h. The reaction was stopped by immersing in an 85° C. water bath for 5 min followed by centrifugation at 14,000×g for 10 min. Analytical HPLC was carried out as described above. Product peaks were detected using absorbance at 210 nm, collected, and characterized with ESI-MS: 564.2215 $[M-H]^-$ calculated, 564.2 observed.

To synthesize descarbmoyl-$C_{15}$-farnesyl-EF-disaccharide 4, purified Trx-MoeGT4 was incubated with dried $C_{15}$-farnesyl-F-amido-monosaccharide 3 and 1 mM UDP-GlcNAc in Buffer 4 (20 mM Tris-HCl/pH 7, 10% glycerol, 5 mM $MnCl_2$) at 30° C. with mild shaking for 10 h. The reaction was quenched and analyzed as described for the MoeGT1 reaction. The formation of product was detected with ESI-MS: 767.3009 $[M-H]^-$ calculated, 767.3 observed.

The $C_{15}$-farnesyl-EF-disaccharide 5 was synthesized by adding 1 mM carbamoyl phosphate and 20 mM Tris-HCl/pH 7 to a tube containing dried descarbamoyl-$C_{15}$-farnesyl-EF-disaccharide 4. The reaction was initiated by addition of purified MoeM5, and allowed to incubate at 30° C. with mild shaking for 2 h. The reaction was quenched and analyzed as described for the MoeGT1 reaction. The formation of product was detected with ESI-MS: 810.3140 $[M-H]^-$ calculated, 810.3 observed.

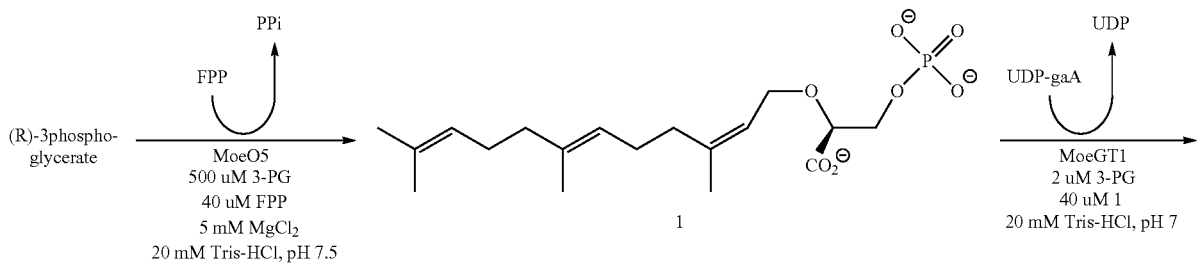

-continued
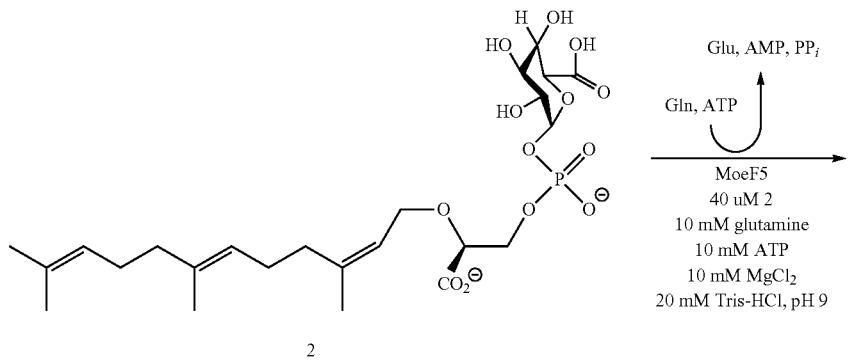
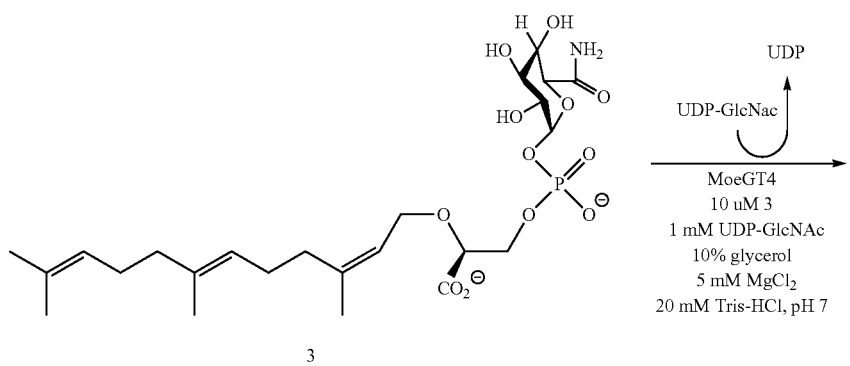
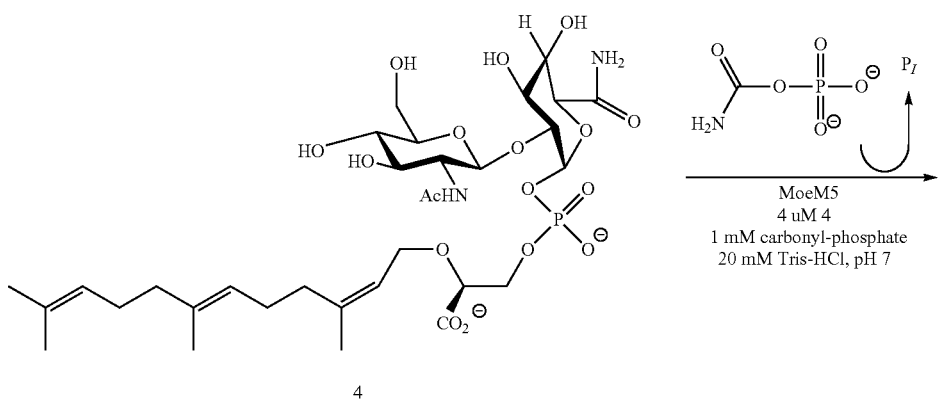

-continued

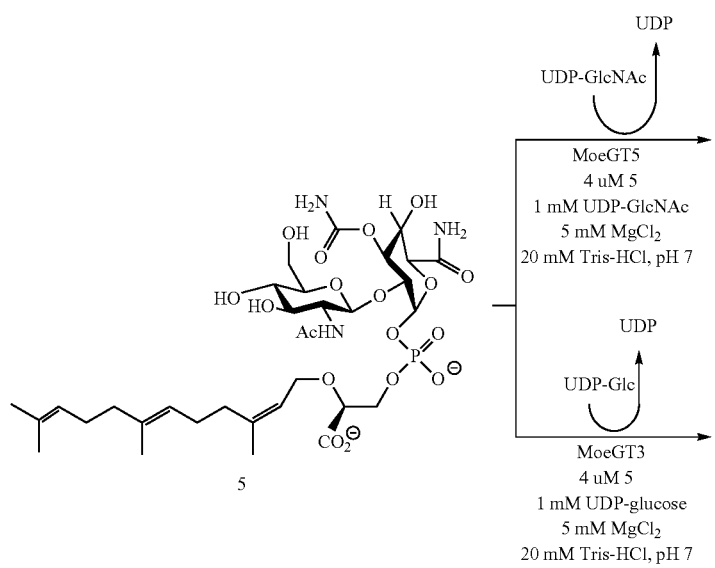
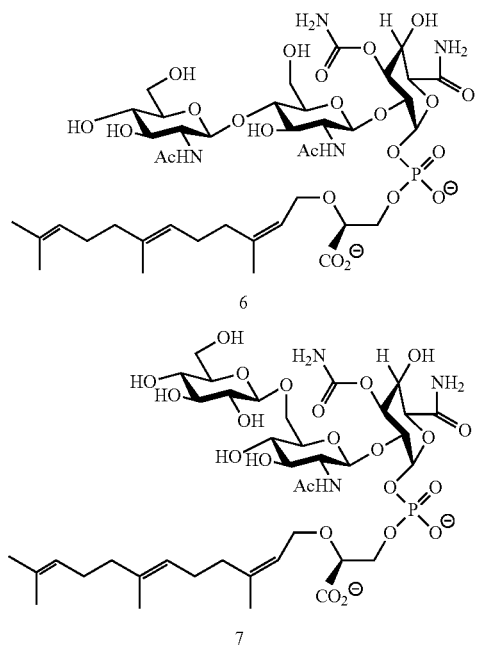

Reconstitution of $C_{15}$-farnesyl-EF-disaccharide 5, $C_{15}$-farnesyl-CEF-trisaccharide 6, and $C_{15}$-farnesyl-DEF-trisaccharide 7.

$C_{15}$-farnesyl-CEF-trisaccharide 6 Biosynthesis.

To synthesize $C_{15}$-farnesyl-CEF-trisaccharide 6, purified MoeGT5 was incubated with dried $C_{15}$-farnesyl-E, F-disaccharide 5 and 1 mM UDP-GlcNAc in Buffer 5 (20 mM Tris-HCl/pH 7, 5 mM $MgCl_2$) at 30° C. with mild shaking for 2 h. The reaction was quenched and analyzed as described for the MoeO5 reaction. The formation of product was detected with ESI-MS: 1011.4141 [M−H]⁻ calculated, 1011.4 observed.

$C_{15}$-farnesyl-DEF-trisaccharide 7 Biosynthesis.

To synthesize $C_{15}$-farnesyl-DEF-trisaccharide 7, purified MoeGT3 was incubated with dried $C_{15}$-farnesyl-E, F-disaccharide 5 and 1 mM UDP-glucose in Buffer 3 (20 mM Tris-HCl/pH 7, 3 mM $MgCl_2$) at 30° C. with mild shaking for 2 h. The reaction was quenched and analyzed as described for the MoeO5 reaction. The formation of product was detected with ESI-MS: 972.3668 [M−H]⁻ calculated, 972.4 observed.

Chemoenzymatic Synthesis of $C_{15}$-farnesyl-E(3'-amino) F-disaccharide 9 and $C_{15}$-farnesyl-C/DE(3'-amino)F-trisaccharides 10 and 11 MmA Analogs.

All reaction conditions are identical to those described for the natural disaccharide and trisaccharide MmA derivatives, except that 5 mM UDP-3-amino-3-deoxy-GlcNAc 8 is used as the sugar donor in the MoeGT4 reaction instead of 1 mM UDP-GlcNAc. All products were detected with ESI-MS. $C_{15}$-farnesyl-E(3'-amino)F-disaccharide 9: ESI-MS: 809.3140 [M−H]⁻ calculated, 809.3 observed. $C_{15}$-farnesyl-CE(3'-amino)F-trisaccharide 10: 1010.4301 [M−H]⁻ calculated, 1010.4 observed. $C_{15}$-farnesyl-DE(3'-amino)F-trisaccharide 11: 971.3828 [M−H]⁻ calculated, 971.4 observed.

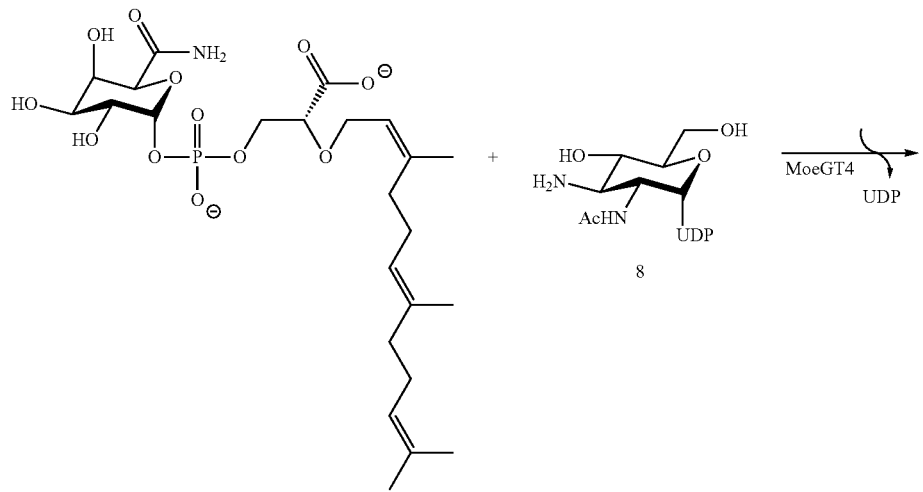

-continued
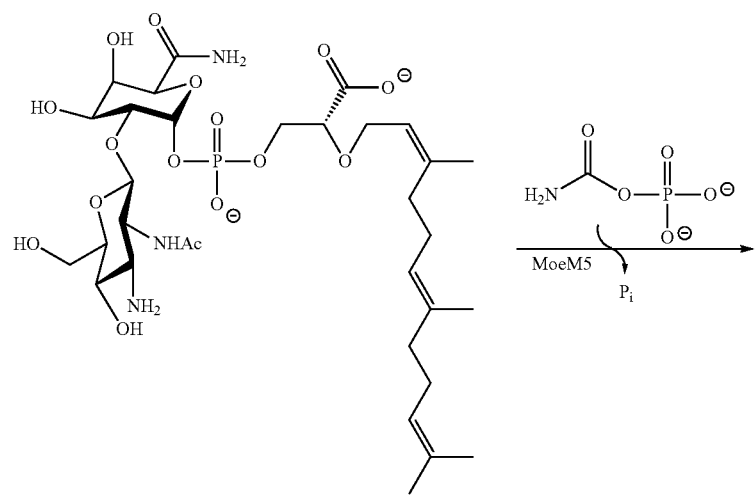
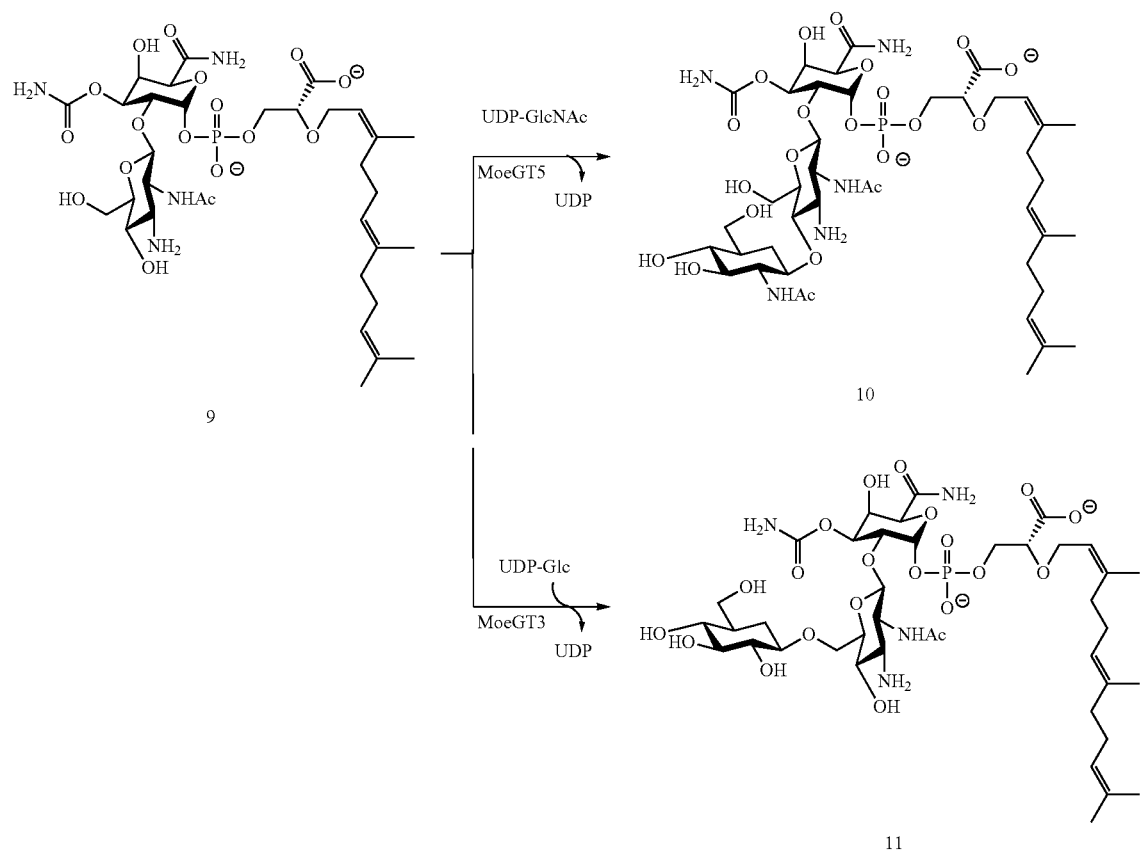

Reconstitution of $C_{15}$-farnesyl-E(3'-amino)F-disaccharide 9 and $C_{15}$-farnesyl-C/DE(3'-amino)F-trisaccharide 10/11 MmA analogs.

Chemoenzymatic Synthesis of $C_{15}$-farnesyl-C(3'-amino) EF-trisaccharide 12 MmA.

All reaction conditions were identical to those described for the CEF-trisaccharide synthesis, except that 5 mM UDP-3-amino-3-deoxy-GlcNAc 8 is used as the sugar donor in the MoeGT5 reaction instead of 1 mM UDP-GlcNAc. The formation of product was detected with ESI-MS: 1010.4301 [M−H]⁻ calculated, 1010.4 observed.

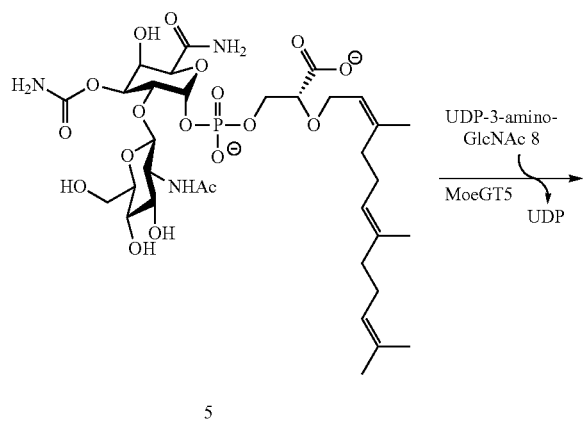

Reconstitution of $C_{15}$-farnesyl-C(3'-amino)EF-trisaccharide 12 MmA analog.

Chemoenzymatic Synthesis of $C_{15}$-farnesyl-C(3'-amino) E(3'-amino)F-trisaccharide 13 MmA.

All reaction conditions were identical to those described for the CEF-trisaccharide synthesis, except that 5 mM UDP-3-amino-3-deoxy-GlcNAc 8 is used as the sugar donor in the MoeGT4 and MoeGT5 reactions instead of 1 mM UDP-GlcNAc. The formation of product was detected with ESI-MS: 1009.4461 [M−H]⁻ calculated, 1009.4 observed.

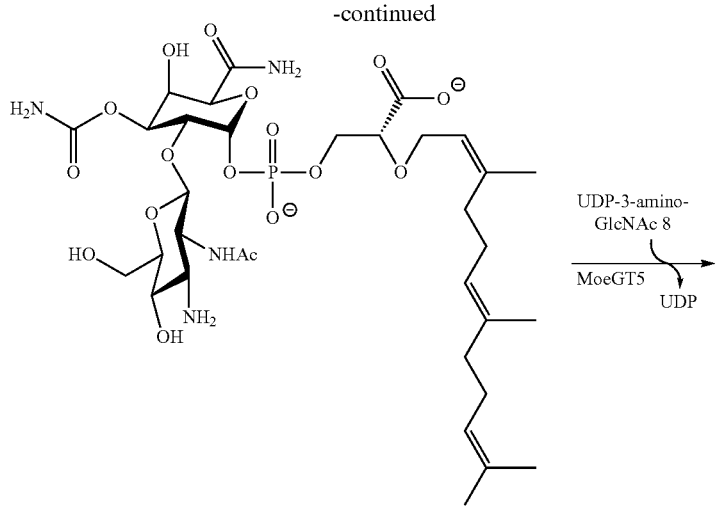

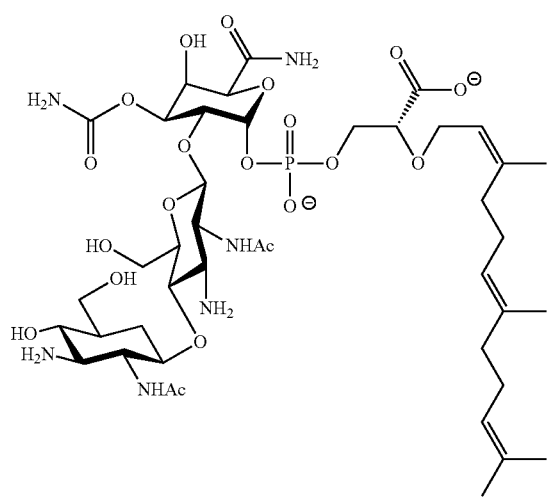

13

Reconstitution of C$_{15}$-farnesyl-C(3'-amino)E(3'-amino)F-trisaccharide 13 MmA analog.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

---

What is claimed is:

1. A compound of formula (I):

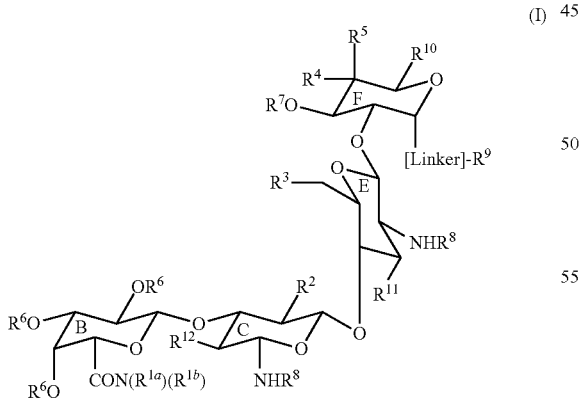

or a pharmaceutically acceptable salt thereof; wherein:

$R^{1a}$ and $R^{1b}$ are, independently, H, an amino protecting group, optionally substituted aryl, optionally substituted heteroaryl, optionally substituted aliphatic, or optionally substituted heteroaliphatic;

each instance of $R^2$, $R^4$, and $R^5$ is, independently, H, $-OR^z$, $-N(R^z)_2$, optionally substituted aryl, optionally substituted heteroaryl, optionally substituted aliphatic, or optionally substituted heteroaliphatic, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety;

$R^3$ is, independently, H, $-OH$, $-NH_2$, $-SH$, $-OR^w$, $-NH(R^w)$, $-N(R^w)_2$, $-SR^w$, $-O(C=O)R^w$, $-NH(C=O)R^w$, $-O(C=NH)R^w$, $-NH(C=NH)R^w$, $-S(C=NH)R^w$, $-NH(C=S)R^w$, $-S(C=O)R^w$, $-O(C=S)R^w$, $-S(=S)R^w$, optionally substituted aryl, optionally substituted heteroaryl, optionally substituted aliphatic, or optionally substituted heteroaliphatic, wherein $R^w$ is a carbohydrate moiety, optionally substituted aryl, optionally substituted heteroaryl, optionally substituted aliphatic, or optionally substituted heteroaliphatic;

each instance of $R^6$ and $R^7$ is, independently, H, a hydroxyl protecting group, optionally substituted aryl, optionally substituted heteroaryl, optionally substituted aliphatic, optionally substituted heteroaliphatic, a carbohydrate moiety, $-C(=O)N(R^Z)_2$, $-C(=O)OR^Z$, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety; and each instance of $R^8$ is, independently, H, an amino protecting group, optionally substituted aryl, optionally substituted heteroaryl, optionally substituted aliphatic, optionally substituted heteroaliphatic, a carbohydrate moiety, or —C(=O)$R^w$, wherein $R^w$ is a carbohydrate moiety, optionally substituted aryl, optionally substituted heteroaryl, optionally substituted aliphatic, or optionally substituted heteroaliphatic;

[Linker] is the group:

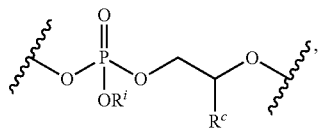

wherein:

$R^c$ is hydrogen, halogen, optionally substituted heteroaryl, —O$R^q$, —N($R^q$)$_2$, —S$R^q$, —NO$_2$, —CN, —N$_3$, —N($R^q$)=N$R^q$, —CHO, —C(=O)$R^q$, —C(=S)$R^q$, —C(=N$R^q$)$R^q$, —C(=O)O$R^q$, —C(=N$R^q$)O$R^q$, —C(=N$R^q$)N($R^q$)$_2$, —C(=O)N($R^q$)$_2$, —C(=S)O$R^q$, —C(=O)S$R^q$, —C(=S)S$R^q$, —P(=O)(O$R^q$)$_2$, —P(=O)$_2$(O$R^q$), —S(=O)(O$R^q$), —S(=O)$_2$(O$R^q$), —P(=O)N($R^q$)$_2$, —P(=O)$_2$N($R^q$)$_2$, —C(=O)N$R^q$S(=O)$_2$$R^q$, —S(=O)N($R^q$)$_2$, —S(=O)$_2$N($R^q$)$_2$, or optionally substituted heteroaryl; wherein each instance of $R^q$ is H, optionally substituted aliphatic, optionally substituted heteroaliphatic, optionally substituted aryl, optionally substituted heteroaryl, or a protecting group;

$R^i$ is H, optionally substituted aliphatic, optionally substituted heteroaliphatic, optionally substituted aryl, optionally substituted heteroaryl, or a hydroxyl protecting group; and $R^9$ is H or an optionally substituted $C_{1-30}$ aliphatic moiety, wherein 0 to 10 methylene units are optionally replaced with —O—, —N$R^x$, —S—, —C(=O)—, —C(=N$R^x$)—, —S(=O)—, —S(=O)$_2$—, —N=N—, —C($R^y$)=C($R^y$)—, an optionally substituted arylene, or an optionally substituted heteroarylene moiety, wherein each instance of $R^x$ is, independently, H, optionally substituted aliphatic, optionally substituted heteroaliphatic, optionally substituted aryl, optionally substituted heteroaryl, or an amino protecting group, and each instance of $R^y$ is, independently, H, optionally substituted aliphatic, optionally substituted heteroaliphatic, optionally substituted aryl, or optionally substituted heteroaryl, $R^{10}$ is —C(=O)NH$R^8$, —CH$_2$O$R^6$, or —C(=O)O$R^6$;

$R^{11}$ is —O$R^6$ or —NH$R^8$;

$R^{12}$ is —O$R^6$ or —NH$R^8$;

with the proviso that the compound is not moenomycin A; moenomycin $A_{1\cdot2}$; moenomycin $C_1$; moenomycin $C_3$; moenomycin $C_4$; AC326-alpha; pholipomycin; decahydromoenomycin A; decahydromoenomycin $A_{1\cdot2}$; decahydromoenomycin $C_1$, decahydropholipomycin; octahydro-AC326-alpha; dihydromoenomycin A; [$^3$H] moenomycin A; [$^2$H] moenomycin A; or a moenomycin compound wherein $R^9$ is:

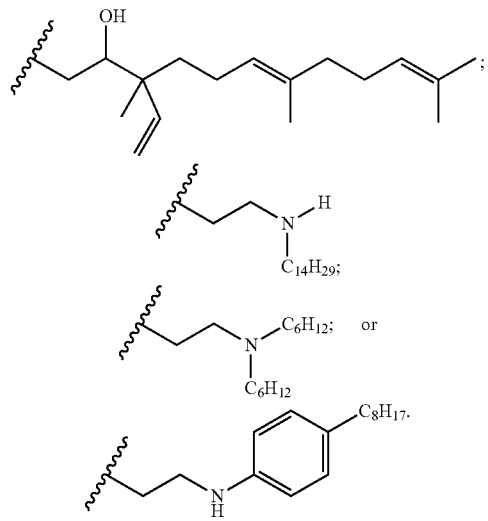

2. A compound of formula (III):

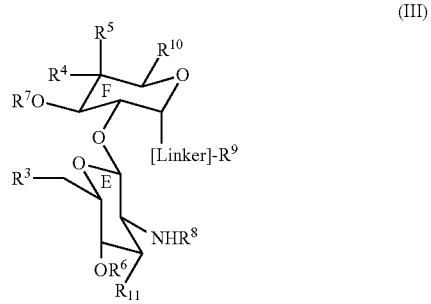

or a pharmaceutically acceptable salt thereof;
wherein:

$R^3$ is, independently, H, —OH, —NH$_2$, —SH, —O$R^w$, —NH($R^w$), —N($R^w$)$_2$, —S$R^w$, —O(C=O)$R^w$, —NH(C=O)$R^w$, —O(C=NH)$R^w$, —NH(C=NH)$R^w$, —S(C=NH)$R^w$, —NH(C=S)$R^w$, —S(C=O)$R^w$, —O(C=S)$R^w$, —S(=S)$R^w$, optionally substituted aryl, optionally substituted heteroaryl, optionally substituted aliphatic, or optionally substituted heteroaliphatic, wherein $R^w$ is a carbohydrate moiety, optionally substituted aryl, optionally substituted heteroaryl, optionally substituted aliphatic, or optionally substituted heteroaliphatic;

each instance of $R^4$ and $R^5$ is, independently, H, —O$R^z$, —N($R^z$)$_2$, optionally substituted aryl, optionally substituted heteroaryl, optionally substituted aliphatic, or optionally substituted heteroaliphatic, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety;

each instance of $R^6$ and $R^7$ is, independently, H, a hydroxyl protecting group, optionally substituted aryl, optionally substituted heteroaryl, optionally substituted aliphatic, optionally substituted heteroaliphatic, a carbohydrate moiety, —C(=O)N($R^z$)$_2$, —C(=O)O$R^z$, wherein $R^z$ is H, a hydroxyl protecting group, an amino protecting group, optionally substituted aryl, optionally substituted heteroaryl, or optionally substituted aliphatic, optionally substituted heteroaliphatic, or a carbohydrate moiety; and each instance of $R^8$ is, independently, H, an amino protecting group, optionally substituted aryl, optionally substituted heteroaryl, optionally substituted aliphatic, optionally substituted heteroaliphatic, a carbohydrate moiety, or —C(=O)$R^w$, wherein $R^w$ is a carbohydrate moiety, optionally substituted aryl, optionally substituted heteroaryl, optionally substituted aliphatic, or optionally substituted heteroaliphatic;

[Linker] is the group:

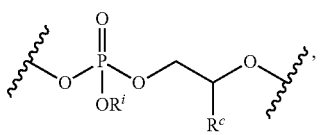

wherein:

$R^c$ is hydrogen, halogen, optionally substituted heteroaryl, —O$R^q$, —N($R^q$)$_2$, —S$R^q$, —NO$_2$, —CN, —N$_3$, —N($R^q$)=N$R^q$, —CHO, —C(=O)$R^q$, —C(=S)$R^q$, —C(=N$R^q$)$R^q$, —C(=O)O$R^q$, —C(=N$R^q$)O$R^q$, —C(=N$R^q$)N($R^q$)$_2$, —C(=O)N($R^q$)$_2$, —C(=S)O$R^q$, —C(=O)S$R^q$, —C(=S)S$R^q$, —P(=O)(O$R^q$)$_2$, —P(=O)$_2$(O$R^q$), —S(=O)(O$R^q$), —S(=O)$_2$(O$R^q$), —P(=O)N($R^q$)$_2$, —P(=O)$_2$N($R^q$)$_2$, —C(=O)N$R^q$S(=O)$_2$$R^q$, —S(=O)N($R^q$)$_2$, —S(=O)$_2$N($R^q$)$_2$, or optionally substituted heteroaryl; wherein each instance of $R^q$ is H, optionally substituted aliphatic, optionally substituted heteroaliphatic, optionally substituted aryl, optionally substituted heteroaryl, or a protecting group;

$R^i$ is H, optionally substituted aliphatic, optionally substituted heteroaliphatic, optionally substituted aryl, optionally substituted heteroaryl, or a hydroxyl protecting group; and $R^9$ is H,

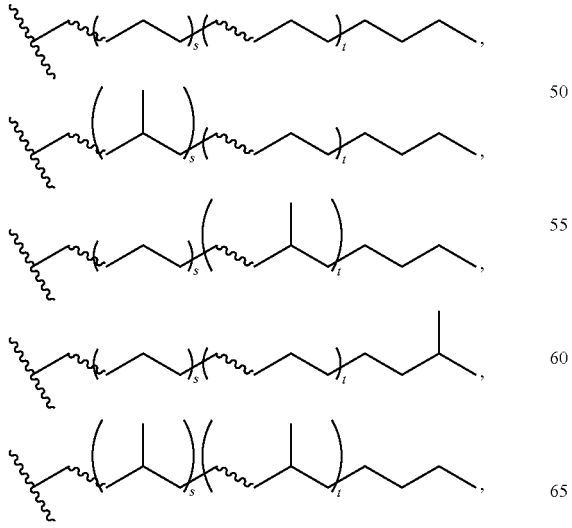

-continued

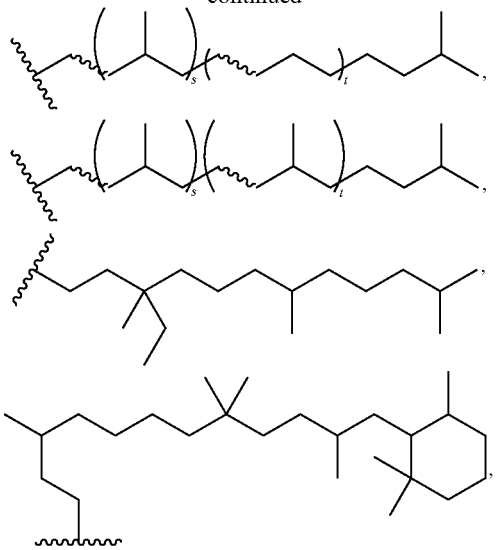

unsubstituted or saturated hydrocarbon chain, unsubstituted or unsaturated hydrocarbon chain, substituted or unsaturated hydrocarbon chain, an optionally substituted aryl, or an optionally substituted heteroaryl moiety, wherein each instance of s and t is independently 0, 1, 2, 3, 4, or 5;

each instance of $R^x$ is, independently, H, optionally substituted aliphatic, optionally substituted heteroaliphatic, optionally substituted aryl, optionally substituted heteroaryl, or an amino protecting group, and each instance of $R^y$ is, independently, H, optionally substituted aliphatic, optionally substituted heteroaliphatic, optionally substituted aryl, or optionally substituted heteroaryl;

$R^{10}$ is C(O)NH$R^8$, —CH$_2$O$R^6$, or —C(=O)O$R^6$; and $R^{11}$ is —O$R^6$ or —NH$R^8$.

3. The compound according to claim 1, wherein $R^{1a}$ and $R^{1b}$ are, independently, H or the group:

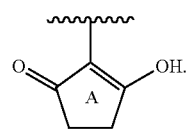

4. The compound according to claim 1, wherein $R^2$ is —CH$_3$ or —CH$_2$OH.

5. The compound according to claim 1, wherein $R^3$ is —OH or —O$R^w$.

6. The compound according to claim 1, wherein $R^3$ is O$R^w$, wherein $R^w$ is a carbohydrate moiety.

7. The compound according to claim 1, wherein $R^4$ and $R^5$ are, independently, H, —CH$_3$, —N($R^z$)$_2$, or —O$R^z$.

8. The compound according to claim 1, wherein each instance of $R^6$ is, independently, H or —C(=O)CH$_3$.

9. The compound according to claim 1, wherein $R^7$ is H, —C(=O)CH$_3$, or —C(=O)NH$_2$.

10. The compound according to claim 1, wherein $R^8$ is H or —C(=O)CH$_3$.

11. The compound according to claim 1, wherein $R^c$ is —C(=O)H, —C(=O)OH, or —C(=O)NH$_2$.

12. The compound according to claim 1, wherein $R^i$ is H or a hydroxyl protecting group.

13. The compound according to claim 1, wherein $R^9$ is an optionally substituted, optionally unsaturated, $C_{10-20}$ hydrocarbon chain, wherein 0 to 8 methylene units are optionally replaced with —O—, —NR$^x$—, —S—, —C(=O)—, —C(=NR$^x$)—, —S(=O)—, —S(=O)$_2$—, —N=N—, —C(R$^y$)=C(R$^y$), an optionally substituted arylene or an optionally substituted heteroarylene moiety.

14. The compound of claim 1, wherein $R^9$ is an optionally substituted, optionally unsaturated, $C_{10}$-$C_{16}$ aliphatic moiety.

15. The compound of claim 1 wherein $R^9$ is of one of the formulae:

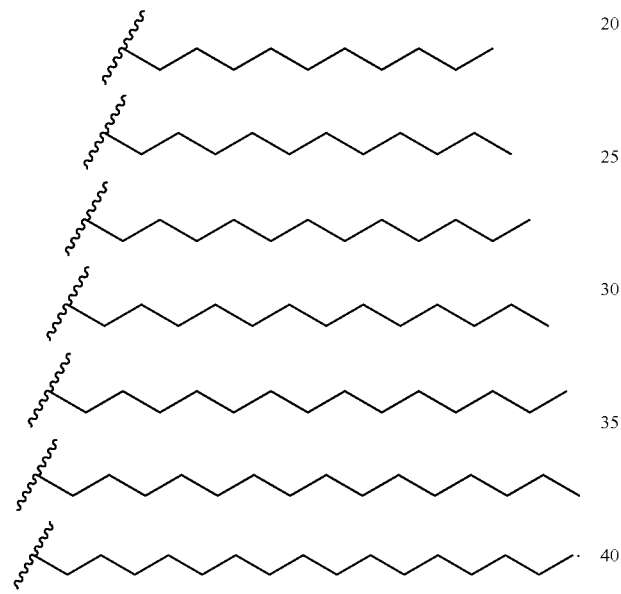

16. The compound of claim 1, wherein $R^9$ is a fluorinated, $C_8$-$C_{16}$ alkyl moiety.

17. The compound of claim 1, wherein $R^9$ is of one of the formulae:

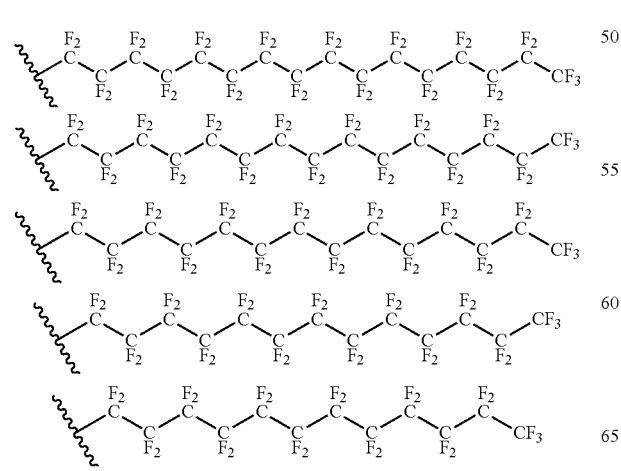

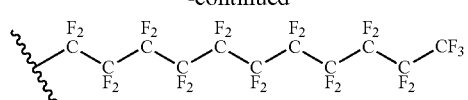

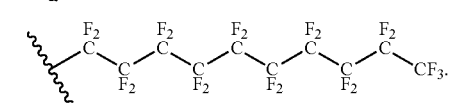

18. The compound of claim 1, wherein $R^9$ is of one of the formulae:

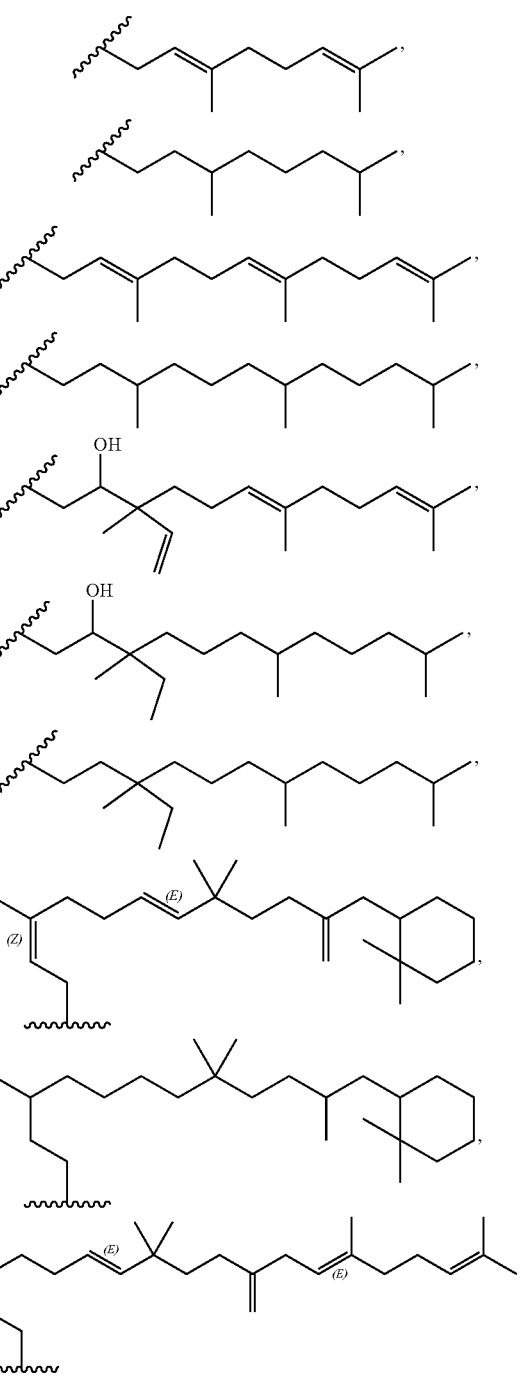

-continued

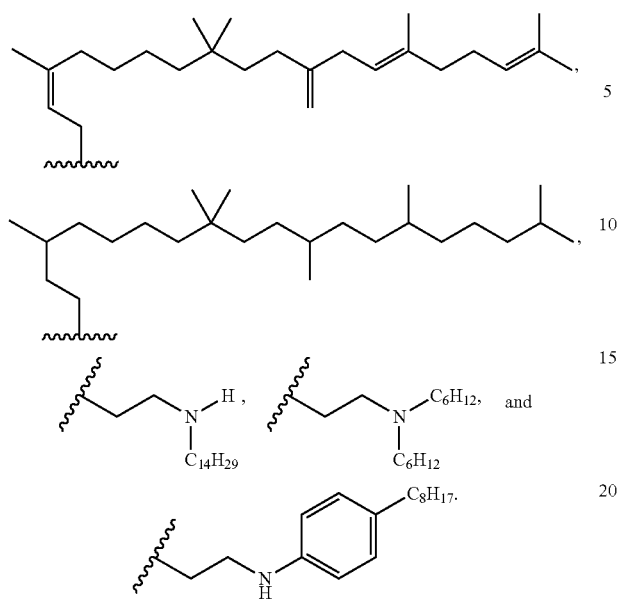

19. The compound of claim 1, wherein $R^9$ is of the formula:

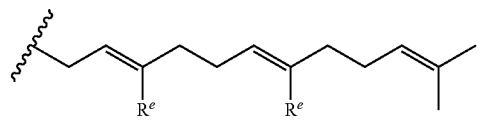

wherein each occurrence of $R^e$ is independently hydrogen or an optionally substituted aliphatic moiety.

20. The compound of claim 1, wherein [Linker] is of formula:

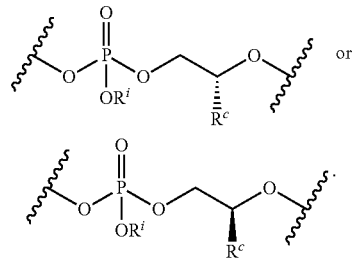

21. The compound of claim 1, wherein $R^{10}$ is —C(=O)NHR$^8$.

22. The compound of claim 1, wherein $R^{10}$ is —C(=O)NH$_2$.

23. The compound of claim 1, wherein $R^{11}$ is —OR$^6$.

24. The compound of claim 1, wherein $R^{11}$ is —OH.

25. The compound of claim 1, wherein $R^{12}$ is —OR$^6$.

26. The compound of claim 1, wherein $R^{12}$ is —OH.

27. A pharmaceutical composition comprising a compound of claim 1.

28. A compound of formula (IV):

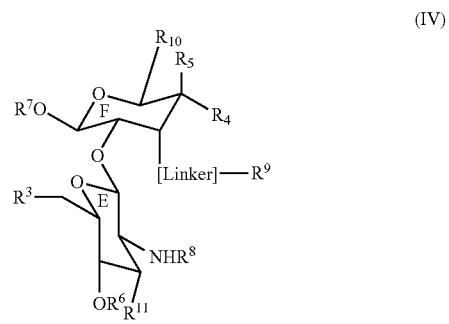

or a pharmaceutically acceptable salt thereof;
wherein:
 $R^3$ is, independently, H, —OH, —NH$_2$, —SH, —OR$^w$, —NH(R$^w$), —N(R$^w$)$_2$, —SR$^w$, —O(C=O)R$^w$, —NH(C=O)R$^w$, —O(C=NH)R$^w$, —NH(C=NH)R$^w$, —S(C=NH)R$^w$, —NH(C=S)R$^w$, —S(C=O)R$^w$, —O(C=S)R$^w$, —S(=S)R$^w$, optionally substituted aryl, optionally substituted heteroaryl, optionally substituted aliphatic, or optionally substituted heteroaliphatic, wherein R$^w$ is a carbohydrate moiety, optionally substituted aryl, optionally substituted heteroaryl, optionally substituted aliphatic, or optionally substituted heteroaliphatic;
 each instance of $R^4$ and $R^5$ is, independently, H, —OR$^z$, —N(R$^z$)$_2$, optionally substituted aryl, optionally substituted heteroaryl, optionally substituted aliphatic, or optionally substituted heteroaliphatic, wherein R$^z$ is H, a hydroxyl protecting group, an amino protecting group, optionally substituted aryl, optionally substituted heteroaryl, or optionally substituted aliphatic, optionally substituted heteroaliphatic, or a carbohydrate moiety;
 each instance of $R^6$ and $R^7$ is, independently, H, a hydroxyl protecting group, optionally substituted aryl, optionally substituted heteroaryl, optionally substituted aliphatic, optionally substituted heteroaliphatic, a carbohydrate moiety, —C(=O)N(R$^Z$)$_2$, —C(=O)OR$^Z$, wherein R$^z$ is H, a hydroxyl protecting group, an amino protecting group, optionally substituted aryl, optionally substituted heteroaryl, or optionally substituted aliphatic, optionally substituted heteroaliphatic, or a carbohydrate moiety; and
 each instance of $R^8$ is, independently, H, an amino protecting group, optionally substituted aryl, optionally substituted heteroaryl, optionally substituted aliphatic, optionally substituted heteroaliphatic, a carbohydrate moiety, or —C(=O)R$^w$, wherein R$^w$ is a carbohydrate moiety, optionally substituted aryl, optionally substituted heteroaryl, optionally substituted aliphatic, or optionally substituted heteroaliphatic;
[Linker] is the group:

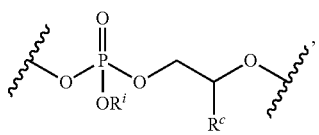

wherein:

R$^c$ is hydrogen, halogen, optionally substituted heteroaryl, —OR$^q$, —N(R$^q$)$_2$, —SR$^q$, —NO$_2$, —CN, —N$_3$, —N(R$^q$)=NR$^q$, —CHO, —C(=O)R$^q$, —C(=S)R$^q$, —C(=NR$^q$)R$^q$, —C(=O)OR$^q$, —C(=NR$^q$)OR$^q$, —C(=NR$^q$)N(R$^q$)$_2$, —C(=O)N(R$^q$)$_2$, —C(=S)OR$^q$, —C(=O)SR$^q$, —C(=S)SR$^q$, —P(=O)(OR$^q$)$_2$, —P(=O)$_2$(OR$^q$), —S(=O)(OR$^q$), —S(=O)$_2$(OR$^q$), —P(=O)N(R$^q$)$_2$, —P(=O)$_2$N(R$^q$)$_2$, —C(=O)NR$^q$S(=O)$_2$R$^q$, —S(=O)N(R$^q$)$_2$, —S(=O)$_2$N(R$^q$)$_2$, or optionally substituted heteroaryl; wherein each instance of R$^q$ is H, optionally substituted aliphatic, optionally substituted heteroaliphatic, optionally substituted aryl, optionally substituted heteroaryl, or a protecting group;

R$^i$ is H, optionally substituted aliphatic, optionally substituted heteroaliphatic, optionally substituted aryl, optionally substituted heteroaryl, or a hydroxyl protecting group; and R$^9$ is H, an optionally substituted C$_{1-30}$ aliphatic moiety, wherein 0 to 10 methylene units are optionally replaced with —O—, —NR$^x$—, —S—, —C(=O)—, —C(=NR$^x$)—, —S(=O)—, —S(=O)$_2$—, —N=N—, —C(R$^y$)=C(R$^y$)—, an optionally substituted arylene, or an optionally substituted heteroarylene moiety, wherein each instance of R$^x$ is, independently, H, optionally substituted aliphatic, optionally substituted heteroaliphatic, optionally substituted aryl, optionally substituted heteroaryl, or an amino protecting group, and each instance of R$^y$ is, independently, H, optionally substituted aliphatic, optionally substituted heteroaliphatic, optionally substituted aryl, or optionally substituted heteroaryl;

R$^{10}$ is —C(O)NHR$^8$, —CH$_2$OR$^6$, or —C(=O)OR$^6$; and

R$^{11}$ is —OR$^6$ or —NHR$^8$.

* * * * *

UNITED STATES PATENT AND TRADEMARK OFFICE
CERTIFICATE OF CORRECTION

PATENT NO. : 8,604,004 B2
APPLICATION NO. : 12/681052
DATED : December 10, 2013
INVENTOR(S) : Daniel Evan Kahne et al.

Page 1 of 2

It is certified that error appears in the above-identified patent and that said Letters Patent is hereby corrected as shown below:

*In the Claims*

In claim 2, at column 196, line 42, the text "$R^{10}$ is C(O)NHR$^8$," should read as follows: --$R^{10}$ is C(=O)NHR$^8$,--.

In claim 2, at column 196, lines 33-40, definitions of $R^x$ and $R^y$ should be removed.

In claim 18, at column 198, lines 45-60, the formula:

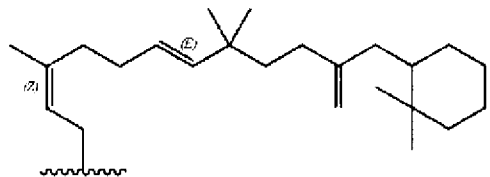

should be changed to the formula: 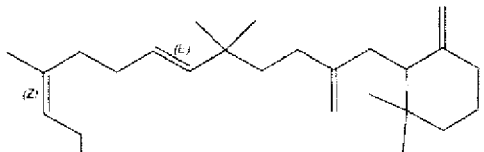.

In claim 18, at column 198, lines 55-60, the formula:

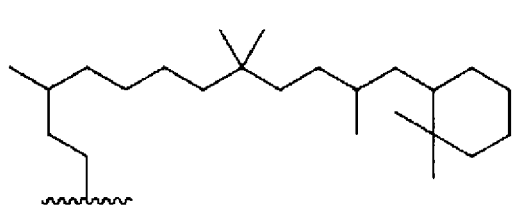

Signed and Sealed this
Twenty-sixth Day of August, 2014

Michelle K. Lee
*Deputy Director of the United States Patent and Trademark Office* should be changed to the formula: 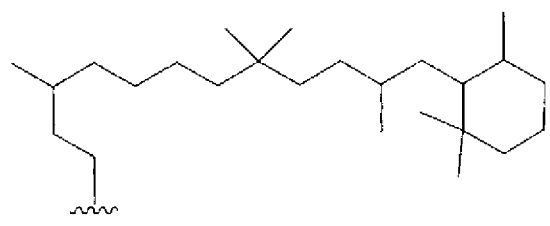.
In claim 28, at column 202, line 16, the text "$R^{10}$ is –C(O)NHR$^8$," should read as follows: --$R^{10}$ is –C(=O)NHR$^8$--.

UNITED STATES PATENT AND TRADEMARK OFFICE
CERTIFICATE OF CORRECTION

PATENT NO. : 8,604,004 B2
APPLICATION NO. : 12/681052
DATED : December 10, 2013
INVENTOR(S) : Kahne et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 694 days.

Signed and Sealed this
Second Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,604,004 B2
APPLICATION NO. : 12/681052
DATED : December 10, 2013
INVENTOR(S) : Daniel Evan Kahne et al.

It is certified that error appears in the above-identified patent and that said Letters Patent is hereby corrected as shown below:

In the Specification

At Column 1, Lines 39-41, please replace the current "Government Support" section as shown below:

"This invention was made with Government support under Grant GM66174 awarded by the National Institutes of Health. The Government has certain rights in the invention."

with the following new section:

--This invention was made with government support under grant number GM066174 awarded by the National Institutes of Health. The government has certain rights in the invention.--

Signed and Sealed this
Twenty-eighth Day of March, 2017

Michelle K. Lee
*Director of the United States Patent and Trademark Office*